(12) United States Patent
Ranum et al.

(10) Patent No.: US 11,035,867 B2
(45) Date of Patent: Jun. 15, 2021

(54) USE AND TREATMENT OF DI-AMINO ACID REPEAT-CONTAINING PROTEINS ASSOCIATED WITH ALS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/851,690

(22) Filed: Apr. 17, 2020

(65) Prior Publication Data
US 2020/0341012 A1    Oct. 29, 2020

Related U.S. Application Data

(62) Division of application No. 16/362,908, filed on Mar. 25, 2019, now Pat. No. 10,663,475, which is a division of application No. 14/775,278, filed as application No. PCT/US2014/022670 on Mar. 10, 2014, now Pat. No. 10,295,547.

(60) Provisional application No. 61/883,219, filed on Sep. 27, 2013, provisional application No. 61/786,258, filed on Mar. 14, 2013.

(51) Int. Cl.
| | |
|---|---|
| *G01N 33/68* | (2006.01) |
| *A61K 35/28* | (2015.01) |
| *B01D 21/26* | (2006.01) |
| *C07K 16/18* | (2006.01) |
| *C12Q 1/6883* | (2018.01) |

(52) U.S. Cl.
CPC ......... *G01N 33/6896* (2013.01); *A61K 35/28* (2013.01); *B01D 21/262* (2013.01); *C07K 16/18* (2013.01); *C12Q 1/6883* (2013.01); *C07K 2317/34* (2013.01); *C12Q 2600/158* (2013.01); *G01N 2800/285* (2013.01); *G01N 2800/2835* (2013.01)

(58) Field of Classification Search
None
See application file for complete search history.

(56) References Cited

U.S. PATENT DOCUMENTS

| | | |
|---|---|---|
| 5,011,912 A | 4/1991 | Hopp et al. |
| 6,204,008 B1 | 3/2001 | Borneman et al. |
| 6,342,581 B1 | 1/2002 | Rosen et al. |
| 7,481,997 B1 | 1/2009 | Hardy |
| 8,993,663 B2 | 3/2015 | Megeney et al. |
| 9,448,232 B2 | 9/2016 | Petrucelli et al. |
| 10,295,547 B2 * | 5/2019 | Ranum ............... C07K 16/18 |
| 10,509,045 B2 | 12/2019 | Ranum et al. |
| 10,663,475 B2 * | 5/2020 | Ranum ............... C12Q 1/6883 |
| 2002/0165355 A1 | 11/2002 | Meheus et al. |
| 2003/0233675 A1 | 12/2003 | Cao et al. |
| 2007/0004729 A1 | 1/2007 | Timmer et al. |
| 2007/0014810 A1 * | 1/2007 | Baker ................... A61K 39/12 |
| | | 424/186.1 |
| 2007/0036760 A1 | 2/2007 | Wilson et al. |
| 2007/0093426 A1 | 4/2007 | Wormser |
| 2008/0227699 A1 | 9/2008 | Chiba et al. |
| 2009/0312395 A1 | 12/2009 | El-Tanani et al. |
| 2012/0076785 A1 | 3/2012 | Nikolaev et al. |
| 2012/0094299 A1 | 4/2012 | Ranum et al. |
| 2012/0220534 A1 | 8/2012 | Levin et al. |
| 2013/0115603 A9 | 5/2013 | Ranum et al. |
| 2014/0336133 A1 | 11/2014 | Miller et al. |
| 2015/0361166 A1 | 12/2015 | Edbauer et al. |
| 2016/0025747 A1 | 1/2016 | Ranum et al. |
| 2016/0096800 A1 | 4/2016 | Walter et al. |
| 2018/0292416 A1 | 10/2018 | Ranum et al. |
| 2019/0142858 A1 | 5/2019 | Ranum et al. |
| 2019/0285652 A1 | 9/2019 | Ranum et al. |
| 2020/0140846 A1 | 5/2020 | Ranum et al. |
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |

FOREIGN PATENT DOCUMENTS

| | | |
|---|---|---|
| EP | 2 837 390 A1 | 2/2015 |
| EP | 2 948 471 A1 | 12/2015 |
| WO | WO 2001/75067 A2 | 10/2001 |
| WO | WO 2006/083800 A2 | 8/2006 |
| WO | WO 2010/115033 A2 | 10/2010 |
| WO | WO 2010/132982 A1 | 11/2010 |

(Continued)

OTHER PUBLICATIONS

Ash et al., Unconventional Translation of C9ORF72 GGGGCC Expansion Generates Insoluble Polypeptides Specific to C9FTD/ALS, Feb. 20, 2013, Neuron 77:639-646 (Year: 2013).*
Mori et al., The C9orf72 GGGGCC Repeat Is Translated into Aggregating Dipeptide-Repeat Proteins in FTLD/ALS, Mar. 15, 2013, Epub Feb. 7, 2013 (Year: 2013).*
Extended European Search Report, dated Sep. 30, 2016, in connection with Application No. EP 14776090.4.
International Search Report and Written Opinion, dated Aug. 22, 2014, in connection with Application No. PCT/US2014/022670.

(Continued)

*Primary Examiner* — John D Ulm
(74) *Attorney, Agent, or Firm* — Wolf, Greenfield & Sacks, P.C.

(57) ABSTRACT

Disclosed herein are methods and compositions for identifying and/or treating subjects having or likely to have amyotrophic lateral sclerosis (ALS) or frontotemporal dementia (FTD). Antibodies specific for one or more di-amino acid repeat-containing proteins are also provided herein.

3 Claims, 35 Drawing Sheets
Specification includes a Sequence Listing.

(56) References Cited

FOREIGN PATENT DOCUMENTS

| WO | WO 2013/030588 A1 | 3/2013 |
|----|-------------------|--------|
| WO | WO 2014/114303 A1 | 7/2014 |
| WO | WO 2014/114660 A1 | 7/2014 |
| WO | WO 2014/116865 A1 | 7/2014 |
| WO | WO 2017/176813 A1 | 10/2017 |
| WO | WO 2018/035408 A1 | 2/2018 |

OTHER PUBLICATIONS

International Preliminary Report on Patentability, dated Sep. 24, 2015, in connection with Application No. PCT/US2014/022670.
International Search Report and Written Opinion, dated Sep. 21, 2016, in connection with Application No. PCT/US2016/034738.
International Preliminary Report on Patentability, dated Dec. 14, 2017, in connection with Application No. PCT/US2016/034738.
Supplementary Partial European Search Report, dated Oct. 18, 2019, in connection with Application No. EP 17779695.0.
Extended European Search Report, dated Jan. 7, 2020, in connection with Application No. EP 17779695.0.
Extended European Search Report, dated Dec. 17, 2020, in connection with Application No. EP 18786964.9.
International Preliminary Report on Patentability, dated Oct. 31, 2019, in connection with Application No. PCT/US2018/028015.
International Search Report and Written Opinion, dated Jan. 15, 2019, in connection with Application No. PCT/US2018/052913.
International Preliminary Report on Patentability, dated Apr. 9, 2020, in connection with Application No. PCT/US2018/052913.
International Search Report and Written Opinion, dated Dec. 6, 2019, in connection with Application No. PCT/US2018/052745.
International Preliminary Report on Patentability, dated Apr. 9, 2020, in connection with Application No. PCT/US2018/052745.
[No Author Listed], Abstracts. Medgen. Mar. 4, 2016; 28(1):84-232. doi: 10.1007/s11825-016-0083-5.
[No Author Listed] EBNA1—Epstein-Barr nuclear antigen 1—Epstein-Barr virus (strain GD1) (HHV-4)—EBNA1 gene & protein, 2018 Jan. 2018. Retrieved from the internet under https://www.uniprot.org/uniprot/Q3KSS4 on Sep. 12, 2018. 6 pages.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular α-synuclein prevents cell-to-cell aggregate transmission. J Neurosci. Sep. 26, 2012;32(39):13454-69.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Functional genomics in *Drosophila* models of human disease. Briefings in Functional Genomics. Aug. 22, 2012;11(5):405-415.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.
Duan et al., Generation of polyclonal antiserum for the detection of methylarginine proteins. J Immunol Methods. Mar. 30, 2007;320(1-2):132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.
Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.
Jin et al., Metformin Protects Cells from Mutant Huntingtin Toxicity Through Activation of AMPK and Modulation of Mitochondrial Dynamics. Neuromolecular Med. Dec. 2016;18(4):581-592. doi: 10.1007/s12017-016-8412-z. Epub May 25, 2016.
Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.
Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.
Satoh et al., Dystrophic neurites express C9orf72 in Alzheimer's disease brains. Alzheimers Res Ther. Aug. 16, 2012;4(4):33. doi: 10.1186/alzrt136. 13 pages.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12):1563-9.
Trouth et al., Myasthenia gravis: a review. Autoimmune Dis. ;2012:874680. doi: 10.1155/2012/874680. Epub Oct. 31, 2012.
Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi:10.1038/srep26120.
Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.
Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.
Yu et al., Developing therapeutic antibodies for neurodegenerative disease. Neurotherapeutics. Jul. 2013;10(3):459-72. doi: 10.1007/s13311-013-0187-4.
Zhang et al., Aggregation-prone c9FTD/ALS poly(GA) RAN-translated proteins cause neurotoxicity by inducing ER stress. Acta Neuropathol. 2014;128:505-24.
Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.

* cited by examiner

CMV-(G₄C₂)ₑₓₚ-3T
| CMV | 6xStops | (GGGGCC)exp | (GR)HA-(GP)Flag-(GA)Myc | SV40 poly (A) |
*FIG. 2A*
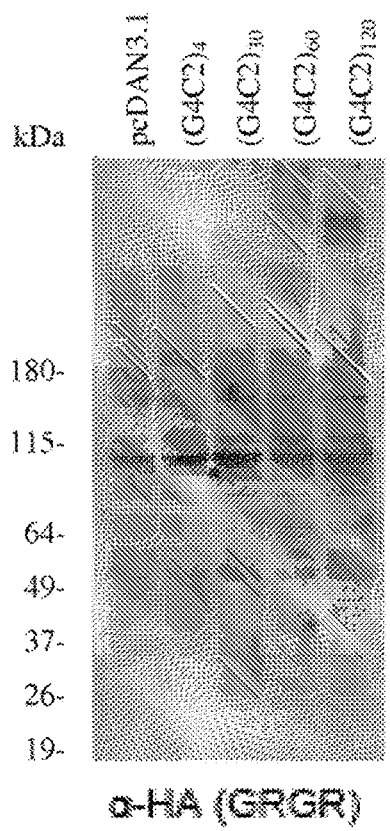
α-HA (GRGR)
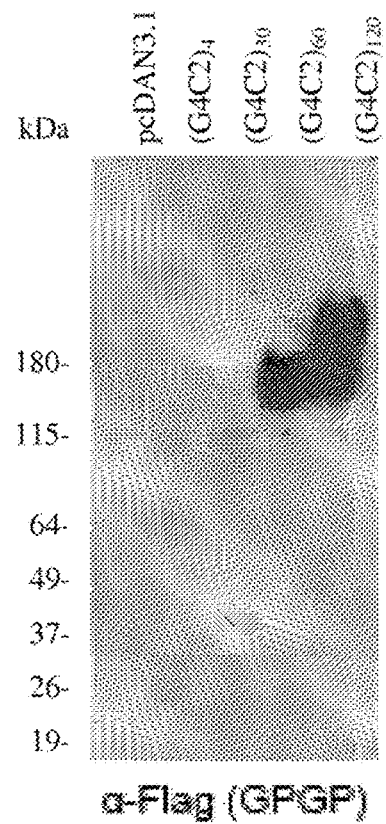
α-Flag (GPGP)
*FIG. 2B*

|  | Case Information | | | | | RAN Inclusions | | | | |
|---|---|---|---|---|---|---|---|---|---|---|
|  | Case | C9 EXP | Age | Sex/Race | PMD | DX | GP | PA | PR | GR | GA |
| Hippocampus | 1 | + | 59 | F/W | 4 | ALS | +++ | + | - | ++ | ++ |
|  | 2 | + | 42 | M/W | 10 | A/F | +++ | + | NA | NA | NA |
|  | 3 | + | 74 | F/W | 16 | FTD | +++ | +++* | +++* | ++ | + |
|  | 4 | + | 45 | M/W | 3 | ALS | +++ | - | + | ++ | + |
|  | 5 | + | 82 | F/W | 17 | FTD | +++ | + | + | ++ | + |
|  | 6 | + | 86 | F/W | 10 | A/F | ++ | - | - | ++ | - |
|  | 7 | - | 76 | M/W | 7 | ALS | - | - | - | - | - |
|  | 8 | - | 55 | M/W | 7.5 | ALS | - | - | NA | NA | NA |
|  | 9 | - | 60 | M/W | 16 | CON | - | - | NA | NA | NA |
|  | 10 | - | 81 | M/W | 6 | FTD | - | - | NA | NA | - |
|  | 11 | - | 83 | M/W | 17 | FTD+ | - | - | - | - | - |
|  | 12 | - | 77 | M/W | 16 | CON | - | - | - | - | - |
| Motor Cortex | 1 | + | 59 | F/W | 4 | ALS | +++ | - | - | ++ | ++ |
|  | 2 | + | 42 | M/W | 10 | A/F | +++ | + | + | + | + |
|  | 7 | - | 76 | M/W | 7 | ALS | - | - | - | - | - |
|  | 8 | - | 55 | M/W | 7.5 | ALS | - | - | - | - | - |
|  | 9 | - | 60 | M/W | 16 | CON | - | - | - | - | - |
| Spinal Cord | 2 | + | 42 | M/W | 6 | A/F | + | - | - | - | - |
|  | 13 | + | 53 | M/W | 10 | ALS | + | - | - | - | - |
|  | 14 | + | 55 | F/W | 7 | A/F | + | - | - | - | - |
|  | 7 | - | 76 | M/W | 7 | ALS | - | - | - | - | - |
|  | 8 | - | 55 | M/W | 7.5 | ALS | - | - | - | - | - |
|  | 9 | - | 60 | M/W | 16 | CON | - | - | - | - | - |
|  | 15 | - | 64 | F/W | 0 | ALS | - | - | - | - | - |
|  | 16 | - | 79 | M/W | 33 | ALS | - | - | - | - | - |
|  | 17 | - | 79 | M/W | 10 | ALS | - | - | - | - | - |

(-) no inclusions, (+) occasional, (++) moderate, (+++) numerous inclusions. (.) Variable staining from section to section. DX =diagnosis. FTD=frontotemporal dementia, ALS=amyotrophic lateral sclerosis. F=female, M=Male, PMD=post-mortem interval. NA = not available. HIPPO=hippocampus, M Cortex = motor cortex. The apparent differences in the frequencies of the various inclusions may reflect differences in protein conformation and epitope availability or differences in the affinities of these antibodies.

FIG. 18

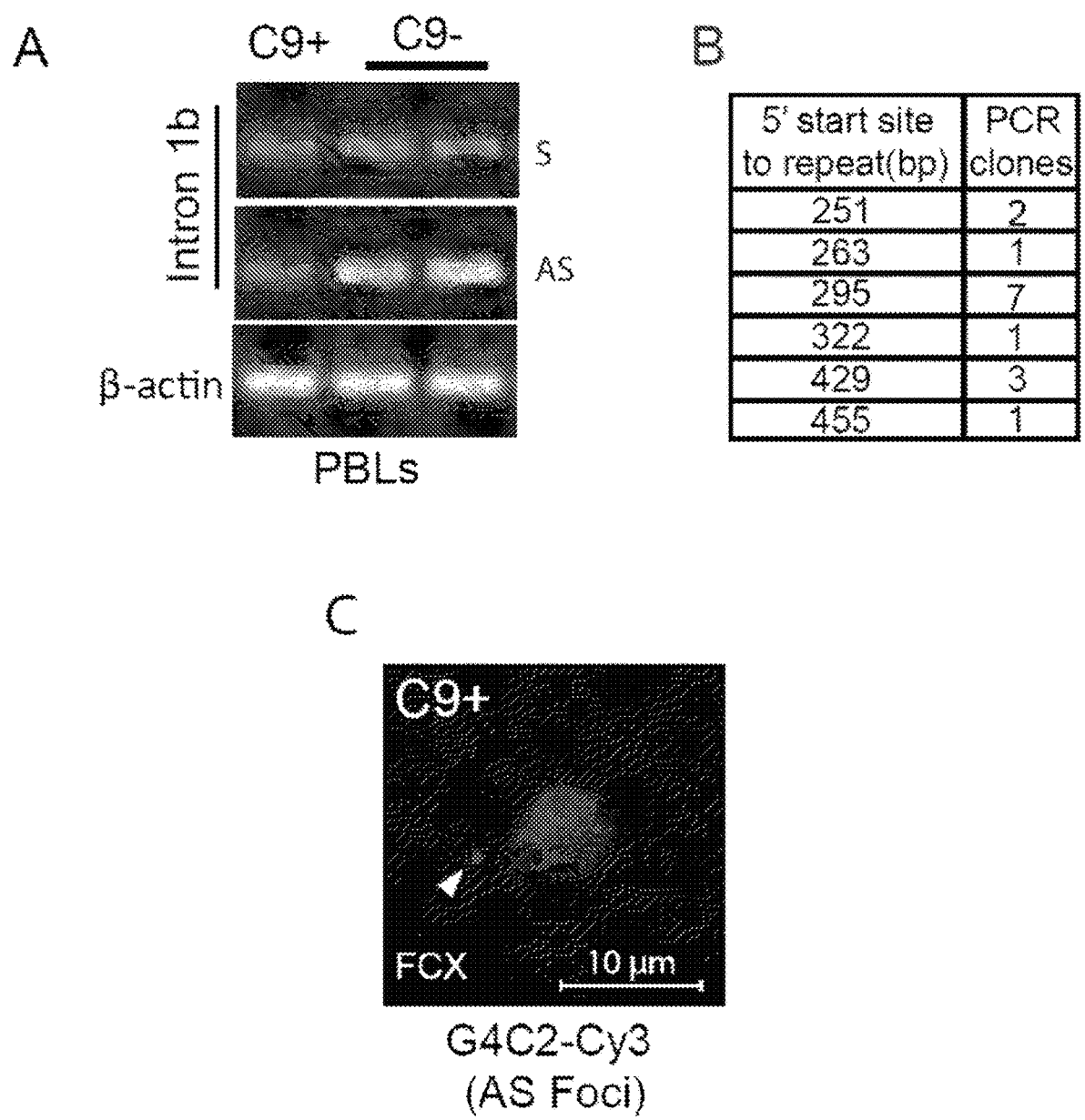
FIG. 19A-C

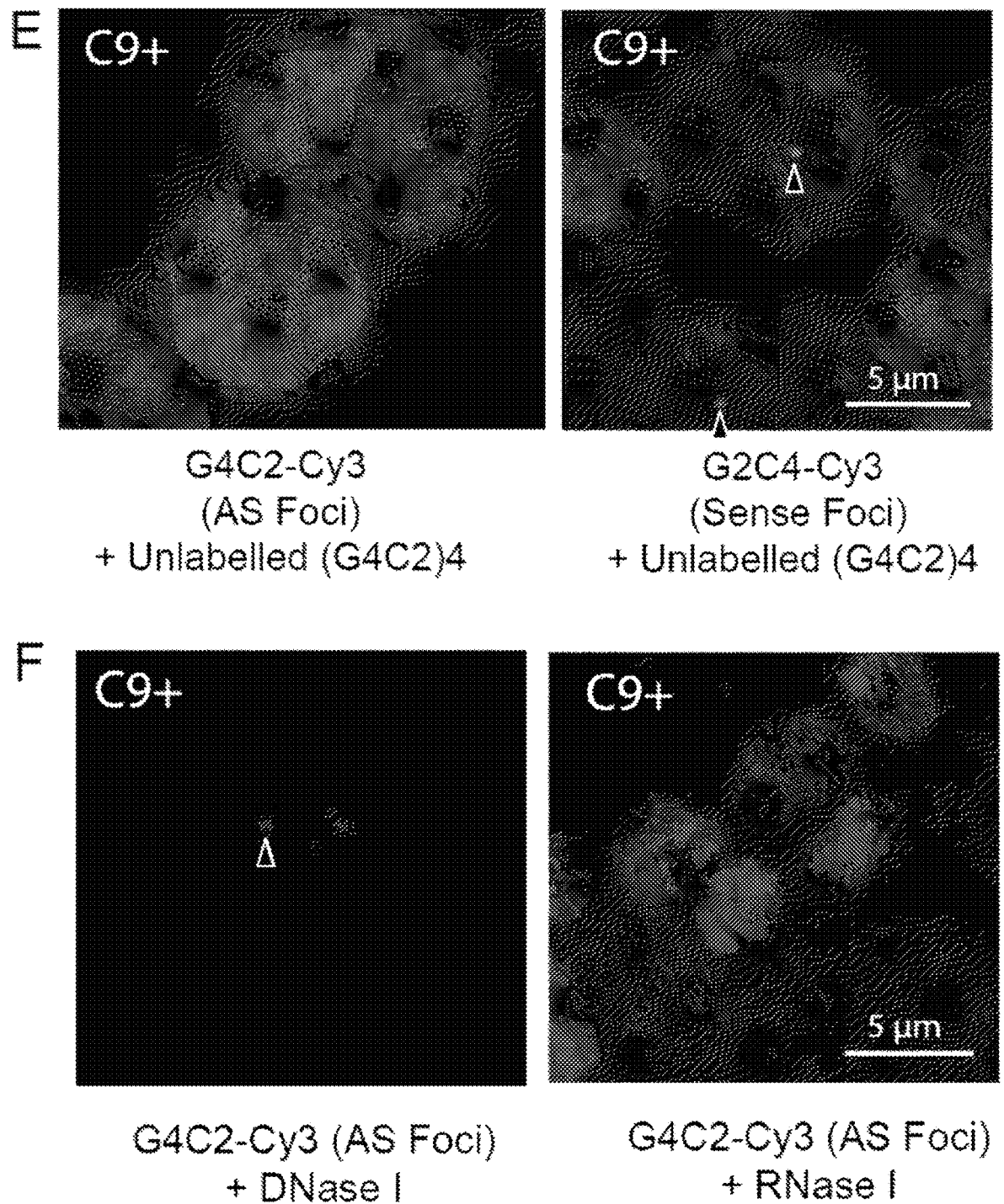
FIG. 19E-F

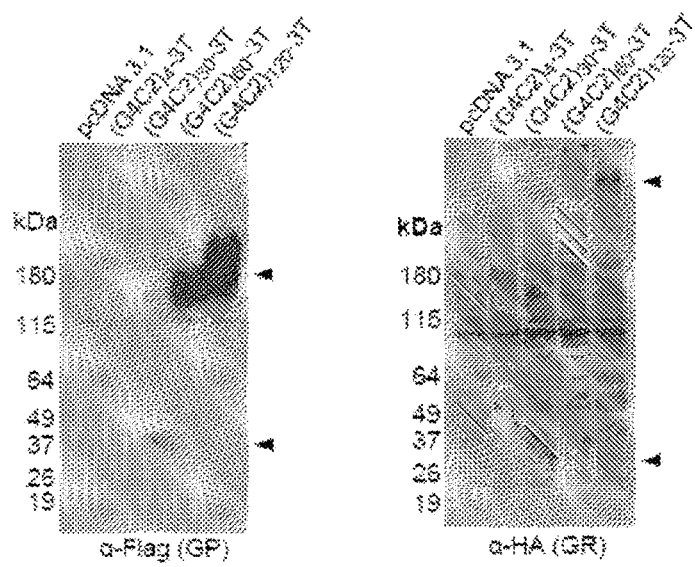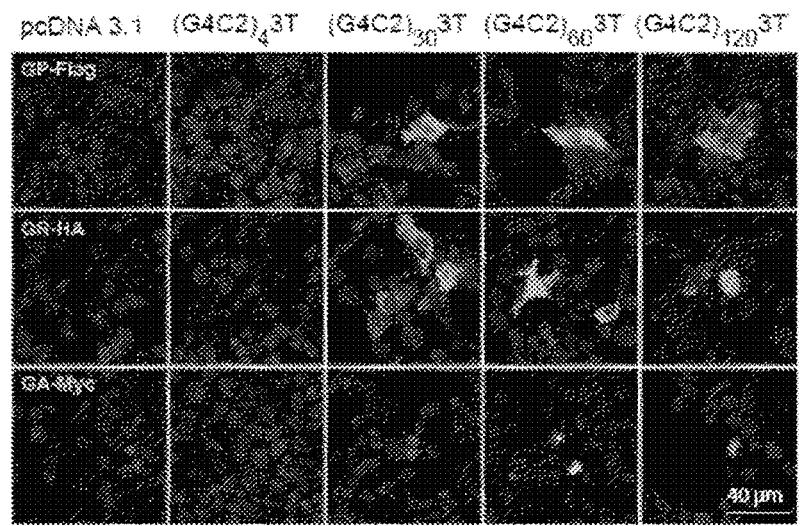
FIG. 20

G₂C₄ strand

Frame 1
*GEPPLLPAPLPGSRTPNSHPPGCRLLTHPLATACASAAAGAGTATAAPPRARPRARPDHAPAPA
PAPAPAPAPAPAPA(PA)₁₇₀PAPAPSARLLSSRACYRLRLEPSLESSG*

Frame 2
MQAIPPVARGESPTPSFGQRNERESKNASSSEESPRFYPRLFPAAEPQTATRQDAASSLTHSPPP
APPPPRAQAPQPQPRPGPAPGPAPTTPRPRPRPRPRPRPRPRPR(PR)₁₇₀PRPRPLARDS*

Frame 3
MRGKVKMRRALRRAPASTRASSRQPNPKQPPARMPPPHSPTRHRLRLRRRGRHRNRSPAPGPPP
GPPRPRPGPGPGPGPGPGPGPGP(GP)₁₇₀GPGP*

G₄C₂ strand

Frame 1
*GPGPGPGPGPGPGPGPGP(GP)₁₇₇GPGPGRGRGGPGGGPGAGLRLRCLRPRRRRRRWRVGE*

Frame 2
*RLTRRKQGGKQPQPVASSGTQESRARGRGRGRGRGRGRGRGR(GR)₁₇₇GRGRGVVGAGPGAG
PGRGCGCGACARGGGGAGGGENVSEEAASWRVAVWGSAAGKRRG*

Frame 3
*DALELRSRALGAGAGAGAGAGAGAGAGA(GA)₁₇₇GAGANSGRARGRARGGAAVAVPAPAAAE
AQAVASG*

*FIG. 21*

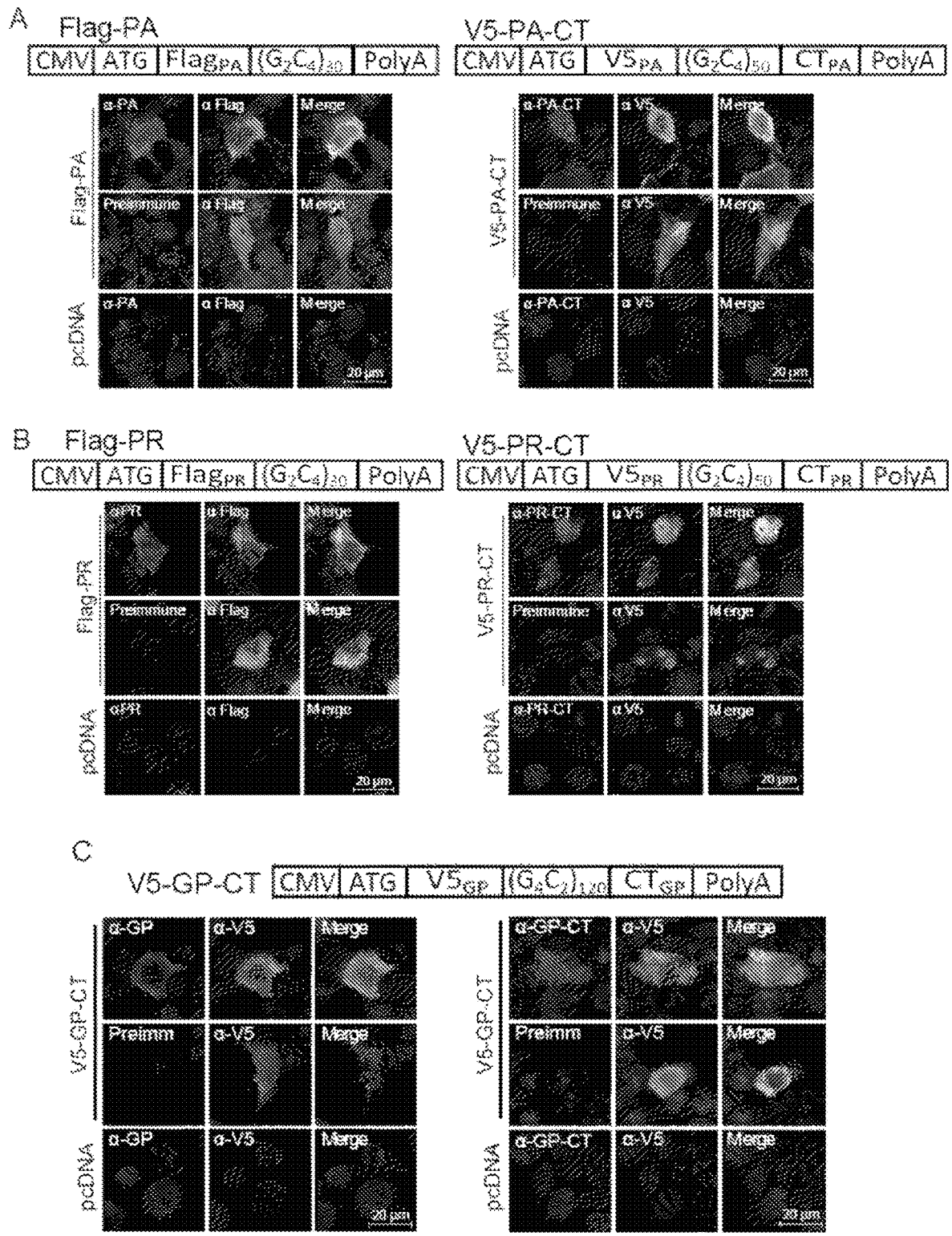
FIG. 22A-C

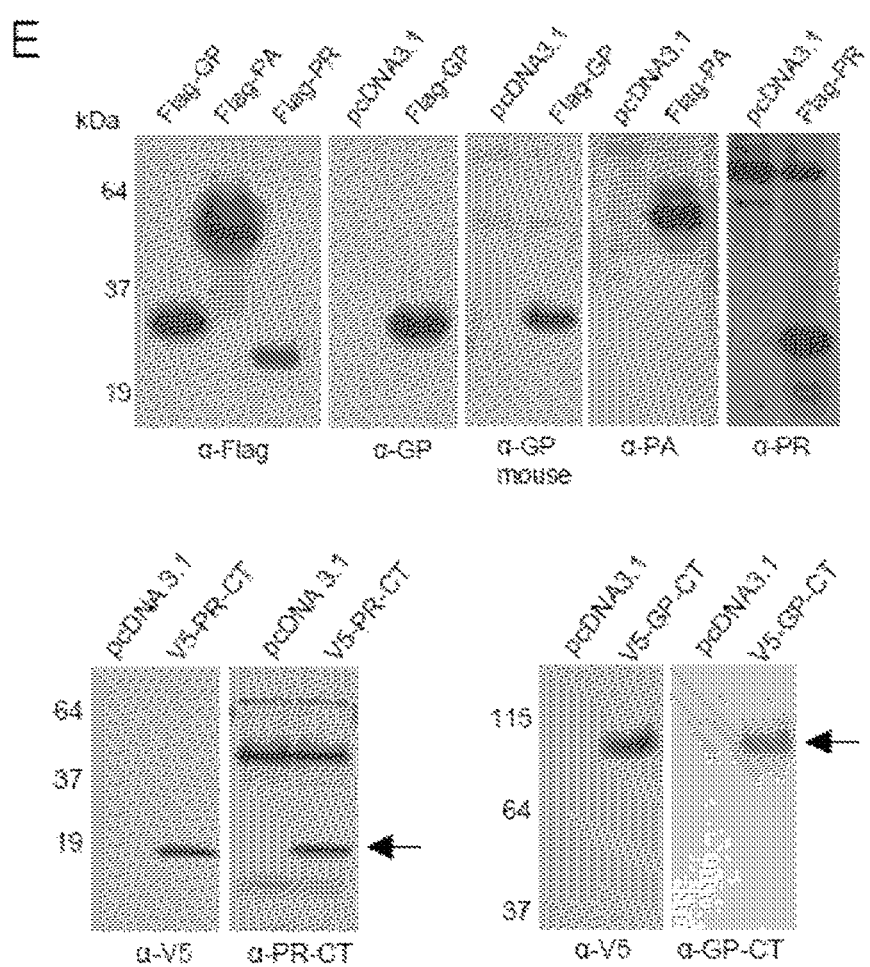
FIG. 22D-E

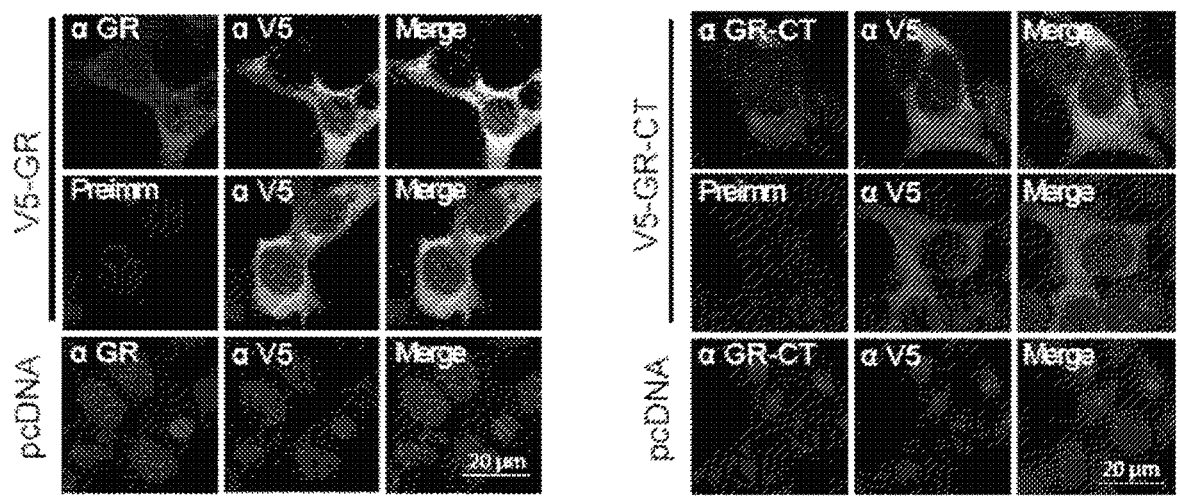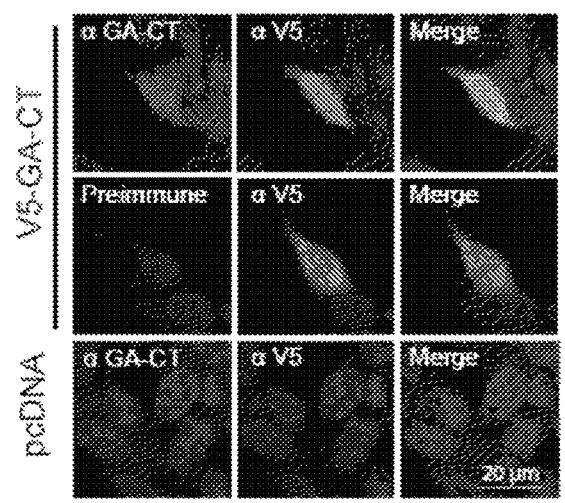
FIG. 23A-B

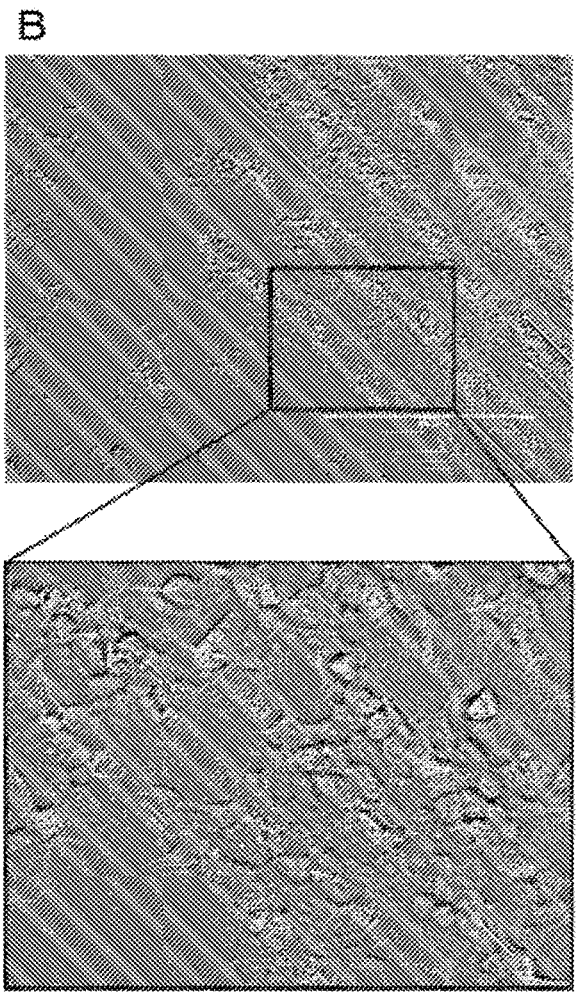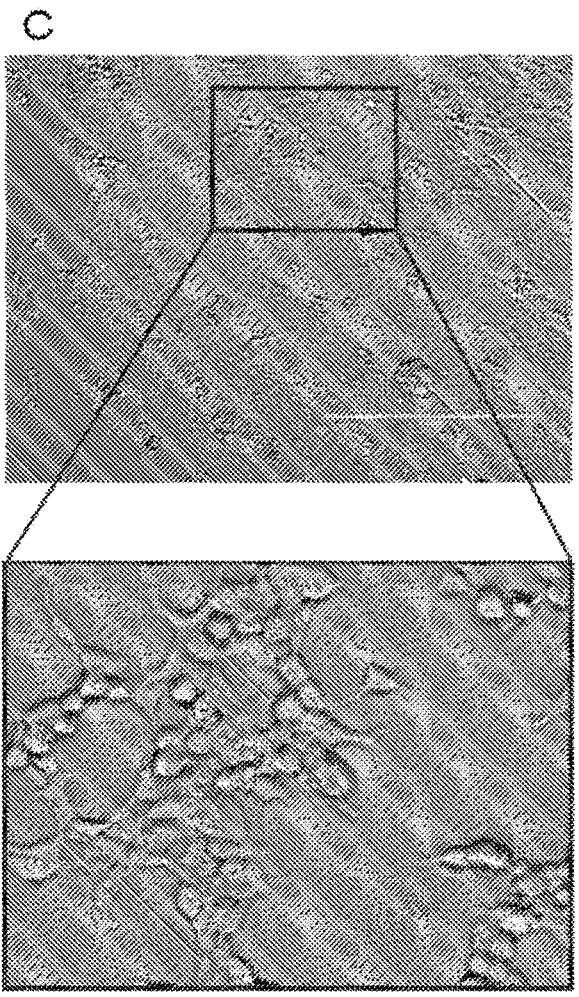
FIG. 26B-C

| Primer Name | Primer Sequence (5' to 3') |
|---|---|
| ASORF-F | AGTCGCTAGAGGCGAAAGC |
| ASORF-R | CGAGTGGGTGAGTGAGGAG |
| LK-ASORF-R | CGACTGGAGCACGAGGACACTGACGAGTGGGTGAGTGAGGAG |
| LK-ASORF-F | CGACTGGAGCACGAGGACACTGAAGTCGCTAGAGGCGAAAGC |
| 1a-F | GCCCACGTAAAAGATGACGC |
| 1a-R | CCTCCTAAACCCACACCTGC |
| LK-1a-R | CGACTGGAGCACGAGGACACTGACCTCCTAAACCCACACCTGC |
| LK-1a-F | CGACTGGAGCACGAGGACACTGAGCCCACGTAAAAGATGACGC |
| LK | CGACTGGAGCACGAGGACACTGA |
| 5'GSP1 | GCTTTCGCCTCTAGCGACT |
| 5'GSP2 | TCTAGCGACTGGTGGAATTGCCT |
| 3'GSP1 | CTGCGGTTGTTTCCCTCCTT |
| 3'GSP2 | TTTCTTGTTCACCCTCAGCGA |
| ACTB3 | CTGGAACGGTGAAGGTGACA |
| ACTB4 | GGGAGAGGACTGGGCCATT |
| 3xTag-Fw | ACGACATCGATTACAAGGACG |
| 3xTag-RV | ATCAGCTTCTGCTCGCTATG |

*FIG. 27*

| Strand | Antigen | ID # | Sequence | Species | IB | IHC | IF |
|---|---|---|---|---|---|---|---|
| AS-G₂C₄ | poly(PA) | H3152 | H2N-APAPAPAPAPAPAPAPACKKKK-amide | Rabbit | Y | Y | Y |
| | PA C-term | H3159 | Ac-CYRLRLFPSLFSSG-OH | Rabbit | Y | Y | Y |
| | poly(PR) | H3150 | Ac-RPRPRPRPRPRPRPRC-amide | Rabbit | Y | Y | Y |
| | PR C-term | H3162 | Ac-CRPRPLARDS-OH | Rabbit | Y | Y | Y |
| Both Strands | poly(GP) | H3154 | H2N-GPGPGPGPGPGPGPGPGCKK-amide | Rabbit | Y | Y | Y |
| | poly(GP) | F3M1 | H2N-GPGPGPGPGPGPGPGPGCKK-amide | Mouse | Y | Y | Y |
| S-G₄C₂ | GP C-term | H3157 | Ac-CRRRRWRVGE-OH | Rabbit | Y | Y | Y |
| | poly(GR) | H3148 | Ac-RGRGRGRGRGRGRGRGRC-amide | Rabbit | Y | Y | Y |
| | GR C-term | H3160 | Ac-CRVAVWGSAAGKRRG-OH | Rabbit | Y | Y | Y |
| | GA C-term | H3184 | Ac-CSGRARGRARGGA-amide | Rabbit | Y | Y | Y |

Summary of sense and antisense antibodies including antigen recognized, identification number (ID#), and peptide sequence used for injections in rabbits or mice. Detection of recombinant proteins by various methods is summarized on right. IB=immunoblot, IHC=immunohistochemistry, IF=immunofluorescence, Y=yes, N=no, AS=Antisense, S=Sense.

*FIG. 28*

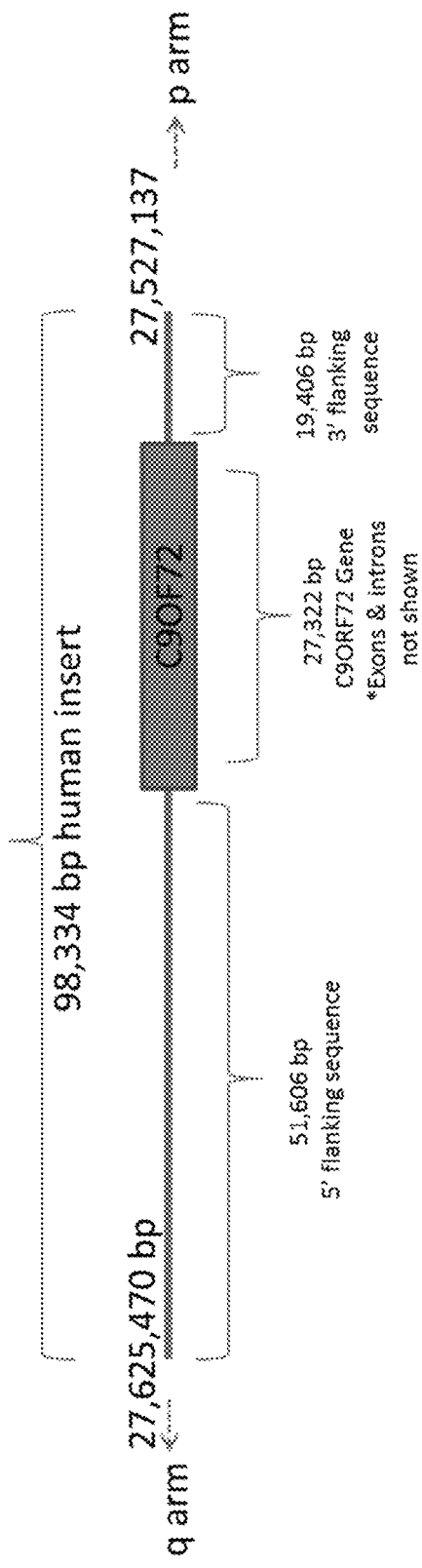

*Map of BAC insert used to make mouse models*

1) BAC insert extends from bp27,625,470 to 27,527,137 of human genome reference sequence on Chromosome 9.
2) The insert was cloned from a patient with ~800 GGGGCC repeats - size estimate above does not include extra repeats from this patient.
3) BAC insert DNA contains about 800 repeats in some clone preps but is very unstable
4) BAC repeat size in the mice is ~500 repeats but this varies between progeny and may grow or shrink in size as mouse colony is expanded and additional generations of mice are propagated in the laboratory.
5) BAC expansion mice express both sense and antisense versions of the C9ORF72 gene

*FIG. 29*

SEQUENCE LISTING

```
<160> NUMBER OF SEQ ID NOS: 65

<210> SEQ ID NO 1
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 1

Trp Ser Gly Arg Ala Arg Gly Arg Ala Arg Gly Gly Ala Ala Val Ala
1               5                   10                  15

Val Pro Ala Pro Ala Ala Ala Glu Ala Gln Ala Val Ala Ser Gly
            20                  25                  30

<210> SEQ ID NO 2
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 2

Gly Arg Gly Arg Gly Gly Pro Gly Gly Gly Pro Gly Ala Gly Leu Arg
1               5                   10                  15

Leu Arg Cys Leu Arg Pro Arg Arg Arg Arg Arg Arg Trp Arg Val
            20                  25                  30

Gly Glu

<210> SEQ ID NO 3
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 3

Gly Val Val Gly Ala Gly Pro Gly Ala Gly Pro Gly Arg Gly Cys Gly
1               5                   10                  15

Cys Gly Ala Cys Ala Arg Gly Gly Gly Gly Ala Gly Gly Glu Trp
            20                  25                  30

Val Ser Glu Glu Ala Ala Ser Trp Arg Val Ala Val Trp Gly Ser Ala
```

Ala Gly Lys Arg Arg Gly
    50

<210> SEQ ID NO 4
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 4

Pro Ser Ala Arg Leu Leu Ser Ser Arg Ala Cys Tyr Arg Leu Arg Leu
1               5                   10                  15

Phe Pro Ser Leu Phe Ser Ser Gly
            20

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Pro Leu Ala Arg Asp Ser
1               5

<210> SEQ ID NO 6
<211> LENGTH: 780
<212> TYPE: DNA
<213> ORGANISM: H. sapiens

<400> SEQUENCE: 6
ccccatttcg ctagcctcgt gagaaaacgt catcgcacat agaaaacaga cagacgtaac      60
ctacggtgtc ccgctaggaa agagaggtgc gtcaaacagc gacaagttcc gcccacgtaa     120
aagatgacgc ttggtgtgtc agccgtccct gctgcccggt tgcttctctt ttggggggcgg    180
ggtctagcaa gagcaggtgt gggtttagga ggtgtgtgtt tttgttttc ccaccctctc      240
tccccactac ttgctctcac agtactcgct gagggtgaac aagaaaagac ctgataaaga     300
ttaaccagaa gaaacaagg agggaaacaa ccgcagcctg tagcaagctc tggaactcag      360
gagtcgcgcg ctaggggccg gggccgggc cggggcgtgg tcgggcgggg cccggggggcg     420
ggcccggggc gggctgcgg ttgcggtgcc tgcgcccgcg gcggcggagg cgcaggcggt      480
ggcgagtggg tgagtgagga ggcggcatcc tggcgggtgg ctgtttgggg ttcggctgcc     540
gggaagaggc gcgggtagaa gcgggggctc tcctcagagc tcgacgcatt tttactttcc    600
ctctcatttc tctgaccgaa gctgggtgtc gggctttcgc ctctagcgac tggtggaatt     660
gcctgcatcc gggccccggg cttccggcg gcgcggcgg cggcggcgg gcagggacaa       720
gggatgggga tctggcctct tccttgcttt cccgccctca gtacccgagc tgtctccttc     780

<210> SEQ ID NO 7
<211> LENGTH: 780
<212> TYPE: DNA
<213> ORGANISM: H. sapiens

<400> SEQUENCE: 7
gaaggagaca gctcgggtac tgagggcggg aaagcaagga agaggccaga tccccatccc      60
ttgtccctgc gccgccgccg ccgccgccgc cgccgggaag cccggggccc ggatgcaggc     120

```
aattccacca gtcgctagag gcgaaagccc gacacccagc ttcggtcaga gaaatgagag      180
ggaaagtaaa aatgcgtcga gctctgagga gagcccccgc ttctacccgc gcctcttccc      240
ggcagccgaa ccccaaacag ccacccgcca ggatgccgcc tcctcactca cccactcgcc      300
accgcctgcg cctccgccgc cgcgggcgca ggcaccgcaa ccgcagcccc gccccgggcc      360
cgccccgggg cccgccccga ccacgccccg gccccggccc cggcccctag cgcgcgactc      420
ctgagttcca gagcttgcta caggctgcgg ttgtttccct ccttgttttc ttctggttaa      480
tctttatcag gtcttttctt gttcaccctc agcgagtact gtgagagcaa gtagtgggga      540
gagagggtgg gaaaaacaaa aacacacacc tcctaaaccc acacctgctc ttgctagacc      600
ccgcccccaa aagagaagca accgggcagc agggacggct gacacaccaa gcgtcatctt      660
ttacgtgggc ggaacttgtc gctgtttgac gcacctctct ttcctagcgg gacaccgtag      720
gttacgtctg tctgtttctc atgtgcgatg acgttttctc acgaggctag cgaaatgggg      780
```

```
<210> SEQ ID NO 8
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GA repeats

<400> SEQUENCE: 8

Gly Ala Trp Ser Gly Arg Ala Arg Gly Arg Ala Arg Gly Gly Ala Ala
1               5                   10                  15

Val Ala Val Pro Ala Pro Ala Ala Ala Glu Ala Gln Ala Val Ala Ser
            20                  25                  30

Gly

<210> SEQ ID NO 9
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AG repeats

<400> SEQUENCE: 9

Ala Gly Ala Trp Ser Gly Arg Ala Arg Gly Arg Ala Arg Gly Gly Ala
1               5                   10                  15

Ala Val Ala Val Pro Ala Pro Ala Ala Ala Glu Ala Gln Ala Val Ala
            20                  25                  30

Ser Gly

<210> SEQ ID NO 10
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GP repeats
```

```
<400> SEQUENCE: 10

Gly Pro Gly Arg Gly Arg Gly Gly Pro Gly Gly Gly Pro Gly Ala Gly
1               5                   10                  15

Leu Arg Leu Arg Cys Leu Arg Pro Arg Arg Arg Arg Arg Arg Trp
            20                  25                  30

Arg Val Gly Glu
        35

<210> SEQ ID NO 11
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PG repeats

<400> SEQUENCE: 11

Pro Gly Pro Gly Arg Gly Arg Gly Gly Pro Gly Gly Gly Pro Gly Ala
1               5                   10                  15

Gly Leu Arg Leu Arg Cys Leu Arg Pro Arg Arg Arg Arg Arg Arg
            20                  25                  30

Trp Arg Val Gly Glu
        35

<210> SEQ ID NO 12
<211> LENGTH: 56
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GR repeats

<400> SEQUENCE: 12

Gly Arg Gly Val Val Gly Ala Gly Pro Gly Ala Gly Pro Gly Arg Gly
1               5                   10                  15

Cys Gly Cys Gly Ala Cys Ala Arg Gly Gly Gly Ala Gly Gly Gly
            20                  25                  30

Glu Trp Val Ser Glu Glu Ala Ala Ser Trp Arg Val Ala Val Trp Gly
                35                  40                  45

Ser Ala Ala Gly Lys Arg Gly
        50              55

<210> SEQ ID NO 13
<211> LENGTH: 57
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RG repeats

<400> SEQUENCE: 13

Arg Gly Arg Gly Val Val Gly Ala Gly Pro Gly Ala Gly Pro Gly Arg
1               5                   10                  15

Gly Cys Gly Cys Gly Ala Cys Ala Arg Gly Gly Gly Ala Gly Gly
            20                  25                  30
```

Gly Glu Trp Val Ser Glu Glu Ala Ala Ser Trp Arg Val Ala Val Trp
        35                  40                  45

Gly Ser Ala Ala Gly Lys Arg Arg Gly
    50                  55

<210> SEQ ID NO 14
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AP repeats

<400> SEQUENCE: 14

Ala Pro Ala Pro Ser Ala Arg Leu Leu Ser Ser Arg Ala Cys Tyr Arg
1               5                   10                  15

Leu Arg Leu Phe Pro Ser Leu Phe Ser Ser Gly
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 15

Pro Ala Pro Ser Ala Arg Leu Leu Ser Ser Arg Ala Cys Tyr Arg Leu
1               5                   10                  15

Arg Leu Phe Pro Ser Leu Phe Ser Ser Gly
            20                  25

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PR repeats

<400> SEQUENCE: 16

Pro Arg Pro Leu Ala Arg Asp Ser
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RP repeats

<400> SEQUENCE: 17

Arg Pro Arg Pro Leu Ala Arg Asp Ser
1               5

<210> SEQ ID NO 18

```
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 18

Arg Gly Arg Gly Arg Gly Arg Gly Arg Gly Arg Gly Arg Gly Arg Gly
1               5                   10                  15

Arg Cys

<210> SEQ ID NO 19
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 19

Arg Pro Arg Pro Arg Pro Arg Pro Arg Pro Arg Pro Arg Pro Arg Pro
1               5                   10                  15

Arg Cys

<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 20

Ala Pro Ala Pro Ala Pro Ala Pro Ala Pro Ala Pro Ala Pro Ala Cys
1               5                   10                  15

Lys Lys Lys Lys
            20

<210> SEQ ID NO 21
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 21

Gly Pro Gly Pro Gly Pro Gly Pro Gly Pro Gly Pro Gly Pro Gly Pro
1               5                   10                  15

Gly Cys Lys Lys
            20

<210> SEQ ID NO 22
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 22

Cys Arg Arg Arg Arg Trp Arg Val Gly Glu
1               5                   10

<210> SEQ ID NO 23
<211> LENGTH: 14
<212> TYPE: PRT
<213> ORGANISM: Artificial sequence
<220> FEATURE:
```

```
<223> OTHER INFORMATION: Synthetic polypeptide

<400> SEQUENCE: 23

Cys Tyr Arg Leu Arg Leu Phe Pro Ser Leu Phe Ser Ser Gly
1               5                   10

<210> SEQ ID NO 24
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 24

Cys Arg Val Ala Val Trp Gly Ser Ala Ala Gly Lys Arg Arg Gly
1               5                   10                  15

<210> SEQ ID NO 25
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 25

Cys Arg Pro Arg Pro Leu Ala Arg Asp Ser
1               5                   10

<210> SEQ ID NO 26
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 26

Cys Ser Gly Arg Ala Arg Gly Arg Ala Arg Gly Gly Ala
1               5                   10

<210> SEQ ID NO 27
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 27

Ala Trp Ser Gly Arg Ala Arg Gly Arg Ala Arg Gly Gly Ala Ala Val
1               5                   10                  15

Ala Val Pro Ala Pro Ala Ala Ala Glu Ala Gln Ala Val Ala Ser Gly
            20                  25                  30

<210> SEQ ID NO 28
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 28

Pro Gly Arg Gly Arg Gly Gly Pro Gly Gly Pro Gly Ala Gly Leu
1               5                   10                  15

Arg Leu Arg Cys Leu Arg Pro Arg Arg Arg Arg Arg Arg Trp Arg
            20                  25                  30

Val Gly Glu
```

<210> SEQ ID NO 29
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 29

Arg Gly Val Val Gly Ala Gly Pro Gly Ala Gly Pro Gly Arg Gly Cys
1               5                   10                  15

Gly Cys Gly Ala Cys Ala Arg Gly Gly Gly Gly Ala Gly Gly Gly Glu
            20                  25                  30

Trp Val Ser Glu Glu Ala Ala Ser Trp Arg Val Ala Val Trp Gly Ser
        35                  40                  45

Ala Ala Gly Lys Arg Arg Gly
    50                  55

<210> SEQ ID NO 30
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 30

Ala Pro Ser Ala Arg Leu Leu Ser Ser Arg Ala Cys Tyr Arg Leu Arg
1               5                   10                  15

Leu Phe Pro Ser Leu Phe Ser Ser Gly
            20                  25

<210> SEQ ID NO 31
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 31

Arg Pro Leu Ala Arg Asp Ser
1               5

<210> SEQ ID NO 32
<211> LENGTH: 99
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (92)..(93)
<223> OTHER INFORMATION: PR repeats

<400> SEQUENCE: 32

Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ser Ser Leu Thr His Ser Pro Pro
    50                  55                  60

```
Pro Ala Pro Pro Pro Pro Arg Ala Gln Ala Pro Gln Pro Gln Pro Arg
 65                  70                  75                  80

Pro Gly Pro Ala Pro Gly Pro Ala Pro Thr Thr Pro Arg Pro Leu Ala
                 85                  90                  95

Arg Asp Ser
```

<210> SEQ ID NO 33
<211> LENGTH: 74
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (73)..(74)
<223> OTHER INFORMATION: GP repeats

<400> SEQUENCE: 33

```
Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
                20                  25                  30

Arg Met Pro Pro Pro His Ser Pro Thr Arg His Arg Leu Arg Leu Arg
            35                  40                  45

Arg Arg Gly Arg Arg His Arg Asn Arg Ser Pro Ala Pro Gly Pro Pro
    50                  55                  60

Pro Gly Pro Pro Arg Pro Arg Pro Gly Pro
65                  70
```

<210> SEQ ID NO 34
<211> LENGTH: 68
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (67)..(68)
<223> OTHER INFORMATION: GP repeats

<400> SEQUENCE: 34

```
Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
                20                  25                  30

Ser Pro Thr Arg His Arg Leu Arg Leu Arg Arg Arg Gly Arg Arg His
            35                  40                  45

Arg Asn Arg Ser Pro Ala Pro Gly Pro Pro Pro Gly Pro Pro Arg Pro
    50                  55                  60

Arg Pro Gly Pro
65
```

<210> SEQ ID NO 35
<211> LENGTH: 41
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (40)..(41)
<223> OTHER INFORMATION: GP repeats

<400> SEQUENCE: 35

```
Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro
            20                  25                  30

Gly Pro Pro Arg Pro Arg Pro Gly Pro
        35                  40
```

<210> SEQ ID NO 36
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 36
agtcgctaga ggcgaaagc                                                    19

<210> SEQ ID NO 37
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 37
cgagtgggtg agtgaggag                                                    19

<210> SEQ ID NO 38
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 38
cgactggagc acgaggacac tgaagtcgct agaggcgaaa gc                          42

<210> SEQ ID NO 39
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 39
cgactggagc acgaggacac tgacgagtgg gtgagtgagg ag                          42

<210> SEQ ID NO 40
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 40
cgactggagc acgaggacac tga                                               23

<210> SEQ ID NO 41
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 41

```
Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
                20                  25                  30

Glu Ser Pro Arg Phe Tyr Pro Arg Leu Phe Pro Ala Ala Glu Pro Gln
            35                  40                  45

Thr Ala Thr Arg Gln Asp Ala Ala Ser Ser Leu Thr His Ser Pro Pro
    50                  55                  60

Pro Ala Pro Pro Pro Arg Ala Gln Ala Pro Gln Pro Gln Pro Arg
65                  70                  75                  80

Pro Gly Pro Ala Pro Gly Pro Ala Pro Thr Thr
                85                  90
```

<210> SEQ ID NO 42
<211> LENGTH: 72
<212> TYPE: PRT
<213> ORGANISM: Artificial sequence
<220> FEATURE:
<223> OTHER INFORMATION: Synthetic polypeptide

<400> SEQUENCE: 42

```
Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
                20                  25                  30

Arg Met Pro Pro Pro His Ser Pro Thr Arg His Arg Leu Arg Leu Arg
            35                  40                  45

Arg Arg Gly Arg Arg His Arg Asn Arg Ser Pro Ala Pro Gly Pro Pro
    50                  55                  60

Pro Gly Pro Pro Arg Pro Arg Pro
65                  70
```

<210> SEQ ID NO 43
<211> LENGTH: 66
<212> TYPE: PRT
<213> ORGANISM: Artificial sequence
<220> FEATURE:
<223> OTHER INFORMATION: Synthetic polypeptide

<400> SEQUENCE: 43

```
Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
                20                  25                  30

Ser Pro Thr Arg His Arg Leu Arg Leu Arg Arg Arg Gly Arg Arg His
            35                  40                  45

Arg Asn Arg Ser Pro Ala Pro Gly Pro Pro Pro Gly Pro Pro Arg Pro
    50                  55                  60

Arg Pro
65
```

<210> SEQ ID NO 44
<211> LENGTH: 39
<212> TYPE: PRT
<213> ORGANISM: Artificial sequence
<220> FEATURE:
<223> OTHER INFORMATION: Synthetic polypeptide

<400> SEQUENCE: 44

```
Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro Pro
            20                  25                  30

Gly Pro Pro Arg Pro Arg Pro
            35
```

<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 45
gcccacgtaa aagatgacgc                                         20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 46
cctcctaaac ccacacctgc                                         20

<210> SEQ ID NO 47
<211> LENGTH: 43
<212> TYPE: DNA
<213> ORGANISM: Artificial sequence
<220> FEATURE:
<223> OTHER INFORMATION: Synthetic polynucleotide

<400> SEQUENCE: 47
cgactggagc acgaggacac tgacctccta aacccacacc tgc               43

<210> SEQ ID NO 48
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 48
cgactggagc acgaggacac tga                                     23

<210> SEQ ID NO 49
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 49
gctttcgcct ctagcgact                                          19

<210> SEQ ID NO 50
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 50

-continued

```
tctagcgact ggtggaattg cct                                    23

<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 51
ctgcggttgt ttccctcctt                                        20

<210> SEQ ID NO 52
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 52
tttcttgttc accctcagcg a                                      21

<210> SEQ ID NO 53
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 53
ctgggaacgg tgaaggtgac a                                      21

<210> SEQ ID NO 54
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 54
gggagaggac tgggccatt                                         19

<210> SEQ ID NO 55
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 55
acgacatcga ttacaaggac g                                      21

<210> SEQ ID NO 56
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 56
atcagcttct gctcgctatg                                        20

<210> SEQ ID NO 57
<211> LENGTH: 106
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: REPEAT
<222> LOCATION: (78)..(79)
<223> OTHER INFORMATION: AP repeats

<400> SEQUENCE: 57
```

Gly Glu Pro Pro Leu Leu Pro Leu Pro Gly Ser Arg Thr Pro
1               5                   10                  15

Asn Ser His Pro Pro Gly Cys Arg Leu Leu Thr His Pro Leu Ala Thr
            20                  25                  30

Ala Cys Ala Ser Ala Ala Ala Gly Ala Gly Thr Ala Thr Ala Ala Pro
        35                  40                  45

Pro Arg Ala Arg Pro Arg Ala Arg Pro Asp His Ala Pro Ala Pro Ala
50                  55                  60

Pro Ala Pro Ala Pro Ala Pro Ala Pro Ala Pro Ala Pro Ala Pro Pro
65                  70                  75                  80

Ala Pro Ala Ser Ala Arg Leu Leu Ser Ser Arg Ala Cys Tyr Arg Leu
            85                  90                  95

Arg Leu Phe Pro Ser Leu Phe Ser Ser Gly
            100                 105

```
<210> SEQ ID NO 58
<211> LENGTH: 119
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (108)..(109)
<223> OTHER INFORMATION: PR repeats

<400> SEQUENCE: 58
```

Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ala Ser Ser Leu Thr His Ser Pro Pro
    50                  55                  60

Pro Ala Pro Pro Pro Arg Ala Gln Ala Pro Gln Pro Gln Pro Arg
65                  70                  75                  80

Pro Gly Pro Ala Pro Gly Pro Ala Pro Thr Thr Pro Arg Pro Arg Pro
            85                  90                  95

Arg Pro Arg Pro Arg Pro Arg Pro Arg Pro Arg Pro Arg Pro Arg Pro
            100                 105                 110

Arg Pro Leu Ala Arg Asp Ser
        115

```
<210> SEQ ID NO 59
<211> LENGTH: 94
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (89)..(90)
<223> OTHER INFORMATION: GP repeats
```

<400> SEQUENCE: 59

```
Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
            20                  25                  30

Arg Met Pro Pro Pro His Ser Pro Thr Arg His Arg Leu Arg Leu Arg
        35                  40                  45

Arg Arg Gly Arg Arg His Arg Asn Arg Ser Pro Ala Pro Gly Pro Pro
    50                  55                  60

Pro Gly Pro Pro Arg Pro Arg Pro Gly Pro Gly Pro Gly Pro Gly Pro
65                  70                  75                  80

Gly Pro Gly Pro Gly Pro Gly Pro Gly Pro Gly Pro
                85                  90
```

<210> SEQ ID NO 60
<211> LENGTH: 56
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (17)..(18)
<223> OTHER INFORMATION: GP repeats

<400> SEQUENCE: 60

```
Gly Pro Gly Pro Gly Pro Gly Pro Gly Pro Gly Pro Gly Pro Gly Pro
1               5                   10                  15

Gly Pro Gly Pro Gly Pro Gly Arg Gly Arg Gly Gly Pro Gly Gly
            20                  25                  30

Pro Gly Ala Gly Leu Arg Leu Arg Cys Leu Arg Pro Arg Arg Arg
        35                  40                  45

Arg Arg Arg Trp Arg Val Gly Glu
    50                  55
```

<210> SEQ ID NO 61
<211> LENGTH: 98
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (39)..(40)
<223> OTHER INFORMATION: GR repeats

<400> SEQUENCE: 61

```
Arg Leu Thr Arg Arg Lys Gln Gly Gly Lys Gln Pro Gln Pro Val Ala
1               5                   10                  15

Ser Ser Gly Thr Gln Glu Ser Arg Ala Arg Gly Arg Gly Arg Gly Arg
            20                  25                  30

Gly Arg Gly Arg Gly Arg Gly Arg Gly Arg Gly Arg Gly Val Val Gly
        35                  40                  45

Ala Gly Pro Gly Ala Gly Pro Gly Arg Gly Cys Gly Cys Gly Ala Cys
    50                  55                  60

Ala Arg Gly Gly Gly Ala Gly Gly Gly Glu Trp Val Ser Glu Glu
65                  70                  75                  80

Ala Ala Ser Trp Arg Val Ala Val Trp Gly Ser Ala Ala Gly Lys Arg
                85                  90                  95
```

Arg Gly

<210> SEQ ID NO 62
<211> LENGTH: 65
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (29)..(30)
<223> OTHER INFORMATION: GA repeats

<400> SEQUENCE: 62

Gln Ala Leu Glu Leu Arg Ser Arg Ala Leu Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Trp Ser Gly Arg Ala Arg Gly Arg Ala Arg Gly Gly Ala Ala
        35                  40                  45

Val Ala Val Pro Ala Pro Ala Ala Glu Ala Gln Ala Val Ala Ser
    50                  55                  60

Gly
65

<210> SEQ ID NO 63
<211> LENGTH: 98334
<212> TYPE: DNA
<213> ORGANISM: H. sapiens
<220> FEATURE:
<221> NAME/KEY: repeat_region
<222> LOCATION: (51933)..(51938)
<223> OTHER INFORMATION: GGGGCC repeats

<400> SEQUENCE: 63
aagcttgata atattatcaa atattagata aatgtaatat tagaagaaaa ctttttttgaa      60 aagatatata aaaataattt cattcaaaat ttttatattt aatttaaatt tttaatgaaa     120
atatatctaa gttttgtacg ctttaaatgt aattatgttt gataatttaa tcatttacta     180
ttcgttctct attgctgccc taacaaatta ccatagttca gtggcttaca aaacacaaat     240
ttattatctt accattctgt gagtcaaaat tccaaaatag gtgtcactag gctaaaatga     300
aggactgcat ttcttcctgc aggctccagg agagatctat gtcttactct tttcggcttc     360
taaaggctgc ccacattcct cgactagtgg cgtccctcct tcgtctctaa acccagcaac     420
aacaggttga gtcctcatgt cacatctttc ttacctttct gtcatctcat ctcgctgact     480
gctgctggga aaaattctcc acttttaagg gctatcatga ttagactatg cccactagat     540
aatacaagat ctcagatcct taacttccat cacatctgca aagtcgcttt tgcctcataa     600
aagagtctga ggtttagacg ggagatctta aggggggctat taatatgcct accataatca     660
ctgagaataa gtacaagtta agattataat agcaatagaa tatacaaacg tgaagctcca     720
aaagaacaac aacaacaaaa aaggtgaaca ggaaaaagaa actgaaaatc tttaaaaagg     780
cagtctgttt aaatctataa aaactggaaa aaatgagag tggacaaata tctggtaagc     840
atgatggact taaatttgt gactagggca ttacatttttt tatattaata taatgaagat     900
tgaattactg atcaaaacaa ttaaaaagca agagaactat tctcatcaaa tctgcaacac     960
gaaaagttca gacaaaattc caacaacttc acattctgaa ctaaatgagg actaattacc    1020
agttcgagca atgagaatat atgaggtcct ccgtttgcac tttgccaggg atctgaaaac    1080

```
gttgggagta ggtcggcttc accctgaagc cagaccatcg acagccagtt ttccctccct      1140
tctccaccca caggtcttag gccctcatcc ttcccagcct cagaactagt ctccaaagaa      1200
gaggaaagtt agaggagaga gtaaatcgtt gaataggatg aaggagatgt gggaaaaaga      1260
aaaagagagg ctgcaagaga gagggtccca gggataactc tgctcttgga agggtggcca      1320
cagtcatgtg gtcccaagag gcaacaacaa gcttaggaag ccagagaaac cagttacaat      1380
cactgctact cttttcgatt ctgtgttgtt taagaaatat cacccgccag gagttctcca      1440
gaaacatttt ccctgattcc atgtaagtgc tcaaccagtg aatggtaatc ccattttggt      1500
ttagtctgta ccatcccta ttccaaaata aagggaaaaa tggtgggttt atatcttaaa       1560
ttttctactt tactaaactc aagggaaata gccaagcaaa aacgaaagct gagactcttg      1620
ctaattatcc tttccataga atgtttgcta aaattccttg tcaaggaagg aataacaaag      1680
ctagtccacg ctctgtatag ggtgtttcca attagttata ctttaaagta taagtattta      1740
acaaaatcta taaattttgt taattattta cttgtagtga aaaatgagcc attctcaagc      1800
aaatcacttt ttattacaca ttccagagaa taaccataaa aggacattta ttatagcaaa      1860
aataaccaca tctggatgga acttcaatca ccagtattta ctaaataaat gcccagaaaa      1920
aaaatagttc atctttaatt tcagtcatca ttaataaaag ctgaagtacc tcttcagatc      1980
ttttgatcat tttctgttgg attgttttct ttttactgag ttgcaaatgc tctttatata      2040
ttttggatac aaagctttat cacataggca ttttgcaagt atttttttcca agttttttta     2100 tcttttcatt tatttaataa tatctttcaa agaacgggaa ttttataatt tttatgaagt      2160
ccatttataa ttttttcttt tatgggttgg tggggttgg gggttgtgtt gtcctaagaa       2220
atcttggctc aacacaaaaa gattagtttc tatattttct tctagaagtt ttatagtacg      2280
atctcagatc catttcagat gatgaataag cacataaaaa aaggatactc atcgttagtc      2340
attagagaaa tgcatattaa aaccataagg aaatactact atatacatat attagatagg      2400
atgaagagca actggaatct catacagtgc tgattgaaat gcaaaatggc aaaacaactt      2460
tagaaaccaa tttggaagca gctgtactga catggaattt tgagctggaa gaatcttaga      2520
aaaagaatac tttaccacct cccccattct cttcaccctg gggaactgtt aaatgaggaa      2580
attgtggttc aaggaggaac ttgtctatat gctttctcag cttccccgtg gtaattacca      2640
tcttgataat ataacgtaat gtatgtatat gttatcaaat aatataatat cttcatcata      2700
tatttatcat cttcataatg ttagctgtct agtggtaact ttttttttgct ctttattgcc      2760 tccctctttt ttccctcttt gttgtttttt gtcatacaat tatgatatat gtgtatatat      2820
tctcactgta aagatgtaaa caacacaaag attattgaac aaatcacgaa agtaaccctt      2880
ccttcattct taccctatcc aaccctcatc tcctcagaag aatacaccat tttagttgta      2940 aatgttttc tagctctttt tcaatgtttc tacctatatg catgtatgta taatgtatat       3000
acatacatat atacatacat attgatatat acatatatag aggtatggtt ttttaactta     3060
aatggaattg cattgtggat attgtcctat gacttgcttt caaccaaatt atatgtcttg      3120
gaaatacata catatattta aaaaatatgt tatgtatatg taacatacta tatgtgcata      3180
atatatatta catagatata ataaggccta ggaagaaatt gtgtgcaacc tctagtacat     3240
cttcctctat atctactgta catacataca acccattctt ttttttaattt tttttattttt    3300 ttagacagaa tcttgctctg tcgcccaggc tggagtgcag tggcacaatc tcggctcact      3360
gcaagctcca cctcctgggt tcacgccatt ctcctgcctc agcctcccaa gtagctggga      3420
atacaggcac ctgccatcag gcccagctaa tttttttttttg tatttttagt acagatgggg    3480
```

```
tttcaccgtg ttagccagga tggtctccat ctcctgacct cgtgatccgc ccacctcatc    3540
ctcccaaagt gctgggattt acaggcgtga gccaccgcgc ccagccacaa ctcattgcag    3600
agtagtccaa aatatggatg gactgtagct taattactta ttctcccatt gatagacact    3660
taggactttt ctaattttta taatttaaaa atatgctgca attaacaaac attcttgtgt    3720 atcttttgc tgtatgtatg catatttctt tagtatgggt tttggaagag gaatcacaaa     3780
ggaggcatag aatataaata ttttattttt gaaaaataca gttgtaattt aataacccac    3840
caaaagactc taacagttta gattcacatc aacagtgtaa gaacatgtct gttttactgc    3900
atccttaccc ccactggtta taatacttt aattaacaat cttatggatg aagaatacta     3960
tcgcaatgtt gtttaatgc attttccaa ttactagtga gattgaacat taattctttt      4020
attttatgga tcactggctt ttctccttct gtgaactacc tgttcacatc ctctgctttt    4080
cagctcttga gctgttatct ttttcttatt gatttatatg agctctttat atattcaaga    4140
tgttaatcat ttgtatttta tgtatatggc aatgattttc ttccaaacca atgcttgtct    4200
tttatttatt tatttatta tttatttatt tgagaccgag tctcgctctg tcgcccaggc     4260
tggagtgcag tggcgcgatc tcggctcact gcaagctccg cctcccgggt tcacgccatt    4320
ctcctgcctc agcctcctga gtaggtggga ctacaggcgc ccgctgccac acccggctaa    4380
ttttttgtat ttttagtaga cagggtttt caccgtgtta gccaggatgc tctctatctc     4440
ctgacctcgt gatccgcccg cctcggcctt ccaaagtggt cggattacag gcatgagcca    4500
ccacgcctgg ccaatgcttg tcttttatc tctgtttatg gcatcttca tactatggac      4560 attttatttt ttattttta tgttgattta ttcttgaatt gtatacatgt taattatacc     4620
taagttattg taatacccctt aaagccaagt tctacacata tatttaattt gctttcccaa    4680
taggtctctg agggaacaca tttttcaaa tcactttgtt tcatcttttt taggtgttga     4740
tcaattatta aggagtttga aataatcatt taaacggaat tcttcagatg aaaacataaa    4800
gacatttatc gggtcagagc attggtcggt tcacatactc aggatcagtg gcctgggtgg    4860
gcaggcactg ggtgaatgga gagctgcagg tattggaaga gagcccagtt ggatatgtag    4920
tttccaaaga tcatcaaggc agacaaccaa agggaaaccg tgggaaacac ctgctttggg    4980
ccatctaaga tgagatgata aagtaaggaa agagttgagc ccaacacagt gatagccaat    5040
ctgaaagcgg gcagaactga caagaccaaa caagtaggtg aactggctgc aggcagccag    5100
ccaccacagg gacagcgtgt actccaggga caagctcaag gctataggta gttagttcaa    5160
ggctactagg gtgagaagag caggaactga gttctatacc agtgcttctc aaaactaatg    5220
tgcatcctaa tcacctggaa atcttgtaaa aatgtagatt ctgattcagt gagtctgaag    5280
cagagcttaa gatactacat gcttaacaag agcctagttg atgctgacac tgctggtccc    5340
tggagctctc tttgagtagc aggcttctgg aaggcttgtg tcactaagca cagagaagcc    5400
tcacttatca aatctgcacc aaaacaggaa aactaatgtg aagaataatg tgatgcacac    5460
gtcagagcat gaggcagttg ctttgtccct gaggttgcgc tccagatggc ttcctaagat    5520
gcgacaggct gatcttgtgc gtggggtcc cggaggcttg ggccacggga gagacaggac     5580
ctcagaggct gggagacagg cagagacaga agagtgacat cctgctgctt ttgaatttgc    5640
acattctgta gaataataac agcagtaaac tgttacacaa tatctattct cagcatcttg    5700
aagccctttc acatattgtt acttccatta atggggccct ttgctgctat ttctactttt    5760
ctcttcagct atcaacaata tggctttcca cacctccatc agacagtagc cagatgaaat    5820
```

```
aaaatgtgcc agaatgaaaa cttgttcatt tgtctacttt ttgccaagac tagacaggca    5880
ggaaattgaa tgtatttta cagaaaaggt tttcaaaact ttttccctc tgtggctcat      5940 ttaggtaaac taaaaggcat aagacccacc taaaacatgg gttcccgctt tttattggag    6000
aaagaacata gtactttaaa aaatacata aaataataaa aaggaaagac aaagataatg     6060
aaggttgtac atggtaccaa attttttgtat cccataataa cacatgagta gatcactact   6120
aagtaggttt tagtgacata taggaaacat taaaatctac agaaatttgc attatttct     6180 gtcaaaaagg atcatttcac agcctttcag ggggaaccca ttgcccacag gaactcatgc    6240
attccatgct ttgaggatca ctagatctaa gaagccttcc ttggaggttc tagcctccaa    6300
cccttatttt agtaaaagaa gctccagttt tatctgtttc taagtcagac taccacacaa    6360
cattgggctt aaagaaaggt ttccagggct aaagcagact ttgaggatta ctaattccga    6420
gttaaatttc tgtgtattat ctctggattt gacttattca cactggacta tcactcataa    6480
atatacataa tacagagtta actatttaaa tttataaaga gagtattttc cttttttatg    6540
agcaaaacat gctgccaact acttggacca catactgatc cataaatact gacagctttg    6600
taattggaaa taataaatac acactaatga agcatctcaa aagggaagag ccacaggtaa    6660
tctgagtgat taggcattca tgttaggtta ggctttgatc attgttttta atcgcaattt    6720
cattgcagtg catctataaa tccatgtcca gaagtatgaa gtggttctat agtaagaata   6780
agatgctaca gataatgcga ctaaataaga cactataggt aatgacacag attcaagtct    6840
tattgttgat gggaagaggt caataatgga tgatataata tactacagca atgagaatta    6900
ttgaatgttt tccagactca cttgtataat tggccataac agcaaacaaa aaacaggttc   6960
tgatagcaaa atgatataca gtactaacaa aggtgaatct tgaggtgaac cttctcttta    7020
taagtttaaa tagtttaccc ccgacctttt cccatagtag aacagcctaa aaagtatctt    7080
tcagtagaat gctagtgctt atgaggtttt cttaagatat cattttttcaa ttaaaattta   7140 tttcacaaaa gactcacatc cttgccagcc ttcagggtga gtgttgattc aggctgtgtc    7200
caacggcaac gatgagtgaa cttctcaccc tcagaatcac atgagcattc ctgagatgtt    7260
ttatcagagt gataccaact tcattattag aatattgagt ccctatttcc tatattcaat    7320
gtcctttcaa gccctaactt tgtccgggtt gaaggcaaag atccaaataa tcacatttgt    7380
ctttgataac tgaaactggg agaactggga ctgtctcaag agttctacgt gactgtaggt    7440
tgcaagtact gtggttgcat ctccaaatat taaccaatcc cagtgacaat tcaatggggt    7500
ctcctgaacc atgatcctca tgtctccagt gaaggaaatg ggcaaagggg attcaaaaat    7560 ccctttgga ggaataggaa acttctgctt tccttcattt cataacattt gcgatggaac     7620
aaaggctttt ttagaatgga gcaaccagat cctttttttgg gggaatcagc ttaaatgtcc   7680
cttcttctca tactactttt atctatgtga tcctattctt ttctgttgtg gattgaatca    7740
tgtccctcaa aaagattgaa tttagagtgt gctctaaatt caatgtggag aaatttggac    7800
acagaggcag acacacaggg agaaccccgt gtgacaatgg aggaagagga tgcatttatg    7860
ctgccacaag ccaaggaaca ccaaagattg tcagcagcca ccagaagcta ggataaaggc    7920
atggcacatc actccctctg agcccccaaa aggagccaag actgctaata tctgatctc     7980 ggacttctgg cctgaaacag tgagagaata aggttctgtt gtttcaagct acccagcttg    8040
cggtattttg tcacagaagc acaaggaatc aagtacattt tctttctcag cacttgtgat    8100
aatttgattt tttctttact cagtggttgt ttcacaccta tgtccccatc agactgtaag    8160
cttaaagaga cctggatctg gtctgtcttc accactgttg attcattacc agcacagtgc    8220
```

```
ctggcccatg gtcactgaat aaacgtttgt tgagagaatg aatgtgctta accagaagta   8280
ctattgacct attaggccaa gttcaaggtg cctaacagct cagctgtgaa ggatacctct   8340
cctttcagtc ctctgttaca tatgtccctg atagatgtgt tatttgtatc tcctcctggc   8400
cctcaagttt gtttgagggc aggaccctt tttgtatatc tgtagagctt cgtagtacct    8460
aaatactact ttgcatatat aataaagttt cgataaatat tcattaaata aagaaataaa   8520
tgaaatgact aagttttcta agatgttaca actagattga agatatttag ctcattattt   8580
aacaagaaaa ctatggttaa ttatggtgtc ctgtgtgaaa atggttatag tttgtttttt   8640
aattaatata agcatgtatg tgcattatca gtatacacaa tttgtggtat gagtgttttg   8700
tgtccctgca cacagaccac ggaaatcctg agaaacaaac tgccacccca gagcaggtgc   8760
ctaacacaga gacttttaat ccttaaagtt tttctataac taagcaatgt ttttcaaat    8820 gcaataacac tgatatgcag acatattgat tgtccactca caaagccatt cctcaatatc   8880
attacaacat gcctctttga atgtcattaa aaatagatgt ctcattttc taggacaagt    8940 tggctgaagt tctgcttgaa aactggtaat agaaaataca atttctcaac ccgctttggc   9000
cttttaattc tgttctacaa ccttgccagt tcactttcaa agtcaaggga tgcatcttgc   9060
aaaaccatga catcttttga gtaactcctt ctgttcttaa cacatattcc caggagctta   9120
ataaatattg ttttttgcaac ttgtttagtg gcaaaataat gagtccttgg tgtatgctta  9180
tcctctgctt tgctattaga aagatatat tcagactgtt ttaaacaaat taattcaagg    9240
gcagggaaca gtcctaaaac ctgttaaaat tcaaatactt ggtcactgta tgtgcagcat   9300
gtgtgttcta gaaagtcct ttattttaaa atataaattg aatcttgttg agaaattaat    9360
gtcatatgaa tatattaata actgaaatgc tgccaagttt acaaaaagcc ctcaatgaaa   9420
ctgtgacctt gtatagacaa gggcctgtgg agggacattt ttaaaccatc tctttttta    9480 tttcctcatg agatctacaa tgtaagtgca ttaaagttga tgaatgaatt gcagtgcaac   9540
ttttcctgcc tcttttgcct ttcatttgtc tatatttcaa gcttcactga agtgatagat   9600
tttgggcttt gccacattgt cctctgattg cttccctctg ctcctccttt tcctagtgaa   9660
tctttgtttt actggtggaa aaatctacat cttttgtatct tggcatttta ctttcacatt   9720
atctcataga ttttatttca agttgctata aagttatcaa cttttatttt taactaatat   9780 tattttaac aattagaaaa ttgttgacca ggtaattcca gcactttggg aagctgaagc    9840
gggaggatca cgtgagccca ggagctcgag accagcctgg gcaatgcaag gagactgtct   9900
ctacaaaata taaaaataca ttagccaggt ttggcggtgc atgcctgggg tccagctatt   9960
caggaagctg aggtgggagg atcacttgag ctggagaggt tgaggctgca gtgagcagtg   10020
atcgcaccac tgcactccag tctgggtgac agagggagac cctatctcga aaaaaggaa    10080 aagaagagga ttttgctggc aagatggctg aataggaata gctccgttct gcagctccca   10140
gtgagatcaa tgcagaaggc aggtgatttc tgcatttcca acagaggtac ctggttcatc   10200
tcactgggac tggttggacg gtgggtgcag cccatggagg gtgagcagaa gtagggtggg   10260
gcgttgcctc actcaggaag tgcaagggt ccctcttcta gccaagtgaa gccgtcaggg    10320
actgtgccat aagaacagtg cactctggtc caggcttttc ccacagtctt tgcaacccac   10380
agaccaggag ataacaagcg gtgcctatgc caccagggcc cggggtttca agcacaaaac   10440
tgggtggcca tttgggcaga catcaagcta gctgcaggag tttttattt catacccag     10500 tggtgcctgg aacgccagtg agacagaacc gttcactccc ctggataagg ggcagaatcc   10560
```

```
agggagccaa gtggtctggc ttggcgggtc ccacacccac ggcgcccagc aagctaagat    10620
ccactggctt gaaactctcg cttccagcac agcagtctga ggtccacctg agacgcccgg    10680
gcttggtgtg gggaggggca tccaccattg ctgaggcttg agtaggcggt tttaccctca    10740
cggtgtaaac aaagctgcct ggaaggtcca gctgggcaca gcccaccaca gctcaccaag    10800
gccgctgtgg ccagagtgcc cctctggatt cctcctctct gggcaaggca tctctgaaaa    10860
aaaggcagca gcgccagtca gagacttata gataaaaccc ccatcaccct gggacagagc    10920
acctcaggga aggagtggct gtgggtgcag tttcagcaga tttaaacgtt cctgcctgac    10980
agctctgaga gagcaacaga tctcccagca cagcgttcaa gctctgttaa agatcagact    11040
gcctcctcaa gtgggtccct gactcccatg tctcctgatt gagagacacc tcccagtagg    11100
ggctgacaaa cacctcataa aggagagctc cagctggcat ctggcaggtg ccctctggg     11160 acgaagcttc cagaggaagg aacaggcagc aatctttgct gttctgcagt ctcagctgat    11220
gatacccagt caaacaggtc ctggagtgga cctccagcaa actccagcag acctgcagca    11280
gaggggcctg accgttagaa ggaaaattaa caaatagaaa ggaatagtat caacatcaac    11340
aaaaaggacg tccactcaga gaccccatcc aaaagtcacc aacatcaaag accaaaggta    11400
gataaatcca caaagatggg gagaaaccag tgcaaaaaag tctgaaaatt ccaaaaacca    11460
gaacgcctct tctcctccaa agaatcacca ctcctcacta gcaaggtaac aaaactggac    11520
agagaatgag tttgacaaat tcacagaatt agtgttcaga aggtgggcaa taacaaactc    11580
ctccaagcta acggagcatg caaggaagct aagaaccttg aaaaaagtta gagcaattgc    11640
taactagaat aaccagttta gagaagaaca taaatgacct gatggagctg aaaaacacag    11700
cacgagaact ttgtgaagca tacacaagta tcaatagcca aatcgatcac gtggaagaaa    11760
ggatatcaga gattaaagat caacttaatg aaataaattg agaagacaag attagagaaa    11820
aaagaatgaa aaggaatgaa caaagcctcc aagcaatata ggactatgtg aaaagaccaa    11880
atctatgttt gactggtgta ccagaaagtg acggggagca tggaaccaag ctggaaaaca    11940
ctcttcagga tattatccag gagaacgtcc ccaacctagc aaaacaggcc aacatttaaa    12000
ttcaagaaat acagacaaca ccacaaagat actcctcgag aagaccaacc caagacaca     12060 taatcgtcag attcaccaag gttgaaatga agaaaaaaat gttaagggca gccagagaga    12120
aaggtcaggt tacccacaaa ggaagcccat cagactaaca gcagatctct ctgcagaaac    12180
cctacaagcc agaagagagt gggggccaat attcaacatt tttaaagaaa agaattttca    12240
acccagaatt tcatgtccag ccaaactaag cttcataagt gaaggagaaa taaaatcctt    12300
tacagacaac caaatgctga gagattttgt caacagcaag cgtgccttac aagagctcct    12360
gaaggaagca ctaaacgtgg aaaggaacaa tcggtaccag ccactgcaaa agcacaccaa    12420
attttaaagt ccattgacac tatgaaaaaa ctgcatcaac taacaggcaa ataaccagc     12480 tagcatcata atgacaggat caaattaacc ttaattaagt tagccttaaa tgtaaacggg    12540
ctaaatgccc cagttaaaag acacagactg gccacctgta taaagagtaa agacccatca    12600
gtgtgctata ttcaggagac ccatctcaca tgaaaagaca cataggct caaaataaag      12660 ggatggagga atatttacta agcaaatggg aagcaaagaa acaaaaagc agggggttgca    12720 atcctagtct ctgataaaac agactttaaa ccaacaaaga tcaaaataga caacaagggg    12780
cattacataa tggtaaaggg atcaatgcaa caagaacagc taactatcct aaatatatat    12840
gcacccaata caggagcacc cagattcata aagcaagttc ttagagacct acaaagagac    12900
ttagactccc acacaataat aatgggagac tttaacactc cactgtcaat attagacaga    12960
```

```
tcaatgagat aggaaattaa caaggatact caggacttga actcagttct ggatcaagtg    13020
gtcctaatag atacctacag aactctccac cccaaatcaa cagaatttac attcttctca    13080
gcaccacatc gcacttattc taaaattcac cacatagttg gaagtaaaac actcctcagc    13140
aaatgcaaaa gaacggaaat cataacagtc tcttagacca cagtgcagtc aaattagaac    13200
tcaggattaa gaaactcact caaaaccgca caactacatg gaaactgaac ctgttcctga    13260
atgactactg ggtaaataat gaaatgaagg gcaaaataaa gaagttcttt gaaaccaatg    13320
acaacaaaca cacaatgtac cagaatctct gggacacatt taaagcagtg ttaagaggga    13380
aatttatagc actagatgcc caaaaagaa agcagaaaag atctaaaatc gacaccctag     13440
catcacaatt aaaagaacta gagaagcaag agcaaacaaa ttcaaaagct agcagaagac    13500
aataaataag atcagagcag aactgaagag gagagagaca tgaaaaaccc ttcaaaaaaa    13560
tcaatgaatc caggagctgg tttttgaag agattgacaa aacagataga ccactagcca     13620
gacaataaag aaggagagaa gaatcaaata gatgcaataa aaatgataa agggggtatc     13680 accactgatc ccacagaaat acaaactacc atcagagaga atactataaa caactacaca    13740
aataaactag aaatctaga agaaatggat aaattcctgg acacatacac cctcccaagt     13800
ctaaaccagg aagaagttga atccctgaat agaccaataa caagttctga aattcaggta    13860
gtaattaata gcctaccaac caaaaaagt ccaggaccag acagattcac agccgaattc      13920
tatcagaggt acaaacagga gctggtacca ttccttctga aactattcca atagaaaaag    13980
agggaatcct ccctaactga ttgtatgaag ccagcatcat cgtgatacca aaacctggca    14040
gagacacaac aaaaaaaaga aattttcagg ccaatatccc tgatgaacat tgatgcgaaa    14100
atcctcaata aaatactggc aagcggaatc cagcagcgca tcaaaaagct tatccgccag    14160
gatcaagtcg gcttcatctc tgggatgcaa ggctggttca acatacgcaa atcaataaac    14220
catcattctc agcaaattat cacaagaaca gaaaaccaaa caccgcatgt tctcactcat    14280
aagagggagt tgaacaatga gaacacgtgg acccaaggag gggaacatca catactgcgg    14340
cctgtcgagg gatttggggt tgagggagtg atagcattag gagaaatacc taatgtaggt    14400
aacaggttga tgggtgcagc aaaccacaat gcgatgtgta tacctaccta acaaacctgc    14460
acgttctgca catgcactcc agaacttaaa gtataataat aaaaggcgct gcctcaggat    14520
gtaaagtgta acaagggggc tggggtgggc agcgtgggcc tctgagacct ttggttgccc    14580
gtgtccgcag ctcgccccgc agccggctcc acaatggtcc gctccgtttg ccacgtgcgg    14640
attcgggttc cagactgaag gctgcgtgtt ctctgccgcc cacagcccaa gtttattgtg    14700
gcaaccgccg gagcagcctt ccccgctgtg gaggagcctg ggctacccc tcagcggtat      14760 ttggggctgg tcctggggga gctaagcagg gttgtgcag cactgcctga aagtgtgaga      14820
ccagactcta atccttatgg ttttccatgg gagttggtga tatgtgcagc tgtacatgga    14880 tttttgctg ttctcttttt ttgtgtggag aagttttaga tcggtggga gtcggcttta       14940 tgtgggaaga gaaaaaagc ttgctgtaat gctttctgga ctaattgaag aaaagcataa      15000
actacttgaa aaatttagcc atgttcaaaa agagtatgaa ggctatgaag tagagtcatc    15060
tttaaagaat gccagctttg agaaggaggc aacctgtgaa aagctaaaca ggtccaattc    15120
tgaacttgag gatgaaatac tctgtctaga aaagagtta aataagaga atctaaaca        15180 ttctgaacaa ggtgaattga tggtggatat ttgcaaaagg atacagtctc tagaagatga    15240
gtcaaaatcc ctcaaatgac aagtagctga agccaaaatg aacttgacga tatttcaaat    15300
```

```
gaatgaagaa cgactgaaga tagcaataaa agatgctttg aatgaaaatt ctcaactcca   15360
ggaaaacgag agacagcttt tgcaagaagc tgaggtatgg aaagaacaag tgagtgaact   15420
taataaacag aaaataacat ttgaagactc caaagtacat gcagaacaag ttctaaatga   15480
taaagaaaat cacatcaaga ctctgaacgc ttgctaaaaa tgaaagatca ggctgctatg   15540
cttggagaag acataacgga tgatggtaac ttggaattag aaatgaacag tgaatcggaa   15600
aatggtgctt acttagataa tcctccgaaa ggagctctga agaaactgat ttatgctgct   15660
aagttaaatg cttcttaaa aaccttacaa ggagaaagaa accaaattta tagtcagtta   15720
tctgaagttg ataaaggaag agcttacaga gcatattaaa aatcttcaga ctgaacaagc   15780
atctttgcag tcagaaaaca cacattttga aagtgagaat cagaagcttc aacaaaaact   15840
taaagtaatg attgaatttt atcaagaaaa tgaaatgaaa ctccagagga aattaacagt   15900
agatgaaatt accggttaga aaggaagaa aaactttcta aagtacacga aaagatcagc   15960
cgtgccactg aagagttgga gacctataga aagtgagcca aagatcttga agaagagttg   16020
gcgagaacta ttcattctta tcaaggatgg attatttccc acgagaaaaa agcacataat   16080
aattggttgg cagcttggac tgctgaaaga aacctcaatg gtttaaggaa agaaagtgct   16140
cacaacagac aaaaattaac tgaagcagag tttaaatttg aacttttaga aaagatcct   16200 tatgcacttc atgttccaaa tacagcattt ggcagagagc attccccata tggtccctca   16260
ccactgggtc ggccttcatc ctaaacaaga gcttttctct gagggccac tgagactctc   16320 atctttgcta acaggaggag gaggaagagg ctcaagaggt ccagggaatc tctggacca   16380 tcagattacc aatgaaagag gagaatcaag atgtgacagg ttaaccaatc ctcacagggc   16440
ttctctgaca ctgggtccct gtcacctcca tgggaacagg accgtaggat gatgtttctt   16500
ccaccaggac aatcatatcc tgattcagct cttcctccac aaaggcaaga cagattttat   16560
tctaattctg gcacactgtc tggaccagca gaactcagaa ggtttaatat gacttctttg   16620
gataaagtgg atgggtcaat gctttcagaa atggaatcca gcagaaatga taccaaagat   16680
gaccttggta atttaaatgt gcctgattca tctctccctg ctgaaaatga agcaactggc   16740
ccttactttt ctcctccacc tcttgctcca atcagaggtc cattgtttcc gggggataca   16800
aggagcctgt tcatgagaag aggacctcct ttccccccac ctcctccagg aaccatgttt   16860
ggagcttctc aagattattt tccaccaagg gatttcccag atccaccaca tgctccatt   16920 gcaatgagaa atgtctatcc agcgaggcgt ttcctcctta ccttccccca aaacctggat   16980
ttttccccat aaaccccaca ttctgaaggt agaagtgagt tccctgcagg gctgattctg   17040
ccttcaaatg agcctgctac tgaacatcca gaaccacagc aagaaacctg acaatatttt   17100
tgctctcttc aaaagtaatt ttgactgatc tcattttcag tttaagtaac tgctgttact   17160
taagtgatta cacttttgct cccactgaag cttaatggaa ttataattct caggatagtg   17220
ttttctaaat aaagatgatt taaatatgaa tcttatgagt aaattattc cattttatgt   17280 tattctggat agtataacta ttttaatttg ataaactaat ccacgattat ataaacaata   17340
atgggagttt tatatatgta atcttgcagg tagggaggct ttaaattata aaggttgtgt   17400
ctttatgcca agaactgtat taactgtggt tgtagacaaa tgtgaaagta attttatgct   17460
tcattaaata aattttagtt gattttttt taaaaaaga aaatggttaa tctatcattt   17520
aggtgcatca tcagttgttt aaccattctc tcttactgaa cattgggttg tttaaaaagt   17580
gttgttattt ttgaatcatg gttcagtgaa caatttggga cacataactt tttatctgat   17640
gagttatttc ctaaggatcc agctcagaaa ctcagcacat aaacctaata agaaaaaaac   17700
```

```
aatttgaagt ggctaacctc ttatcccaat aaaaatgttg tatttatgtt tggatttaga      17760
tgcctttcag tggtcatacc ttcacctaac ttttatggat tctactttta acatgtagag      17820
tgactgttta aatcacctaa actcactgag ttttaagttc cttttattc aacaagactg       17880 gattgtatgt tccagctcct caaacttagt taccaaccac catcctagag aagtgaattc      17940
acatgaggcc tgtccagaag aacaatctcc ctttcagtgt cctcatgcat gcagtgacca      18000
gagaccaacc ttgataaatt atggaaaaag tacagcacat tctggaagag ccatgaaaga      18060
tccagatcat ctggtgctgg ataagaatat taatggacag gctgggcgcg gtggctcacg      18120
cctgtaatcc tagcactttg ggaggccgag gcgggcggaa catgaggtca ggagatcgag      18180
accatcctgg ctaacacggt gaaacccgt ctctactgaa aatacaaaaa attagccggg       18240
catggtggcg gcgcctgta gtcccagcta cacgagaggc tgaggcagga aatggcgtg       18300 aacccgggag gcagagcttg tagtgagccc agatggcgcc attgcacttc agcctgggcg      18360
acagagtgag actccgtttc aaaaaaaaaa aaaaagaat attaatggac aaaaagatta       18420
atgaaagaac atattgaagc atccaattac ctggtgtctg ctcaaatgag gaatcggtga      18480
gataggtcag ttagcagtca agatttataa aagagacgat ggccttggga ggggctgccc      18540
tactcgactt tttaatggct agaagctatt aagggctaag ccagaaccct tcagtatggt      18600
tcagtgagga tcccaatttg gggtccaaaa gtaaatgaca actcccagga accattaaga      18660
ataaaaatca tggagcatta ctgagaattt atgttatcta agtctgagga aaattaatgt      18720
taaggaagct ttcaaaagtc taatatttac accgaattcc agggcaccat gctctaagac      18780
aaagcactct ggtcctgccc ctctccttc ctcatgtttt ttggttcttg ggatccttaa       18840
gggtcaatgt tattcttaaa atacagagca tcctggaaac taaaaagtg gaagatattc       18900 aaattctaat gaatgtactg gcagtattgt agatcatgga gtataacata aagacaagaa      18960
tccctagcct cttccaccat actttgtaat ggtaaggaga aaggatagaa ttttgagaag      19020
tctgggaaga caatgtatga taacatctgg agaagctctg cataagttac ttttgttcag     19080
gcttaagaaa aattctagct tgcccctgca ctgtcatcag gtatcatgaa agtaaataaa      19140
acctttaaag attcttcaag ccagcagact tctatcttct ctatactatc ctgtgatcct      19200
aaactcttaa cagttactac gtataattc cctacatttg ctactagtat tttatcatac       19260
acaatattac actcaatatt tcaaaagtgg atgattcatc tcccgaagag actgcaaaat      19320
tcatgagtta agatttgaga atactatttt agacaagatt tagtcagatt ttagagagtt      19380
agaaacctgt aacaattctc taacaatact gcttctcctt ttgtgtatta aggaatttt      19440 gtctatcaaa gatagtacga ggtagaccag aagataactt gccttcaaaa tgtctggaat     19500 gtaaatggc aacagtagta tttggggact tcgtagggga tggccaatat acacccattc      19560
ttagaggtac tgatgatata atgtataaga caaaatcaag tggtctccat caccatataa      19620
tgtttaaaat ggcaaagagg gagcagaaca aacacccttt gcaaatctct tcatagaatc      19680
taccgtaata aacttgtact tgcttaaagt gtgtctcttc agtggtctta ttaccactac      19740
tttggggaaa atgaggctgc ttaaaagatt aacagacatt acattttaca tatctgtggc      19800
agagaaaaca ctatgtattc accaaaccac ttctttcct tcccagtcac tcgggaagag       19860
gtcatttctt tgtcccttt catctaattg aggtgccgtg actacttcta gacaggcaat       19920
gtgagcagaa ggtatgcacg ccacgtatag gcctggtctt caaaaatccc tcagatatga      19980
tcttcttctc tcgtctcttt catggacaaa ctacaggcca tgtaataagg atggtggggt      20040
```

```
tccaaactga aagagcctgg atttctgatt tactgttttg agaagagttc accagggaaa    20100
cagcctggaa atacgcacag gaaaatatgc acaggaccct gtgtgagcaa gatataaaga    20160
tctattacat ggtgccatta aggtgagagt attgtgctta tagtatccag cattaattat    20220
cctcactact acaacttctt tgtatccatc atgtggaaaa gtagagtatt taataaatga    20280
ttattgagtt tattaccttt tttatattcc aatcattgct aattgtacgt tacctcattt    20340
caaggtaaag gtgaccaagg gctaaagcag tgctatccaa accaagccag acatcaaaat    20400
cacacaaaac cttttgaaaa tacaactttg aagatgccat tcacatagat atttattcag    20460
tgggttttca aatggaaccc tggaatctac agtctttaac aaggcttccc aagttattct    20520
gatatacagc aggcaaatct gagaaccact ggacaagaag aaaataaagg ctatatcttt    20580
cgacaacaaa gacaatgcct taaacataga atgtattcaa ttaaagcttg tagaaagata    20640
ggtttgtgaa caggcacagg gactagcctc gagcaaatta ataagggcag caatgttttt    20700
cactgaaacc attattcccc ctattttatt tcttctgggg ctctgtgttt cctttctcct    20760
atcaaaatcc attctaaggt tggaggttgg gggtatctct tgcctactcc atacagcaag    20820
gaataaaatt agtatttctc gaactatctg tgacagcaga cccattgtag gccagtactt    20880
ttgtaaaatg caataaaaat taacttctag agaatgaaat tttaaaatca cagacattca    20940
aaatacaaat tccaatttt ttattattaa ctgtaagaaa tttaaaatta aatctcaata    21000
aataaaatta aagcaaacat aagatagaaa aaaataagca ttatggattg gcccagtctg    21060
caaactgtat acactttgcc aaacatgggc ataaattact aagaagcaaa atcttccatc    21120
tgtaaacatt tccatttcca ttgacaatat gtgtgaggga aaggagggat gcttctgttt    21180
tagaatgcca ggcgtcagct aacaagtgac aaatacgtat tgagactgag atctccccag    21240
cctctcagta gtcagcaaga acatgttgag gcctctgttt ttgactaaaa aattggccag    21300
tgcatgggca acatgcatag gtcctgaatg aaaaaaatag cagcagcaga aatttaaaag    21360
aattttcaca gctaggccac agtaaattct caagcccttc atcagaagcc actgtggggc    21420
ctcatttatg cctttgtttt tattaaattg gatgtgatct taagattctt ctgtcaaaat    21480
tccactagca tgtgaaggca ccaaaagttt aaaatgtaaa attaacccaa gttaagctat    21540
tccattatta agcaatagca gatatatttg ttattatatg agaagaaagt taacagggag    21600
ctaagattga tgttactgat aagaaacaga aacaagactt taaaattaaa taatgaatt    21660
atttatttaa taagaaccaa ttgacagatt ctcgataaag actgtaagat gtcttaaaac    21720
attaggtgta tggagataac atttgtaact ttgacaattt atatgatgag aaaaatcaag    21780
gaatgttatt gtttattggc agagttctag aattacaatt ccatcattct gttttgggga    21840
agtttccctt gaagtaaatg ataacagggc ttgaaatagt acacctcagc attttgttta    21900
taaaactgtg gaataggtaa ggtttgtatt gtaactgaac ccaggttcag ctgcttgctg    21960
ctctaaagct agacataaga gaggaaggtt ggtgggagga aaagcgattt taatcggaga    22020
agcagcaaac caagaagatg gtgaacaata gtcacagaac catcttaaat tttaaaattt    22080
accatagagt gttcaaagga aaacttggta tgggaggcat gcaggagggg tgcaggggggc    22140
ggggtctgtg tgtcttgttc caatggctat ctcagatagt cacccatctg gaggtctagt    22200
tggtattatt ttgaattcag cccagtggtg gtggactgtc agtgactcct cgctaagcag    22260
gaggattctg cactcagggc tccatgcatg gtttgtttca agattggcct ctggaatttc    22320
tcaagcaaga acataattaa ataagcaggc attgccagag gggagtgtct ggaaaggaaa    22380
ggaatgaaga gatgaaagga aagtgggtgg ttaaactata tttttaaaac tgaggttccc    22440
```

```
agttatagta tgtttcgcac gctcccccca ttttagcacc cctgacagaa tttagtaatc   22500
tcctcatctt gtcctctact tcaggtcccc tatctgtcct tgtactctcc agggtttcct   22560
tttcttcttc acgaccttcc ttccctgcaa ttttataagc tattcctatc ccagtgattt   22620
agtttcagct tataaaactg tgtctttgcc attgtaatca aattgaaggg cctctgcttc   22680
atggttggat tctgtgacca ggagactctt acgaggagtt ggccaggtct ctgttaggaa   22740
agcaaaaaag aacaatggag gcaattatcc cattgatttc agctataaat cctattttgc   22800
ctgaattgtc tgaacgatga gtattctgtg aaaatgctgc tctctagtgc aatagaactg   22860
caaataatgc acatctattt cttataatct catccaacat acccacagag attcagatct   22920
aacaaaacag aggtgatttg gttattgaat cataatataa atatggggaa gaggagggaa   22980
atttcaagcc tgaggaaact gtagtaggag taagtatgct gtgtttaaga ggtcacagat   23040
aaaattaata ttaccaatcc atcaataggc aattactaat agcttactac acacacagga   23100
ataaaatgtg aagacagagg aagtgtaaaa tggagccgcc aactctacgg agttgtttgc   23160
aatttggtct ggtagaaagc tatgaaataa ggaagtacat gattgagagc tagagaatgt   23220
ggcacaggct ctgaacccgg accgttcaat gtagtaagct ctagccacac tggacacttg   23280
caatgtggct tgtccaaact gacatgtgct ttaagtataa aatataatcc agatttctaa   23340
gacttcaaaa aaaatggaaa tatctcatta ataatcttaa gtttattaca ggtagaaatg   23400
atagattaaa taaactatat tgtcaaaatt catttgatct gtttctacag tataacaaac   23460
ttacttgtgt ggtttgcatt ttatttctac tggataacat ggcttttaaaa atggtatttt   23520 agaggaagga aagcttggta gagaatggac taatccggat ccctggaaga aatggaccct   23580
gaatgggtct tgatgacttg gagaggcaga gagagaaaaa gaaaagtcaa acataggaa   23640 ttggttgata aaatgaaggt gaggggagaa ggaacagagg gaggagaaga tccagtttga   23700
gggatattac agcgagcagc ctgagaaaga aggataagaa aggagagaaa aaatgcaagg   23760
gaagtaaccc ttcaaagcca gtcagaagtt tctgggttcc tcagcagcca gaaaagaagc   23820
cgttgaaaag atctgagtaa cggagattct ggacgaaaac tgaagttatg gaagggaagt   23880
ttagacatgg gttattaaac gctttagcgc attagaagtt tcttatgtaa tcactaaatt   23940
cagatcctga ataatgcca caagaactat acagctcagc cacccaattc aataagaagt   24000
tacagcacag tctcacacat atccaattaa ccttggcctt tagtcaacat ctgggttctt   24060
tttgtcattt tcaaatacta tcacccagag gtgctatgat ttatattggg gaggggatta   24120
aaagaaaata agtaagttgg tgataagaaa aagctttcag atgattccat ctgaattaac   24180
agccctcttt agttgtctag gaaagaggat gcttttctt gaaagtgctt tgaaatgatg   24240
atgtgcttgt tagtaaacat caattatttt caaatcgtaa tgtttgcaag tttgtcttcc   24300
tgtagctcac cctttatgta ggtccagaat atgattgtca caaatatctg ggtgagcaag   24360
actatgaaat gtggtcataa agtaagtgat tatttctaaa ctcatctttg tcactcgtag   24420
tgcttcacaa agcacctttt cctggactac aattcatttt aattgatccc atcagcacta   24480
tatctgtatc ctgagtgact tcacaatacc ctctatttca agagaaacca atcaggttat   24540
gggtttgtta gtaataaaaa ttaccaagga gcagttgtg gatggtaaaa gcaatgcaaa   24600
ttctaaagag aagtcataag agcaataata agcatcctcc tcacttcttg gaagtgaaca   24660
attccaagct ccctgaagca acacttaacc tatcatatta aacagtaatg gacaaatatt   24720
agaaatgttg atgtcagctt tcagaatctg tgggcatcaa aacatcactt aagttctccg   24780
```

```
aagtattctc tgtcaagttt ccttctacag tattctttc ctactaggac agagccttaa    24840
gccctagaag aataattttg cttgtgtgtt aattatttgt ttactggttc attccagagt    24900
gtgagctgga aaaaggggga agtgtcataa atagtttttt atggcccatg gttttttcaac   24960 tacgtcacta ttggtagcag tttccactgc aggatctatt tgcaaagcct aggaaattag    25020
cattaagcaa gctgctagga agacttcaac agtaactagg ccacaggcct cacacatttt    25080
tcctccaccc cagcctcctc tggagagtac ttgctaaacc tctgtgacac ataatgaagc    25140
aaagaaagtg atagaacaac agaattacac gggcagatcc ttgtttcttc ttctctctct    25200
aaagaattcc ttggactgaa aagcagttta ttttggagga gtgagaaagt ggtgacagaa    25260
ttagaagggc ctgggagggc ttcattttag agacagttt taggctgaaa agagatttca    25320
tgagtgtgat ttacctgagg tgacttttgg gggctcttat aaaaaggaag ttcatgctga    25380
atgggaggtg gcttctgaga tgcagattct ggtgagctaa gagggctcgg taaagaggag    25440
gcaggagtta agtagcgtga actatgcagt agcagcctt ttccccctt gcttggggca    25500 ggtcatcaca acccttctca ataaaggggt ccaggaacca ctaggaataa atgggcattt    25560
gcacttcagg tgaaacccat ttgtcataac tgcttggact ttaagcttac aaataaaaag    25620
aaccacatat ttcccttgc agcttgattt agttaatgtc attttgagaa agaagaaga    25680 cattgttatc ccgtccctt ttttttttt tttttttt tatgaagaga ctgggactca    25740
gagaagtcaa gtgattttcc cagaaccaga aaacacagaa gtagcagagc tgagatgact    25800
actccggtct tctgattcca aattccaaat tcattcttct aagcgatttc ccaaaacggg    25860
aaatgggttt atcttctat tatgggaagt gatagtggta ttctatttag agaacttata    25920
taaaatctta ctttaaaata aataatattt caaaagtaa gcttaattta agaaaataa    25980 tcaagaaagt ctggtatatt ttacaaata taccaaatga ccttgctcta aaatacatct    26040
actttccagc aagccaaagt gaaacaattt gaaataagtg gcatttactg accactccct    26100
aaagttcaca caaagaggt agtactctaa cttaaatata caaggtgaag aaatagctta    26160
ctcagcctgt tgggcttcct cttctacact cttgggaaat gccctccgtg ttaaccaaga    26220
attctcaggc cttggaggga gttttccatt ctcagtaaac tgagattgca gttgcggaaa    26280
ttaagaggta tctgtccagc acttcattcc cttaaggtca ggatctgtgc ttttaataat    26340
gacaattagc taacatatac aattaagcca tgcaaatgaa gtaagagaaa gctagaggag    26400
aaattcagga gccagttgcc ttttccagac atcttgtaca aatagtgttc aaaggactaa    26460
ttcaaaagat gggattcttc gcttgaaccc aggaggtgga gtttgcagtg agcggagatc    26520
gctccactgc actccagcct gggtgacaaa gtgagacccc atccaaaaa aaaaaaaaa    26580 aaaaaaaaa aagatgggat tctttttaa aaaataaatt ttactgcgta tttttaaggt    26640
atacaacgtg atgttataag atggatatag atagtgaaaa ggtaactgta gtgaagcaaa    26700
ttaacatatt catcatctca catagttatc ttttatttgt tttgttttga tgggattttt    26760
aagatagtag aaaggaatgg tagacaataa acatttgagg gaaagtgggg ctttgtagaa    26820
ctcctaaaat gacagcacgc acaaatgtcc ccattatgtc taaagggtaa ctcgttccta    26880
cttctaggga cagctgaggg acatcaatgt aaatttctaa atgacttcct gaactttta    26940 ttttatttt ttgtattttt agaggaaatt ataataacat caagccacct ctggaccata    27000
tcgctgctga tatcatcagc aaatggcact attcctaaat cctaagatgc acttttccct    27060
tcacatttca acatttgtga aactcgattg tacctcacc tgatttata tacaatgcag    27120 cctttccttt tcttttgtca ttgcatctta cgcctgattt ctccttggaa ttgagtaaat    27180
```

```
ataatgctta catgtgttaa taagaattga ggtcactcat aattttttgaa atatgccacc   27240 aaatataagc ctttctacat attgttgact ttgaagtcat ttcttttttt aactactaaa   27300
caataacact ttttgttgag aaaaattgca tatgaacaag agaccaagca ggtagagaga   27360
aaaaaacttt taataatcaa gagaatgtta ctgtgtccca aaggctaaag tcaccttact   27420
atcaagagag aaggacagga acagagagaa ccaggtaaat tacgaattga aaattccatg   27480
gttcatttat ctttatttt aataattcca tttgtgtgat tgtgttgacc acaaggtcat    27540
aatgttactc ttcatactga cttctcatgt aaattataaa taagttttta tgctaatgat   27600
ttatggagta agctattcat cttttccgaca gagagttacc tacaaagaaa taattattct  27660
acctctgaga tgaaatatca tgaaaggagt ggtttccaga tattttgact tttaaaagct   27720
taaagaatat atgtagtata aaattctaaa gcaggcaaaa ttaatccttt tagcaatcaa   27780
gatagcggct acttttggtg agaaggacaa ggtagtgata gagaaggggc tcagggtct    27840 ttcctgaaga cagtgaggtg ggcaatggta ttttccttga cctggatggt gattaaacag   27900
atgtgtttac tttgtgataa ttgactaggc tgtgcaccta tgaactgcat acttttccat   27960
atatgtactg tattcttata cttaaaaaga agtttaaaaa taaatgcaac agatatagga   28020
cttcctatat tactcgttga ccaaaaaaat ggattcattt ttctttcagg taaaacgtac   28080
tagtggtttt aatattatat tgaccaggga gtaaatgttt accttaggaa ccttaatctt   28140
gatgttctcc aaagtcatta tctgttcttt ctgattatca gaatagagta tatctctata   28200
taaatgaaaa tttctggtca ttctcaaaaa ataacactaa gcatgaaaat cagaaatatt   28260
gatcttgttt tgtaatgatg tttctattga tgtgaagtag tttctagtag agttgctgtc   28320
ctaacacaca aatgaaattg cactgtttgg aagacacaac tgtgaatgac ttgcttcagt   28380
aaggaatttc caacatgatg gtttagggat agaggtgctc gattcctctg tctccggtta   28440
cccaggttat tgaggacagg gaggtcaata agtaatgccc tcctcccacc catagcacaa   28500
aacagagcgg ggttcagaga ataggtaagg cttttggccag ggtgttgagg agacttacat  28560
ccctgggaac cagtcagaat gggggcgctg aaaacaatgt tttaaattct agcacccagc   28620
aacatatgtg tgaagattaa atgtactcgt gctaaattca cttgctccat tactgaattt   28680
gggtggtgtc tgttaaagat gggaacaaag gcattcaggt cctggtatct tctaccactc   28740
ccagcatgaa cagactcatg tcagtgggta agggatggta tttcccgaga aggctttgaa   28800
ctcttgtagt gggtcaaata atggccccc acttaaaaat gttcatgtcc aaatccctgg    28860
aagctgtgaa aaggggtttt tgcacatgta attaagtcaa agatattgaa attagatcat   28920
cctggattac ataggtgggc cctacatta atgacaagta tcctcataac agaagaggag    28980
aaggtgatgt gagatttgga gcagcagaga ttggagtgat gtggccacca atcaaggaaa   29040
ccaaggactt ccagcagcca ccagaagctg gaagaggcaa ggaaggactc ttccctaaag   29100
cctttaaagg agcacagccc tactaacacc ttgcttttgg gctctggccc gcaaaactgt   29160
gaaaggatac attgctgtta tttgaagcca cagttcgtag taaatttatt acagcagccc   29220
tagaaactga tacaactcct aaatacaccc ttagcaacac tgctcaacaa gaagtaggca   29280
atttcctcct gactgaaaaa tactgatact gttatgggat ccttgggggt gttgcttttc   29340
tgtccagaaa cctctgtggc ggtggcacct ttgcatgagt tttgctcggg tccactgggc   29400
ccactcatcc tggcaggctg cgctcagctg acactactgg cgtggatccc atgcctccaa   29460
agagactgga gcgaagcggt gagggatgtg tgaggaagtg agcgtggggt ctggcacaca   29520
```

```
gtcaggctca atggctgcta cagcgggatg ggcagcttca ggtgctggca cgggtgctgg    29580
ctcactgcaa ggctgtggct gcaccaagca gcgcagcaac ggaacgcatt ggtgcctgga    29640
aacttggaga ctccaggaac ctcagggctc caaaaggcaa atcacagccc tagcttcggg    29700
agctcccagg tctgggctgc caaagggctg cagctcttct ctcctctctc tctcttcgct    29760
cctctccctt tctctcttca ctcctccctc tttctctctt cactcctcct gtcgcctatg    29820
aacagcgaat tcaaccttcc agttttcaga ctaggaatgc tggagttgtc cttgattact    29880
ctgaattgtt cactccgcat atgggcactg aggatacgtt gatgaactac acagacaaaa    29940
aggatagaaa ttcctgtcaa gactacattc aatagggatg aagcaggcaa taatgaataa    30000
acatactaag ttgaatatga ctatttaaat atatataaca catgacttt gtataatgtt     30060 aaatatttta agtttttaa attcttccct tcatagattt tacattatag tagaagaggc     30120 attttttgttg ttgttctttt tgtttggat tcagagggta aatgtgcggg gttgttacat    30180
gggtatattg cataatgctg atgatggtcc catcacccag gtggtaaaca tagtacgtaa    30240
taggtgaatt tttagcccgt gcttccctct cccatctagt cgtcctgagt gtttatcgtt    30300
gctacgttta tgtcaatgtg tattcaatat ttagctccca cttataattg agaatatgca    30360
gtatttcgtt ttttgttctc gtgttaattt gtttaggata atggcctaca agaacatga     30420 tttcattatt tttatggaca tgtagtattt catggtgtat atgtaccacg gtttctttat    30480
acaatcccac tgttgatggg cacctaggtt gattctattg ctgttgtgaa tagggctgca    30540
atgaacatac aagtgcatgt atcttttgg taacaaaaat tttatatttg gattacccag     30600
tagaattgct gggttgaata atagtttgg tttaagttct ctgagaaatc tccaaactgc     30660
tttccacagt agctgaacta atttacattt ccactagcag tgtataagcg ttctctttc     30720 tccacaatct tttcaccagc atctgttatg tttggcttt taatagcct tttgatgact      30780 gtgaaatggt atctcactgt ggtttggatt tccatttctc taatgattag tgaatgttga    30840
gcattttttt catatgttta ttggccgttt gtatgtcttc ttttgataag cgtctgttca    30900
tgtcctttac acattttcaa ttaaaatatt tgttttttgc ttgctgattt aagttctttg    30960
tatattctgg aaattagatc tttgtcagat gcatagtttg caaatatttt ctcccattct    31020
gtagcctgtt tactctgttg gtaatttctt ttgctgtaca gaaactcttt aattaggtcc    31080
cacttgccta ttttagttt tgttgcaatt attctctgga acttagccat aaattgtttg    31140
ccaaagccaa cgtggagaag gatattttct aggttttctt ctaggatttt atagtttaag   31200
ttttacattt aaatctttaa tccatcttga gttaattttt gtatatgttg agaagcagga    31260 gtctaattc attcttctgc atagggctag ccattatctt ggcaccattt attgaataga    31320
gagtcctttc cttattgctt atttctgtca attttgttga atatcagatc gtcgtaggtg    31380
tatgggtcca tttctgggtt ttctattctg ttctatttgt ctctgtgtct gtttttgtac    31440
cagaaccatg ctgcttggtt actgtagcct tttagtatag tttgaagttg ggtaatgtga    31500
tgtctctggc ttcgttcttt ttgcttagga ttgctttggc tattcaggct ccttttggt     31560 tccatatgaa ttttagaata tttttctgat tctgtgaaaa atgacttgat attttgctag    31620
ggatagcatt ggagtggtaa cttgctttgg acagtgtggc cattttaatg atattgatta    31680
ttccaatcca tgagcatgga gtattttat atttattcag tcatcttgat ttctttcagc     31740
agtgttttgt agttcacct gtagaacatt tcacttccat ggttagatgt attcctattt     31800
tgtggctatt gtaaatggca ttgtattttt tttatttgg ccctaaacta gaatgttatt     31860
ggtgtataga attgctactg atttttgtac attgattttg tatccttaaa ctttactgaa    31920
```

```
gttatttatc agttctagga gacttttgga gaagtcttta gggttttcta tgtatgaaat   31980
catatcatca gcaaagagag acagtttgac ttcttcttct ttttggatgc catttatttc   32040
tttctcttgc ctagttgctc tgactaggac ttccagggca atgctgaata ggagtggtga   32100
gagtgggcat ccttgtcttg ttccagtact caagagaaat gcttccagca tttacctgtt   32160
tagtatgatg ttggctgtgg tttgtcatag gtggatctta ttattctaag gtatattcct   32220
ttgatgccta gcctgtcgag ggttttaat catgaatgga tattgaattt tattgaaggt   32280
tttttctgaa actattgaga tgatcatatg gttttgttt tttcattctg tttatgtggt   32340
gaatcacact tattgatttg ttatgttgaa ccagccttgc atcccaggaa taaagcctac   32400
ttgattgttg tgaattaact ttttgatgtg cttcttgatt tagtttgctc atattttgtt   32460
gaggattttc gtgtttatgt taatcagaga tattgtcctg aagttttctt ttttcattgt   32520
gtctctggca gattttgata tcaggatgat gctggcattg tagaatgagt tagggaggag   32580
cccctctcct taatattatg gaatagtttc agtaagatta ctatcagttc ttctttgtat   32640
gcttggtaga attcagttgt gaatccatct ggtccagggc taaatttggt tggtaggttt   32700
tttattactg attcaattt ggaacttgtt ataggtctgt tcaagttttc acttccgtcc   32760
tggttcaatc ttgggaggtt gtatgtttcc aggaatttat ccatttcctc tagatttcct   32820
actttgtgtg catagaggtg ttcataacgg tctctgaaaa tctttggcat ttctgtggga   32880
ttggtcgtaa tgtcattttt gtcatttctt gtgctttttg gaacttctgt ctgttttcc   32940 tcgttttct agctagcagt ctattagtct tgtttattct tatgaaaaac caactctttg   33000
tttcactaac atttatgga cttttgcatc tcaattttat ttagtcatta tctgatttta   33060
gttatgtctt ttcctctgct agctgtgaga ttgaattgtg ctctttttt ctagttcctc   33120 tagtgttatg ttagattgtt tagttgagat cttttctaacc tcttgatgaa ggcattttag   33180
cactataaac tttcctctta acactgcttt tgctacatcc caaagatttt ggaaagttgt   33240
gtctctattt tcattaattt caaataattt tttgatttct gccttaattt cattgttcac   33300
ccaacagtta ttcgggagca tgtggcttaa tttccatgct tttgtgtagt tttgagagat   33360
cttcttggta ttgatttcta ttgttatttc actatgattt gagagtggcc tttgtatgat   33420
tttaattttt tttaattat tgagacttgc tttatgactg agcatgtggg gcaatcttag   33480
aatacgttcc atgtgcatat gagaagaatg tgtgttctgt cattgttggc ttgagtatcc   33540
tagagaggtc tattaggtcc aactggtcaa gtgtcaagtt taattccaga attccttcgt   33600
cagttttctg cctcagtgat ctgtctaatg ctatcagtgg agtgataaag cccccactaa   33660
tattgtgctg ccatctacgt tttattgtag gccaataatt tgttttatga atctgagtgc   33720
tccagtgttg ggtgcatata tgtttagaat agttaagtct ttttgttcaa ttgaaccttt   33780
tatcatttta taatgccctt ctttgtcctt cctgattgtt gttggtttaa agtatgtttt   33840
aatctgattt aagggtagca actcctgctc tttttgttt tcatttgca tggtagatct   33900 ttcttcattc tttcactttg agcctgtgag tgtcattcat gtaggatgca tcttctgaaa   33960
acagcagaca gttgtgtctt gtcttttat ccagcttacc actttatgca ttttaaaggg   34020
agagtgtaga ctgtttacat ttagggttag cattgacatg tgagattttg ctcctgtcat   34080
tgtgttgttt agctggttgt tttgtagact tcattgtgta ataagtgtat ttttattggt   34140
agcaggtttc gtctttcatt tccatgttta gcaatcactt acggatttcc tgtaagaatc   34200
atctggtggt aatgaatctc cttggtgctt gcttgtctga gaaggattgt atttctcctt   34260
```

```
cacttatgaa actcagtttg gtgggatatg agttcttggt tgaaatttat tttctttaat   34320
aatgctgaaa atataggccc ccccatatct tctggcttgt aaggtttctg ctgacagaac   34380
tgttgctggc ctgatgaggt tcttttgta ggtgacctga cctttctcac tagctgcctt   34440 aacaatttt tcttttgcat tgaccttggt gaatctgatg actatgtgac ttggcaatgg   34500
ttgtcttgta tagtgtctca caggagttct ctgtatttct tgaatttgta tgcccacctc   34560
tctggtgaga tagggaaat tttcatggac tgcatcctca gatgtatgtt ctaagttgct   34620
tactctcttt ctcaggaatg actgtgagtc atagacttgg tctctttaca taacctcata   34680
aatcttgaag gttttgttca tgttttaaat tctttttct ttattttgt ccaaccaagt   34740 tgattcaaat aactggtctt caaactctga gattctttcc tcagcttggt ctgttctgct   34800
gttaatgcct ctgactatat tatgaaattt ttgaagttga tccctcaatt tctgaagttc   34860
agttttgttc tttcttaaaa tagctatttc atctttaagc tctttgatca ttttctgga   34920 ttccttgagt tccttgtatt gggtttcaat gatctcctgg atcttgatgt acttccttgc   34980
catccagatt ctgaattcta tgtatgtcat ttgagtcatt ttaatctggt taaaatcctt   35040
tgctggagga cttgtgtgtt tgtctggagg taaggagaca ccagctttt tgaattgcta   35100 gagttcttga gatgactctt taacatatga gggctggtgt tccattaaca atagtgtaca   35160
ttgagtatag tcagttggct tcattctgag tgctttcaaa gggccaaagc tctgtacagc   35220
atctttattt gtggctagat ttttgcttta ggtttcacag gtgctgtata ttggaaaaat   35280
gtttttggtg ttgtcatttg gggtgcaatc cagtaggtga tgcttaagag tggtagctgg   35340
cagataggct cttactcagt ccacagctct tttgtatttt ggtgcagtcc tcagtagtgc   35400
tctgtggtgg tagggagaga tgaccccctc accagataca ttcctgggcc ttggggagc   35460 cctctcttat tactggcact gcacctgcat ttcatttatt aggtgtcctg ggctgcaggg   35520
tgccctcagg cagaggctgc ggctggaaaa tagaccatac ccttccctgg ctggccctgc   35580
acaaggaggc acaccctgtt cctgagccag tccatgaacc cagctgtctc accctctca   35640 gtgttctgag agtaggggat cccccactgc ttgagcacca tgagcccctc ctggctacag   35700
gcagtggggg taggtatagt ctctcaaccc actgtccaac tgatttccag ggtaacagag   35760
agctgtgcct gcccacagag ttcaggcaga ggccaggcca ttgtgctgga agctgatgct   35820
aagccttgtc tgatgatggg gagtgaagca atgtaacggc tccctaactg tggcttctct   35880
cagggctatg gcagctggca tgagactgct ccaggtccaa ggcctgtggg acttcctgtg   35940
gacttgagtt ttgcctctgc aaacactcca gcaactctct atgtcagtct agaggcccag   36000
ggacacggat caggtattgg gatgaagggg ttctccagtt cccaggattt cacaggtccc   36060
tgtggaaagt gaggatcccc caggggctct cactcactca ccctttctct atgtggggga   36120
gcttcccctg gctccatgcc catcttgggt ggccagctgc ccagcttcac tcttccctgt   36180
tctctgtgtc ccctcactcc cttaattgtc ctgatatcgt tccttaggtg atctacttgc   36240
agaggcagtg tttactcgcc acttgttttc tctctgtgag agtagcacac actagctgct   36300
actcatctag catcttgaat tcttcccatc tgaaaaagtt tcaactgcaa tcacagttaa   36360
agaaatacaa aaacaatagc actctaagtt acaacttctc acctatagaa ttcaaaaaca   36420
tccaaatgat taactaaaca tttgtttggt agatctgtgg gaaaacatga attccttgtg   36480
aattactgga gaaatgaaa atgatgcaac acttatggaa gaaatttgg ggattttgg   36540 gggggagggg aacaatatat ttaaaactat aaatgcattt atcctagcaa ttctatgaat   36600
ggggatttat cttagggtac acctgcacac ttaggaaata atgtatgcag tcattcatta   36660
```

```
cagaattgtt tgtaatagca acaacctgaa aagcaactca tatatccatc catcacacag   36720
ggactggttt catgactacg gttcatgaat actctgcagc ccttagaaag aatgaggaag   36780
tggccgggca cggtggctca tgcctgtaat cccagcactt tgggaggccg aggcgggtgg   36840
atcacgaggt caggagatca agaccatcct ggctaacacg gtgaaacccc gtctctacta   36900
aaaacaatac aaaaaaatta gccaggcagg cgcctatagt cccagctatt cgggaggctg   36960
aggccggaga atggcatgaa cccgggaggc agagcttgca gtgagccgag ataacgccac   37020
tgcactccat ccagcctggg cgacagagcg agactccgtc aaaaaaaaaa aaaagagga   37080
agttctctat gcgctgacat ggaaggaaga cagatggttg aatgaaaaaa gtacataatt   37140
agccataaag tgtaagactt tttgtctaaa aagaagggt gatataattg catatttata    37200
tttcttcca tttatattaa gagataataa aggtacacaa attggctaga ataaagtggt    37260
ttcctataaa gggtaagagt aattgagtgg atgaagacta gggttaggga tagatttctc   37320
agtgtattca ttttaatata tgtattcatt ttatatatgt actaattttt atatatgtat   37380
ttattttata ttttgatttt cttaacataa atatattatt ccttcataaa attaaacttg   37440
atacatttt gattactaga tatgtagaaa gcattatgtt cagtaccaca gtaatacttt    37500
caaaccagct acaattagta tttatgagca tctatgtgcc agacattgtg ttctgctttg   37560
gttggtgggg gtagaggagg aaaggaaacc atggcttaca taggagtgga agtcttgtct   37620
ttcactttgc acctctctcc ttcagaccta gcataaatat gaccttaggg gaggcagaac   37680
acatatgata aagagataac tagcaagaga cataatagta gctaaataaa tactgaagga   37740
aaaattcagg aagaggtagg aaggatatgc ctcatcactt ccacctgtta agaaaaactt   37800
tagacattct tgccaatatt ccttattgcc tgtcttttga acaaatgcca ttatcactag   37860
agtgaaatga tatttcattg tagttttgat ttgcatttct ctcatgatcg gtgatgttga   37920
gcaccttttt atatacctgt ttgccatttg tatgtcttct cttgaaaaat gtctattcag   37980
atctttgccc atttttaaat ggcgtaatac atttttttcct attgagttgt ttgagttctt   38040
tatatattct ggttattaat cccttgtcag atgaataatt tgcaaatatt ttctcccatt   38100
ctgaggatta ccagaggctc agaggggtaa tggtggtggg ggagaataaa aatggttaat   38160
gagtacaaaa atatagatag gagtaataag atctagtatc tgatagcaca acagggtaat   38220
tacagccaac aaaaatttat tgtgcatttc aaaataacta agagtataat tggaatgtct   38280
gtaacacaaa gaagcaataa atgcttgagg tgatgtgagg ggatggatat ctaatttacc   38340
ttgatgtgat tattacatat tgtatgcctg catcaaaata gctcatgtat cttataagta   38400
tatacaccta ttatgtaccc attaaatttt ttaagaactt taaacaaatc aaatttaaca   38460
gagtttaatt gggcaaagaa tgatttgagg atcaggcaac ccccagaaac agaagaggtt   38520
caaagcaact cagtgctgtc acatggttgg agaggattta tgggcagaaa agggaaagag   38580
agatacagaa aatggaagtg aggtacacaa acagctggat tggttacagc ttgccatttg   38640
cgttatttga acataatctg aacagttggc tgtctttgct tgaccaaaac ttggtgtttg   38700
gtacaagagc agattacagt ctatttacac atccagttag tttacagttc actatacacg   38760
aagaagaaac ctttaagcag aacttaaaat atgcaaagag gaagctttaa gttaaactta   38820
atttaacaca cccaattatc aaaaaatgag tagctctgca aaagtggatt ttcctggtca   38880
tctttggtac ttccttaaaa aagagaaaag tagtactcac gataaaaaaa aaaagtcct    38940
caagtcttta ttttattcct ttccaattta aaatgttaca tcatctgagg aaggttttc    39000
```

```
cctttgaccg ctttcataga catttcttct gcatgggttg gccagaatca gaagagtaat    39060
tgtaactttc tgttcttgtc ctacagttac aaagcggttt cactttgtaa atgctctttg    39120
gatggcagga accaagcagc catgaaaaga ggagttacac ctttaaagga gtcattccat    39180
catgactctc aggactggaa catggaatac ctgaatggcc tctttggcac agataggcca    39240
cccttgaaag gtgttccaag ctaggaactc actaccactg ttacatcgat gcaactctgt    39300
gagaagtttt tatctggtga tggaaaatct catctcttca acacactgac tactaccagt    39360
ctcagaaccc tgtaaacaag attcattcat ctcaaattgg gttaaagcag tcaccctgcc    39420
ttacattagt ttggaataag gatgtgggga tggtggtaga ggaggggagt ggatgatgat    39480 tttttttattg ttatttgatt ctaaagaaac ttctatacat tttgcattta aaataattat    39540
gtttttaaca atgtttggat taattcaaaa taggatatta tatcctatta tattaaatat    39600
actatttaat catcttgttg accaaatgca acttaaacat gtaaaatggt aaatagcata    39660
ataattgtct tctaagcctg cactataaag tatttcagtg gcctcattat taaaggacca    39720
aggtgcccaa agaaacaaaa tttagtaatc ataaacaaga gacaaaccta cttcttttcc    39780
cccagagttc tggccacatt gaaataaggt gtttgaatgc ttaataagaa ttattttggc    39840
ccacacagtg gctcatgcct gtaatctcag cactttggga tgccaaggtg agcagatcac    39900
ttgaggccag gagttcaaga ccagcgtggc caacgtggtg aaaccccatc tctactaaaa    39960
atacaaaaat tagcccggtg tggtggtaca cgcctatagt cccagctact cgggagactg    40020
aggtgggaga atcacttgaa cccgggaggc caaggctgca atatcgagat cacaccactg    40080
cactctagcc tgggcaacag agtgagagtg agactctttc tcggaaaaaa aaaaaagaa    40140 ttatttttgaa caaagtgctg tcacctaagt tagcaaaact ccaagcaagg tttttggctc    40200
tgtaaggaaa gaattagcct actcatttgg aaatttagtg gtgtttgtaa tgcagaaagt    40260
gacagtgaga ctggaaaggg attggctttg gggcttgttc tgctttataa ataataatga    40320
atcttctcca acatgaagta atgtgaatta aaaaaaaaaa atctgtcctt agagtacaaa    40380
attacttcat aacccaatct gcatttctcc actccaagca tattttctgg gagttctact    40440
tagagagtga aagctgctgt gtgtgtgata attaattta acaaacactt ggcaaactga    40500
gctggactat gtataagcta ccctagacta agcatgaatt tgaactgcac ttttttatggt    40560 gttttttcca caatgacatt atttaggcat ttaaagttat ctgaactgca attttttgtt    40620 ctttttttttt taatttgact ttttaaaaaa aattattcct gaataaagag gcagtttgta    40680
aaaactcgag aactgtgaga gataattgga tctttgtgta gcaaaactag aagggtgttg    40740
ggtatctgct ctttatcaaa tggaccactt acttttcttt tctttttttgc cctgtgttca    40800 gaaaacaaat gtgcgtgtct cctgatttat aatgtatagt tcattaatgg agaaagtgct    40860
tgagaattag atcctaatgt catttcccat gcagcatctt cattctttc taaagcacta    40920 tttggtaaaa acaactgata gtcgtcagag gtgatcagca atgtttgagc actatttcct    40980
ttttatatcc tgcacatgga atatggacag gcaaacaaat catttccaag taagaaaata    41040
aattttgagg gagttaatac tataatttga agtaataac ctcctattta tccatctagt    41100
ttgttgttct gtactaaatt atttgtgcat gtctctgtgt ctataattta tgtgaaactt    41160
tgcacaatct taaataggac aaaatagaca ttctgtaatt tcccaggcaa gctatttaag    41220
gtgactatct ctctacatat ttgagatgaa aaacaataac atgacaatcc atcccttctt    41280 aggttttttgt aagcagactt actacctgtg actcagtttt gttctcacag gtactaatt    41340 aatccttcac gataataact tgtcaaattc cattacttct gtaaaggcaa tactttatat    41400
```

```
ttgtttgtat tcaaatttta aactgatgtt aaatgccgtg ggtgcaactg caggttaaaa    41460
atatgtgttt gaatctctta ttcttttgc ttggcaatgt atgaaataac tgctctttct    41520
agaaatcttg atgatgaagt ggcctgttgt tttgtcacct aaaaatgcaa taatgttcaa    41580
attaagcttt tctttattaa catcacttga ttgtgtgcca tatttagagc ttagtgaaat    41640
tttaatctac acattgatta aatacatttt atttattctt gtttctaatg ggaactttct    41700
ttgtttctaa tgggaacttt cttaaattaa attacatcca acatttatta aagacctaaa    41760
acataggcaa ttactgtgct tagaggaaaa gcgcagacga aagtgaatca gacaagttcc    41820
ctgccctccg gaagctttca gtctagtgat gagaaagacg tatacacacc ttatgttgat    41880
ttaaaaaaaa aaaagctct tacctggttg ctggcatatg aaagtgttag ttacagatct    41940
gccccaaact aaaggtgtca cctcgagtaa atctctttcc ctttcccttt caatctcttc    42000
atctataaac taggggttgg gaatacattt attaacaaac acaaattgag cgtctaccat    42060
gtgataatag tagctaaact tactgagcaa ttaccatggg gcaggtatca agataaaccc    42120
tttatgatgg taacctcatt taatcctcaa agcaattcca ttttcaagag gaggaaattg    42180
aggctcaaaa atgttaagta actcccccaa ggatgcaaag tgattgagcc agaattcaag    42240
actaggttgg tttgactcca aaactcatgc cattaaaccc tattgtgtca ctgcaaacaa    42300
ctctaatagt ttcaaattat tagttctatt aatattatat taccattatt tgcccccaaa    42360
atgtaaaatg taaatacaaa gagtttggtt tttgtattac tagtggaggt taaaggtgca    42420
caatggaatt attcaaactg ggaaaatcca ggaagacttc atggaggagg cagcatatgg    42480
ctgcagttaa taaggtttgc tcacacaaaa tggagaggtg aggacatttc aggcagagag    42540
aattatatga gaggttacag agcagtaaac agtcatgcgt ctgcaagatc aaagggaaag    42600
ggcggtaaga gagaagcttg aaagtcaagt ggagccagat tgtggaaaaa ctagagagtc    42660
atgccaagga ccttgacata tagaaaatgg gaagcccctg aaaggtgaag aacatgagag    42720
tgaaatgatt agtaacttt tggtttagga cttgtttctt ttgtgttttg gttgctttct    42780
tgttttgttt tgtttgtggt ttttaaattt acaaccaata agaatattta gtaaggtttc    42840
caaatacatc atgaatatat aaaactagcc tgactcaagg ataataattc tgggtagttg    42900
gagtgaagtt tcaatcagct acgtggcatt tgctaatcat ctgatatgag ctaacaataa    42960
aggagttaac aaataaactg tcagcctaca gtccagggtc tcaaatagca tgtgacatag    43020
ttgagaagca gttttccata tcatacatga aataactaaa gaaactactt acaaagcact    43080
ataccagtaa ctacaataaa atacaactat acatgcaaaa taatgctgaa agctgcaagt    43140
agaggggtaa agctaggcca gttgctcagg gaaccattct gaagtggatt tgggaagtat    43200
gtctagaagg ggagccattg ctgtgagagt gctgaggctc atctgctact agtccccac    43260 tactcaggca tatggtaggt cagtaacaaa accatcattg tgcactgttc tttccatcta    43320
aattccatca aattatgacc aacctatcaa ggtactagtt caaattctct cttcctctat    43380
aagctagtgg tcttctctaa aatttaagaa gatcgtgctc atcttcctac ttcttgttct    43440
ctttcttctg tgtttctga ggctgcaatg aactaggaac ttcctctccc cagaactctg    43500
tattccaggc cttagatcac tcaaaactgt tgcttataaa gtgcagagaa tcaacagaga    43560
aggaatagag gttaatgtct ggtcaaagat gtgattctct tgttgaaaag ttcattagct    43620
tattatttat agaatcataa gtcccaggaa aaaccaaaag gaaatatata ttggatccta    43680
atgatattct cttttttct tttttctttt cccccactcc attgcccagg ctggagtgca    43740
```

```
gtggcataat ctcagctcac tgcaacctcc acctcccggg ttcaagggac tctcctgcct   43800
cagccttcca agtagatggg attacaggca tgtgccacca catctggcta attttttttt   43860
gtatttttag tagagatggg gtttcaccat gttagtcagg ctggtgttga actcctgacc   43920
tcaaatgatc caccagcctc ggcctcccag tgtgctggga ttgcaggcgt gagccaccac   43980
acccggcctg atattctctt gcaagggcat tgtttacatt gtctatcatc agaactgtag   44040
agtgttggct ccaggcacag aaccoctaga gttttgtaaa ccatttatat cacactggca   44100
accagaagta actttatata ctcaagaatc aagatttcac ctagaagtac ctcaggtagg   44160
tgttggttca ttcacattcc aaccaaaaga taatgtacca taaagtgcat accgcctagt   44220
ccgtaatgat taaggcaacc acataaaatc tcattattta aaagaaatta agtccaggca   44280
cggtggctca cacctgtaat ctcagcactt cgggaggcca aggagggcag atcacctgag   44340
gttgggagtt tgagaccagc ctgatcaaca tggagaaatc ccatctctac taaaaataca   44400
aaattagcgg ggcatggtgg tgcatgccta atcccagc tactcaggag gctgaggcag   44460
gagaatcact tgaacccagg aggtggaggt tgagatcgtg ccattgcact ccagcctgga   44520
caacaagagt gaaactctgt ctcaaaaaag aaaaaagaa aagaaatta aatgcactat   44580 ggtttatgga gcggtattcc tcctccatgt cctacataag atctttcaca tgccagtcac   44640
agttaaatct aatttgctgt aatctggata aatgggagct aatcaacaag ctctcagctc   44700
tagctctgaa tcagcagcag atattgcatt tttgaaatac actaatagca agaatgcctt   44760
cctgacaaca actggcattt ttgacacagc aggaagttta tctggattct gatataatag   44820
ttattggaat catacatagg tacatagtt aaaaggctaa taagtcattt gttattgctt   44880
ttattatctc tgcatagtta gtaaaattga gattagaacc acttctcgaa tgtactgttc   44940
taaatcctta gcttgcttga tcacacatga ccctcacaat gatcctagga gaaattattc   45000
tgcatgccat tttgtagctg gggaaactga ggcacagaga aatacagtac tgcccaaaat   45060
gtcataacta atcaaaggca aagacaatac tcacaccagc tctgattcca gagcccactc   45120
tcttaaccat atgctttct gcttccctag ttgtagagtc tttttgtatg actgcattaa   45180
ttatatgtga agagttcaaa aatttctata aaggtctttt aagggtgtc attctggttg   45240 aaaatggagg actaggcttc tcacttgaag acatatttct gtagaaaaac ctattttcat   45300
ttagatgcta cagttacttg atgtggttaa taaaccagtt aacagagtat gaaaaggata   45360
agggttaaag ccctcccaag ccatctttca tgctgctaat atgaatcaca ttactagata   45420
cttaaatatc attttctctt tggttcccag aagactgcat atatgctaga atattttgtcc  45480 tcctctttta cccttttcagg caataaagta ttttggacca ctgtactatg ttataattat   45540
tgtttctctc ctgattttt tgctccaatc taatgaaaga catacaagct actatactgc   45600
tacacaatga ctaaataccct gttggattag gtgggggaa gatacacagt cactggctag   45660
aaagcatcat gcatacagag ccattttcac catatatttt atttctcatg atcatgtaga   45720
atttaggctt tggtgttgat tatttctctc ttaggaaaca tagttgtttc agggttgata   45780
tcacaaaaaa acagaaaaac ctattcgaga aaaggaaaat tatttgtctg taggccaaat   45840
tttgaagtag gaaaacctgc ttttggagtt gtattcccct cccaggcact taatccaagt   45900
tccagtctta ttctaaactg gggatgctag tattaaccac cataggagtt atctgagatg   45960
agttatcatc aacttggtac caggttgttg tcctctggac tcagtgagct ctagaattgc   46020
atgaaactgg cctaatttat caaagtatgt agccttgggt aaataattca agctctcaga   46080
ggtccagtta tctcctctgt aaaacatatc tacatcctag ggatgacaat atctacatcc   46140
```

```
tagagatgtc aggaggatta agtgtaattt tttttaattg tatgtattta aaatgggcaa   46200
cataatgttt tgatatacac gtgtatagtg attactacag tcaagcaaat taacatatcc   46260
atcatttcat agctacctt  tatgtatgtg ataagattat ctaaaatcta ttctcttacc   46320
aaatttccag tatacaatat tgatatggtt tgatccatat ccccatccaa atctcatgtt   46380
cagttgcaat ccccaacgtt ggagatgag  cctggttgga ggtgattgga tcacaggggt   46440
ggcttctaat ggttcagcac catcctttct tggtactgta tagtgagtaa gttctcacga   46500
gatctggttg tttaaaagtg tgtaacacct cccccacttt ccctctctct gttcctcctg   46560
ctcccgctat gtgaagtgcc agctccctct ttgccttccg ccatgattgt aagttctctg   46620
aggcatcccc agaagctgat gctgccatgc ttcctataca gcctgcagaa ccatgagtca   46680
attaaacctc ttttctttgt aaattaccca gtctcaagta tttctttata gcaatgcaag   46740
aatggactaa tacagaaaat tgttactgag aagaagggca ttgctataaa gatacctgaa   46800
aatgtagaag tgactttgga accggctaac aggcagaagt tgaaacattt tagagggctc   46860
agaagaagac agaaagatga gagaaagttt ggaactcgct aggaacttgt tgagtggttg   46920
taaccaaaat actgatagtg atatagacag tgaagtccag gctgaggagg tctcagatgg   46980
aaatgagaaa tttattggga atgagtaaag gtcaggtttg ctatgcttta gcaaagagct   47040
tagctgcatt gttcctctgt tctagggatc tgtgaaatct tagacttaag aatgatgatt   47100
tagggtatct ggcagaagaa atttctaagc agcagagtgt tcaagaagta acctagctgc   47160
ttctaatagc ctatgctcat aggcatgagc acagaaatga cctgaaattg gaacttacac   47220
ttaaaaggga agcagagcat aaaagtttgt aaattttgca gcctggccat gtggtagtaa   47280
agaaaagctc gttctcagga gaggaagtca agcaggctgc ataaatttgc ataactaaaa   47340
ggaaggcaag ggctgataac caaaacaatg gggagaaaga ctcataggac taacaggcat   47400
tttattttat tttatttta  ttttattatt attatactt  aagttttagg gtacatgtgc   47460
acaatgtgca ggttagttgc atatgtatac atgtgccatg ctggtgtgct gcacccatta   47520
actcgtcatt tagcattagg tatatctcct aatgctatcc ctcccccctc ccccaccca   47580 caacagtccc cagagtgtga tgttcccctt cctgtgtcca tgtgttctca ttgttcaatt   47640
cccacctatg agtgagaaca tgtggtgttt ggttttttga ccttgcaata gtttactgag   47700
aatgacgatt tccaatttca tccatgtccc tacaaaggac atgaactcat catttttat   47760 ggctgcatag tattccatgg tgtatatgtg ccacattttc ttaatccagt ctatcactgt   47820
tggacatttg ggttggttcc aagtctttgc tattgtgaat agtgccacaa taaacatagt   47880
gtgcatgtgt ctttatagca gcaggattta tagtcctttg ggtatatacc cagtgatggg   47940
atggctgggt caaatggtat ttctagttct agatccctga ggaatcgcca cactgacttc   48000
cacaatggtt gaactagttt acagtcccac caacagtgta aaagtgttcc taataggcat   48060
tttaggcttt catggtggtc cctctcatca caggccccga ggcctaggag gactgaatca   48120
tttcctgggc caggcctagg gccctgctc  cctcttacag ccttgggact ctgctccctg   48180
aatcccagct gctcaagggg gcccaggtac tgttacagta ggtagctaat caggcatgag   48240
tggggtaaga gagaagtccc caccaccca  caggaatgtc aggcaaccat cagatgatgg   48300
tcaggcagtt gtcatactgc ctctctaaaa tagtaattgg ttgcagccag caccagggag   48360
aggcaacttc tcaatagata gaaacacctg aaattggtaa ctgggcgctt ccaataagat   48420
ctcaggaact gagagagtgg gcttaacatg cacattaaga ggcaaaatgg tgaagtatga   48480
```

```
cctttgggggg cattccaccg gaaaagggaa gaaagcctca ggtaagcatg tatacaactc    48540
cagtaaacac actgcacacg ctcaccttcc aagtgcaagc agggcaccat gcatgcggca    48600
agctcaccct tagggaagga ccaagggaaa ggggcacaag atgtcagaag taggccagtg    48660
tataagatcc taggttcaag gtcaaacagg gcacttgacc tccaaggtgc ccacttgggc    48720
ctcttccaaa tgtactttcc tttcattcct gttctaaagc ttttaataa acttttactc    48780 ctgctctgaa acttgtcgca gtctcttttt ctgccttatg cctcttggtc aaattctttc    48840
ttctgaggag gcaagaattg aggttgctgc agacccacat ggatttgcag ctggtaactc    48900
agataacttt caccagtaag aatacagttc aggctgctgc ttcacagggt gccaggcata    48960
agccttggtg gcttccataa gctgtgaagc cggcgggcgc acataatgca agagttgagg    49020
cttaagaagc tctgcctaga ttttagagga tgtatgaaaa agcctggatg tccagacaga    49080
agcctgttac tggggtggaa tcctcatgga gaacatctac tagggaagca aggagaagaa    49140
atgtggggtt gcagccccca cagagagtcc cctgggcac tgcctagcag agctatgaca    49200
agacagccac cgtcctccag accccagaat ggtagatcca ccaacaactt gcaccctgca    49260
gcctggaaaa gctgcaagca ctcaatgcta gcccatgaga gcagctgtgg gagatgaacc    49320
ctggaaaacc cagggggtgg ttctgcccaa ggttttggga gccccactcat tgcatcagtg    49380 ttccctgggt gtgagtcaaa ggagattatt tcagagcttt aacatttaat gactgcccgg    49440
ctggctttca gacttgcaat ggggcccctat agcctctttc ttttggcaga tttctcccctt    49500 tcggaatggc agtatctgcc caatgcctat accccccattg tatctttgaa gcaattacct    49560
tgtttttgat tttacaggtt cataggtaga agggactagc ttcgtctcag gtgagacttg    49620
ggactttgga cttttgaatg aatgctggat cgagttaaga ctttggggaa ctgttggtaa    49680
ggcacgacag tattttgcaa tatgagaagg acattagatt tggggagggggc cagagttgga    49740 ataacatggt ttggatctct gtccccaccc aaatctcatg ttcaactgta atccccagtg    49800
ttggaggttg ggcctggtgg gaggtgagtg gattatgggg tggcttctaa tggttttgta    49860
cagtcccctc ttggtactat atagtgagtt ctgacaagat ctagttgttt aaacgtatgt    49920
agcacctccc atttctctct tccccccagtt cctgccatgt gaagtctggg gtctccctat    49980
gccttccatc atgattttaa gttccctatg gcctgcccag aagctgatcc agccatgctt    50040
cttgtacagc ctgcagaact gtgagccatt aaacttttct ttataaatta cccagtttca    50100
gttatttctt tatagcagtg taagaatgga ctaacacaat tattaacgct agtcctcatg    50160
ttgtacatta aatctctaga tgtattagac gtaactgcaa cttttgtaccc taccctacaa    50220 ttttctttcc ccccaagccc cccaaccaag ggtctactct gtttctataa attcagttgt    50280
tttttaattc cacgtataag tgaagtacaa ctcagtgtag aaacttggta aatgctagct    50340
acttgttata agctgtcagt caaaatataaa atacagagat gaatctctaa attaagtgat    50400
ttatttggga agaaagaatt gcaattaggg catacatgta gatcagatgg tcttcggtat    50460
atccacacaa caaagaaaag ggggaggttt tgttaaaaaa gagaaatgtt acatagtgct    50520
ctttgagaaa attcattggc actattaagg atctgaggag ctggtgagtt tcaactggtg    50580
agtgatggtg gtagataaaa ttagagctgc agcaggtcat tttagcaact attagataaa    50640
actggtctca ggtcacaacg ggcagttgca gcagctggac ttggagagaa ttacactgtg    50700
ggagcagtgt catttgtcct aagtgctttt ctaccccta cccccactat tttagttggg    50760
tataaaaaga atgacccaat ttgtatgatc aactttcaca aagcatagaa cagtaggaaa    50820
agggtctgtt tctgcagaag gtgtagacgt tgagagccat tttgtgtatt tattcctccc    50880
```

-continued

```
tttcttcctc ggtgaatgat taaaacgttc tgtgtgattt ttagtgatga aaaagattaa    50940
atgctactca ctgtagtaag tgccatctca cacttgcaga tcaaaaggca cacagtttaa    51000
aaaacctttg ttttttttaca catctgagtg gtgtaaatgc tactcatctg tagtaagtgg   51060
aatctataca cctgcagacc aaaagacgca aggtttcaaa aatctttgtg ttttttacac    51120
atcaaacaga atggtacgtt tttcaaaagt taaaaaaaaa caactcatcc acatattgca    51180
actagcaaaa atgacattcc ccagtgtgaa aatcatgctt gagagaattc ttacatgtaa    51240
aggcaaaatt gcgatgactt tgcaggggac cgtgggattc ccgcccgcag tgccggagct    51300
gtcccctacc agggtttgca gtggagtttt gaatgcactt aacagtgtct tacggtaaaa    51360
acaaaatttc atccaccaat tatgtgttga gcgcccactg cctaccaagc acaaacaaaa    51420
ccattcaaaa ccacgaaatc gtcttcactt tctccagatc cagcagcctc ccctattaag    51480
gttcgcacac gctattgcgc caacgctcct ccagagcggg tcttaagata aagaacagg    51540
acaagttgcc ccgccccatt tcgctagcct cgtgagaaaa cgtcatcgca catagaaaac    51600
agacagacgt aacctacggt gtcccgctag gaaagagagg tgcgtcaaac agcgacaagt    51660
tccgcccacg taaagatga cgcttggtgt gtcagccgtc cctgctgccc ggttgcttct     51720
cttttggggg cggggtctag caagagcagg tgtgggttta ggaggtgtgt gttttttgttt  51780
ttcccaccct ctctccccac tacttgctct cacagtactc gctgagggtg aacaagaaaa    51840
gacctgataa agattaacca gaagaaaaca aggagggaaa caaccgcagc ctgtagcaag    51900
ctctggaact caggagtcgc gcgctagggg ccggggccgg ggccggggcg tggtcggggc    51960
gggcccgggg gcgggcccgg ggcggggctg cggttgcggt gcctgcgccc gcggcggcgg    52020
aggcgcaggc ggtggcgagt gggtgagtga ggaggcggca tcctggcggg tggctgtttg    52080
gggttcggct gccgggaaga ggcgcgggta gaagcggggg ctctcctcag agctcgacgc    52140
attttttactt tccctctcat ttctctgacc gaagctgggt gtcgggcttt cgcctctagc   52200
gactggtgga attgcctgca tccgggcccc gggcttcccg gcggcggcgg cggcggcggc    52260
ggcgcaggga caaggatgg ggatctggcc tcttccttgc tttcccgccc tcagtacccg     52320
agctgtctcc ttcccgggga cccgctggga gcgctgccgc tgcgggctcg agaaaaggga   52380
gcctcgggta ctgagaggcc tcgcctgggg aaggccgga gggtgggcgg cgcgcggctt     52440
ctgcggacca agtcggggtt cgctaggaac ccgagacggt ccctgccggc gaggagatca    52500
tgcgggatga gatgggggtg tggagacgcc tgcacaattt cagcccaagc ttctagagag    52560
tggtgatgac ttgcatatga gggcagcaat gcaagtcggt gtgctcccca ttctgtggga    52620
catgacctgg ttgcttcaca gctccgagat gacacagact tgcttaaagg aagtgactat    52680
tgtgacttgg gcatcacttg actgatggta atcagttgtc taaagaagtg cacagattac    52740
atgtccgtgt gctcattggg tctatctggc cgcgttgaac accaccaggc tttgtattca    52800
gaaacaggag ggaggtcctg cactttccca ggaggggtgg ccctttcaga tgcaatcgag    52860
attgttaggc tctgggagag tagttgcctg gttgtggcag ttggtaaatt tctattcaaa    52920
cagttgccat gcaccagttg ttcacaacaa gggtacgtaa tctgtctggc attacttcta    52980
cttttgtaca aaggatcaaa aaaaaaaaag atactgttaa gatatgattt ttctcagact    53040
ttgggaaact tttaacataa tctgtgaata tcacagaaac aagactatca tataggggat    53100
attaataacc tggagtcaga atacttgaaa tacggtgtca tttgacacgg gcattgttgt    53160
caccacctct gccaaggcct gccactttag gaaaaccctg aatcagttgg aaactgctac    53220
```

```
atgctgatag tacatctgaa acaagaacga gagtaattac cacattccag attgttcact   53280
aagccagcat ttacctgctc caggaaaaaa ttacaagcac cttatgaagt tgataaaata   53340
ttttgtttgg ctatgttggc actccacaat ttgctttcag agaaacaaag taaaccaagg   53400
aggacttctg tttttcaagt ctgccctcgg gttctattct acgttaatta gatagttccc   53460
aggaggacta ggttagccta cctattgtct gagaaacttg gaactgtgag aaatggccag   53520
atagtgatat gaacttcacc ttccagtctt ccctgatgtt gaagattgag aaagtgttgt   53580
gaactttctg gtactgtaaa cagttcactg tccttgaagt ggtcctgggc agctcctgtt   53640
gtggaaagtg gacggtttag gatcctgctt ctctttgggc tgggagaaaa taaacagcat   53700
ggttacaagt attgagagcc aggttggaga aggtggctta cacctgtaat gccagagctt   53760
tgggaggcgg aggcaagagg atcacttgaa gccaggagtt caagctcaac ctgggcaacg   53820
tagaccctgt ctctacaaaa aattaaaaac ttagccgggc gtggtgatgt gcacctgtag   53880
tcctagctac ttgggaggct gaggcaggag ggtcatttga gcccaagagt ttgaagttac   53940
cgagagctat gatcctgcca gtgcattcca gcctggatga caaaacgaga ccctgtctct   54000
aaaaaacaag aagtgagggc tttatgattg tagaattttc actacaatag cagtggacca   54060
accacctttc taaataccaa tcagggaaga gatggttgat ttttttaacag acgtttaaag   54120
aaaaagcaaa acctcaaaact tagcactcta ctaacagttt tagcagatgt taattaatgt   54180
aatcatgtct gcatgtatgg gattatttcc agaaagtgta ttgggaaacc tctcatgaac   54240
cctgtgagca agccaccgtc tcactcaatt tgaatcttgg cttccctcaa aagactggct   54300
aatgtttggt aactctctgg agtagacagc actacatgta cgtaagatag gtacataaac   54360
aactattggt tttgagctga ttttttttcag ctgcatttgc atgtatggat ttttctcacc   54420
aaagacgatg acttcaagta ttagtaaaat aattgtacag ctctcctgat tatacttctc   54480
tgtgacattt catttcccag gctatttctt ttggtaggat ttaaaactaa gcaattcagt   54540
atgatctttg tccttcattt tctttcttat tctttttgtt tgtttgtttg tttgtttttt   54600
tcttgaggca gagtctctct ctgtcgccca ggctggagtg cagtggcgcc atctcagctc   54660
attgcaacct ctgccacctc cgggttcaag agattctcct gcctcagcct cccgagtagc   54720
tgggattaca ggtgtccacc accacacccg gctaattttt tgtattttta gtagaggtgg   54780
ggtttcacca tgttggccag gctggtcttg agctcctgac ctcaggtgat ccacctgcct   54840
cggcctacca aagagctggg ataacaggtg tgacccacca tgcccggccc attttttttt   54900
tcttattctg ttaggagtga gagtgtaact agcagtataa tagttcaatt ttcacaacgt   54960
ggtaaaagtt tccctataat tcaatcagat tttgctccag ggttcagttc tgttttagga   55020
aatacttttta ttttcagttt aatgatgaaa tattagagtt gtaatattgc ctttatgatt   55080
atccaccttt ttaacctaaa agaatgaaag aaaaatatgt ttgcaatata attttatggt   55140
tgtatgttaa cttaattcat tatgttggcc tccagttttgc tgttgttagt tatgacagca   55200
gtagtgtcat taccatttca attcagatta cattcctata tttgatcatt gtaaactgac   55260
tgcttacatt gtattaaaaa cagtggatat tttaaagaag ctgtacggct tatatctagt   55320
gctgtctctt aagactatta aattgataca acatatttaa aagtaaatat tacctaaatg   55380
aattttttgaa attacaaata cacgtgttaa aactgtcgtt gtgttcaacc atttctgtac   55440
atacttagag ttaactgttt tgccaggctc tgtatgccta ctcataatat gataaaagca   55500
ctcatctaat gctctgtaaa tagaagtcag tgctttccat cagactgaac tctcttgaca   55560
agatgtggat gaaattcttt aagtaaaatt gtttactttg tcatacattt acagatcaaa   55620
```

-continued

```
tgttagctcc caaagcaatc atatggcaaa gataggtata tcatagtttg cctattagct    55680
gctttgtatt gctattatta taaatagact tcacagtttt agacttgctt aggtgaaatt    55740
gcaattcttt ttactttcag tcttagataa caagtcttca attatagtac aatcacacat    55800
tgcttaggaa tgcatcatta ggcgattttg tcattatgca aacatcatag agtgtactta    55860
cacaaaccta gatagtatag cctttatgta cctaggccgt atggtatagt ctgttgctcc    55920
taggccacaa acctgtacaa ctgttactgt actgaatact atagacagtt gtaacacagt    55980
ggtaaatatt tatctaaata tatgcaaaca gagaaaaggt acagtaaaag tatggtataa    56040
aagataatgg tatacctgtg taggccactt accacgaatg gagcttgcag gactagaagt    56100
tgctctgggt gagtcagtga gtgagtggtg aattaatgtg aaggcctaga acactgtaca    56160
ccactgtaga ctataaacac agtacgctga agctacacca aatttatctt aacagttttt    56220
cttcaataaa aaattataac tttttaactt tgtaaacttt ttaattttt aacttttaaa    56280 atacttagct tgaaacacaa atacattgta tagctataca aaaatatttt ttctttgtat    56340
ccttattcta gaagcttttt tctattttct attttaaatt tttttttta cttgttagtc    56400 gttttttgtta aaaactaaaa cacacacact ttcacctagg catagacagg attaggatca    56460
tcagtatcac tcccttccac ctcactgcct tccacctcca catcttgtcc cactggaagg    56520 ttttttagggg caataacaca catgtagctg tcacctatga taacagtgct ttctgttgaa    56580
tacctcctga aggacttgcc tgaggctgtt ttacatttaa cttaaaaaaa aaaaagtag    56640 aaggagtgca ctctaaaata acaataaaag gcatagtata gtgaatacat aaaccagcaa    56700
tgtagtagtt tattatcaag tgttgtacac tgtaataatt gtatgtgcta tactttaaat    56760
aacttgcaaa atagtactaa gaccttatga tggttacagt gtcactaagg caatagcata    56820
ttttcaggtc cattgtaatc taatgggact accatcatat atgcagtcta ccattgactg    56880
aaacgttaca tggcacataa ctgtatttgc aagaatgatt tgttttacat taatatcaca    56940
taggatgtac cttttagag tggtatgttt atgtggatta agatgtacaa gttgagcaag    57000
gggaccaaga gccctgggtt ctgtcttgga tgtgagcgtt tatgttcttc tcctcatgtc    57060
tgttttctca ttaaattcaa aggcttgaac gggcccctatt tagcccttct gtttttctacg    57120 tgttctaaat aactaaagct tttaaattct agccatttag tgtagaactc tctttgcagt    57180
gatgaaatgc tgtattggtt tcttggctag catattaaat attttatct ttgtcttgat    57240 acttcaatgt cgttttaaac atcaggatcg ggcttcagta ttctcataac cagagagttc    57300
actgaggata caggactgtt tgcccatttt ttgttatggc tccagacttg tggtatttcc    57360
atgtcttttt tttttttttt tttttgacc ttttagcggc tttaaagtat ttctgttgtt    57420
aggtgttgta ttacttttct aagattactt aacaaagcac cacaaactga gtggctttaa    57480
acaacagcaa tttattctct cacaattcta gaagctagaa gtccgaaatc aaagtgttga    57540
caggggcatg atcttcaaga gagaagactc tttccttgcc tcttcctggc ttctggtggt    57600
taccagcaat cctgagtgtt cctttcttgc cttgtagttt caacaatcca gtatctgcct    57660
tttgtcttca catggctgtc taccattgt ctctgtgtct ccaaatctct ctccttataa    57720
acacagcagt tattggatta ggccccactc taatccagta tgaccccatt ttaacatgat    57780
tacacttatt tctagataag gtcacattca cgtacaccaa gggttaggaa ttgaacatat    57840 cttttttgggg gacacaattc aacccacaag tgtcagtctc tagctgagcc tttcccttcc    57900 tgttttctc cttttagtt gctatgggtt aggggccaaa tctccagtca tactagaatt    57960
```

| | | | | | |
|---|---|---|---|---|---|
| gcacatggac | tggatatttg | ggaatactgc | gggtctattc | tatgagcttt | agtatgtaac | 58020 |
| atttaatatc | agtgtaaaga | agccctttt | taagttattt | ctttgaattt | ctaaatgtat | 58080 |
| gccctgaata | aagtaacaa | gttaccatgt | cttgtaaaat | gatcatatca | acaaacattt | 58140 |
| aatgtgcacc | tactgtgcta | gttgaatgtc | tttatcctga | taggagataa | caggattcca | 58200 |
| catctttgac | ttaagaggac | aaaccaaata | tgtctaaatc | atttggggtt | ttgatggata | 58260 |
| tctttaaatt | gctgaaccta | atcattggtt | tcatatgtca | ttgtttagat | atctccggag | 58320 |
| catttggata | atgtgacagt | tggaatgcag | tgatgtcgac | tctttgccca | ccgccatctc | 58380 |
| cagctgttgc | caagacagag | attgcttaa | gtggcaaatc | accttatta | gcagctactt | 58440 |
| ttgcttactg | ggacaatatt | cttggtccta | gagtaaggca | catttgggct | ccaaagacag | 58500 |
| aacaggtact | tctcagtgat | ggagaaataa | ctttcttgc | caaccacact | ctaaatggag | 58560 |
| aaatccttcg | aaatgcagag | agtggtgcta | tagatgtaaa | gttttttgtc | ttgtctgaaa | 58620 |
| agggagtgat | tattgtttca | ttaatctttg | atggaaactg | gaatggggat | cgcagcacat | 58680 |
| atggactatc | aattatactt | ccacagacag | aacttagttt | ctacctccca | cttcatagag | 58740 |
| tgtgtgttga | tagattaaca | catataatcc | ggaaaggaag | aatatggatg | cataaggtaa | 58800 |
| gtgattttc | agcttattaa | tcatgttaac | ctatctgttg | aaagcttatt | ttctggtaca | 58860 |
| tataaatctt | attttttaa | ttatatgcag | tgaacatcaa | acaataaatg | ttatttattt | 58920 |
| tgcatttacc | ctattagata | caaatacatc | tggtctgata | cctgtcatct | tcatattaac | 58980 |
| tgtggaaggt | acgaaatggt | agctccacat | tatagatgaa | aagctaaagc | ttagacaaat | 59040 |
| aaagaaactt | ttagaccctg | gattcttctt | gggagccttt | gactctaata | ccttttgttt | 59100 |
| cccttcatt | gcacaattct | gtcttttgct | tactactatg | tgtaagtata | acagttcaaa | 59160 |
| gtaatagttt | cataagctgt | tggtcatgta | gcctttggtc | tctttaacct | ctttgccaag | 59220 |
| ttcccaggtt | cataaaatga | ggaggttgaa | tggaatggtt | cccaagagaa | ttccttttaa | 59280 |
| tcttacagaa | attattgttt | tcctaaatcc | tgtagttgaa | tatataatgc | tatttacatt | 59340 |
| tcagtatagt | tttgatgtat | ctaaagaaca | cattgaattc | tccttcctgt | gttccagttt | 59400 |
| gatactaacc | tgaaagtcca | ttaagcatta | ccagttttaa | aaggcttttg | cccaatagta | 59460 |
| aggaaaaata | atatctttta | aaagaataat | tttttactat | gtttgcaggc | ttacttcctt | 59520 |
| ttttctcaca | ttatgaaact | cttaaaatca | ggagaatctt | ttaaacaaca | tcataatgtt | 59580 |
| taatttgaaa | agtgcaagtc | attctttcc | ttttgaaac | tatgcagatg | ttacattgac | 59640 |
| tgttttctgt | gaagttatct | tttttcact | gcagaataaa | ggttgtttg | attttatttt | 59700 |
| gtattgttta | tgagaacatg | catttgttgg | gttaatttcc | tacccctgcc | cccattttt | 59760 |
| ccctaaagta | gaaagtattt | ttcttgtgaa | ctaaattact | acacaagaac | atgtctattg | 59820 |
| aaaaataagc | aagtatcaaa | atgttgtggg | ttgtttttt | aaataaattt | tctcttgctc | 59880 |
| aggaaagaca | agaaaatgtc | cagaagatta | tcttagaagg | cacagagaga | atggaagatc | 59940 |
| aggtatatgc | aaattgcata | ctgtcaaatg | ttttctcac | agcatgtatc | tgtataaggt | 60000 |
| tgatggctac | atttgtcaag | gccttggaga | catacgaata | agcctttaat | ggagctttta | 60060 |
| tggaggtgta | cagaataaac | tggaggaaga | tttccatatc | ttaaacccaa | agagttaaat | 60120 |
| cagtaaacaa | aggaaaatag | taattgcatc | tacaaattaa | tatttgctcc | cttttttttt | 60180 |
| ctgtttgccc | agaataaatt | ttggataact | tgttcatagt | aaaaataaaa | aaattgtct | 60240 |
| ctgatatgtt | cttaaggta | ctacttctcg | aaccttccc | tagaagtagc | tgtaacagaa | 60300 |
| ggagagcata | tgtacccctg | aggtatctgt | ctggggtgta | ggcccaggtc | cacacaatat | 60360 |

```
ttcttctaag tcttatgttg tatcgttaag actcatgcaa tttacatttt attccataac    60420
tattttagta ttaaaatttg tcagtgatat ttcttaccct ctcctctagg aaaatgtgcc    60480
atgtttatcc cttggctttg aatgcccctc aggaacagac actaagagtt tgagaagcat    60540
ggttacaagg gtgtggcttc ccctgcggaa actaagtaca gactatttca ctgtaaagca    60600
gagaagttct tttgaaggag aatctccagt gaagaaagag ttcttcactt ttacttccat    60660
ttcctcttgt gggtgaccct caatgctcct tgtaaaactc caatatttta aacatggctg    60720
ttttgccttt ctttgcttct ttttagcatg aatgagacag atgatacttt aaaaaagtaa    60780
ttaaaaaaaa aaacttgtga aaatacatgg ccataataca gaacccaata caatgatctc    60840
ctttaccaaa ttgttatgtt tgtacttttg tagatagctt tccaattcag agacagttat    60900
tctgtgtaaa ggtctgactt aacaagaaaa gatttccctt tacccaaaga atcccagtcc    60960
ttatttgctg gtcaataagc agggtcccca ggaatggggt aactttcagc accctctaac    61020
ccactagtta ttagtagact aattaagtaa acttatcgca agttgaggaa acttagaacc    61080
aactaaaatt ctgcttttac tgggattttg ttttttcaaa ccagaaacct ttacttaagt    61140
tgactactat taatgaattt tggtctctct tttaagtgct cttcttaaaa atgttatctt    61200
actgctgaga agttcaagtt tgggaagtac aaggaggaat agaaacttaa gagattttct    61260
tttagagcct cttctgtatt tagccctgta ggattttttt ttttttttt tttttggtg     61320 ttgttgagct tcagtgaggc tattcattca cttatactga taatgtctga gatactgtga    61380
atgaaatact atgtatgctt aaacctaaga ggaaatattt tcccaaaatt attcttcccg    61440
aaaaggagga gttgccttt gattgagttc ttgcaaatct cacaacgact ttattttgaa    61500
caatactgtt tggggatgat gcattagttt gaaacaactt cagttgtagc tgtcatctga    61560
taaaattgct tcacagggaa ggaaatttaa cacggatcta gtcattattc ttgttagatt    61620
gaatgtgtga attgtaattg taaacaggca tgataattat tactttaaaa actaaaaaca    61680
gtgaatagtt agttgtggag gttactaaag gatggttttt ttttaaataa aactttcagc    61740
attatgcaaa tgggcatatg gcttaggata aaacttccag aagtagcatc acatttaaat    61800
tctcaagcaa cttaataata tggggctctg aaaaactggt taaggttact ccaaaaatgg    61860
ccctgggtct gacaaagatt ctaacttaaa gatgcttatg aagactttga gtaaaatcat    61920
ttcataaaat aagtgaggaa aaacaactag tattaaattc atcttaaata atgtatgatt    61980
taaaaaatat gtttagctaa aaatgcatag tcatttgaca atttcattta tatctcaaaa    62040
aatttactta accaagttgg tcacaaaact gatgagactg tggtggtag tgaataaatg     62100 agggaccatc catatttgag acactttaca tttgtgatgt gttatactga attttcagtt    62160
tgattctata gactacaaat ttcaaaatta caatttcaag atgtaataag tagtaatatc    62220
ttgaaatagc tctaaaggga attttttctgt tttattgatt cttaaaatat atgtgctgat    62280
tttgatttgc atttgggtag attatacttt tatgagtatg gaggttaggt attgattcaa    62340
gttttcctta cctatttggt aaggatttca aagtcttttt gtgcttggtt ttcctcattt    62400
ttaaatatga aatatattga tgacctttaa caaattttt ttatctcaaa ttttaaagga     62460
gatcttttct aaaagaggca tgatgactta atcattgcat gtaacagtaa acgataaacc    62520
aatgattcca tactctctaa agaataaaag tgagctttag ggccgggcat ggtcagaaat    62580
ttgacaccaa cctggccaac atggcgaaac cccgtctcta ctaaaaatac aaaaatcagc    62640
cgggcatggt ggcggcacct atagtcccag ctacttggga ggatgagaca ggagagtcac    62700
```

```
ttgaacctgg gaggagaggt tgcagtgagc tgagatcacg ccattgcact ccagcctgag    62760
caatgaaagc aaaactccat ctcaaaaaaa aaaaagaaa agaaagaata aaagtgagct      62820
ttggattgca tataaatcct ttagacatgt agtagacttg tttgatactg tgtttgaaca    62880
aattacgaag tattttcatc aaagaatgtt attgttgat gttattttta tttttttattg    62940 cccagcttct ctcatattac gtgattttct tcacttcatg tcactttatt gtgcagggtc    63000
agagtattat tccaatgctt actggagaag tgattcctgt aatggaactg ctttcatcta    63060
tgaaatcaca cagtgttcct gaagaaatag atgtaagttt aaatgagagc aattatacac    63120
tttatgagtt ttttgggtt atagtattat tatgtatatt attaatattc taattttaat     63180
agtaaggact ttgtcataca tactattcac atacagtatt agccacttta gcaaataagc    63240
acacacaaaa tcctggattt tatggcaaaa cagaggcatt tttgatcagt gatgacaaaa    63300
ttaaattcat tttgtttatt tcattacttt tataattcct aaaagtggga ggatcccagc    63360
tcttatagga gcaattaata tttaatgtag tgtcttttga aacaaaactg tgtgccaaag    63420
tagtaaccat taatggaagt ttacttgtag tcacaaattt agtttcctta atcatttgtt    63480
gaggacgttt tgaatcacac actatgagtg ttaagagata cctttaggaa actattcttg    63540
ttgttttctg attttgtcat ttaggttagt ctcctgattc tgacagctca gaagaggaag    63600
ttgttcttgt aaaaattgtt taacctgctt gaccagcttt cacatttgtt cttctgaagt    63660
ttatggtagt gcacagagat tgttttttgg ggagtcttga ttctcggaaa tgaaggcagt    63720
gtgttatatt gaatccagac ttccgaaaac ttgtatatta aaagtgttat ttcaacacta    63780
tgttacagcc agactaattt ttttatttt tgatgcattt tagatagctg atacagtact    63840
caatgatgat gatattggtg acagctgtca tgaaggcttt cttctcaagt aagaattttt    63900
cttttcataa aagctggatg aagcagatac catcttatgc tcacctatga caagatttgg    63960
aagaaagaaa ataacagact gtctacttag attgttctag ggacattacg tatttgaact    64020
gttgcttaaa tttgtgttat ttttcactca ttatatttct atatatattt ggtgttattc    64080
catttgctat ttaaagaaac cgagtttcca tcccagacaa gaaatcatgg cccccttgctt   64140 gattctggtt tcttgtttta cttctcatta aagctaacag aatcctttca tattaagttg    64200
tactgtagat gaacttaagt tatttaggcg tagaacaaaa ttattcatat ttatactgat    64260
ctttttccat ccagcagtgg agtttagtac ttaagagttt gtgcccttaa accagactcc    64320
ctggattaat gctgtgtacc cgtgggcaag gtgcctgaat tctctataca cctatttcct    64380
catctgtaaa atggcaataa tagtaatagt acctaatgtg tagggttgtt ataagcattg    64440
agtaagataa ataatataaa gcacttagaa cagtgcctgg aacataaaaa cacttaataa    64500
tagctcatag ctaacattc ctatttacat ttcttctaga aatagccagt atttgttgag     64560
tgcctacatg ttagttcctt tactagttgc tttacatgta ttatcttata ttctgttta    64620 aagtttcttc acagttacag attttcatga aatttactt ttaataaaag agaagtaaaa    64680
gtataaagta ttcacttta tgttcacagt ctttttctttt aggctcatga tggagtatca    64740
gaggcatgag tgtgtttaac ctaagagcct taatggcttg aatcagaagc actttagtcc    64800
tgtatctgtt cagtgtcagc cttttcataca tcatttttaaa tcccatttga ctttaagtaa    64860
gtcacttaat ctctctacat gtcaatttct tcagctataa aatgatggta tttcaataaa    64920
taaatacatt aattaaatga tattatactg actaattggg ctgttttaag gctcaataag    64980
aaaatttctg tgaaaggtct ctagaaaatg taggttccta tacaaataaa agataacatt    65040
gtgcttatag cttcggtgtt tatcatataa agctattctg agttatttga agagctcacc    65100
```

```
tacttttttt tgttttagt ttgttaaatt gttttatagg caatgttttt aatctgtttt    65160
ctttaactta cagtgccatc agctcacact tgcaaacctg tggctgttcc gttgtagtag    65220
gtagcagtgc agagaaagta aataaggtag tttattttat aatctagcaa atgatttgac    65280
tctttaagac tgatgatata tcatggattg tcatttaaat ggtaggttgc aattaaaatg    65340
atctagtagt ataaggaggc aatgtaatct catcaaattg ctaagacacc ttgtggcaac    65400
agtgagtttg aaataaactg agtaagaatc atttatcagt ttattttgat agctcggaaa    65460
taccagtgtc agtagtgtat aaatggtttt gagaatatat aaaatcaga tatataaaaa    65520 aaattactct tctatttccc aatgttatct ttaacaaatc tgaagatagt catgtacttt    65580
tggtagtagt tccaaagaaa tgttatttgt ttattcatct tgatttcatt gtcttcgctt    65640
tccttctaaa tctgtccctt ctagggagct attgggatta agtggtcatt gattattata    65700
ctttattcag taatgtttct gaccctttcc ttcagtgcta cttgagttaa ttaaggatta    65760
atgaacagtt acatttccaa gcattagcta ataaactaaa ggattttgca cttttcttca    65820
ctgaccatta gttagaaaga gttcagagat aagtatgtgt atctttcaat ttcagcaaac    65880
ctaatttttt aaaaaaagtt ttacatagga aatatgttgg aaatgatact ttacaaagat    65940
attcataatt ttttttgta atcagctact ttgtatattt acatgagcct taatttatat    66000
ttctcatata accatttatg agagcttagt atacctgtgt cattatattg catctacgaa    66060
ctagtgacct tattccttct gttacctcaa acaggtggct ttccatctgt gatctccaaa    66120
gccttaggtt gcacagagtg actgccgagc tgctttatga agggagaaag gctccatagt    66180
tggagtgttt tttttttttt ttttaaacat ttttcccatc ctccatcctc ttgagggaga    66240
atagcttacc ttttatcttg ttttaatttg agaaagaagt tgccaccact ctaggttgaa    66300
aaccactcct ttaacataat aactgtggat atggtttgaa tttcaagata gttacatgcc    66360 ttttattt tcctaataga gctgtaggtc aaatattatt agaatcagat ttctaaatcc    66420
cacccaatga cctgcttatt ttaaatcaaa ttcaataatt aattctcttc tttttggagg    66480
atctggacat tctttgatat ttcttacaac gaatttcatg tgtagaccca ctaaacagaa    66540
gctataaaag ttgcatggtc aaataagtct gagaaagtct gcagatgata taattcacct    66600
gaagagtcac agtatgtagc caaatgttaa aggttttgag atgccataca gtaaatttac    66660
caagcatttt ctaaatttat ttgaccacag aatccctatt ttaagcaaca actgttacat    66720
cccatggatt ccaggtgact aaagaatact tatttcttag gatatgtttt attgataata    66780
acaattaaaa tttcagatat cttt cataag caaatcagtg gtcttttac ttcatgtttt    66840 aatgctaaaa tattttcttt tatagatagt cagaacatta tgccttttc tgactccagc    66900 agagagaaaa tgctccaggt tatgtgaagc agaatcatca tttaaatatg agtcagggct    66960
ctttgtacaa ggcctgctaa aggtatagtt tctagttatc acaagtgaaa ccacttttct    67020
aaaatcattt ttgagactct ttatagacaa atcttaaata ttagcattta atgtatctca    67080
tattgacatg cccagagact gacttccttt acacagttct gcacatagac tatatgtctt    67140
atggatttat agttagtatc atcagtgaaa caccatagaa tacccttgt gttccaggtg    67200 ggtccctgtt cctacatgtc tagcctcagg acttttttt ttttaacaca tgcttaaatc    67260
aggttgcaca tcaaaaataa gatcatttct ttttaactaa atagatttga attttattga    67320
aaaaaaattt taaacatctt taagaagctt ataggattta agcaattcct atgtatgtgt    67380
actaaaatat atatatttct atatataata tatattagaa aaaaattgta ttttctttt    67440
```

```
atttgagtct actgtcaagg agcaaaacag agaaatgtaa attagcaatt atttataata    67500
cttaaaggga agaaagttgt tcaccttgtt gaatctatta ttgttatttc aattatagtc    67560
ccaagacgtg aagaaatagc tttcctaatg gttatgtgat tgtctcatag tgactacttt    67620
cttgaggatg tagccacggc aaaatgaaat aaaaaaattt aaaaattgtt gcaaatacaa    67680
gttatattag gcttttgtgc attttcaata atgtgctgct atgaactcag aatgatagta    67740
tttaaatata gaaactagtt aaaggaaacg tagtttctat ttgagttata catatctgta    67800
aattagaact tctcctgtta aaggcataat aaagtgctta atacttttgt ttcctcagca    67860
ccctctcatt taattatata attttagttc tgaaagggac ctataccaga tgcctagagg    67920
aaatttcaaa actatgatct aatgaaaaaa tatttaatag ttctccatgc aaatacaaat    67980
catatagttt tccagaaaat acctttgaca ttatacaaag atgattatca cagcattata    68040
atagtaaaaa aatggaaata gcctctttct tctgttctgt tcatagcaca gtgcctcata    68100
cgcagtaggt tattattaca tggtaactgg ctaccccaac tgattaggaa agaagtaaat    68160
ttgttttata aaaatacata ctcattgagg tgcatagaat aattaagaaa ttaaaagaca    68220
cttgtaattt tgaatccagt gaatacccac tgttaatatt tggtatatct ctttctagtc    68280
ttttttcccc ttttgcatgt attttcttta agactcccac ccccactgga tcatctctgc    68340
atgttctaat ctgcttttt cacagcagat tctaagcctc tttgaatatc aacacaaact    68400
tcaacaactt catctataga tgccaaataa taaattcatt tttatttact taaccacttc    68460
ctttggatgc ttaggtcatt ctgatgtttt gctattgaaa ccaatgctat actgaacact    68520
tctgtcacta aaactttgca cacactcatg aatagcttct taggataaat ttttagagat    68580
ggatttgcta aatcagagac catttttta aattaaaaaa caattattca tatcgtttgg    68640
catgtaagac agtaaatttt ccttttattt tgacaggatt caactggaag ctttgtgctg    68700
cctttccggc aagtcatgta tgctccatat cccaccacac acatagatgt ggatgtcaat    68760
actgtgaagc agatgccacc ctgtcatgaa catatttata atcagcgtag atacatgaga    68820
tccgagctga cagccttctg gagagccact tcagaagaag acatggctca ggatacgatc    68880
atctacactg acgaaagctt tactcctgat ttgtacgtaa tgctctgcct gctggtactg    68940
tagtcaagca atatgaaatt gtgtctttta cgaataaaaa caaacagaa gttgcattta    69000 aaagaaaga aatattacca gcagaattat gcttgaagaa acatttaatc aagcatttt    69060 ttcttaaatg ttcttctttt tccatacaat tgtgtttacc ctaaaatagg taagattaac    69120
ccttaaagta aatatttaac tatttgttta ataaatatat attgagctcc taggcactgt    69180
tctaggtacc gggcttaata gtggccaacc agacagcccc agcccagcc cctacattgt    69240 gtatagtcta ttatgtaaca gttattgaat ggacttatta acaaaaccaa agaagtaatt    69300
ctaagtcttt ttttcttga catatgaata taaaatacag caaaactgtt aaaatatatt    69360
aatggaacat tttttactt tgcattttat attgttattc acttcttatt ttttttaaa    69420 aaaaaaagcc tgaacagtaa attcaaaagg aaaagtaatg ataattaatt gttgagcatg    69480
gacccaactt gaaaaaaaa atgatgatga taaatctata atcctaaaac cctaagtaaa    69540
cacttaaaag atgttctgaa atcaggaaaa gaattatagt atacttttgt gtttctcttt    69600
tatcagttga aaaaggcac agtagctcat gcctgtaaga acagagcttt gggagtgcaa    69660
ggcaggcgga tcacttgagg ccaggagttc cagaccagcc tggcaacat agtgaaaccc    69720 catctctaca aaaaataaaa aagaattatt ggaatgtgtt tctgtgtgcc tgtaatccta    69780
gctattccga aagctgaggc aggaggatct tttgagccca ggagtttgag gttacaggga    69840
```

```
gttatgatgt gccagtgtac tccagcctgg ggaacaccga gactctgtct tatttaaaaa    69900
aaaaaaaaaa aaaatgcttg caataatgcc tggcacatag aaggtaacag taagtgttaa    69960
ctgtaataac ccaggtctaa gtgtgtaagg caatagaaaa attggggcaa ataagcctga    70020
cctatgtatc tacagaatca gtttgagctt aggtaacaga cctgtggagc accagtaatt    70080
acacagtaag tgttaaccaa aagcatagaa taggaatatc ttgttcaagg gacccccagc    70140
cttatacatc tcaaggtgca gaaagatgac ttaatatagg acccattttt tcctagttct    70200
ccagagtttt tattggttct tgagaaagta gtagggggaat gttttagaaa atgaattggt    70260
ccaactgaaa ttacatgtca gtaagttttt atatattggt aaattttagt agacatgtag    70320
aagtttctta attaatctgt gccttgaaac attttctttt ttcctaaagt gcttagtatt    70380
ttttccgttt tttgattggt tacttgggag cttttttgag gaaatttagt gaactgcaga    70440
atgggtttgc aaccatttgg tattttttgtt ttgttttttta gaggatgtat gtgtattta    70500
acatttctta atcattttta gccagctatg tttgttttgc tgatttgaca aactacagtt    70560
agacagctat tctcattttg ctgatcatga caaaataata tcctgaattt ttaaattttg    70620
catccagctc taaattttct aaacataaaa ttgtccaaaa aatagtattt tcagccacta    70680
gattgtgtgt taagtctatt gtcacagagt cattttactt ttaagtatat gttttacat     70740
gttaattatg tttgttattt ttaattttaa ctttttaaaa taattccagt cactgccaat    70800
acatgaaaaa ttggtcactg gaatttttttt tttgactttt attttaggtt catgtgtaca    70860
tgtgcaggtg tgttatacag gtaaattgcg tgtcatgagg gtttggtgta caggtgattt    70920
cattacccag gtaataagca tagtacccaa taggtagttt tttgatcctc acccttctcc    70980
caccctcaag taggccctgg tgttgctgtt tccttcttty tgtccatgta tactcagtgt    71040
ttagctccca cttagaagtg agaacatgcg gtagttggt ttctgttcct ggattagttc     71100
acttaggata atgacctcta gctccatctg gtttttatgg ctgcatagta ttccatggtg    71160
tatatgtatc acattttctt tatccagtct accattgata ggcatttagg ttgattccct    71220
gtctttgtta tcatgaatag tgctgtgatg aacatacaca tgcatgtgtc tttatggtag    71280
aaaaatttgt attcctttag gtacatatag aataatgggg ttgctagggt gaatggtagt    71340
tctattttca gttatttgag aaatcttcaa actgcttttc ataatagcta aactaattta    71400
cagtcccgcc agcagtgtat aagtgttccc ttttctccac aaccttgcca acatctgtga    71460
tttttttgact tttaataat agccattcct agagaattga tttgcaattc tctattagtg    71520
atattaagca ttttttcata tgcttttag ctgtctgtat atattcttct gaaaaatttt     71580
catgtccttt gcccagtttg tagtggggtg ggttgtttt tgcttgttaa ttagttttaa     71640
gttccttcca gattctgcat atcccttgtt tggatacatg gtttgcagat atttttctcc    71700
cattgtgtag gttgtctttt actctgttga tagtttcttt tgccatgcag gagctcgtta    71760
ggtcccattt gtgtttgttt tgttgcagt tgcttttggc gtcttcatca taaaatctgt      71820
gccagggcct atgtccagaa tggtatttcc taggttgtct tccagggttt ttacaatttt    71880
agattttacg tttatgtctt taatccatct tgagttgatt tttgtatatg gcacaaggaa    71940
ggggtccagt ttcactccaa ttcctatggc tagcaattat cccagcacca tttattgaat    72000
acggagtcct ttccccattg cttgtttttt gtcaactttg ttgaagatca gatggttgta    72060
agtgtgtggc tttatttctt ggctctctat tctccattgg tctatgtgtc tgttttata     72120
acagtaccct gctgttcagg ttcctatagc cttttagtat aaaatcggct aatgtgatgc    72180
```

```
ctccagcttt gttcttttg cttaggattg ctttggctat ttgggctcct tttgggtcc    72240 atattaattt taaaacagtt ttttctggtt ttgtgaagga tatcattggt agtttatagg    72300
aatagcattg aatctgtaga ttgctttggg cagtatggcc attttaacaa tattaattct    72360
tcctatctat gaatatggaa tgttttcca tgtgtttgtg tcatctcttt atacctgatg    72420
tataaagaaa agctggtatt attcctactc aatctgttcc aaaaaattga ggaggaggaa    72480
ctcttcccta atgaggccag catcattctg ataccaaaac ctggcagaga cacaacagaa    72540 aaagaaaac ttcaggccaa tatccttgat gaatatagat gcaaaatcc tcaacaaaat     72600 actagcaaac caaatccagc agcacatcaa aaagctgatc tactttgatc aagtaggctt    72660
tatccctggg atgcaaggtt ggttcaacat acacaaatca ataagtgtga ttcatcacat    72720
aaacagagct aaaaacaaaa accacaagat tatctcaata ggtagagaaa aggttgtcaa    72780
taaaatttaa catcctccat gttaaaaacc ttcagtaggt caggtgtagt gactcacacc    72840
tgtaatccca gcactttggg aggccaaggc gggcatatct cttaagccca ggagttcaag    72900
acgagcctag gcagcatggt gaaaccccat ctctacaaaa aaaaaaaaaa aaaaaatta    72960 gcttggtatg gtgacatgca cctatagtcc cagctattca ggaggttgag gtgggaggat    73020
tgtttgagcc cggaggcag aggttggcag cgagctgaga tcatgccacc gcactccagc     73080
ctgggcaacg gagtgagacc ctgtctcaaa aagaaaaat cacaaacaat cctaaacaaa     73140
ctaggcattg aaggaacatg cctcaaaaaa ataagaacca tctatgacag acccatagcc    73200
aatatcttac caaatgggca aaagctggaa gtattctcct tgagaaccgt aacaagacaa    73260
ggatgtccac tctcaccact ccttttcagc atagttctgg aagtcctagc cagagcaatc    73320
aggaaagaga aagaagaaa gacattcaga taggaagaga agaagtcaaa ctatttctgt     73380
ttgcaggcag tataattctg tacctagaaa atctcatagt ctctgcccag aaactcctaa    73440
atctgttaaa aatttcagca aagttttggc attctctata ctccaacacc ttccaaagtg    73500
agagcaaaat caagaacaca gtcccattca caatagccgc aaaacgaata aaataccatg    73560
gaatccagct aaccagggag gtgaaagatc tctatgagaa ttacaaaaca ctgctgaaag    73620
aaatcagaga tgacacaaac aaatggaaat gttcttttt aacaccttgc tttatctaat    73680
tcacttatga tgaagatact cattcagtgg aacaggtata ataagtccac tcgattaaat    73740
ataagcctta ttctctttcc agagcccaag aaggggcact atcagtgccc agtcaataat    73800
gacgaaatgc taatatttt ccccttacg gtttctttct tctgtagtgt ggtacactcg     73860
tttcttaaga taaggaaact tgaactacct tcctgtttgc ttctacacat acccattctc    73920
tttttttgcc actctggtca ggtataggat gatccctacc actttcagtt aaaaactcct    73980
cctcttacta aatgttctct taccctctgg cctgagtaga acctagggaa aatgaaagag    74040 aaaagatga aagggaggtg gggcctggga agggaataag tagtcctgtt tgtttgtgtg     74100
tttgctttag cacctgctat atcctaggtg ctgtgttagg cacacattat tttaagtggc    74160
cattatatta ctactactca ctctggtcgt tgccaaggta ggtagtactt tcttggatag    74220
ttggttcatg ttacttacag atggtgggct tgttgaggca aacccagtgg ataatcatcg    74280
gagtgtgttc tctaatctca ctcaaatttt tcttcacatt ttttggtttg ttttggtttt    74340
tgatggtagt ggcttatttt tgttgctggt ttgttttttg ttttttttg agatggcaag    74400 aattggtagt tttatttatt aattgcctaa gggtctctac tttttttaaa agatgagagt    74460
agtaaaatag attgatagat acatacatac ccttactggg gactgcttat attctttaga    74520
gaaaaaatta catattagcc tgacaaacac cagtaaaatg taaatatatc cttgagtaaa    74580
```

```
taaatgaatg tatattttgt gtctccaaat atatatatct atattcttac aaatgtgttt    74640
atatgtaata tcaatttata agaacttaaa atgttggctc aagtgaggga ttgtggaagg    74700
tagcattata tggccatttc aacatttgaa ctttttttctt ttcttcattt tcttcttttc   74760
ttcaggaata tttttcaaga tgtcttacac agagacactc tagtgaaagc cttcctggat    74820
caggtaaatg ttgaacttga gattgtcaga gtgaatgata tgacatgttt tctttttttaa   74880 tatatcctac aatgcctgtt ctatatattt atattcccct ggatcatgcc ccagagttct    74940
gctcagcaat tgcagttaag ttagttacac tacagttctc agaagagtct gtgagggcat    75000
gtcaagtgca tcattacatt ggttgcctct tgtcctagat ttatgcttcg ggaattcaga    75060
cctttgttta caatataata aatattattg ctatctttta aagatataat aataagatat    75120
aaagttgacc acaactactg ttttttgaaa catagaattc ctggtttaca tgtatcaaag    75180
tgaaatctga cttagctttt acagatataa tatacata tatatatcct gcaatgcttg      75240
tactatatat gtagtacaag tatatatata tgtttgtgtg tgtatatata tatagtacga    75300
gcatatatac atattaccag cattgtagga tatatatatg tttatatatt aaaaaaaagt    75360
tataaactta aaaccctatt atgttatgta gagtatatgt tatatatgat atgtaaaata    75420
tataacatat actctatgat agagtgtaat atattttta tatatatttt aacatttata    75480
aaatgataga attaagaatt gagtcctaat ctgttttatt aggtgctttt tgtagtgtct    75540
ggtctttcta aagtgtctaa atgatttttc cttttgactt attaatgggg aagagcctgt    75600
atattaacaa ttaagagtgc agcattccat acgtcaaaca acaaacattt taattcaagc    75660
attaacctat aacaagtaag ttttttttttt tttttgaga aagggaggtt gtttatttgc    75720
ctgaaatgac tcaaaatat ttttgaaaca tagtgtactt attttaaataa catctttatt    75780 gtttcattct tttaaaaaat atctacttaa ttacacagtt gaaggaaatc gtagattata    75840
tggaacttat ttcttaatat attacagttt gttataataa cattctgggg atcaggccag    75900
gaaactgtgt catagataaa gctttgaaat aatgagatcc ttatgtttac tagaaatttt    75960
ggattgagat ctatgaggtc tgtgacatat tgcgaagttc aaggaaaatt cgtaggcctg    76020
gaatttcatg cttctcaagc tgacataaaa tccctcccac tctccacctc atcatatgca    76080
cacattctac tcctacccac ccactccacc ccctgcaaaa gtacaggtat atgaatgtct    76140 caaaccata ggctcatctt ctaggagctt caatgttatt tgaagatttg ggcagaaaaa     76200
attaagtaat acgaaataac ttatgtatga gttttaaaag tgaagtaaac atggatgtat    76260
tctgaagtag aatgcaaaat ttgaatgcat ttttaaagat aaattagaaa acttctaaaa    76320
actgtcagat tgtctgggcc tggtggctta tgcctgtaat cccagcactt tgggagtccg    76380
aggtgggtgg atcacaaggt caggagatcg agaccatcct gccaacatgg tgaaaccccg    76440
tctctactaa gtatacaaaa attagctggg cgtggcagcg tgtgcctgta atcccagcta    76500
cctgggaggc tgaggcagga gaatcgcttg aacccaggag gtgtaggttg cagtgagtca    76560
agatcgcgcc actgcacttt agcctggtga cagagctaga ctccgtctca aaaaaaaaa     76620 aaaatatcag attgttccta cacctagtgc ttctatacca cactcctgtt aggggcatc     76680 agtggaaatg gttaaggaga tgtttagtgt gtattgtctg ccaagcactg tcaacactgt    76740
catagaaact tctgtacgag tagaatgtga gcaaattatg tgttgaaatg gttcctctcc    76800
ctgcaggtct ttcagctgaa acctggctta tctctcagaa gtactttcct tgcacagttt    76860
ctacttgtcc ttcacagaaa agccttgaca ctaataaaat atatagaaga cgatacgtga    76920
```

```
gtaaaactcc tacacggaag aaaaacctttt gtacattgtt ttttttgtttt gtttcctttg    76980 tacattttct atatcataat ttttgcgctt cttttttttt tttttttttt ttttttttcca    77040 ttattttag gcagaaggga aaaagccct ttaaatctct tcggaacctg aagatagacc       77100
ttgatttaac agcagagggc gatcttaaca taataatggc tctggctgag aaaattaaac    77160
caggcctaca ctcttttatc tttggaagac ctttctacac tagtgtgcaa gaacgagatg    77220
ttctaatgac tttttaaatg tgtaacttaa taagcctatt ccatcacaat catgatcgct    77280
ggtaaagtag ctcagtggtg tggggaaacg ttcccctgga tcatactcca gaattctgct   77340
ctcagcaatt gcagttaagt aagttacact acagttctca caagagcctg tgaggggatg    77400
tcaggtgcat cattacattg ggtgtctctt ttcctagatt tatgcttttg ggatacagac    77460
ctatgtttac aatataataa atattattgc tatcttttaa agatataata ataggatgta    77520
aacttgacca caactactgt ttttttgaaa tacatgattc atggtttaca tgtgtcaagg    77580
tgaaatctga gttggctttt acagatagtt gactttctat cttttggcat tctttggtgt    77640
gtagaattac tgtaatactt ctgcaatcaa ctgaaaacta gagcctttaa atgatttcaa    77700
ttccacagaa agaaagtgag cttgaacata ggatgagctt tagaaagaaa attgatcaag    77760
cagatgttta attggaattg attattagat cctactttgt ggatttagtc cctgggattc    77820
agtctgtaga aatgtctaat agttctctat agtccttgtt cctggtgaac cacagttagg    77880
gtgttttgtt tattttattg ttcttgctat tgttgatatt ctatgtagtt gagctctgta    77940
aaaggaaatt gtattttatg ttttagtaat tgttgccaac ttttaaaatt aattttcatt    78000 attttgagc caaattgaaa tgtgcacctc ctgtgccttt tttctcctta gaaaatctaa     78060
ttacttggaa caagttcaga tttcactggt cagtcatttt catcttgttt tcttcttgct    78120
aagtcttacc atgtacctgc tttggcaatc attgcaactc tgagattata aaatgcctta   78180
gagaatatac taactaataa gatcttttttt tcagaaacag aaaatagttc cttgagtact    78240
tccttcttgc atttctgcct atgttttga agttgttgct gtttgcctgc aataggctat    78300
aaggaatagc aggagaaatt ttactgaagt gctgttttcc taggtgctac tttggcagag    78360
ctaagttatc ttttgttttc ttaatgcgtt tggaccatttt tgctggctat aaaataactg    78420
attaatataa ttctaacaca atgttgacat tgtagttaca caaacacaaa taaatatttt    78480
atttaaaatt ctggaagtaa tataaaaggg aaaatatatt tataagaaag ggataaaggt    78540
aatagagccc ttctgccccc cacccaccaa atttacacaa caaaatgaca tgttcgaatg    78600
tgaaaggtca taatagcttt cccatcatga atcagaaaga tgtggacagc ttgatgttt     78660 agacaaccac tgaactagat gactgttgta ctgtagctca gtcatttaaa aaatatataa    78720 atactaccttt gtagtgtccc atactgtgtt ttttacatgg tagattctta tttaagtgct    78780
aactggttat tttctttggc tggtttattg tactgttata cagaatgtaa gttgtacagt    78840
gaaataagtt attaaagcat gtgtaaacat tgttatatat cttttctcct aaatggagaa    78900
ttttgaataa aatatatttg aaattttgcc tctttcagtt gttcattcag aaaaaaatac    78960
tatgatattt gaagactgat cagcttctgt tcagctgaca gtcatgctgg atctaaactt    79020
tttttaaaat taatttgtc ttttcaaaga aaaatatttt aaagaagctt tataatataa      79080
tcttatgtta aaaaaacttt ctgcttaact ctctggattt cattttgatt tttcaaatta    79140
tatattaata tttcaaatgt aaaatactat ttagataaat tgttttaaa cattcttatt    79200 attataatat taatataacc taaactgaag ttattcatcc caggtatcta atacatgtat    79260
ccaaagtaaa aatccaagga atctgaacac tttcatctgc aaagctagga ataggtttga    79320
```

```
cattttcact ccaagaaaaa gttttttttt gaaaatagaa tagttgggat gagaggtttc   79380 tttaaagaa gactaactga tcacattact atgattctca aagaagaaac caaaacttca    79440
tataatacta taaagtaaat ataaaatagt tccttctata gtatatttct ataatgctac   79500
agtttaaaca gatcactctt atataatact attttgattt tgatgtagaa ttgcacaaat   79560
tgatatttct cctatgatct gcagggtata gcttaaagta acaaaaacag tcaaccacct   79620
ccatttaaca cacagtaaca ctatgggact agttttatta cttccatttt acaaatgagg   79680
aaactaaagc ttaaagatgt gtaatacacc gcccaaggtc acacagctgg taaaggtgga   79740
tttcatccca gacagttaca gtcattgcca tgggcacagc tcctaactta gtaactccat   79800
gtaactggta ctcagtgtag ctgaattgaa aggagagtaa ggaagcaggt tttacaggtc   79860
tacttgcact attcagagcc cgagtgtgaa tccctgctgt gctgcttgga gaagttactt   79920
aacctatgca aggttcattt tgtaaatatt ggaaatggag tgataatacg tacttcacca   79980
gaggatttaa tgagaccttat acgatcctt agttcagtac ctgactagtg cttcataaat   80040 gcttttcat ccaatctgac aatctccagc ttgtaattgg ggcatttaga acatttaata   80100
tgattattgg catggtaggt taaagctgtc atcttgctgt tttctatttg ttcttttttgt  80160 tttctcctta cttttggatt tttttattct actatgtctt ttctattgtc ttattaacta   80220
tactctttga tttattttag tggttgtttt agggttatac ctctttctaa tttaccagtt   80280
tataaccagt ttatatacta cttgacatat agcttaagaa acttactgtt gttgtctttt   80340
tgctgttatg gtcttaacgt ttttatttct acaaacatta taaactccac actttattgt   80400
tttttaattt tacttataca gtcaattatc ttttaaagat atttaaatat aaacattcaa   80460
aacaccccaa ttaaaagtca gagattgtta ataccacatg atctcactta cacacagaat   80520
tgaaaaactt ggaactcata gaagcagaga gtaaaaacat ggttaccagg tgctggggag   80580
aggcggtggg ctgggagat gttggtcaaa gttagacagg aggaataagt tcaagagatc   80640
tattgtacaa cttattcagt tagataggag gaataagcta aagatcaaga gatctattgt   80700
acaatgtgac tataaccaac aacatatatt gtacacttga aaattgctaa cagtatcttt   80760
taagtgttct ctctacaaat aaatatgtga ggtaatgtat atattaatta actgtagtca   80820
tttcacaatg tatacttatt tcaaaacatc atattgtatg ctataaatat atacaacttt   80880
tatttttcaa ttttagaaat gtccttaaaa aatcagattt tcagatcaga taaaaaagca   80940
agacccaact atatgctgcc aacaggaaac acaccttaaa aataaaggac gaacaaacag   81000
attaaaagta aaaggatgga gaaaagatac atcatattgg taattagaag aaaactggag   81060
tgacaatatg aaacaaaata gatttcagag caaagaatat taccaggggt aaaaatgatc   81120 atttataat gataaaagag tcagttcagc aaaaggatat aacagtccta aatgtttttt    81180
cacctcatag ctgtgtcaaa atagatgaag caaaaactga tagaactgta agaagtagac   81240
aagtccacaa ttatgtttgg agattttttt tttttttttt tttgtcgccc aggctggagt   81300
gcagtggcag gatctcagct cactgcaagc tccgcctccc aggttcacgc cattctcctg   81360
cttcagcctc cccagtagct gggactacag gcggccacca ccacgcctgg ctaattttt   81420 tgtattttta gtagagacgg ggtttcaccg tgttagccag gatggtctcg atctcctgac   81480
ctcgtgatct gcctgcctcg gcctcccaaa gtgctgggat tacaggcatg agccactgca   81540
cgcagcctgg agatttttaat atcctttcaa tgtttagtag aacaagaata cacaaaatca   81600
gtaaggatat agaagattag aacaagacta tcaaacaatt tgacttaaat gacatttgta   81660
```

```
gagcacagca gtccccaaca acaataaatc acacattctt tccaagagta catgaaacat   81720
gtaccaagat agaccgtatt ttgagccatg aaacaaatct tgataaattt aaaaggattc   81780
aagtcataga aaatatgttc tctgaccaca atggaattaa attattaacc aataacaaat   81840
atctgggaaa acctcaaaaa cttggacacc agcgctttta aaagactaaa taatttctaa   81900
attatctgtg ttgggggaa aagagaaatg gattagagag caaaagggt atcagagtgc     81960 tgtggtacga ttttatgaa gagtggaaca gaatctgcct ttggcgtttc cccactacag    82020
cccattcttc acattgataa cagcatgatc cttctaaaat taaatctaac gatcacttct   82080
gcttaatggc tctccaacac ttacagaatt aggtccaaaa ttctagcaca gtttctgttc   82140
atctttctaa cctttcttcc cacaggtcta gctagtacgt atttcttta ttgcatttat    82200 tacactattc ctttgcttat ctatctcccc acctaggcta agaacaaga ttcttgtctt    82260 tttcattttt gtgtctcagt gcctagcatg gtgccaggca cacagcatgc ttccagtaaa   82320
tgttagctgg atggatgtaa tgagtatatt aaatattaat ttatttgttt ttccccaaaa   82380
agaattattt cctgcaaatc aaggaaattg ctttctttat ataatcaaaa acttattttc   82440
ccagaagatt cttcattaaa aattaagcct atgcacaacc tagctctaaa gtttcaaaga   82500
ttttaggcag caattttca atcttttga agtaatacat ttgaatcttt tcaaatttct     82560
gtttctgcat ttgtgccaca ccatctcatc tcttgctgaa atgttttgt taaattaatt    82620 gcttgataaa ttgctaagta cttttcatca gaccaattag gacaatagta agtatccatc   82680
tgtggagcgc ggacattcaa gaaatctgat ccagtattta gaaagtcatt cctgagctga   82740
gttggctcaa actggcacct tctggcattt gcttgtgggt ggggaatgtg gaatgctttg   82800
aaagctgaat gagtttgtca gttttaaaa ttcccttatg gctaaaggaa aacaacattc    82860
attgtttaaa aacaccattg tttgtttttt ctgcttttt gttctttgga gcctgaatct    82920
gcaaaaacac tcacacccag cattttgctt catgtaccac tcctaagatg ttttagaga    82980 cttgaatagt gtctccgcac tactttttat tgtgattgtt cagaatgttc ataacaaatg   83040
gtaaaaagtc agttttagtg ctcaaattga gttttatgga gaaagaccat aatttatgtt   83100
tgtcattgta aattgatagg agaatttttg gaagtttgcg tcctagaacc agatttccaa   83160
ggctcagatc cttatttct cacttcctag ctgtgtgacc ttagacaagg tattaaacct    83220
gtctgtgctg cctcagtgtc ctcatctatt ctttaagagt aagaatagaa cctacccgat   83280
agagtcactt gaagattaag tgggttagta aattcagaat gcttggaaca gtaactagca   83340
cagaataagt gtccaataaa attgggttgc agctattatc agtattattc ctgtcataat   83400
catcatcacc attaagcaat taaatgtaga gttccaaaat ttgattatga aactacagtt   83460
atacagccat gattcccggt gataccacgt cagtaacaag attatttcct tagcttgagc   83520
cagtcactac ctcattgcat gtggcagagt gtgttgccgt aggcaaatgt cattgtaggg   83580
aatgaaaaaa aaattgcctg tgagctgctc tccagaggcc tcatcccatt ttcccatcgt   83640
ccactttact ccatctccac tgccactatt aggaccttat catttcttgt ctagattaat   83700
tcaacagctt ccttccttct agtctccatg atttcaccca ctagccatcc cctcccttt    83760 gcccaatttt ctccatttat ggtagagtga tctttctaat aggaaactcc tgacttgcct   83820 taaaagccc tcattgaggc cggacgtggt ggctcatgcc tgtaatccca gcactttggg    83880
aggccgaggc aggtggatca cgaggtcaag agattgagac catcgtgact aacacagtga   83940
aaccccatct gtactaaaaa tacaagaaat tagccaggcg tggtggcggg tgcctgtagt   84000
cgcagctact tgggaggctg aggcaggaga atggcgtgaa cccgggaggc agagcttgca   84060
```

```
gtgagccgag attgcgccac tgcactccag cctgggcgac agagtgagac tccgtctcaa   84120
aaaaaaaaag ccctcattga caaccttcaa cccacaatcc atggtgaagc acaggagcct   84180
tggggatctg cccccagcac acctctccac ccttgtctct cactgctcct gccttcatgg   84240
agagccctga tgaactattt gtagtttccc ctgactcacc ttgctgttac tgggcctgtg   84300
tgcgtgttgc tcccactacc tgcaatacgc ttacccactt cacctgggtg aactttactt   84360
aggattcacc ttaggtgggc atcatgttct tccaggcccc tcctctaact tttagttgag   84420
agtattccag acttaaggct ccatgggata gggatcttgt ctatgcacca gcttattccc   84480
aactgcctgg cacgtaatgc atttattaaa tatatattga attgattacc ctacttgggg   84540
ctcttgtttg cttctacact tacagttcta gcatagcact taactcatta tcatgcatca   84600
ttattatggg tttgttttgt ctcccattag actgtgagct ccacaaggct gtgtccttgt   84660
cttatacatc attgtatttc cagcttccaa catagtgctt gccatgacac aggaagtcag   84720
taagctctga tgaatgaat agtatctaca taccattaat ctgaggttta agtttcccc   84780 aaattctgaa gcaaggggat ttacggactt ccctgacaat ttttggatgt catcccaatg   84840
ataccactaa cattttaagg gacagcttgc atatatacat ttttctggat ggcagttttt   84900
tttcccacag gcttcatcag atatttctcc atagccttcc tcagattctc aaaggggtct   84960
ctgattcccc caaagataa gaaactgtca taaaaaatta tttctaaata tcaattgtta   85020
aataaaatgt ttgcaaagca gcctgatgaa tcatttcagg ccacttgacc ccgatgagtt   85080
agagagtttg tgctctgcaa tctgactgct tccagcagtc tcactgctgc tggactgtgg   85140
cacttccaat tggcagcagg gcaagtttct tctggatgaa tattctgtca tagggtccc   85200 ccttccacac atacctgtag gagcagtttg aaactcatat gcatggtctt cctggttcta   85260
ggcacatgag tcatttaagc tgctggagcc aggaccagct agtatgctag cccggcattc   85320
agaaagttaa aatttggggt caaaactgag aaccttcttt gatccacctt ggccagacat   85380
tttctctggc ttccattaat agcctcaaca tttttttttt ttctggccta gacccacaca   85440
ggcaagagac cagagcttct ctaaggagct aagggaaagc acatttaaa ataacttga   85500 gcaaatgaat tcatctggca aaagcaaccc cactacgtaa aataaacctt tttagtttcg   85560
caatagcagt tcctgaaaat gtaaacaacc tcagggtcta catgcactga atcatttgct   85620
gaacagaaag tccctggtcc aaattctgca agaataaaca ccttacaaaa ctaggggtca   85680
atgaccttca tatgggaaca aggagggtgt gggggggcagc aacccacccct gaggacaatg   85740 agaaagtctt gagacttgat attcaaaatg ctggctttct aaaccaaaaa ctggcatgag   85800
tggagggaga aggggagggt gggcacagtc tatgcctcag gctcttgctc agaccctacc   85860 aggccctgc cttccctagg gaaagcgaga gtctactcac tgtcatgaag ccagaggaag   85920
gccctgcagg tttcactgtg tgttctgttg acaagatgat ggttccattg aaactgtaat   85980
aacatacttg gccaactaag cccatacgat cgtagtaact ttgtacccag tcctagcttt   86040
tcaaacataa tgataatatg ttctttctaa tgtggcccat actgttctaa tgaacttatg   86100
ctgagttttt ctgagtacta gaataatatt cgccataaat aatagatata attattctca   86160
tttaatattt gcgtagctct tctttaaagc agaaagtatt ttctcattcc ttactagaac   86220
ctttctgtgt gaggagcact gagctagaac ccatatctta gaatggtcag aatttggaga   86280
aattcaggga aaaggcactg gactcatttt taaagactag aaaatgcaac ctccagaaaa   86340
agattcaaga gttttttact cccagagatg taggaaagat tggagtaaat cttaatatta   86400
```

```
tatttcaggt aaacaaagga tcactgtcaa aatagcagca tttattgagt aatggctgtg    86460
tgccaggtac tttacagttt cacatttaac cctcataata accttgtaaa gtggatatcc    86520
cctcagtaca tgatgagaac actgaagctt aggttaaatg attgtccaaa tcggacaatc    86580
attttcaaaa tctcccccct tttttctcct ttcttatctg caaggcagat tgcccttttcc   86640 ctttcagtga aacttgtgca tgaccacatg actctctttg gccaatgaaa catgaacaag    86700
cagcgtttat cactttcaga tggaaggctt tgcatgagct ttgcctcctt ttcactctgc    86760
cacagtggcc actaacattc cagatagtgg cgctctgcag gctaggtcct atagtgggag    86820
ctatgggcag agccccctt cccacccca tcaagatgtg catgctgcat aagccatgca      86880
ttaatctttg cagttttaag ccactaagtt ttggagttat attaatcatt aatcatggtt    86940
ctcaagagaa acagagtggg ggagtggtat tcattatggg aattggctta catgattatg    87000
gaagctgagt agtcccccag tctgctgttt ttgagctgga gaactagagg agccagtggt    87060
ataattcagc ccaagcctga aggcctgaga aatgggatgg gggaattggg agggtgggtg    87120
tgctagggta ggataagtcc tgaagttcaa aggccagcca gaaggtggat gtttcagcac    87180
cagaagagag agcaaattcg cttttcttct gccttttgt cctctctggg ccctcaatgg     87240
attggatgat gccctcccac attggtaagg gtggatcttc tatactcagt ctgctaattt    87300
cttccagaaa catcttcaca gacacatcca gaaataatgt tttaccagct atctcggtat    87360
cccttagcct agtccatatt taaaaattaa tgatcacaag cagttgtttg tttccacagc    87420
aaaacctggg tgacagacca agtgacccag atgactagaa tttgaccttc ttttgttgcc    87480
cacaccatac tctgaactaa catgctgtgc tgccttccaa gtggagaatg atggctaagt    87540
atcttctacc taatttgagt cacagaaaaa aaaaaaaaag gttattaact gcagtgacaa    87600
gaattgtgat tccccagggg gcagatcaag actgatagat aagagaagtg aggaacatct    87660
ggggaatgtc cattgaaaat ttactcagaa gagaagaata attaatataa taatatgata    87720
tattgaatta taataaataa tattttgatg tatttccttc caggcatgtt taagtttatag   87780 actttgagta tattttctca aaggggggttc tatgtaagag actatttctt aatatagttc   87840
ctagcttgga attgctcttg ctggtttaag ctgagcttat tttattacag acttcacaac    87900
aataacgttt tccttcacta gtcagtacac aagatggtct tcatttccag tttggaatcc    87960
cacactatca gagcctgaga caaggactag tatgcagtta gtttgtttgg gaggtgattc    88020
caggaagtgg gaatgagaga tcagtcagcc tgcaacacga aggaggaaaa gtcaatataa    88080
ggatgaattt ggcaattggc cgtttcatgc aactgggggct aaattttgct tggctctcta   88140
agaaatgtaa agaatgcctc ccgtaattgc tcacctcaag tatttattca ttggctctca    88200
tgctccattg gttgtccatg agaactttag ccctccctcg ctgcagcaca gacactgtgc    88260
tttctcctag gctgagcaag ctcctgcatc tgtggaaacc gtcccggggc agatagtgaa    88320
ataatgactg ctgcgtgctt gagatctggg aaagaggcca catcataagt gcactgaaat    88380
cagagatgtg tcaagagatg tgacacaggg catctgaggt gtctactgca ccagctataa    88440
ctccctaaac gctaatctca gttcttacag aggggatgga tgcaagggaa cagtcatgat    88500
tgagagcacc gaagaagctc tgtatgaacc ttaggcaagt ttcctaatct ccaaaatgaa    88560
ggtaataata cccaccatcc aagatcttcg ggaggaatag atgaactaat gtatgtgaaa    88620
atgtccagca caggtcctaa cccatagtag gtgctcacca aatgttagtt ccctgccctc    88680
cacgttgtgt gtatccggag ctgcactaga tgctgaggca aatggtctca aatgtacttt    88740
aacacttaat gactgagatt ttttctgagc tgcctacagg ttattgacta tattcattat    88800
```

```
taataataat atatatggcc acttcaggca actggggcta aatttttgctt ggctctctaa    88860 gaaatgtaaa gaatgcctcc tgtaattgct cacctcaagt atttattcat tggctctcgt    88920
gctttattgg ttgtccctga ggactttagc cctctctcac tgcagcacag acactgtgct    88980
ttctcctagt ttctgtggca agtgacagga gcccacctca aactaaagca aaagggactt    89040
cattggctct tgtagctagg aattccaggg ttggcactgg ctttgggcac tactggatgc    89100
aggaattcaa acaatgtctt caactctttc ttttggtgtt tctctcagct gtgcttctct    89160
tgtcgtttct ttttcccatt ttacagataa gttcatccgt aactgagaga ggtgaaaagg    89220
ggatggctgc agagaactct ggcttatatc atccttgctt gctgacctca aggtccatgt    89280
ataaattctc agagaagaag ccctctggtt ggtgatgctt ggaacatgcc ctggagggtg    89340 ggcccctttga agtggagctt gctggaacca catgggctgg agcaaggcgc tagggccaga    89400
agagagaggt aggcagggct gctggccagg cactcttcac caagacaagg caagaggagg    89460
ggcatgattg aggcagtgat acagaaagca gacagtagag gtcgtggcaa gtgtgccgtt    89520
acttgctacc tgtggttgat gggagagtca caccacattt aggaggagag aatccatttg    89580
ccacttctga caatgccaca agaatcacat atttcatcca gaggttgaat ttggcccatg    89640
ctgagcttta aaatacagag ctgtcttgga acaatggctc agtacattca tttggtgtcc    89700
aacaaagcct gcctctgttg ccttccctct ctctgtgtgc ccttcaagat cttcattgtg    89760
ctttggggag agaaagagaa aatgtcatat cagggtagct caccccatgt gtcctggact    89820
caggaaaaga gtatcttatc accttactct tttgttatta taaaaaataa agttgaacgt    89880
cttcaaataa aataaagaag tatagaaaaa attttaaatt aacctgttat gattctacct    89940
agagaaccat tgtcaacatc ttggtatatg tacttccaga tactttccta tgaatatata    90000
cattgtagat tttttaatat taaaaggcta tcatgctgct ttgtatacag gctttcttta    90060
ctgatatgta atataataca cagacaaata tacaaatcct aagccatcaa ctcattgaat    90120
ttttattcat tgtttttaat acctgcattg tgttccattg ttaggctatg tcacaacata    90180
tttaattaag cccctattga tgaatattaa tttactctat ttgccagttc attccagtcc    90240
aacatttatt gagtgtctac ttacgggcca ggcactcttg tattcatcaa gatcaccaca    90300
ttatctgtat cagttattta ttgccacaat aaaactgcat aacaaatcac tccaaaatgt    90360
agcaccttaa aactacaact acttattatt tctcaagagt caatgggtca gctgagcagt    90420
tctgccgata ggggtcaagg tcaacacatt tcaactagac tacttgtaaa aagaatgag    90480 tgtctgggta ggtgtgttct tctaaaaata aacaaggaa tgaggaaatt gcaggtagga    90540
taagaggggt ggttggcaac caaaccccac aaaaggcaga caaatttttaa ggaaacataa    90600 tgccagactc ctatgtcatc atccaagtag atgcagtgaa gtataacctg gggcgtagta    90660
gggtaggagt ggggagagca gaggagaagg aagggagatt gcttttcatc acttttggat    90720
tccctaataa cagacatgac tgccagtatt aaaatttaac aaaggatatc tgatcattaa    90780
ttttcctgta taagtcactg gtgatcttca acatctctcc ctcccttcct cccttccttc    90840
ctcccaccct cccttccttc cttctttcct cttttgcttt caacttcctt ttctcgtttc    90900
cttttgcttt ctttctcttc tccctttttt ctgtcactct gggcgtatgt agtagtgtaa    90960
aaaggttgac agagaaatca aatataacag gagcagggcc ctgagaaaag cacctggcat    91020
cctgtaggca aaccattgtt tctaaaagaa gggactgaga gattgaggag ctcaggacat    91080
tgccaaatga acaaggcaag cacatttatt cagtaccaaa caaacggaaa acggcctttc    91140
```

```
caaataactg acctataaaa cagccttttc acaagagtac cgtaattact ggccaacagc  91200
aacaatgaaa aacaactccc aaacaaagaa atatttctgg attaaaagcc atgagatctg  91260
gattctaaca agctgtgctc ctcaaactac aagtacaaaa tctggctcta aactaacaag  91320
ctatgagcct caaactgatg actggcatgt ttgggtctcc atctccttct tgggggttgg  91380
ggtcttagag acccttttcc acgccctgat tctcttacta gtgtgtatgc tttccttttg  91440
acttctcatg ctgaccgtct gagcaggagt gagaagcaat ttcaaaggaa aacatcgttt  91500
atcatctgct gaaagaaacc aaaaagaaca caggaaaaca aaaagacaag gaaagggaat  91560
gaaaatgtaa ttcattttat taaaaagaag aattattctt ctgggacact ggatagaaac  91620
cttaatgagt tacctagcta tcataaatcc tctaacagag aagagaagag aaagaaacaa  91680
agacggaaga gggcaggata aaagaaagaa aaaggaagg gaaaaatgaa ggaaggaagt  91740
tatctattca tttctacaga gactctgctg agcagtagac aagaagactt gggaaaaatt  91800
taactgaaac ttttccaaaa atcttttcag agggattttt tccctctgaa aagcatcatt  91860
agaggctgtt caatacccaa ggcaagcctc tttcatatta cttactgtac atgaaacact  91920
catgcaattg aggctagcca gaggccattt agaaattcaa taattattca acccaagggg  91980 cttccaaat ggtgaagtag cttcttaaga ggaaattaat attgagcagt atagcaaacc  92040
taattggaat cttgagaaaa tagttctgtg tcgttagaac agctagaggc taaagaagat  92100
caggttggat gataccttca tttttgtctc tttccttaat tatgatgtaa agggaaaaat  92160
cttgtttatt ttctatgcca ggagggtaga gggtgatttg gagaggttcc aagtttatca  92220
aaatctacct tcagtctggc agtagaaaag tttacttcct tcatttcttt cctatagaca  92280
ttcaaagaga gctaaggaga tccaaaaacc ttttttttcta tatttgcaat gcaaggcagt  92340
tgggaattaa tgactgattt gttggtgagg gcagtgggca ttgatcacaa aagcagtaaa  92400
gctgtgtttc tcaaagagag aaagtctctt tgagatcttc attattttac tatttagaag  92460 agaaggggc gttatatcac gttggaagca tccatgagtc actagtctct tctctatctt  92520
tctatgcctt tctgtattaa ttactttgaa agcacaacat tccaaaccca ttgagcacac  92580
agtggtctga tttctccact tgtgaaaggt gctaaagtct cactgtagga ttaatttggg  92640
ggtccaggct atgggcttgt agatatgact accttagact ttggttctcc tggcaactaa  92700 cccttttttgg atcgtatcta agttgacctg tttcacagtg agagaactcc tctccattac  92760
tcagaatact gaggcagatc acaagtgtac cacacctggc taatgttaag ccagacagaa  92820
acatcaggct catctcttga gaagaagggt cgcttattaa ggatacaaac tatttttttt  92880 ttttttttt gagacagggt ctcattgccc aggttagagt gcagtggtgc aatcatagct  92940
cactgcagcc tcaaccacat gggtattttt aaataagaaa aaaataccat ctgatagata  93000
tgaaggagca ttgggtcact ataaacaaaa cagattctaa gagcaggaag aaagagtaca  93060
gtctcttttc aataattttt ttttaaactt gggaagaac actcactcta ttcctataga  93120
ccagaaagca gataattgtc cattatgatt ccacatgaca ctatcttgtt cagctgtcac  93180
tgaaacaact ttgaacactg tcatatgttc ttcccagctc ctgaactctg acctttttat  93240
gccttagttc cactttcaca aaagggatt gatgtaatgt gcatttcaga ggaaacgact  93300
atagacattt agtgtcatta taaatgttga gaagtatgct ggcagaaatt atgccttaag  93360
atcatatatg gattcttgta tggttttgaaa ttgcttaaaa gatatatatg atctctaaaa  93420
tgtgtgtgta tatatatatg atgtcttctt atatatctat atgtgatata tttatatata  93480
tataaatctg tgtatatcac atatataaat ttgctgttat ttgaattgcc attacctcag  93540
```

```
tgcttagggg aagccatgca cgtttgtttc ttttcagtac ccagagttaa ttaacataag    93600
ttatcacaga agctcccata agcattgaga caatttctct atacctgtga ctatttaagg    93660
ttttgaaaac aaaacagaag caggtaagga ggaagtacgc tttactattg aagatttatt    93720
aggtacacat ttagatttgt gaactcacat tgcttaggat gaaagggact cttgaggatg    93780
tctgctgttt gttagtgaac tgcctgtaac aattacaatt agcacacaca tgagcacaat    93840
gaactgggta gtcagactca gccaaaatga atagaaatag cctcttacca aatttacttt    93900
gagtagccct tggactctga gcactgctgc ccagagcaat atgactgtag gtccaagttt    93960
gtcaatgact atgcaaatgt gctttcttcg cttttactct attgtcatct gtctattaca    94020
atgttgctat ggtgacacct ttccaatatc cctgtgcttc tttggtatcc tctaagggga    94080
agctgtaatg aagtggcttg gcaaaagaat cctcttggaa tttttttttt ttcatatgct    94140
actgaaaacc agcatgattt tcctcttatg ggaaatgtat aaagtatgag ttggaaatga    94200
tggaaattaa tctgtactga cttgggcaag gaatgtgaat gttattcatt ctgttccaaa    94260
ctacctgaaa atattctctt tctgttccta cttttcagga gataacatct taagggacac    94320
tgaagcttgt gcgtgtgtga gtagaacacg tgctgggggc tcttgagctc atgagggagg    94380
ggctacatgt cggtggggtg ataactgtat gctggaaaca atgataggtg gtgaccctgg    94440
agcacttacc atgtgacagg tgttatgcta agcatgttgt atgcattcct tcattgaatg    94500
acagctacct atattatcct catttttataa gatgaggtaa cagagcttca gaaaggttag    94560
actcagctgc tatgggtctg tctgactctg gtgttcttcc tcttaaaaac tggggcactt    94620
tggaaatgag attcctcggt gatgaacaga aatattgctt agcggctgta ttttgtatc     94680 tggcagtttt cccatatttg agtcttatat tcacaatcgg tatctttaca ttacacaaaa    94740
gtgacacaga attagagtca tttaatccag ggttgatatc attaagtcat gactatttat    94800
taaatgtttc ttacaatatc tgagatgata ttgcaaaaga tgtaagtgat tttagaagtt    94860
ctcacttcgt agttagttgc agaaacctct tttggaggag ggatgttttc tctatatatc    94920
ctaatttcta cttaatatat ttccacacct ctttgaagtg tgtagtaaga atggtaaaat    94980
gcagtacttc gtcatttggt acagttcaat caatatgcat taagatgtga tcatatgggt    95040
aatagaaaaa tgtgaaagat ccaattcttt ttctccagaa ggcaggaagc tcatatttga    95100
tttctgttac tataaactat aaaaacgttt caaatgtagt ttacccgtaa ccatcaccct    95160
gcaagggtga tattgctccc cgccaattta cggaggagaa tactgaggct ttaaggttgt    95220
agatagacca agaccacaca agtagagagt ggcgggctgt gggttgagct ttaaaatcca    95280
ggttcatcca tgactcccag tgtgttctag taaatccact agaatctgag tattttccaa    95340
tgatttatgc tccgctctgt gtcaggcagt tcatggtatt tttcaacaat cagaaaatcc    95400
tggggaaggc aaactgtttc cccctctcta ggtgccttgg aagtggccgt tgtgaccca    95460 gagatcatcc tttctgatct gacaccttct tcactgccct ggcccagtgt cttttctgca    95520
aggctggaag cccccttaga ctggtcatgt cccatctctt tccggaggga agatgatccc    95580
aaagacgact tttctctcca cggtgctgcc ataccgcagg cggccgccag gggtccccgc    95640
tcggcgtccc cgcgagacag tcgagccccg gccggctgcg cggcgcgctg ggtgcatgag    95700
ggggctgctc cggagcgacg gcggctgcag ctggagccag gcgctcgccc gtccgccggt    95760
tggctcgccg ggaccctcgcg caccggcggc agagtcccctt gcgtggattg gcaagcgacg    95820
ccccacctgc cccgagctca ccatttttctt tcgcgctggc tgcagctgac ccggcgaagg    95880
```

```
gagccgaccg ggccctgggc tggaggtaaa accccacggt gagtaagaac ccgctccaag  95940
ctaggggagg cggcgcagcc cggtggctgc tcgctcccga tctcgcccgg gcgggcggcg  96000
aggtttgggg cgcacctggg cgcgggtgca agaaggtgcg ggaggcggcg gaccggtctt  96060
ctgcccgccg gccacgggct tccggggctg gagtcctctt cagacccctg ccggcgcctg  96120
ggtttctggc cggctcctcg tgtgcacttc ccggcaggaa caagggtcgc ccactttcca  96180
ccccgggatc ttgatttgtc cttgatttga aagatataa atcaataaga tcgtccttct  96240
ttcggggtgc aagactccga gcccatcccc agccgcggac gcctgcaggg tgcgtgttgg  96300
gctgtgggtg gcgggaagac aaacttttac aaaagtgcgc ctgggctggg ggacaacgct  96360
tgggcgtcct gatcctgagg gaggagtctc ggcttgggc agcgtagggg aagtccgcac  96420
cgtcagccag gtcgccccg gggctgacga tgcctcacgg aggtggggag cgtgtaaagg  96480
ccgtacaaat cgcgcttaac tttggggcca acaactgtca aacatctgga atcccagccc  96540
ctccctttcc ctgaactggg gaagaaggtg aaaaccttc aagttttctt tgattgcccc  96600
ttcccacctt cagacccctg ctgggagggt aaagcgccga cccctggtgc ctggcaagta  96660
ccagagactc taaatctctc gggatccccc ccctcgcgct cttttcctgac cctctcccct  96720 aaccctcccc acagagatct ctctacgcag ccgactgaga tcgtggcgaa tggccttttg  96780
tttctccgcg tttcccctat tgtttgcctt ccaacatct ggcggggctt ggggagagaa  96840 ggaagccccct ctggtccccc tcccggccc cacgcagc tccggcaggg gatcccagct  96900
gggaaagtgg aggagcccga ccccagcgag gccgcccac ccgcccttg tggttagagg  96960 gcggagggaa agttgttcct tccccgcctc cgctgctgcc tgtggcccag ggcgcatttc  97020
tcagatctca gcccaggcgc gccgcaaagg ctcaaatccg agaaggtgct gctttcgaga  97080
cagtggaagc gcgttccgcc ccaatccaga gcgtccagtg gttggttcca gaggatttca  97140
atctctagcc aaaggcgttg gggctgggcc gctgctaggg cagtgggagg ggatcggggc  97200
acctttggta ggcggaaagc tgagattctg gggtccacaa gtttccaagg gcgggagggc  97260
aggctagtcg ccaaaaagag aacgaagatg caaataacga ggaagcctta tgacgttgcc  97320
tggaaatagt agtgtggtgg ttcactccgg aatgaacgtg gagttctggc tttgagtacc  97380
gctccaagtt taaatcccaa gtccccttc ttcattgtag aaaaagagga ctcagacgac  97440
gcaacacaga tacggctaga gcacagttcc tgcttccacg tcccagagaa caagtggctt  97500
aggatggtcc cgagttcccc tgtgggtgcg cttgttgggt tgcaggcggc cctgtttccc  97560
tgcacaagtc agatgcttac acattgtgtt cattcttagt gtggattatt gattaaagaa  97620 ctgggcaaa agcaaagtag ctactctgag aagtcagggt cccagatgg tgcccagcga  97680 gttgtcttgc ctctgagggg aggctgactg agactgtgca cctgttagaa cctatgctac  97740
cccatagcct tgcagttgac ttgctgttgc cagcttttcc tgtgggatcc ccaatgagtc  97800
cctcttccaa ggaagctcaa ttacactttt gattcctcct caacccaggg gaagaaagag  97860
gcttctgtag gaacattatg atctatgtac ccactcagac attgtcagtg ataccagaa  97920 gcttggctct gcacagctct gagagttttc cctttgcgaa ctcaacagaa cttttgagtt  97980
tccatttaac ataaagaag tgagactgct aagccaggaa tgcgacacat agagcacttt  98040
ctctagtgat ttctgggtat tatatctctt taccttccca acggtggaac caggaaaaga  98100
aaaaaaagca acatctttga agtactgcaa ggcactttac aaacatttca ttatgaaaat  98160 gatcccaag gaaggattcc tttgaaattt agcagcagca acccagaagc aacaaaaaag  98220
accaaagtta ctcaagaagt acccaaaggc atcattaaca aaataaaaga gcatttcttg  98280
```

```
tcttggccta ccccgctaag gaaaacaggg taattatagt ggaagttaag cttg        98334
```

<210> SEQ ID NO 64
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 64

```
cccggggccg gggccggggc cggggccc                                       28
```

<210> SEQ ID NO 65
<211> LENGTH: 212
<212> TYPE: DNA
<213> ORGANISM: Artificial sequence
<220> FEATURE:
<223> OTHER INFORMATION: Synthetic polynucleotide

<400> SEQUENCE: 65

```
cccggggccg gggccggggc cccggggccc ggggcccggg gcccggggcc cggggcccgg     60
ggcccggggc ccggggcccg gggccggggg cccggggccc ggggcccggg gcccggggcc    120
cggggcccgg ggcccggggc ccggggcccg gggcccgggg cccggggccc ggggcccggg    180
gcccggggcc cggggcccgg ggcccggggc cc                                  212
```

USE AND TREATMENT OF DI-AMINO ACID REPEAT-CONTAINING PROTEINS ASSOCIATED WITH ALS

CROSS-REFERENCE TO RELATED APPLICATIONS

This application is a Divisional Application of U.S. application Ser. No. 16/362,908, filed Mar. 25, 2019, which is a Divisional Application of U.S. application Ser. No. 14/775,278, filed Sep. 11, 2015, which is a national stage filing under 35 U.S.C. § 371 of International PCT application PCT/US2014/022670, filed Mar. 10, 2014, which claims the benefit of the filing date of U.S. Provisional Application No. 61/786,258, filed Mar. 14, 2013, and the benefit of the filing date of U.S. Provisional Application No. 61/883,219, filed Sep. 27, 2013. The entire contents of each of these referenced applications are incorporated by reference herein.

FEDERALLY SPONSORED RESEARCH OR DEVELOPMENT

This invention was made with government support under P01NS058901 and R01NS040389 awarded by the National Institutes of Health. The Government has certain rights in the invention.

BACKGROUND OF THE INVENTION

Expansion of a GGGGCC hexanucleotide sequence within the intron of the human C9ORF72 gene is associated with both amyotrophic lateral sclerosis and frontotemporal dementia in humans. Amyotrophic lateral sclerosis (ALS) is a debilitating disease with varied etiology characterized by rapidly progressing weakness, muscle atrophy, muscle spasticity, difficulty speaking (dysarthria), difficulty swallowing (dysphagia), and difficulty breathing (dyspnea). Although the order and rate of symptoms varies from person to person, eventually most subjects are not able to walk, get out of bed on their own, or use their hands and arms. Most subjects with ALS will eventually die from respiratory failure, usually within three to five years from the onset of symptoms. Riluzole (Rilutek) is the only currently available treatment for ALS and only slows progression and increases survival to a modest extent. Frontotemporal dementia (FTD) is also a devestating group of disorders resulting from atrophy or shrinkage of the frontal and temporal lobes of the brain. This shrinkage or atrophy results in severe behavioral changes. There is currently no cure for FTD and limited medications for managing the symptoms of FTD. New methods for diagnosing and treating ALS and/or FTD would greatly benefit ALS and FTD subjects.

SUMMARY OF THE INVENTION

Expansion of a GGGGCC hexanucleotide sequence within the intron of the human C9ORF72 gene is associated with both amyotrophic lateral sclerosis and frontotemporal dementia in humans. As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. These sense and anti-sense transcripts were found to be translated to produce di-amino acid repeat-containing proteins. The sense transcript (containing 5'-GGGGCC-3' hexanucleotide repeats) was found to be translated through repeat-associated non-ATG (RAN) translation such that poly-(Gly-Ala), poly-(Gly-Pro), and poly-(Gly-Arg) proteins were produced. The anti-sense transcript (containing 5'-GGCCCC-3' hexanucleotide repeats) was found to be translated through repeat-associated non-ATG (RAN) translation such that poly-(Pro-Ala), poly-(Pro-Arg), poly-(Gly-Pro) proteins were produced. Additionally, the anti-sense transcript was found to be translated through ATG-initiated translation to produce Met . . . poly-(Pro-Arg) and Met . . . poly-(Gly-Pro) proteins.

These di-amino acid repeat-containing proteins were found to be present in ALS subject blood samples. Accordingly, aspects of the disclosure relate to a method of detection of di-amino acid-repeat containing protein levels in sample (e.g., blood) obtained from a subject, the method comprising measuring di-amino acid-repeat-containing protein levels in the sample of the subject. In some aspects, detection of di-amino acid-repeat containing protein levels may identify (or diagnose) or aid in identification (or aid in diagnosis) of a subject having ALS or FTD or likely to develop ALS or FTD. Alternatively or additionally, detection of di-amino acid-repeat containing protein levels, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject. Aspects of the disclosure also relate to treatment of a subject having ALS or FTD by decreasing or stabilizing di-amino acid-repeat-containing protein levels in the blood of the subject.

Additionally, expression of the anti-sense transcript (containing 5'-GGCCCC-3' hexanucleotide repeats) was found to be highly elevated in subjects having the expanded GGGGCC hexanucleotide repeat compared to controls. Foci of sense and anti-sense transcripts were also detectable using fluorescent in situ hybridization (FISH) in brain and blood cells of patients having the expanded GGGGCC hexanucleotide repeat sequence within the intron of the C9ORF72 gene. Thus, other aspects of the disclosure relate to a method of detection of a hexanucleotide repeat-containing transcript, the method comprising measuring a level a hexanucleotide repeat-containing transcript and/or measuring the presence or absence of a hexanucleotide repeat-containing transcript focus. In some aspects, detection of a hexanucleotide repeat-containing transcript may identify (or diagnose) or aid in identification (or aid in diagnosis) of a subject as having ALS or FTD or likely to develop ALS or FTD. Alternatively or additionally, detection of a hexanucleotide repeat-containing transcript, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject.

In some aspects, the disclosure relates to a method for identifying a subject as having ALS or FTD or likely to develop ALS or FTD, the method comprising determining, in a blood sample obtained from a subject, a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pr) protein, wherein a level of the one or more di-amino acid repeat-containing proteins that is elevated compared to a control level indicates that the subject has ALS or FTD or is likely to develop ALS or FTD. In some embodiments, the level of the one or more di-amino acid repeat-containing proteins is determined by performing an assay. In some embodiments, the assay comprises an immuno-based assay. In some embodiments, the immuno-based assay comprises an isolated antibody specific for an antigen comprising a sequence as set for in Tables 1, 2, or 3. In some embodiments, the immuno-based assay comprises an isolated antibody specific for the C-terminus of the one or more di-amino acid repeat-containing protein.

In some embodiments, the method further comprises identifying the subject as having ALS or FTD or likely to develop ALS or FTD if the level of the di-amino acid repeat-containing protein is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant.

In some embodiments, the one or more di-amino acid repeat-containing proteins is selected from the poly-(Pro-Ala), poly-(Pro-Arg), Met . . . poly-(Pro-Arg) or Met . . . poly-(Gly-Pro) protein. In some embodiments, the one or more di-amino acid repeat-containing proteins is two or more di-amino acid repeat-containing proteins.

Other aspects of the disclosure relate to a method for treating a subject with ALS or FTD, the method comprising decreasing or preventing an increase in a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein in the blood of the subject. In some embodiments, decreasing or preventing an increase of the level of one or more di-amino acid repeat-containing proteins comprises removing the one or more di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, the bone marrow transplantation is an allogeneic bone marrow transplantation.

In yet another aspect, the disclosure relates to an isolated antibody specific for one or more di-amino acid repeat proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. In some embodiments, the di-amino acid repeat protein is selected from a poly-(Pro-Ala), poly-(Pro-Arg), Met . . . poly-(Pro-Arg) or Met . . . poly-(Gly-Pro) protein. In some embodiments, the isolated antibody is specific for an antigen comprising a sequence or fragment of a sequence as set for in Tables 1, 2, or 3.

Other aspects of the disclosure relate to a method for identifying a subject as having ALS or FTD or likely to develop ALS or FTD, the method comprising determining, in a sample obtained from a subject, a level of a 5'-GGGGCC-3' hexanucleotide repeat-containing RNA and/or a 5'-GGCCCC-3' hexanucleotide repeat-containing RNA, wherein a level of the 5'-GGGGCC-3' hexanucleotide repeat-containing RNA and/or a 5'-GGCCCC-3' hexanucleotide repeat-containing RNA that is elevated compared to a control level indicates that the subject has ALS or FTD or is likely to develop ALS or FTD. In some embodiments, the level is determined by performing an assay. In some embodiments, the assay comprises a nucleic acid-based assay, such as in-situ hybridization (e.g., FISH) or RT-PCR (e.g., quantitative RT-PCR or strand specific quantitative RT-PCR). In some embodiments, the method further comprises identifying the subject as having ALS or FTD or likely to develop ALS or FTD if the level of a 5'-GGGGCC-3' hexanucleotide repeat-containing RNA and/or a 5'-GGCCCC-3' hexanucleotide repeat-containing RNA is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant. In some embodiments, the level of a 5'-GGGGCC-3' hexanucleotide repeat-containing RNA and/or a 5'-GGCCCC-3' hexanucleotide repeat-containing RNA is a level of a 5'-GGCCCC-3' hexanucleotide repeat-containing RNA.

Yet other aspects of the disclosure relate to a method for identifying a subject as having ALS or FTD or likely to develop ALS or FTD, the method comprising determining, in a sample obtained from a subject, the presence or absence of foci containing 5'-GGGGCC-3' hexanucleotide repeat-expansion-containing RNA and/or a 5'-GGCCCC-3' hexanucleotide repeat-expansion-containing RNA, wherein the presence of the foci of the 5'-GGCGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. In some embodiments, presence or absence of foci or elevated C9ORF72 sense or antisense RNA levels is determined by performing an assay. In some embodiments, the assay comprises a nucleic acid-based assay, such as strand specific RT-PCR or in-situ hybridization (e.g., FISH).

Yet other aspects of the disclosure relate to transgenic mice. In some embodiments, the transgenic mouse comprises a human C9ORF72 gene and optionally human flanking sequences. In some embodiments, the transgenic mouse comprises SEQ ID NO: 63.

These and other aspects are described in more detail herein and illustrated by the non-limiting figures and examples.

BRIEF DESCRIPTION OF THE DRAWINGS

The drawings are first described.

FIG. 2A is a diagram of an expression vector for expressing RAN translation proteins in cells. CMV=cytomegalovirus promoter. 6× Stop=6 stop codons, two in each frame. (GGGGCC)exp=a GGGGCC repeat sequence that extends for 4, 30, 60, or 120 repeats. (GR) HA-(GP)Flag-(GA)Myc=a HA, flag or myc tag that corresponds to the poly-(Gly-Arg), poly-(Gly-Pro), and poly-(Gly-Ala) repeat proteins, respectively. SV40 poly(a)=transcription terminator and poly A signal.

FIG. 2B is a photograph of a western blot depicting that GR and GP RAN translation proteins are expressed in cells transfected with 30, 60 or 120 GGGGCC repeat sequences.

FIG. 18 is a table summarizing histopathological findings in C9ORF72 positive ALS/FTD cases and controls.

FIGS. 19A-19F are a series of images and datasets. (A) shows strand-specific RT-PCR detection of sense (S) and antisense (AS) transcripts (across intron 1) of PBLs of C9(+) patient and normal controls. (B) is a summary of 5' RACE products. (C) shows FISH staining of frontal cortex from a C9(+) case showing an example of cytoplasmic RNA foci. (D) shows FISH staining of peripheral blood leukocytes showing the accumulation of antisense (AS) $G_2C_4$ and sense (S) G₄C₂ RNA foci in C9(+) but not C9(−) cells. (E) shows antisense foci specificity assay showing excess unlabeled (G₄C₂)₄ oligo blocks labeling of G4C2-Cy3 antisense (AS) but not G₂C₄-Cy3 labeled sense foci. (F) shows additional controls for antisense RNA foci showing expected DNase I resistance and RNase I sensitivity.

FIG. 20 is a series of images of in vitro evidence for RAN translation of the sense GGGGCC repeat expansion. (A) shows constructs containing varying GGGGCC repeat lengths with upstream 6× Stop cassette and 3' tags in each reading frame. Immunoblots (B) and/or immunofluorescence staining (C) showing RAN translation occurs in all three frames (GP, GR, GA) in cells transfected with constructs containing 30, 60 and 120 repeats.

FIG. 21 is a schematic of putative protein products in sense and antisense directions for all reading frames SEQ ID NOs: 57-62, from top to bottom. Underlined sequences were used to generate polyclonal antibodies. *=Stop codon.

FIGS. 22A-22E are a series of images showing validation of dual antibodies to detect putative polyPA, polyPR, polyGP proteins by immunofluorescence and protein blot (A-D Top): Schematic diagrams of constructs expressing ATG-initiated N-terminal epitope-tagged (V5 or Flag) repeat proteins with or without endogenous C-terminal sequences. (A-D Bottom panels), co-localization of α-Flag or α-V5 staining in transfected HEK293T cells with staining using the following newly developed antibodies: (A) α-PA or α-PA-CT(antisense); (B) α-PR or α-PR-CT (C) rabbit α-GP or α-GP-CT (sense); (D) mouse α-GP. Similar staining was not seen in preimmune or pcDNA3.1 empty vector controls; (E) Corresponding immunoblots showing six of the seven antibodies tested also detect recombinant proteins by Western.

FIGS. 23A-23C are a series of images showing validation of additional sense repeat and C-terminal polyclonal antibodies. (A, B Top): Schematic diagrams of constructs expressing ATG-initiated N-terminal V5-epitope tagged GR or GA repeat proteins with endogenous C-terminal sequences. (A-B Bottom panels), co-localization of α-V5 staining in transfected HEK293T cells with α-GR, α-GR-CT and α-GP-CT respectively. Similar staining was not seen in preimmune or pcDNA3.1 empty vector controls. (C) α-OR detection of recombinant protein in Flag-OR transfected cells by protein blot.

FIGS. 26A-26D are a graph and a series showing images RAN translation and PR protein expression affect cell viability. (A) qRT-PCR shows expression of expansion transcripts are similar in HEK293T cells transfected with (−)ATG-PR-3T and (+)ATG-PR-3T constructs. (B-D) Bright-field microscopy images showing changes in cell morphology in cells expressing RNA and RAN proteins from (−)ATG-PR-3T constructs compared to empty vector control (pcDNA3.1) and worsening effects in (+)ATG-PR-3T cells expressing increased levels of PR protein.

FIG. 27 is a table describing primers used for RT-PCR and RACE (in order: SEQ ID NOs: 36, 37, 39, 38, 45-47, 40, 48-56).

FIG. 28 is a table describing novel sense and antisense antibodies. (in order SEQ ID NOs: 20, 23, 19, 25, 21, 21, 22, 18).

FIG. 29 is a schematic of the BAC insert used to make transgenic mice.

DETAILED DESCRIPTION OF THE INVENTION

Figure 1:
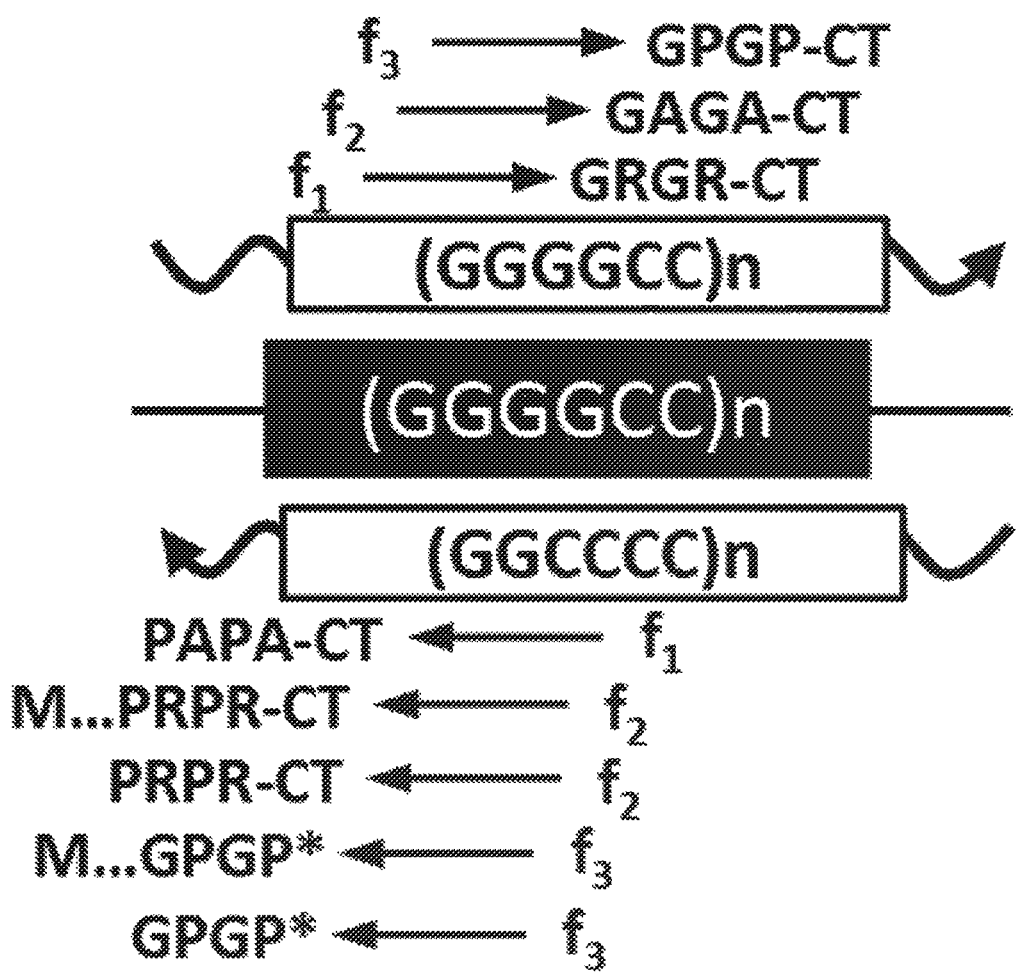
FIG. 1 is a drawing showing that transcripts are produced in the sense and anti-sense direction on the C9ORF72 gene, and that repeat-associated non-ATG (RAN) translation proteins are translated in all three reading-frames from both the sense and anti-sense C9ORF72 transcripts. The drawing also shows that Met . . . poly-(Pro-Arg) and Met . . . poly-(Gly-Pro) proteins are translated through ATG-initiated translation on the anti-sense transcript. CT=predicted to and/or shown to contain a c-terminal domain. *=end of protein (due to stop codon). M=Methionine.

Well-established rules of translational initiation have been used as a cornerstone in molecular biology to understand gene expression and to predict the consequences of disease causing mutations. In general, microsatellite expansion mutations (e.g., CAG, CTG) located in predicted coding- and non-coding regions have been thought to cause disease by protein gain-, or loss-, of-function or RNA gain-of-function mechanisms. It has been previously reported that the canonical rules of translation do not apply for CTG.CAG repeat expansions and that CAG and CUG expansion transcripts express homopolymeric expansion proteins in all three frames without an AUG start codon (see, e.g., T. Zu et al., Non-ATG-initiated translation directed by microsatellite expansions. PNAS 108, 260 (2011)). This translation independent of an AUG start codon is termed repeat-associated non-ATG (RAN) translation. RAN translation is hairpin dependent and occurs without frameshifting or RNA editing. RAN translation has been observed from trinucleotide, tetranucleotide, and pentanucleotide repeats associated with myotonic dystrophy 1, myotonic dystrophy 2, spinocerebellar ataxia type 3, spinocerebellar ataxia type 8 and Huntington disease (see PCT publication WO/2010/115033, which is incorporated herein by reference).

Expansion of a GGGGCC hexanucleotide repeat within the intron of the C9ORF72 gene has been previously associated with both amyotrophic lateral sclerosis and frontotemporal dementia. As described herein, it has been found that this expanded hexanucleotide repeat is contained within RNA transcripts expressed in both the sense and anti-sense direction from the C9ORF72 locus. These hexanucleotide repeat-containing transcripts were found to undergo RAN translation such that poly-(Gly-Ala), poly-(Gly-Pro), poly-(Gly-Arg), poly-(Pro-Ala), or poly-(Pro-Arg) proteins were produced, depending on the frame of the hexanucleotide repeat being mad from the RNA (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense transcript was found to be translated through ATG-initiated translation to produce Met . . . poly-(Pro-Arg) and Met . . . poly-(Gly-Pro) proteins. These RAN and ATG-initiated proteins are referred to as di-amino acid-repeat-containing proteins herein. The sense and anti-sense hexanucleotide repeat-containing transcripts are referred to herein as 5'-GGGGCC-3' hexanucleotide repeat-containing RNA (sense) and 5'-GGCCCC-3' hexanucleotide repeat-containing RNA (anti-sense).

As further described herein, these di-amino acid-repeat-containing proteins unexpectedly were found to be present in blood samples from subjects with ALS. Additionally, expression of the anti-sense 5'-GGCCCC-3' hexanucleotide repeat-containing RNA transcript was found to be highly elevated in subjects having a C9ORF72 gene containing the expanded GGGGCC hexanucleotide repeat sequence. Further, foci of both the sense and anti-sense hexanucleotide repeat-expansion-containing RNA transcripts were found to be present in subjects having a C9ORF72 gene containing the expanded GGGGCC hexanucleotide repeat sequence. Without wishing to be bound by theory or mechanism, it is believed that di-amino acid-repeat-containing proteins in the blood of subjects with ALS accumulate within the brain parenchyma over time, leading to neuroinflammatory changes, CNS dysfunction, and neuronal death. Accordingly, aspects of the disclosure relate to identification of a subject as having ALS or likely to develop ALS by providing novel assays for determining di-amino acid-repeat-containing protein levels in the blood of the subject and/or hexanucleotide repeat-containing RNA levels in a sample from the subject. Aspects of the disclosure also relate to treatment of a subject having ALS or FTD by decreasing or stabilizing di-amino acid-repeat-containing protein levels in the blood of the subject.

Identification of a Subject Having ALS or FTD or Likely to Develop ALS or FTD

Aspects of the disclosure relate to identification of a subject having ALS or FTD or likely to develop ALS or FTD based on a level of one or more di-amino acid-repeat-containing proteins in a blood sample from a subject. In some embodiments, a method comprises, determining, in a blood sample obtained from a subject, a level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid-repeat-containing proteins that is elevated compared to a control level indicates that the subject has ALS or FTD or is likely to develop ALS or FTD. In some embodiments, a level of one or more di-amino acid-repeat-containing proteins is determined by performing an assay. Non-limiting assays are described herein.

Other aspects of the disclosure relate to identification of a subject having ALS or FTD or likely to develop ALS or FTD based on a level of a 5'-GGGGCC-3' hexanucleotide repeat-containing RNA and/or a 5'-GGCCCC-3' hexanucleotide repeat-containing RNA in a sample from a subject. In some embodiments, identification of a subject having ALS or FTD or likely to develop ALS or FTD is based on a level of a 5'-GGCCCC-3' hexanucleotide repeat-containing RNA in a sample from a subject. The sample may be, e.g., a fluid or tissue sample obtained from the subject. In some embodiments, a method comprises, determining, in a sample obtained from a subject, a level of a 5'-GGGGCC-3' hexanucleotide repeat-containing RNA and/or a 5'-GGCCCC-3' hexanucleotide repeat-containing RNA, wherein a level of the hexanucleotide repeat-containing RNA that is elevated compared to a control level indicates that the subject has ALS or FTD or is likely to develop ALS or FTD. In some embodiments, a level of a hexanucleotide repeat-containing RNA is determined by performing an assay. Non-limiting assays are described herein.

Yet other aspects of the disclosure relate to identification of a subject having ALS or FTD or likely to develop ALS or FTD based on the presence or absence of RNA foci containing a 5'-GGGGCC-3' hexanucleotide repeat-expansion-containing RNA and/or a 5'-GGCCCC-3' hexanucleotide repeat-expansion-containing RNA in a sample from a subject, wherein the presence of the focus of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. As used herein, a focus of a 5'-GGGGCC-3' hexanucleotide repeat-expansion-containing RNA and/or a 5'-GGCCCC-3' hexanucleotide repeat-expansion-containing RNA refers to an area of accumulation of the 5'-GGGGCC-3' hexanucleotide repeat-expansion-containing RNA and/or the 5'-GGCCCC-3' hexanucleotide repeat-expansion-containing RNA, which may be detectable using a nucleic acid-based assay, such as FISH. In some embodiments, the focus may be, e.g., 0.1 to 2 micrometers in diameter, 0.1 to 1.5 micrometers in diameter, or 0.1 to 1 micrometers in diameter. In some embodiments, the focus may be at least 0.1 micrometers in diameter. It is to be appreciated that a sample may contain more than one focus and that each focus may be a different size. For example, one focus may be 0.2 micrometers in diameter, while second focus may be 1 micrometer in diameter. Non-limiting examples of foci and methods detecting such foci are provided in Example 3.

It is to be understood that a subject may be identified based on a level of one or more di-amino acid-repeat-containing proteins, a level of a hexanucleotide repeat-expansion containing RNA, the presence or absence of a hexanucleotide repeat-expansion containing RNA, or any combination thereof. In some embodiments, the method further comprises identifying the subject as having ALS or FTD or likely to develop ALS or FTD if the level of the di-amino acid-repeat-containing protein or hexanucleotide repeat-containing RNA is elevated compared to a control level. In some embodiments, the method further comprises identifying the subject as having ALS or FTD or likely to develop ALS or FTD if the focus or foci of the hexanucleotide repeat-expansion-containing RNA are present in the sample. In some embodiments, the method further comprises identifying the subject as not having ALS or FTD or unlikely to develop ALS or FTD if the level of the di-amino acid-repeat-containing protein or hexanucleotide repeat-containing RNA is decreased or the same compared to a control level. In some embodiments, the method further comprises identifying the subject as not having ALS or FTD or unlikely to develop ALS or FTD if the focus or foci of the hexanucleotide repeat-expansion-containing RNA are absent in the sample.

In some embodiments, a level of one or more di-amino acid-repeat-containing proteins or the identity of a subject may be recorded. In some embodiments, recordation comprises inputting a level or identity of subject into a computer, such as a medical record database.

Other aspects of the disclosure relate to treatment of a subject identified as having ALS or FTD or likely to develop ALS or FTD. As used herein, "treat" or "treatment" refers to (a) preventing or delaying the onset of ALS or FTD; (b) reducing the severity of ALS or FTD; (c) reducing or preventing development of symptoms characteristic of ALS or FTD; (d) preventing worsening of symptoms characteristic of ALS or FTD; and/or (e) reducing or preventing recurrence of ALS or FTD symptoms in subjects that were previously symptomatic for ALS or FTD.

In some embodiments, treatment comprises administering an effective amount of a known ALS therapeutic agent, such as Riluzole (Rilutek, Sanofi-Aventis), to a subject identified as having ALS. In some embodiments, treatment comprises administering an effective amount of a known FTD therapeutic agent, such as trazodone (Desyrel, Oleptro) or a selective serotonin reuptake inhibitor (SSRI), to a subject identified as having FTD. In some embodiments, treatment comprises administering an effective amount of a therapeutic agent, such as baclofen, diazepam, phenytoin, trihexyphenidyl and/or amitriptyline, which reduces one or more symptoms of ALS or FTD in a subject identified as having ALS or FD. In some embodiments, treatment comprises one or more of physical therapy, occupational therapy, or speech therapy. In some embodiments, treatment comprises a method as described herein for decreasing or stabilizing di-amino acid-repeat-containing protein levels in the blood of the subject, such as bone marrow transplantation or plasmapheresis. In some embodiments, treatment comprises any combination of the above-mentioned treatments or any other treatments described herein.

An effective amount is a dosage of a therapeutic agent sufficient to provide a medically desirable result, such as treatment of ALS or FTD. The effective amount will vary with the age and physical condition of the subject being treated, the severity of ALS or FD in the subject, the duration of the treatment, the nature of any concurrent therapy, the specific route of administration and the like factors within the knowledge and expertise of the health practitioner.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Other aspects of the disclosure relate to methods for monitoring responsiveness to a treatment in a subject having ALS or FTD or suspected of having ALS or FTD. In some embodiments, the method comprises: determining, in a blood sample obtained from the subject at a first time point, a first level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein; and determining, in a blood sample obtained from the subject at a second time point, a second level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a second level that is elevated or the same compared to a first level indicates that the subject is unresponsive or likely unresponsive to treatment and wherein a second level that is decreased compared to a first level indicates that the subject is responsive or likely responsive to treatment. In some embodiments, the first blood sample is obtained before treatment of the subject and the second blood sample is obtained during or after treatment of the subject. This method may also be performed by determining a level of a hexanucleotide repeat-containing RNA or the presence or absence of a focus or foci of a hexanucleotide repeat-expansion-containing RNA in addition to or in place of the level of di-amino acid protein.

As used herein, "elevated" means that the level of one or more di-amino acid-repeat-containing proteins or a hexanucleotide repeat-containing RNA is above a control level, such as a pre-determined threshold or a level of one or more di-amino acid-repeat-containing proteins or a hexanucleotide repeat-containing RNA in a control sample. Controls and control levels are described in detail herein. An elevated level includes a level that is, for example, 1%, 5%, 10%, 20%, 30%, 40%, 50%, 60%, 70%, 80%, 90%, 100%, 150%, 200%, 300%, 400%, 500%, or more above a control level. An elevated level also includes increasing a phenomenon from a zero state (e.g., no or undetectable di-amino acid-repeat-containing protein expression or hexanucleotide repeat-containing RNA expression) to a non-zero state (e.g., some or detectable di-amino acid-repeat-containing protein expression or hexanucleotide repeat-containing RNA).

As used herein, "decreased" means that the level of one or more di-amino acid-repeat-containing proteins or a hexanucleotide repeat-containing RNA is below a control level, such as a pre-determined threshold or a level of one or more di-amino acid-repeat-containing proteins or a hexanucleotide repeat-containing RNA in a control sample. Controls and control levels are described in detail herein. A decreased level includes a level that is, for example, 1%, 5%, 10%, 20%, 30%, 40%, 50%, 60%, 70%, 80%, 90%, 100%, 150%, 200%, 300%, 400%, 500%, or more below a control level. A decreased level also includes decreasing a phenomenon from a non-zero state (e.g., some or detectable di-amino acid-repeat-containing protein expression or hexanucleotide repeat-containing RNA) to a zero state (e.g., no or undetectable di-amino acid-repeat-containing protein expression or hexanucleotide repeat-containing RNA expression).

Hexanucleotide Repeat-Containing RNAs and Di-Amino Acid Repeat-Containing Proteins As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. The GenBank Gene JD for the human C9ORF72 gene is 203228. Both the sense and anti-sense hexanucleotide repeat-containing transcripts were found to undergo translation independent of an AUG start codon (repeat-associated non-ATG (RAN) translation) such that poly-(Gly-Ala), poly-(Gly-Pro), poly-(Gly-Arg), poly-(Pro-Ala), or poly-(Pro-Arg) di-amino acid repeat-containing proteins were produced, depending on the frame of the hexanucleotide repeat being read (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense hexanucleotide repeat-containing transcript was found to be translated through ATG-initiated translation to produce Met . . . poly-(Pro-Arg) and Met . . . poly-(Gly-Pro) proteins.

Accordingly, aspects of the invention relate to the sense and anti-sense RNAs containing an expanded hexanucleotide repeat and uses thereof. The sense RNA is a 5'-GGGGCC-3' hexanucleotide repeat-containing RNA and the anti-sense RNA is a 5'-GGCCCC-3' hexanucleotide repeat-containing RNA.

The 5'-GGGGCC-3' and 5'GGCCCC-3' hexanucleotide repeat-containing RNAs comprise a repeat nucleic acid sequence of the formula $(GGGGCC)_x$ or $(GGCCCC)_x$, respectively, where X may be at least 10, at least 20, at least 25, or at least 30, or in a range selected from 10-100,000, 10-50,000, 10-5,000, 20-1,000, 20-100,000, 20-50,000, 20-5,000, 20-1,000, 25-100,000, 25-50.000, 25-5,000, or 25-1,000. The hexanucleotide repeat-containing RNA may further comprise additional N- and/or C-terminal nucleic acids. In some embodiments, an N-terminal nucleic sequence comprises a nucleic acid sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal nucleic acid sequence comprises a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript.

Other aspects of the invention relate to one or more di-amino acid repeat-containing proteins and uses thereof. The one or more di-amino acid repeat-containing proteins are selected from poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) proteins.

The sense 5'-GGGGCC-3' hexanucleotide repeat-containing RNA and the anti-sense 5'-GGCCCC-3' hexanucleotide repeat-containing RNA both encode poly-(Gly-Pro) proteins. Accordingly a poly-(Gly-Pro) protein may include a protein translated from the sense strand, the anti-sense strand, or both. It is predicted that the C-terminus of the sense and anti-sense translated poly-(Gly-Pro) proteins may differ (see Table 1). Accordingly, a sense poly-(Gly-Pro) protein may comprise the poly-(Gly-Pro) a C-terminal sequence as described in Table 1, while an anti-sense poly-(Gly-Pro) protein may comprise the repeat region with no additional C-terminal sequence. Methods described herein may comprise use of a poly-(Gly-Pro) protein translated from the sense strand, the anti-sense strand, or both. Antibodies described herein may be specific for a poly-(Gly-Pro) protein translated from the sense strand, the anti-sense strand, or both.

Each di-amino acid repeat-containing protein comprises a repeat amino acid sequence, which contains a di-amino acid repeat unit of the formula $(YZ)_x$, where X can be from 2-10,000, 5-10,000, 2-5,000, 5-5,000, 2-1000, 5-1000, 5-500, 5-300, 5-200, 10-500, 10-300, or 10-200. The di-amino acid repeat unit for each di-amino acid repeat-containing protein is provided in Table 1.

TABLE 1

Di-Amino Acid-Repeat-Containing Proteins

| Di-Amino Acid-Repeat-Containing Protein | Di-Amino Acid Repeat Unit | Predicted C-terminus |
|---|---|---|
| poly-(Gly-Ala) | $(GA)_x$ or $(AG)_x$ | WSGRARGRARGGAAVAVPAPAAAEAQA VASG (SEQ ID NO: 1) or AWSGRARGRARGGAAVAVPAPAAAEAQ AVASG (SEQ ID NO: 27) |
| poly-(Gly-Pro) | $(GP)_x$ or $(PG)_x$ | GRGRGGPGGGPGAGLRLRCLRPRRRRRR RWRVGE (SEQ ID NO: 2, sense), PGRGRGGPGGGPGAGLRLRCLRPRRRRRR RWRVGE (SEQ ID NO: 28, sense) or none (anti-sense) |
| poly-(Gly-Arg) | $(GR)_x$ or $(RG)_x$ | GVVGAGPGAGPGRGCGCGACARGGGGA GGGEWVSEEAASWRVAVWGSAAGKRRG (SEQ ID NO: 3) or RGVVGAGPGAGPGRGCGCGACARGGGG AGGGEWVSEEAASWRVAVWGSAAGKRR G (SEQ ID NO: 29) |
| poly-(Pro-Ala) | $(AP)_x$ or $(PA)_x$ | PSARLLSSRACYRLRLFPSLFSSG (SEQ ID NO: 4) OR APSARLLSSRACYRRRLFPSLFSSG (SEQ ID NO: 30) |
| poly-(Pro-Arg) | $(PR)_x$ or $(RP)_x$ | PLARDS (SEQ ID NO: 5) or RPLARDS (SEQ ID NO: 31) |
| Met . . . poly-(Pro-Arg) | $(PR)_x$ | PLARDS (SEQ ID NO: 5) |

TABLE 1-continued

Di-Amino Acid-Repeat-Containing Proteins

| Di-Amino Acid-Repeat-Containing Protein | Di-Amino Acid Repeat Unit | Predicted C-terminus |
|---|---|---|
| Met . . . poly-(Gly-Pro) | $(GP)x$ | None |

$x$= number of repeats of the sequence in the parentheses

Each di-amino acid repeat-containing protein may further comprise an N- and/or C-terminal amino acid sequence that comprises a non-di-amino acid repeat sequence. In some embodiments, a N-terminal amino acid sequence comprises an amino acid sequence translated from a nucleotide sequence of a C9ORF72 RNA transcript, such as a nucleotide sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal amino acid sequence comprises an amino acid sequence translated from a nucleotide sequence of a C9ORF72 RNA transcript, such as a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript. Such a nucleotide sequence downstream of the 5'-GGGGCC-3' or 5'-GGCCCC-3' hexanucleotide repeat may be translated until a stop codon or multiple stop codons are reached.

A portion of a C9ORF72 gene sequence (sense and anti-sense) is shown below. The 5'-GGGGCC-3' or 5'-GGCCCC-3' hexanucleotide repeat is underlined and in bold. The nucleotide sequence upstream of the 5'-GGGGCC-3' or 5'-GGCCCC-3' hexanucleotide repeat precedes the underlined and bolded sequence. The nucleotide sequence downstream of the 5'-GGGGCC-3' or 5'-GGCCCC-3' hexanucleotide repeat follows the underlined and bolded sequence. It is to be understood that this 5'-GGGGCC-3' or 5'-GGCCCC-3' hexanucleotide repeat can be repeated more than the number of times present in these sequences.

C9ORF72 (partial sequence, sense)

(SEQ ID NO: 6)

CCCCATTTCGCTAGCCTCGTGAGAAAACGTCATCGCACATAGAAAACAGA

CAGACGTAACCTACGGTGTCCCGCTAGGAAAGAGAGGTGCGTCAAACAGC

GACAAGTTCCGCCCACGTAAAAGATGACGCTTGGTGTGTCAGCCGTCCCT

GCTGCCCGGTTGCTTCTCTTTTGGGGGCGGGGTCTAGCAAGAGCAGGTGT

GGGTTTAGGAGGTGTGTGTTTTTGTTTTTCCCACCCTCTCTCCCCACTAC

TTGCTCTCACAGTACTCGCTGAGGGTGAACAAGAAAAGACCTGATAAAGA

TTAACCAGAAGAAAACAAGGAGGGAAACAACCGCAGCCTGTAGCAAGCTC

TGGAACTCAGGAGTCGCGCGCTAGGGGCCGGGGCCGGGGCCGGGGCGTGG

TCGGGGCGGGCCCGGGGGCGGGCCCGGGGCGGGGCTGCGGTTGCGGTGCC

-continued
```
TGCGCCCGCGGCGGCGGAGGCGCAGGCGGTGGCGAGTGGGTGAGTGAGGA

GGCGGCATCCTGGCGGGTGGCTGTTTGGGGTTCGGCTGCCGGGAAGAGGC

GCGGGTAGAAGCGGGGGCTCTCCTCAGAGCTCGACGCATTTTTACTTTCC

CTCTCATTTCTCTGACCGAAGCTGGGTGTCGGGCTTTCGCCTCTAGCGAC

TGGTGGAATTGCCTGCATCCGGGCCCCGGGCTTCCCGGCGGCGGCGGCGG

CGGCGGCGGCGCAGGGACAAGGGATGGGGATCTGGCCTCTTCCTTGCTTT

CCCGCCCTCAGTACCCGAGCTGTCTCCTTC

C9ORF72 (partial sequence, anti-sense)
                                         (SEQ ID NO: 7)
GAAGGAGACAGCTCGGGTACTGAGGGCGGGAAAGCAAGGAAGAGGCCAGA

TCCCCATCCCTTGTCCCTGCGCCGCCGCCGCCGCCGCCGCCGCGGGAAG

CCCGGGGCCCGGATGCAGGCAATTCCACCAGTCGCTAGAGGCGAAAGCCC

GACACCCAGCTTCGGTCAGAGAAATGAGAGGGAAAGTAAAAATGCGTCGA

GCTCTGAGGAGAGCCCCCGCTTCTACCCGCGCCTCTTCCCGGCAGCCGAA

CCCCAAACAGCCACCCGCCAGGATGCCGCCTCCTCACTCACCCACTCGCC

ACCGCCTGCGCCTCCGCCGCCGCGGGCGCAGGCACCGCAACCGCAGCCCC

GCCCCGGGCCCGCCCCGGGCCCGCCCCGACCACGCCCGGCCCCGGCCC

CGGCCCCTAGCGCGCGACTCCTGAGTTCCAGAGCTTGCTACAGGCTGCGG

TTGTTTCCCTCCTTGTTTTCTTCTGGTTAATCTTTATCAGGTCTTTTCTT

GTTCACCCTCAGCGAGTACTGTGAGAGCAAGTAGTGGGGAGAGAGGGTGG

GAAAAACAAAAACACACACCTCCTAAACCCACACCTGCTCTTGCTAGACC

CCGCCCCCAAAAGAGAAGCAACCGGGCAGCAGGGACGGCTGACACACCAA

GCGTCATCTTTTACGTGGGCGGAACTTGTCGCTGTTTGACGCACCTCTCT

TTCCTAGCGGGACACCGTAGGTTACGTCTGTCTGTTTTCTATGTGCGATG

ACGTTTTCTCACGAGGCTAGCGAAATGGGG
```

In some embodiments, a Met . . . poly-(Pro-Arg) or Met . . . poly-(Gly-Pro) protein comprises an N-terminal amino acid sequence comprising an N-terminal methionine. In some embodiments, a Met . . . poly-(Pro-Arg) protein comprises an N-terminal amino acid sequence comprising MQAIPPVARGESPTPSFGQRNERESKNASS-SEESPRFYPRLFPAAEPQTATRQDAASSL THSPP-PAPPPPRAQAPQPQPRPGPAPGPAPTT (SEQ ID NO: 41) or a fragment thereof, wherein the sequence is N-terminal to a poly-(Pro-Arg) repeat amino acid sequence. In some embodiments, a Met . . . poly-(Gly-Pro) protein comprises an N-terminal amino acid sequence comprising MRGKVKMRRALRRAPASTRASSRQPNPKQPPARM-PPPHSPTRHRLRLRRRGRRHRN RSPAPGPPPGPPR-PRP (SEQ ID NO: 42), MRRALRRAPAS-TRASSRQPNPKQPPARMPPPHSPTRHRLRLRRRGRR-HRNRSPAPGP PPGPPRRPRPR (SEQ ID NO: 43), MPP-PHSPTRHRLRLRRRGRRHRNRSPAPPPPPRPRP (SEQ ID NO: 44), or a fragment thereof, wherein the sequence is N-terminal to a poly-(Gly-Pro) repeat amino acid sequence.

In some embodiments, a C-terminal amino acid sequence comprises a C-terminus amino acid sequence shown in Table 1 or a fragment of a C-terminus amino acid sequence shown in Table 1. It is to be understood that C-terminal amino acid sequences other than those in Table 1 are also contemplated.

Exemplary di-amino acid repeat-containing proteins may comprise a sequence provided in Table 2.

TABLE 2

(GA)$_x$WSGRARGRARGGAAVAVPAPAAAEAQAVASG (SEQ ID NO: 8)

(AG)$_x$AWSGRARGRARGGAAVAVPAPAAAEAQAVASG (SEQ ID NO: 9)

(GP)$_x$GRGRGGPGGGPGAGLRLRCLRPRRRRRRRWRVGE (SEQ ID NO: 10)

(PG)$_x$PGRGRGGPGGGPGAGLRLRCLRPRRRRRRRWRVGE (SEQ ID NO: 11)

(GP)$_x$ (PG)$_x$ (GR)$_x$GVVGAGPGAGPGRGCGCGACARGGGGAGGGEWVSEEAASWRVAVW GSAAGKRRG (SEQ ID NO: 12)

(RG)$_x$RGVVGAGPGAGPGRGCGCGACARGGGGAGGGEWVSEEAASWRVAV WGSAAGKRRG (SEQ ID NO: 13)

(AP)$_x$APSARLLSSRACYRLRLFPSLFSSG (SEQ ID NO: 14)

(PA)$_x$PSARLLSSRACYRLRLFPSLFSSG (SEQ ID NO: 15)

(PR)$_x$PLARDS (SEQ ID NO: 16)

(RP)$_x$RPLARDS (SEQ ID NO: 17)

MQAIPPVARGESPTPSFGQRNERESKNASSSEESPRFYPRLFPAAEPQTA TRQDAASSLTHSPPPAPPPPRAQAPQPQPRPGPAPGPAPTT(PR)$_x$PLAR DS (SEQ ID NO: 32)

MRGKVKMRRALRRAPASTRASSRQPNPKQPPARMPPPHSPTRHRLRLRRR GRRHRNRSPAPGPPPGPPRPRP(GP)$_x$ (SEQ ID NO: 33)

MRRALRRAPASTRASSRQPNPKQPPARMPPPHSPTRHRLRLRRRGRRHRN RSPAPGPPPGPPRPRP(GP)$_x$ (SEQ ID NO: 34)

MPPPHSPTRHRLRLRRRGRRHRNRSPAPGPPPGPPRPRP(GP)$_x$ (SEQ ID NO: 35)

$_x$= a number between 2-10,000, 5-10,000, 2-5,000, 5-5,000, 2-1000, 5-1000, 5-500, 5-300, 5-200, 10-500, 10-300, or 10-200.

In some embodiments, the one or more di-amino acid repeat-containing proteins are selected from the poly-(Pro-Ala), poly-(Gly-Pro), poly-(Pro-Arg), Met . . . poly-(Pro-Arg) or Met . . . poly-(Gly-Pro) protein. In some embodiments, the one or more di-amino acid repeat-containing proteins are selected from the poly-(Pro-Ala), poly-(Pro-Arg) protein, Met . . . poly-(Pro-Arg) or Met . . . poly-(Gly-Pro) protein.

In some embodiments, the one or more di-amino acid repeat-containing proteins is two or more, three or more, four or more, or five or more, or six or more, seven or more, or eight di-amino acid repeat-containing proteins.

Subjects

Aspects of the disclosure relate to identification and treatment of a subject, such as a human, with ALS or FTD or likely to develop ALS or FTD. In some embodiments, a subject may have ALS. In some embodiments, a subject may have one or more symptoms of ALS, such as difficulty breathing, difficulty swallowing, muscle cramps, muscle contractions, muscle weakness, paralysis, speech problems, or weight loss. In some embodiments, a subject may not have any symptoms of ALS. In some embodiments, a subject may have a family history of ALS.

In some embodiments, a subject may have frontotemporal dementia (FTD). In some embodiments, a subject may have one or more symptoms of FTD, such as lethargy, aspontaneity, disinhibition, loss of empathy and other interpersonal skills, apathy, progressive nonfluent aphasia, semantic dementia, binge eating, compulsive behavior, tremor, rigidity, muscle spasms, poor coordination, difficulty swallowing, and muscle weakness. In some embodiments, a subject may not have any symptoms of FTD. In some embodiments, a subject may have a family history of FTD.

In some embodiments, a subject may have GGGGCC hexanucleotide repeats within one or both alleles of a C9ORF72 gene (NCBI Entrez Gene ID: 203228). In some embodiments, GGGGCC hexanucleotide repeats are within a promoter and/or intron of the C9ORF72 gene. In some embodiments, the number of GGGGCC hexanucleotide repeats is greater than 25, 50, 100, 150, 200, 250, 300, 500, 5,000, 10,000 or more. The number of repeats may be detected using any assay known in the art, e.g., using as a nucleic acid-based assay such as a southern blot (see, e.g., Dejesus-Hernandez et al. Expanded GGGGCC hexanucleotide repeat in noncoding region of C9ORF72 causes chromosome 9p-linked FTD and ALS. Neuron 72, 245 (2011); Renton et al. A hexanucleotide repeat expansion in C9ORF72 is the cause of chromosome 9p21-linked ALS-FTD. Neuron 72, 257 (2011); and Gijselink et al. A C9orf72 promoter repeat expansion in a Flanders-Belgian cohort with disorders of the frontotemporal lobar degeneration-amyotrophic lateral sclerosis spectrum: A gene identification study. Lancet Neurol. 11, 54 (2011)).

Controls and Control levels

Aspects of the disclosure relate to comparison of a level of one or more di-amino acid repeat-containing proteins and/or hexanucleotide repeat-containing RNAs to a control level. In some embodiments, the control level is a level of one or more di-amino acid repeat-containing proteins and/or hexanucleotide repeat-containing RNAs in sample, such as a fluid sample or tissue sample, obtained from a healthy subject or population of healthy subjects. In some embodiments, the sample is a blood sample. As used herein, a healthy subject is a subject that is apparently free of disease and has no history of disease, such as ALS or FTD. In some embodiments, a healthy subject is a subject that has 25 or fewer GGGGCC hexanucleotide repeats within a C9ORF72 gene.

In some embodiments, a control level is a level of one or more di-amino acid repeat-containing proteins and/or hexanucleotide repeat-containing RNAs that is undetectable or below a background/noise level obtained using standard methods of detection (e.g., Western blot, qPCR, northern blot, or immunohistochemistry). Such a level could be obtained, for example, by measuring a level of one or more di-amino acid repeat-containing proteins and/or hexanucleotide repeat-containing RNAs in a sample that is known to be free of the di-amino acid repeat-containing proteins and/or hexanucleotide repeat-containing RNAs.

The disclosure also involves comparing the level of one or more di-amino acid repeat-containing proteins and/or hexanucleotide repeat-containing RNAs with a predetermined level or value, such that a control level need not be measured every time. The predetermined level or value can take a variety of forms. It can be single cut-off value, such as a median or mean. It can be established based upon comparative groups, such as where one defined group is known not to have ALS or FTD and another defined group is known to have ALS or FTD. It can be a range, for example, where the tested population is divided equally (or unequally) into groups, such as a subject that has 25 or fewer GGGGCC hexanucleotide repeats, a subject that has 25-50 GGGGCC hexanucleotide repeats, and a subject that has 50 or more GGGGCC hexanucleotide repeats.

Samples

Aspects of the disclosure relate to determining a level of one or more di-amino acid repeat-containing proteins in a blood sample (e.g., whole blood, plasma, or serum) obtained from a subject. The blood sample may be obtained by any method known in the art, e.g., using a needle or fingerprick device. The blood may be processed before use in the methods described herein. Such processing includes, for example, addition of an anti-coagulant, removal of blood cells, and/or freezing of the blood. However, it should be appreciated that other samples may be used, such as a tissue sample (e.g., brain tissue) or other fluid samples such as saliva, or urine.

Other aspects of the disclosure relate to determining a level of hexanucleotide repeat-containing RNA in sample obtained from a subject. The sample may be a fluid or tissue sample. In some embodiments, the tissue sample is brain tissue. In some embodiments, the fluid sample is blood (e.g., whole blood, plasma, or serum), saliva, or urine. In some embodiments, the fluid sample is a blood sample (e.g., whole blood, plasma, or serum).

Assays

Aspects of the disclosure relate to performing an assay to determine a level or presence/absence of one or more di-amino acid repeat-containing proteins and/or hexanucleotide repeat-containing RNAs. Assays known in the art for detecting proteins and RNAs (see, e.g., Molecular Cloning: A Laboratory Manual, J. Sambrook, et al., eds., Third Edition, Cold Spring Harbor Laboratory Press, Cold Spring Harbor, N.Y. 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York) can be used alone or in combination with techniques and compositions described herein for measuring a di-amino acid repeat-containing protein level.

Assays for detecting protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are well-known in the art. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329, all of which are incorporated herein by reference in their entirety.

Any suitable binding partner for a di-amino acid repeat-containing protein is contemplated for detection of a di-amino acid repeat-containing protein level. In some embodiments, the binding partner is any molecule that binds specifically to a di-amino acid repeat-containing protein as described herein. As described herein, "binds specifically to a di-amino acid repeat-containing protein" means that the molecule is more likely to bind to a portion of or the entirety of a di-amino acid repeat-containing protein than to a portion of or the entirety of a non-di-amino acid repeat-containing protein.

In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Binding partners also include other peptide molecules and aptamers that bind specifically to a di-amino acid repeat-containing protein. Methods for producing peptide molecules and aptamers are well known in the art (see, e.g., published US Patent Application No. 2009/0075834, U.S. Pat. Nos. 7,435,542, 7,807,351, and 7,239,742). The binding partner may comprise a label including, but not limited to, a fluorescent, enzymatic, affinity or isotopic label.

In some embodiments, an assay comprises an immuno-based assay. In some embodiments, the immuno-based assay comprises an isolated antibody specific for one or more di-amino acid repeat-containing proteins. In some embodiments, the isolated antibody specific for one or more di-amino acid repeat-containing proteins is an isolated antibody as described herein in further detail. In some embodiments, the isolated antibody specific for one or more di-amino acid repeat-containing proteins is an isolated antibody specific for an antigen or sequence, or a fragment of an antigen or sequence described in Table 1, Table 2 or Table 3.

Accordingly, a di-amino acid repeat-containing binding partner (e.g., a di-amino acid repeat-containing-specific antibody) can be labeled with a detectable moiety.

Assays for detecting RNA include, but are not limited to, hybridization-based assays such as Northern blot analysis, RT-PCR, sequencing technology, RNA in situ hybridization (using e.g., DNA or RNA probes to hybridize to RNA molecules present in the sample as in FISH), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer) with addressable locations, such as an Affymetrix microarray (Affymetrix®, Santa Clara, Calif.)). Methods for designing nucleic acid binding partners, such as probes, are well known in the art. In some embodiments, the nucleic acid binding partners bind to a part of or an entire nucleic acid sequence of a hexanucleotide repeat-containing RNA provided herein.

Treatment

As described herein, it was found that di-amino acid repeat-containing proteins were present in samples of blood from patients with ALS. Without wishing to be bound by theory or mechanism, it is believed that di-amino acid repeat-containing proteins in the blood of subjects with ALS accumulate within the brain parenchyma over time, leading to neuroinflammatory changes, CNS dysfunction, and neuronal death. Accordingly, aspects of the disclosure relate to treatment of a subject having ALS or FTD by decreasing or stabilizing di-amino acid repeat-containing protein levels in the blood of the subject.

In some embodiments, decreasing or preventing an increase of the level of one or more di-amino acid repeat-containing proteins comprises removing the one or more (e.g., 1, 2, 3, 4, 5, 6, 7 or 8) di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, it may be advantageous to decrease or prevent an increase of the level of all di-amino acid repeat-containing proteins expressed by a subject. Accordingly, in some embodiments, a method comprises decreasing or preventing an increase of the level of all forms of di-amino acid repeat-containing proteins expressed by a subject.

In some embodiments, the one or more di-amino acid repeat-containing from the blood of the subject is removed using a hematopoietic stem cell (HSC) transplantation. HSC transplantation is the transplantation of hematopoietic stem cells, usually derived from bone marrow, peripheral blood, or umbilical cord blood, into a subject. The source of hematopoietic stem cells may be allogeneic (e.g., from a donor such as a healthy subject). Methods of HSC transplantation are well known in the art (see, e.g., Bishop M R, Pavletic S Z. Hematopoietic stem cell transplantation. In: Abeloff M D, Armitage J O, Niederhuber J E, Kastan M B, McKena W G, eds. Clinical Oncology, 4th ed. Philadelphia, Pa.: Elsevier Churchill Livingstone; 2008:chap 32; and Vose J M. Pavletic S Z. Hematopoietic stem cell transplantation. In: Goldman L, Schafer A I. Cecil Medicine. 24th ed. Philadelphia, Pa.: Saunders Elsevier; 2011:chap 181).

In order to prepare a subject for HSC transplantation, the HSCs present in the subject may be removed or depleted so that the transplanted cells can become the dominant HSC population in the subject. HSCs in the subject may be depleted, for example, by treating the subject with a chemotherapy, radiation, or both in order to cause the HSC cells of the subject to undergo apoptosis or cell cycle arrest.

In allogeneic HSC transplantation, the HSCs are obtained from a donor. The donor is preferably a healthy subject, such as a subject that is apparently free of disease and has no history of disease, such as ALS or FTD. It is preferable that the donor is HLA-compatible with the subject receiving the transplant in order to reduce the risk of graft versus host disease. HLA-compatibility can be determined, e.g., using HLA typing. HLA typing generally involves examination of at least 8 HLA markers: two A, two B, two C, and two DRB1 markers, and optionally also two DQ markers. HLA typing can be accomplished, e.g., through a blood test. HLA allele identities can be determined using serology or a nucleic acid-based assay. Generally, a match of at least 4-6 markers between host and donor is preferred. In some embodiments, the donor is a subject that has 25 or fewer GGGGCC hexanucleotide repeats within a C9ORF72 gene.

HSCs can be obtained from a donor using any method known in the art. Exemplary methods include bone marrow harvest and leukapheresis (see, e.g., Transfusion. 2003 February; 43(2):259-64. Leukapheresis after high-dose chemotherapy and autologous peripheral blood progenitor cell transplantation: a novel approach to harvest a second autograft. Schwella N, Braun A, Ahrens N, Rick O, Salama A). In a bone marrow harvest, the bone marrow is typically removed from the back of one or both hip bones of the donor. Leukapheresis involves separation of HSCs from blood obtained from the donor using, e.g., continuous flow centrifugation or filtering. The growth factor G-CSF may be administered to the donor to stimulate the growth of new HSCs so that more HSCs are present in the blood. Once obtained, the allogeneic HSCs are then administered to the subject receiving the transplant. Any suitable method of administration known in the art is contemplated, e.g., by central venous catheter.

In some embodiments, during or after HSC transplantation, the subject receiving the HSC transplant may receive additional treatments and/or therapies, such as antibiotics, antifungals, antivirals, blood transfusions and/or immunosuppressive therapies. Such treatments and/or therapies may help to prevent infection and/or graft versus host disease during a HSC transplant recovery period.

In some embodiments, the HSC transplantation is bone marrow transplantation. In some embodiments, the bone marrow transplantation is an allogeneic bone marrow transplantation.

Plasmapheresis is a medical procedure that occurs outside the body (an "extracorporeal therapy") and refers to the removal, treatment, and return of (components of) blood plasma from blood circulation. Plasmapheresis is well-known in the art and has been used to treat several diseases including Goodpasture's syndrome, myasthenia gravis, Guillain-Barre syndrome, lupus, and thrombotic thrombocytopenic purpura (see, e.g., Madore, Plasmapheresis Technical aspects and indications, Crit Care Clin 18: 375-392. 2002). During plasmapheresis, blood is initially taken out of the body, e.g., through a needle or previously implanted catheter. Plasma is then separated from the blood cells, e.g., by using a cell separator. After plasma separation, the blood cells are combined with a replacement fluid and readministered to the subject. The replacement fluid may be either the separated plasma treated to remove disease-associated components or a replacement plasma (also called plasma exchange).

Exemplary procedures used to separate the plasma from the blood cells include:

1) Discontinuous flow centrifugation: One venous catheter line is used. Typically, one or more batches of blood are removed at a time and centrifuged to separate plasma from blood cells. The blood cells are then combined with the replacement fluid and returned to the subject.

2) Continuous flow centrifugation: Two venous lines are used. Plasma is continuously spun out of the blood and the separated blood cells are fed through a line that combines with a replacement fluid before return to the subject.

3) Plasma filtration: Two venous lines are used. The plasma is filtered using standard hemodialysis equipment, e.g., a parallel-plate or hollow-fiber filter. The separated blood cells are fed through a line that combines with a replacement fluid before return to the subject. The filters usually have pores of 0.2-0.6 µm diameter, sufficient to allow passage of plasma, while retaining cells. Several membrane plasma separators are commercially available (e.g., Plasmaflo from Asahi Medical Co., Ltd., Tokyo, Japan; Plasmax from Toray Industries, Tokyo, Japan; CPS-10 from Baxter. Deerfield, Ill., USA; Plasmaflux from Fresenius Medical Care AG, Bad Homburg, Germany; Prisma TPE 2000 from Hospal, Lyon, France).

If the separated plasma is to be used as the replacement fluid, the separated plasma is first treated to decrease the levels of di-amino acid repeat-containing proteins present in the separated plasma. In some embodiments, decreasing the levels of di-amino acid repeat-containing proteins present in the separated plasma comprises contacting the separated plasma with one or more isolated antibodies specific for a di-amino acid repeat-containing protein as described herein, whereby the di-amino acid repeat-containing proteins present in the separated plasma bind to the one or more isolated antibodies. In some embodiments, a binding partner for the one or more isolated antibodies is contacted with the separated plasma. A binding partner for the one or more isolated antibodies may be, for example, a capture moiety such as biotin or streptavidin, protein A, or a secondary antibody specific for the one or more isolated antibodies. Such binding partners allow for the one or more isolated antibodies to be removed from the separated plasma.

In some embodiments, the one or more isolated antibodies are attached to a filter, column, and/or solid support. In such embodiments, the separated plasma is contacted with the filter, column, and/or solid support, whereby the di-amino acid repeat-containing proteins bind to the isolated antibodies attached to the filter, column and/or solid support. Without wishing to be bound by theory, it is believed that the di-amino acid repeat-containing proteins may form aggregates in the blood. Accordingly, the di-amino acid repeat-containing proteins may be removed from the separated plasma using a filter, such that the aggregates are isolated from the separated plasma.

In some embodiments, a subject expressing one or more di-amino acid repeat-containing proteins may develop autoantibodies. In some embodiments, autoantibodies to one or more di-amino acid repeat-containing proteins may be removed from the separated plasma. Autoantibodies may be removed using any method known in the art, e.g., using a binding partner (e.g., bound to a solid support or attached to a tag) that recognizes the autoantibodies. In some embodiments, the binding partner may be one or more di-amino acid repeat-containing proteins as described herein.

If plasma exchange is to be used, the subject receives replacement plasma. Replacement plasma may be, e.g., donor plasma or a solution of albumin (e.g., 5-70% albumin in saline). An exemplary replacement plasma is 5% albumin combined with 0.9% saline in a 50%:50% (vol:vol) solution. Medication to keep the blood from clotting (e.g., an anticoagulant such as citrate, acid-citrate dextrose or heparin) may be given to the subject or contacted with the blood of the subject during the procedure.

In some embodiments, decreasing or preventing an increase of the level of one or more di-amino acid repeat-containing proteins comprises decreasing a level of a hexanucleotide repeat-containing RNA. Decreasing a level of a hexanucleotide repeat-containing RNA may comprise administration of an effective amount of an inhibitory nucleic acid molecule such as an shRNA, an siRNA, miRNA, or an antisense nucleic acid molecule that targets the hexanucleotide repeat-containing RNA.

Methods for producing shRNAs, siRNAs, miRNAs, and antisense nucleic acid molecules are well known in the art (see e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition). In some embodiments, a nucleic acid inhibitor comprises or corresponds to at least a portion of sequence of a target hexanucleotide repeat-containing RNA sequence or comprises at least a portion of a sequence complementary to a target hexanucleotide repeat-containing RNA sequence.

In some embodiments, treatment may comprise decreasing or stabilizing a level of an autoantibody to one or more di-amino acid repeat-containing proteins in a subject. A level of autoantibody may be decreased or stabilized using any method known in the art. In some embodiments, decreasing or stabilizing a level of an autoantibody comprises administration of an effective amount of atacicept, belimumab, blisibimod, BR3-Fe, rituximab, ocrelizumab, atumumab, epratuzumab, corticosteroid (e.g., prednisone), mycophenolic acid, methotrexate, cyclophosphamide, azathioprine, and/or cyclosporin. In some embodiments, decreasing or stabilizing a level of an autoantibody comprises plasmapheresis.

Antibodies Aspects of the disclosure relate to isolated antibodies specific for a di-amino acid repeat-containing protein (e.g., a RAN protein) selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. The isolated antibody may recognize a region or regions of the di-amino acid repeat-containing protein (such as a repeat sequence or the C-terminus) or may recognize the entire di-amino acid repeat-containing protein.

An antibody that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically binds to a poly-(Gly-Ala) protein or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically bind to a second target antigen. As such, "specific binding" does not necessarily require (although it can include) exclusive binding. Generally, but not necessarily, reference to binding means specific binding. In some embodiments, antibodies described herein have a suitable binding affinity to a di-amino acid repeat-containing protein (e.g., a RAN protein). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof: or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or 10 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2) at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[$N$][Free]/($Kd$+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the isolated antibody is specific for a di-amino acid repeat-containing protein selected from a poly-(Pro-Ala) poly-(Pro-Arg), Met . . . poly-(Pro-Arg) or Met . . . poly-(Gly-Pro) protein.

In some embodiments, the isolated antibody is specific for an antigen comprising a di-amino acid repeat and/or C-terminus sequence or fragment thereof as defined in Table 1. In some embodiments, the isolated antibody is specific for an antigen comprising a sequence or fragment of a sequence defined in Table 2.

In some embodiments, the isolated antibody is specific for an antigen in Table 3 or in FIG. 28. In some embodiments, an antigen in Table 3 does not contain an N- and/or C-terminal modification.

TABLE 3

Di-Amino Acid Repeat-Containing Protein Antigens

| di-amino acid repeat-containing protein | Label | Antigen | Antigen location in di-amino acid repeat-containing protein |
|---|---|---|---|
| Poly-(Gly-Arg) | GGGGCC F1 repeat | Ac-RGRGRGRGRGRGRGRC-amide (SEQ ID NO: 18) | Repeat sequence |
| Poly-(Pro-Arg) | GGGGCC-AS F2 repeat | Ac-RPRPRPRPRPRPRPRPRC-amide (SEQ ID NO: 19) | Repeat sequence |
| Poly-(Pro-Ala) | GGGGCC-AS F1 repeat | H2N-APAPAPAPAPAPAPAPACKKKK-amide (SEQ ID NO: 20) | Repeat sequence |
| Poly-(Gly-Pro) | GGGGCC F3 repeat | H2N-GPGPGPGPGPGPGPGPGCKK-amide (SEQ ID NO: 21) | Repeat sequence |
| Poly-(Gly-Pro) | GGGGCC F3 CT | Ac-CRRRRWRVGE-OH (SEQ ID NO: 22) | C-terminus |
| Poly-(Pro-Ala) | GGGGCC-AS F1 CT | Ac-CYRLRLFPSLFSSG-OH (SEQ ID NO: 23) | C-terminus |
| Poly-(Gly-Arg) | GGGGCC F1 CT | Ac-CRVAVWGSAAGKRRG-OH (SEQ ID NO: 24) | C-terminus |
| Poly-(Pro-Arg) | GGGGCC-AS F2 CT | Ac-CRPRPLARDS-OH (SEQ ID NO: 25) | C-terminus |
| Poly-(Gly-Ala) | GGGGCC F2 CT | Ac-CSGRARGRARGGA-amide (SEQ ID NO: 26) | C-terminus |

F1 = reading frame 1, F2 = reading frame 2, F3 = reading frame 3, AS F1 = anti-sense reading frame 1, AS F2 = anti-sense reading frame 2, AS F3 = anti-sense reading frame 3.

An isolated antibody may be a monoclonal or polyclonal antibody, or an antigen-binding fragment thereof. An antigen-binding fragment thereof includes, for example, an Fab, F(ab)2, F(ab')2, Fv, single chain antibody, Fab fragment, sFab fragment, Fd fragment, scFv, or dAb fragment. Methods for producing polyclonal and monoclonal antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Also encompassed are antibodies made by recombinant means such as chimeric antibodies (variable region and constant region derived from different species) and CDR-grafted antibodies (complementary determining region derived from a different species) as described in U.S. Pat. Nos. 4,816,567 and 5,225,539, which are incorporated herein by reference in their entirety. Also encompassed are humanized antibodies, typically produced by recombinant methods, wherein the human sequences comprise part or all of the antibody. Also included are fully human antibodies, such as those produced in genetically-altered mice (see PCT Application No. 93/12227, which is incorporated herein by reference in its entirety).

In some embodiments, an isolated antibody specific for a di-amino acid repeat-containing protein is a rabbit polyclonal antibody as listed in Table 4.

TABLE 4

Di-Amino Acid Repeat-Containing Protein
Rabbit Polyclonal Antibodies

| Antigen | Animal | Titer |
|---|---|---|
| GGGGCC F1 repeat | H3147 | 1,575,500 |
| GGGGCC F1 repeat | H3148 | 1,956,500 |
| GGGGCC-AS F2 repeat | H3149 | 2,399,600 |
| GGGGCC-AS F2 repeat | H3150 | 3,225,000 |
| GGGGCC-AS F1 repeat | H3151 | 660,200 |
| GGGGCC-AS F1 repeat | H3152 | 2,082,600 |
| GGGGCC F3 repeat | H3154 | 752,300 |
| GGGGCC F3 repeat | H3155 | 590,500 |
| GGGGCC F3 CT | H3156 | 231,300 |
| GGGGCC F3 CT | H3157 | 616,700 |
| GGGGCC-AS F1 CT | H3158 | 6,300 |
| GGGGCC-AS F1 CT | H3159 | 32,800 |
| GGGGCC F1 CT | H3160 | 573,900 |
| GGGGCC F1 CT | H3161 | 363,000 |
| GGGGCC-AS F2 CT | H3162 | 2,261,700 |
| GGGGCC-AS F2 CT | H3163 | 176,300 |
| GGGGCC F2 CT | H3164 | 1,549,500 |
| GGGGCC F2 CT | H3165 | 115,700 |

Antibodies may be produced in bacterial cells, e.g., *E. coli*, or eukaryotic cells, such as yeast cells or mammalian cells. In one embodiment, antibodies are produced in mammalian cells. Mammalian host cells for expressing the antibodies or antigen-binding fragments thereof include Chinese Hamster Ovary (CHO cells) (including dhfr– CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, and a cell from a transgenic animal, e.g., a transgenic mammal. Antibodies can also be produced by a transgenic animal. For example, U.S. Pat. No. 5,849,992 describes a method of expressing an antibody in the mammary gland of a transgenic mammal.

Isolated antibodies of the disclosure may also have a detectable label attached thereto. The label may be, for example, a fluorescent, enzymatic, affinity or isotopic label. Examples include fluorescein isothiocyanate (FITC) for detection by fluorescence, horseradish peroxidase which allows detection by cleavage of a chromogenic substrate, radioisotopes such as $I^{125}$ for detection by autoradiography and avidin/biotin for antibody detection and affinity purification of antigens and antigen-bearing cells.

Also encompassed by the disclosure are hybridoma cell lines producing a monoclonal antibody specific for a di-amino acid repeat-containing protein selected from a poly-(Gly-Ala), poly-(Gly-Pro), poly-(Gly-Arg), poly-(Pro-Ala), poly-(Pro-Arg) protein, Met . . . poly-(Pro-Arg), Met . . . poly-(Gly-Pro), a C-terminal peptide of a di-amino acid repeat-containing protein as described herein, and/or a combination of two or more thereof.

In some embodiments, an isolated antibody is an isolated auto-antibody obtained from a subject having ALS, wherein the isolated auto-antibody is specific for one or more di-amino acid repeat-containing proteins as described herein.

In some embodiments, an isolated antibody described herein is contained within a buffered solution. In some embodiments, an isolated antibody described herein is attached to a solid support (e.g., the surface of a plate or a bead).

Transgenic Mouse

In another aspect, the disclosure relates to a transgenic mouse comprising a human C9ORF72 gene comprising a GGGGCC hexanucleotide repeat sequence. In some embodiments, the mouse comprises a human C9ORF72 gene comprising a GGGGCC hexanucleotide repeat sequence and flanking human sequences on the 5' and 3' end of the human C9ORF72 gene. In some embodiments, the flanking human sequences on the 5' and 3' end are each independently at least 1 kilobases (kB), at least 5 kB, at least 10 kB, at least 20 kB, at least 30 kB, at least 40 kB, or at least 50 kB in length. In some embodiments, the flanking human sequences on the 5' and 3' end each independently comprise a promoter capable of driving transcription of the human C9ORF72 gene in the sense and anti-sense direction, respectively. Accordingly, in some embodiments, the transgenic mouse expresses both sense and anti-sense transcripts (e.g., 5'-GGGGCC-3' and 5'GGCCCC-3' hexanucleotide repeat-containing RNAs described herein). In some embodiments, the human C9ORF72 gene and flanking sequences comprise the sequence below, wherein $(GGGGCC)_n$ indicates the location of the GGGGCC hexanucleotide repeat sequence:

Chr9:27,527,137-27,625,470 (reverse complement)

(SEQ ID NO. 63)

AAGCTTGATAATATTATCAAATATTAGATAAATGTAATATTAGAAGAAAACTTTTTTGAAAAGATATATAAAAT
AATTTCATTCAAAATTTTTATATTTAATTTAAATTTTTAATGAAAATATATCTAAGTTTTGTACGCTTTAAATGT
AATTATGTTTGATAATTTAATCATTTACTATTCGTTCTCTATTGCTGCCCTAACAAATTACCATAGTTCAGTGGC
TTACAAAACACAAATTTATTATCTTACCATTCTGTGAGTCAAAATTCCAAAATAGGTGTCACTAGGCTAAAATGA
AGGACTGCATTTCTTCCTGCAGGCTCCAGGAGAGATCTATGTCTTACTCTTTTCGGCTTCTAAAGGCTGCCCACA
TTCCTCGACTAGTGGCGTCCCTCCTTCGTCTCTAAACCCAGCAACAACAGGTTGAGTCCTCATGTCACATCTTTC
TTACCTTTCTGTCATCTCATCTCGCTGACTGCTGCTGGGAAAAATTCTCCACTTTTAAGGGCTATCATGATTAGA
CTATGCCCACTAGATAATACAAGATCTCAGATCCTTAACTTCCATCACATCTGCAAAGTCGCTTTTGCCTCATAA
AAGAGTCTGAGGTTTAGACGGGAGATCTTAAGGGGGCTATTAATATGCCTACCATAATCACTGAGAATAAGTACA
AGTTAAGATTATAATAGCAATAGAATATACAAACGTGAAGCTCCAAAAGAACAACAACAACAAAAAGGTGAACA
GGAAAAAGAAACTGAAAATCTTTAAAAAGGCAGTCTGTTTAAATCTATAAAAACTGGAAAAAAATGAGAGTGGAC
AAATATCTGGTAAGCATGATGGACTTAAAATTTGTGACTAGGGCATTACATTTTTTATATTAATATAATGAAGAT
TGAATTACTGATCAAAACAATTAAAAAGCAAGAGAACTATTCTCATCAAATCTGCAACACGAAAAGTTCAGACAA
AATTCCAACAACTTCACATTCTGAACTAAATGAGGACTAATTACCAGTTCGAGCAATGAGAATATATGAGGTCCT
CCGTTTGCACTTTGCCAGGGATCTGAAAACGTTGGGAGTAGGTCGGCTTGACCGTGAAGGCAGACCATCGACAGC
CAGTTTTCCCTCCCTTCTCCACCCACAGGTCTTAGGCCCTCATCCTTCCCAGCCTCAGAACTAGTCTCCAAAGAA
GAGGAAAGTTAGAGGAGAGTAAATCGTTGAATAGGATGAAGGAGATGTGGGAAAAAGAAAAAGAGAGGCTGCA
AGAGAGAGGGTCCCAGGGATAACTCTGCTCTTGGAAGGGTGGCCACAGTCATGTGGTCCCAAGAGGCAACAACAA
GCTTAGGAAGCCAGAGAAACCAGTTACAATCACTGCTACTCTTTTCGATTCTGTGTTGTTTAAGAAATATCACCC
GCCAGGAGTTCTCCAGAAACATTTTCCCTGATTCCATGTAAGTGCTCAACCAGTGAATGGTAATCCCATTTTGGT
TTAGTCTGTACCATCCCCTATTCCCAAATAAAGGGAAAAATGGTGGGTTTATATCTTAAATTTTCTACTTTACTA
AACTCAAGGGAAATAGCCAAGCAAAAACGAAAGCTGAGACTCTTGCTAATTATCCTTTCCATAGAATGTTTGCTA
AAATTCCTTGTCAAGGAAGGAATAACAAAGCTAGTCCACGCTCTGTATAGGGTGTTTCCAATTAGTTATACTTTA
AAGTATAAGTATTTAACAAAATCTATAAATTTTGTTAATTATTTACTTGTAGTGAAAAATGAGCCATTCTCAAGC
AAATCACTTTTTATTACACATTCCAGAGAATAACCATAAAAGGACATTTATTATAGCAAAAATAACCACATCTGG
ATGGAACTTCAATCACCAGTATTTACTAAATAAATGCCCAGAAAAAAAATAGTTCATCTTTAATTTCAGTCATCA
TTAATAAAAGCTGAAGTACCTCTTCAGATCTTTTGATCATTTTCTGTTGGATTGTTTTCTTTTTACTGAGTTGCA
AATGCTCTTTATATATTTTGGATACAAAGCTTATCACATAGGCATTTTGCAAGTATTTTTTCCAAGTTTTTTTA
TCTTTTCATTTATTTAATAATATCTTTCAAAGAACGGGAATTTTATAATTTTTATGAAGTCCATTTATAATTTTT
TCTTTTATGGGTTGGTGGGGGTTGGGGGTTGTGTTGTCCTAAGAAATCTTGGCTCAAGAGAAAAAGATTAGTTTC
TATATTTTCTTCTAGAAGTTTTATAGTACGATCTCAGATCCATTTCAGATGATGAATAAGCACATAAAAAAAGGA
TACTCATCGTTAGTCATTAGAGAAATGCATATTAAAACCATAAGGAAATACTACTATATACATATATTAGATAGG
ATGAAGAGCAACTGGAATCTCATACAGTGCTGATTGAAATGCAAAATGGCAAAACAACTTTAGAAACCAATTTGG
AAGCAGCTGTACTGACATGGAATTTTGAGCTGGAAGAATCTTAGAAAAAGAATACTTTACGACCTCCCCCATTCT
CTTCACCCTGGGGAACTGTTAAATGAGGAAATTGTGGTTGAAGGAGGAACTTGTCTATATGCTTTCTCAGCTTTC
CCGTGGTAATTACCATCTTGATAATATAACGTAATGTATGTATATGTTATCAAATAATATAATATCTTCATCATA
TATTTATCATCTTCATAATGTTAGCTGTCTAGTGGTAACTTTTTTTTGCTCTTTATTGCCTCCCTCTTTTTTCCC
TCTTTGTTGTTTTTTGTCATACAATTATGATATATGTGTATATATTCTCACTGTAAAGATGTAAACAACACAAAG
ATTATTGAACAAATCACGAAAGTAACCCTTCCTTCATTCTTACCCTATCCAACCCTCATCTCCTCAGAAGAATAC
ACCATTTTAGTTGTAAATGTTTTTCTAGCTCTTTTTCAATGTTTCTACCTATATGCATGTATGTATAATGTATAT

-continued

```
ACATACATATATACATACATATTGATATATACATATATAGAGGTATGGTTTTTTAACTTAAATGGAATTGCATTG

TGGATATTGTCCTATGACTTGCTTTCAACCAAATTATATGTCTTGGAAATACATACATATATTTAAAAAATATGT

TATGTATATGTAACATACTATATGTGCATAATATATATTACATAGATATAATAAGGCCTAGGAAGAAATTGTGTG

CAACCTCTAGTACATCTTCCTCTATATCTACTGTACATACATACAACCCATTCTTTTTTTAATTTTTTTATTTTT

TTAGACAGAATCTTGCTCTGTCGCCCAGGCTGGAGTGCAGTGGCACAATCTCGGCTCACTGCAAGCTCCACCTCC

TGGGTTCACGCCATTCTCCTGCCTCAGCCTCCCAAGTAGCTGGGAATACAGGCACCTGCCATCAGGCCCAGCTAA

TTTTTTTTTGTATTTTTAGTACAGATGGGGTTTCACCGTGTTAGCCAGGATGGTCTCCATCTCCTGACCTCGTGA

TCCGCCCACCTCATCCTCCCAAAGTGCTGGGATTTACAGGCGTGAGCCACCGCGCCCAGCCACAACTCATTGCAG

AGTAGTCCAAAATATGGATGGACTGTAGCTTAATTACTTATTCTCCCATTGATAGACACTTAGGACTTTTCTAAT

TTTTATAATTTAAAAATATGCTGCAATTAACAAACATTCTTGTGTATCTTTTTGCTGTATGTATGCATATTTCTT

TAGTATGGGTTTTGGAAGAGGAATCACAAAGGAGGCATAGAATATAAATATTTTTATTTTGAAAAATACAGTTGT

AATTTAATAACCCACCAAAAGACTCTAACAGTTTAGATTCACATCAACAGTGTAAGAACATGTCTGTTTTACTGC

ATCCTTACCCCCACTGGTTATAATACTTTTAATTAACAATCTTATGGATGAAGAATACTATCGCAATGTTGTTTT

AATGCATTTTTCCAATTACTAGTGAGATTGAACATTAATTCTTTTATTTTATGGATCACTGGCTTTTCTCCTTCT

GTGAACTACCTGTTCACATCCTCTGCTTTTCAGCTCTTGAGCTGTTATCTTTTTCTTATTGATTTATATGAGCTC

TTTATATATTCAAGATGTTAATCATTTGTATTTTATGTATATGGCAATGATTTTCTTCCAAACCAATGCTTGTCT

TTTATTTATTTATTTATTTATTTATTTGAGACCGAGTCTCGCTCTGTCGCCCAGGCTGGAGTGCAGTGGCG

CGATCTCGGCTCACTGCAAGCTCCGCCTCCCGGGTTCACGCCATTCTCCTGCCTCAGCCTCCTGAGTAGGTGGGA

CTACAGGCGCCCGCTGCCACACCCGGCTAATTTTTTGTATTTTTAGTAGAGACAGGGTTTCACCGTGTTAGCCAG

GATGCTCTCTATCTCCTGACCTCGTGATCCGCCCGCCTCGGCCTTCCAAAGTGGTCGGATTACAGGCATGAGCCA

CCACGCCTGGCCAATGCTTGTCTTTTTATCTCTGTTTATGGCATCTTTCATACTATGGACATTTTTATTTTTATT

TTTTATGTTGATTTATTCTTGAATTGTATACATGTTAATTATACCTAAGTTATTGTAATACCCTTAAAGCCAAGT

TCTACACATATATTTAATTTGCTTTCCCAATAGGTCTCTGAGGGAACACATTTTTTCAAATCACTTTGTTTCATC

TTTTTTAGGTGTTGATCAATTATTAAGGAGTTTGAAATAATCATTTAAACGGAATTCTTCAGATGAAAACATAAA

GACATTTATCGGGTCAGAGCATTGGTCGGTTCACATACTCAGGATCAGTGGCCTGGGTGGGCAGGCACTGGGTGA

ATGGAGAGCTGCAGGTATTGGAAGAGAGCCCAGTTGGATATGTAGTTTCCAAAGATCATCAAGGCAGACAACCAA

AGGGAAACCGTGGGAAACACCTGCTTTGGGCCATCTAAGATGAGATGATAAAGTAAGGAAAGAGTTGAGCCCAAC

ACAGTGATAGCCAATCTGAAAGCGGGCAGAACTGACAAGACCAAACAAGTAGGTGAACTGGCTGCAGGCAGCCAG

CCACCACAGGGACAGCGTGTACTCCAGGGACAAGCTCAAGGCTATAGGTAGTTAGTTCAAGGCTACTAGGGTGAG

AAGAGCAGGAACTGAGTTCTATACCAGTGCTTCTCAAAACTAATGTGCATCCTAATCACCTGGAAATCTTGTAAA

AATGTAGATTCTGATTCAGTGAGTCTGAAGCAGAGCTTAAGATACTACATGCTTAACAAGAGCCTAGTTGATGCT

GACACTGCTGGTCCCTGGAGCTCTCTTTGAGTAGCAGGCTTCTGGAAGGCTTGTGTCACTAAGCACAGAGAAGCC

TCACTTATCAAATCTGCACCAAAACAGGAAAACTAATGTGAAGAATAATGTGATGCACACGTCAGAGCATGAGGC

AGTTGCTTTGTCCCTGAGGTTGCGCTCCAGATGGCTTCCTAAGATGCGACAGGCTGATCTTGTGCGTGGGGGTCC

CGGAGGCTTGGGCCACGGGAGAGACAGGACCTCAGAGGCTGGGAGACAGGCAGAGACAGAAGAGTGACATCCTGC

TGCTTTTGAATTTGCACATTCTGTAGAATAATAACAGCAGTAAACTGTTACACAATATCTATTCTCAGCATCTTG

AAGCCCTTTCACATATTGTTACTTCCATTAATGGGGCCCTTTGCTGCTATTTCTACTTTTCTCTTCAGCTATCAA

CAATATGGCTTTCCACACCTCCATCAGACAGTAGCCAGATGAAATAAAATGTGCCAGAATGAAAACTTGTTCATT

TGTCTACTTTTTGCCAAGACTAGACAGGCAGGAAATTGAATGTATTTTTACAGAAAAGGTTTTCAAAACTTTTTC

CCCTCTGTGGCTCATTTAGGTAAACTAAAAGGCATAAGACCCACCTAAAACATGGGTTCCCGCTTTTTATTGGAG
```

-continued

```
AAAGAACATAGTACTTTAAAAAAATACATAAAATAATAAAAAGGAAAGACAAAGATAATGAAGGTTGTACATGGT
ACCAAATTTTTGTATCCCATAATAACACATGAGTAGATCACTACTAAGTAGGTTTTAGTGACATATAGGAAACAT
TAAAATCTACAGAAATTTGCATTATTTTCTGTCAAAAAGGATCATTTCACAGCCTTTCAGGGGGAACCCATTGCC
CACAGGAACTCATGCATTCCATGCTTTGAGGATCACTAGATCTAAGAAGCCTTCCTTGGAGGTTCTAGCCTCCAA
CCCTTATTTTAGTAAAAGAAGCTCCAGTTTTATCTGTTTCTAAGTCAGACTACCACACAACATTGGGCTTAAAGA
AAGGTTTCCAGGGCTAAAGCAGACTTTGAGGATTACTAATTCCGAGTTAAATTTCTGTGTATTATCTCTGGATTT
GACTTATTCACACTGGACTATCACTCATAAATATACATAATACAGAGTTAACTATTTAAATTTATAAAGAGAGTA
TTTTCCTTTTTTATGAGCAAAACATGCTGCCAACTACTTGGACCACATACTGATCCATAAATACTGACAGCTTTG
TAATTGGAAATAATAAATACACACTAATGAAGCATCTCAAAAGGGAAGAGCCACAGGTAATCTGAGTGATTAGGC
ATTCATGTTAGGTTAGGCTTTGATCATTGTTTTTTATCGCAATTTCATTGCAGTGCATCTATAAATCCATGTCCA
GAAGTATGAAGTGGTTCTATAGTAAGAATAAGATGCTACAGATAATGCGACTAAATAAGACACTATAGGTAATGA
CACAGATTCAAGTCTTATTGTTGATGGGAAGAGGTCAATAATGGATGATATAATATACTACAGCAATGAGAATTA
TTGAATGTTTTCCAGACTCACTTGTATAATTGGCCATAACAGCAAACAAAAAACAGGTTCTGATAGCAAAATGAT
ATACAGTACTAACAAAGGTGAATCTTGAGGTGAACCTTCTCTTTATAAGTTTAAATAGTTTACCCCCGACCTTTT
CCCATAGTAGAACAGCCTAAAAAGTATCTTTCAGTAGAATGCTAGTGCTTATGAGGTTTTCTTAAGATATCATTT
TTCAATTAAAATTTATTTCACAAAAGACTCACATCCTTGCCAGCCTTCAGGGTGAGTGTTGATTCAGGCTGTGTC
CAACGGCAACGATGAGTGAACTTCTCACCCTCAGAATCACATGAGCATTCCTGAGATGTTTTATCAGAGTGATAC
CAACTTCATTATTAGAATATTGAGTCCCTATTTCCTATATTCAATGTCCTTTCAAGCCCTAACTTTGTCCGGGTT
GAAGGCAAAGATCCAAATAATCACATTTGTCTTTGATAACTGAAACTGGGAGAACTGGGACTGTCTCAAGAGTTC
TACGTGACTGTAGGTTGCAAGTACTGTGGTTGCATCTCCAAATATTAACCAATCCCAGTGACAATTCAATGGGGT
CTCCTGAACCATGATCCTCATGTCTCCAGTGAAGGAAATGGGCAAAGGGGATTCAAAAATCCCTTTTGGAGGAAT
AGGAAACTTCTGCTTTCCTTCATTTCATAACATTTGCGATGGAACAAAGGCTTTTTTAGAATGGAGCAACCAGAT
CCTTTTTTGGGGGAATCAGCTTAAATGTCCCTTCTTCTCATACTACTTTTATCTATGTGATCCTATTCTTTTCTG
TTGTGGATTGAATCATGTCCCTCAAAAAGATTGAATTTAGAGTGTGCTCTAAATTCAATGTGGAGAAATTTGGAC
ACAGAGGCAGACACACAGGGAGAACCCCGTGTGACAATGGAGGAAGAGGATGCATTTATGCTGCCACAAGCCAAG
GAACACCAAAGATTGTCAGCAGCCACCAGAAGCTAGGATAAAGGCATGGCACATCACTCCCTCTGAGCCCCCAAA
AGGAGCCAAGACTGCTAATACTCTGATCTCGGACTTCTGGCCTGAAACAGTGAGAGAATAAGGTTCTGTTGTTTC
AAGCTACCCAGCTTGCGGTATTTTGTCACAGAAGCACAAGGAATCAAGTACATTTTCTTTCTCAGCACTTGTGAT
AATTTGATTTTTTCTTTACTCAGTGGTTGTTTCACACCTATGTCCCCATCAGACTGTAAGCTTAAAGAGACCTGG
ATCTGGTCTGTCTTCACCACTGTTGATTCATTACCAGCACAGTGCCTGGCCCATGGTCACTGAATAAACGTTTGT
TGAGAGAATGAATGTGCTTAACCAGAAGTACTATTGACCTATTAGGCCAAGTTCAAGGTGCCTAACAGCTCAGCT
GTGAAGGATACCTCTCCTTTCAGTCCTCTGTTACATATGTCCCTGATAGATGTGTTATTTGTATCTCCTCCTGGC
CCTCAAGTTTGTTTGAGGGCAGGACCCTTTTTTGTATATCTGTAGAGCTTCGTAGTACCTAAATACTACTTTGCA
TATATAATAAAGTTTCGATAAATATTCATTAAATAAAGAAATAAATGAAATGACTAAGTTTTCTAAGATGTTACA
ACTAGATTGAAGATATTTAGCTCATTATTTAACAAGAAAACTATGGTTAATTATGGTGTCCTGTGTGAAAATGGT
TATAGTTTGTTTTTTAATTAATATAAGCATGTATGTGCATTATCAGTATACACAATTTGTGGTATGAGTGTTTTG
TGTCCCTGCACACAGACCACGGAAATCCTGAGAAACAAACTGCCACCCCAGAGCAGGTGCCTAACACAGAGACTT
TTAATCCTTAAAGTTTTTCTATAACTAAGCAATGTTTTTTCAAATGCAATAACACTGATATGCAGACATATTGAT
TGTCCACTCACAAAGCCATTCCTCAATATCATTACAACATGCCTCTTTGAATGTCATTAAAAATAGATGTCTCAT
TTTTCTAGGACAAGTTGGCTGAAGTTCTGCTTGAAAACTGGTAATAGAAAATACAATTTCTCAACCCGCTTTGGC
CTTTTAATTCTGTTCTACAACCTTGCCAGTTCACTTTCAAAGTCAAGGGATGCATCTTGCAAAACCATGACATCT
```

-continued

```
TTTGAGTAACTCCTTCTGTTCTTAACACATATTCCCAGGAGCTTAATAAATATTGTTTTTGCAACTTGTTTAGTG

GCAAAATAATGAGTCCTTGGTGTATGCTTATCCTCTGCTTTGCTATTAGAGAAGATATATTCAGACTGTTTTAAA

CAAATTAATTCAAGGGCAGGGAACAGTCCTAAAACCTGTTAAAATTCAAATACTTGGTCACTGTATGTGCAGCAT

GTGTGTTCTAGAAAGTCCTATTATTTTAAATATAAATTGAATCTTGTTGAGAAATTAATGTCATATGAATATAT

TAATAACTGAAATGCTGCCAAGTTTACAAAAAGCCCTCAATGTAACTGTGACCTTGTATAGACAAGGGCCTGTGG

AGGGACATTTTTAAACCATCTCTTTTTTTATTTCCTCATGAGATCTACAATGTAAGTGCATTAAAGTTGATGAAT

GAATTGCAGTGCAACTTTTCCTGCCTCTTTTGCCTTTCATTTGTCTATATTTCAAGCTTCACTGAAGTGATAGAT

TTTGGGCTTTGCCACATTGTCCTCTGATTGCTTCCCTCTGCTCCTCCTTTTCCTAGTGAATCTTTGTTTTACTGG

TGGAAAAATCTACATCTTTGTATCTTGGCATTTTACTTTCACATTATCTCATAGATTTTATTTCAAGTTGCTATA

AAGTTATCAACTTTTATTTTTAACTAATATTATTTTTAACAATTAGAAAATTGTTGACCAGGTAATTCCAGCACT

TTGGGAAGCTGAAGCGGGAGGATCACGTGAGCCCAGGAGCTCGAGACCAGCCTGGGCAATGCAAGGAGACTGTCT

CTACAAAATATAAAAATACATTAGCCAGGTTTGGCGGTGCATGCCTGGGTCCAGCTATTCAGGAAGCTGAGGTG

GGAGGATCACTTGAGCTGGAGAGGTTGAGGCTGCAGTGAGCAGTGATCGCACCACTGCACTCCAGTCTGGGTGAC

AGAGGGAGACCCTATCTCGAAAAAAAGGAAAAGAAGAGGATTTTGCTGGCAAGATGGCTGAATAGGAATAGCTCC

GTTCTGCAGCTCCCAGTGAGATCAATGCAGAAGGCAGGTGATTTCTGCATTTCCAACAGAGGTACCTGGTTCATC

TCACTGGGACTGGTTGGACGGTGGGTGCAGCCCATGGAGGGTGAGCAGAAGTAGGGTGGGCGTTGCCTCACTCA

GGAAGTGCAAGGGGTCCCTCTTCTAGCCAAGTGAAGCCGTCAGGGACTGTGCCATAAGAACAGTGCACTCTGGTC

CAGGCTTTTCCCACAGTCTTTGCAACCCACAGACCAGGAGATAACAAGCGGTGCCTATGCCACCAGGGCCCGGGG

TTTCAAGCACAAAACTGGGTGGCCATTTGGGCAGACATCAAGCTAGCTGCAGGAGTTTTTATTTTCATACCCCAG

TGGTGCCTGGAACGCCAGTGAGACAGAACCGTTCACTCCCCTGGATAAGGGGCAGAATCCAGGGAGCCAAGTGGT

CTGGCTTGGCGGGTCCCACACCCACGGCGCCCAGCAAGCTAAGATCCACTGGCTTGAAACTCTCGCTTCCAGCAC

AGCAGTCTGAGGTCCACCTGAGACGCCCGGGCTTGGTGTGGGGAGGGGCATCCACCATTGCTGAGGCTTGAGTAG

GCGGTTTTACCCTCACGGTGTAAACAAAGCTGCCTGGAAGGTCCAGCTGGGCACAGGCCACCACAGCTCACCAAG

GCCGCTGTGGCCAGAGTGCCCCTCTGGATTCCTCCTCTCTGGGCAAGGCATCTCTGAAAAAAAGGCAGCAGCGCC

AGTCAGAGACTTATAGATAAAACCCCCATCACCCTGGGAGAGAGCACCTCAGGGAAGGAGTGGCTGTGGGTGCAG

TTTCAGCAGATTTAAACGTTCCTGCCTGACAGCTCTGAGAGAGCAACAGATCTCCCAGCACAGCGTTCAAGCTCT

GTTAAAGATCAGACTGCCTCCTCAAGTGGGTCCCTGACTCCCATGTCTCCTGATTGAGAGACACCTCCCAGTAGG

GGCTGACAAACACCTCATAAAGGAGAGGTCCAGCTGGCATCTGGCAGGTGCCCCTCTGGGACGAAGCTTCCAGAG

GAAGGAACAGGCAGCAATCTTTGCTGTTCTGCAGTCTCAGCTGATGATACCCAGTCAAACAGGTCCTGGAGTGGA

CCTCCAGCAAACTCCAGCAGACCTGCAGCAGAGGGGCCTGACCGTTAGAAGGAAAATTAACAAATAGAAAGGAAT

AGTATCAACATCAACAAAAAGGACGTCCACTCAGAGACCCCATCCAAAGTCACCAACATCAAAGACCAAAGGTA

GATAAATCCACAAAGATGGGGAGAAACCAGTGCAAAAAGTCTGAAAATTCCAAAAACCAGAACGCCTCTTCTCC

TCCAAAGAATCACCACTCCTCACTAGCAAGGTAACAAAACTGGAGAGAGAATGAGTTTGACAAATTCACAGAATT

AGTGTTCAGAAGGTGGGCAATAACAAACTCCTCCAAGCTAAGGGAGCATGCAAGGAAGCTAAGAACCTTGAAAAA

AGTTAGAGCAATTGCTAACTAGAATAACCAGTTTAGAGAAGAACATAAATGACCTGATGGAGCTGAAAAACACAG

CACGAGAACTTTGTGAAGCATACACAAGTATCAATAGCCAAATCGATCACGTGGAAGAAAGGATATCAGAGATTA

AAGATCAACTTAATGAAATAAATTGAGAAGACAAGATTAGAGAAAAAAGAATGAAAGGAATGAACAAAGCCTCC

AAGCAATATAGGACTATGTGAAAAGACCAAATCTATGTTTGACTGGTGTACCAGAAAGTGACGGGGAGCATGGAA

CCAAGCTGGAAAACACTCTTCAGGATATTATCCAGGAGAACGTCCCCAACCTAGCAAAACAGGCCAACATTTAAA

TTCAAGAAATACAGACAACACCACAAAGATACTCCTCGAGAAGACCAACCCCAAGACACATAATCGTCAGATTCA
```

-continued

```
CCAAGGTTGAAATGAAGAAAAAAATGTTAAGGGCAGCCAGAGAGAAAGGTCAGGTTACCCACAAAGGAAGCCCAT

CAGACTAACAGCAGATCTCTCTGCAGAAACCCTACAAGCCAGAAGAGAGTGGGGGCCAATATTCAACATTTTTAA

AGAAAAGAATTTTCAACCCAGAATTTCATGTCCAGCCAAACTAAGCTTCATAAGTGAAGGAGAAATAAAATCCTT

TACAGACAACCAAATGCTGAGAGATTTTGTCAACAGCAAGCGTGCCTTACAAGAGCTCCTGAAGGAAGCACTAAA

CGTGGAAAGGAACAATCGGTACCAGCCACTGCAAAAGCACACCAAATTTTAAAGTCCATTGACACTATGAAAAAA

CTGCATCAACTAACAGGCAAAATAACCAGCTAGCATCATAATGACAGGATCAAATTAACCTTAATTAAGTTAGCC

TTAAATGTAAACGGGCTAAATGCCCCAGTTAAAAGACACAGACTGGCCACCTGTATAAAGAGTAAAGACCCATCA

GTGTGCTATATTCAGGAGACCCATCTCACATGAAAAGACACACATAGGCTCAAAATAAAGGGATGGAGGAATATT

TACTAAGCAAATGGGAAGCAAAGAAAACAAAAAGCAGGGGTTGCAATCCTAGTCTCTGATAAAACAGACTTTAAA

CCAACAAAGATCAAAATAGACAAACAAGGGCATTACATAATGGTAAAGGGATCAATGCAACAAGAACAGCTAACT

ATCCTAAATATATATGCACCCAATACAGGAGCACCCAGATTCATAAAGCAAGTTCTTAGAGACCTACAAAGAGAC

TTAGACTCCCACACAATAATAATGGGAGACTTTAACACTCCACTGTCAATATTAGACAGATCAATGAGATAGGAA

ATTAACAAGGATACTCAGGACTTGAACTCAGTTCTGGATCAAGTGGTCCTAATAGATACCTACAGAACTCTCCAC

CCCAAATCAACAGAATTTACATTCTTCTCAGCACCATCGCACTTATTCTAAAATTCACCACATAGTTGGAAGT

AAAACACTCCTCAGCAAATGCAAAAGAACGGAAATCATAACAGTCTCTTAGACCACAGTGCAGTCAAATTAGAAC

TCAGGATTAAGAAACTCACTCAAAACCGCACAACTACATGGAAACTGAACCTGTTCCTGAATGACTACTGGGTAA

ATAATGAAATGAAGGGCAAAATAAAGAAGTTCTTTGAAACCAATGACAACAAACACACAATGTACCAGAATCTCT

GGGACACATTTAAAGCAGTGTTAAGAGGGAAATTTATAGCACTAGATGCCCAAAAAAGAAAGCAGAAAAGATCTA

AAATCGACACCCTAGCATCACAATTAAAAGAACTAGAGAAGCAAGAGCAAACAAATTCAAAAGCTAGCAGAAGAC

AATAAATAAGATCAGAGCAGAACTGAAGAGGAGAGAGACATGAAAAACCCTTCAAAAAAATCAATGAATCCAGGA

GCTGGTTTTTTGAAGAGATTGACAAAACAGATAGACCACTAGCCAGACAATAAAGAAGGAGAGAAGAATCAAATA

GATGCAATAAAAAATGATAAAGGGGGTATCACCACTGATCCCACAGAAATACAAACTACCATCAGAGAGAATACT

ATAAACAACTACACAAATAAACTAGAAAATCTAGAAGAAATGGATAAATTCCTGGACACATACACCCTCCCAAGT

CTAAACCAGGAAGAAGTTGAATCCCTGAATAGACCAATAACAAGTTCTGAAATTCAGGTAGTAATTAATAGCCTA

CCAACCAAAAAAGTCCAGGACCAGACAGATTCACAGCCGAATTCTATCAGAGGTACAAACAGGAGCTGGTACCA

TTCCTTCTGAAACTATTCCAATAGAAAAGAGGGAATCCTCCCTAACTGATTGTATGAAGCCAGCATCATCGTGA

TACCAAAACCTGGCAGAGACACAACAAAAAAAAGAAATTTTCAGGCCAATATCCCTGATGAACATTGATGCGAAA

ATCCTCAATAAAATACTGGCAAGCGGAATCCAGCAGCGCATCAAAAAGCTTATCCGCCAGGATCAAGTCGGCTTC

ATCTCTGGGATGCAAGGCTGGTTCAACATACGCAAATCAATAAACCATCATTCTCAGCAAATTATCACAAGAACA

GAAAACCAAACACCGCATGTTCTCACTCATAAGAGGGAGTTGAACAATGAGAACACGTGGACCCAAGGAGGGGAA

CATCACATACTGCGGCCTGTCGAGGGATTTGGGGTTGAGGGAGTGATAGCATTAGGAGAAATACCTAATGTAGGT

AACAGGTTGATGGGTGCAGCAAACCACAATGCGATGTGTATACCTACCTAACAAACCTGCACGTTCTGCACATGC

ACTCCAGAACTTAAAGTATAATAATAAAAGGCGCTGCCTCAGGATGTAAAGTGTAACAAGGGGGCTGGGGTGGGC

AGCGTGGGCCTCTGAGACCTTTGGTTGCCCGTGTCCGCAGCTCGCCCCGCAGCCGGCTCCACAATGGTCCGCTCC

GTTTGCCACGTGCGGATTCGGGTTCCAGACTGAAGGCTGCGTGTTCTCTGCCGCCCACAGCCCAAGTTTATTGTG

GCAACCGCCGGAGCAGCCTTCCCCGCTGTGGAGGAGCCTGGGGCTACCCCTCAGCGGTATTTGGGGCTGGTCCTG

GGGGAGCTAAGCAGGGTTGTGGCAGCACTGCCTGAAAGTGTGAGACCAGACTCTAATCCTTATGGTTTTCCATGG

GAGTTGGTGATATGTGCAGCTGTACATGGATTTTTTGCTGTTCTCTTTTTTGTGTGGAGAAGTTTTAGATCGGT

TGGGAGTCGGCTTTATGTGGGAAGAGAAAAAAGCTTGCTGTAATGCTTTCTGGACTAATTGAAGAAAAGCATAA

ACTACTTGAAAAATTTAGCCATGTTCAAAAAGAGTATGAAGGCTATGAAGTAGAGTCATCTTTAAAGAATGCCAG

CTTTGAGAAGGAGGCAACCTGTGAAAAGCTAAACAGGTCCAATTCTGAACTTGAGGATGAAATACTCTGTCTAGA
```

-continued

```
AAAAGAGTTAAAATAAGAGAAATCTAAACATTCTGAACAAGGTGAATTGATGGTGGATATTTGCAAAAGGATACA

GTCTCTAGAAGATGAGTCAAAATCCCTCAAATGACAAGTAGCTGAAGCCAAAATGAACTTGACGATATTTCAAAT

GAATGAAGAACGACTGAAGATAGCAATAAAAGATGCTTTGAATGAAAATTCTCAACTCCAGGAAAACGAGAGACA

GCTTTTGCAAGAAGCTGAGGTATGGAAAGAACAAGTGAGTGAACTTAATAAACAGAAAATAACATTTGAAGACTC

CAAAGTACATGCAGAACAAGTTCTAAATGATAAAGAAAATCACATCAAGACTCTGAACGCTTGCTAAAAATGAAA

GATCAGGCTGCTATGCTTGGAGAAGACATAACGGATGATGGTAACTTGGAATTAGAAATGAAGAGTGAATCGGAA

AATGGTGCTTACTTAGATAATCCTCCGAAAGGAGCTCTGAAGAAACTGATTTATGCTGCTAAGTTAAATGCTTCT

TTAAAAACCTTACAAGGAGAAAGAAACCAAATTTATAGTCAGTTATCTGAAGTTGATAAAGGAAGAGCTTACAGA

GCATATTAAAAATCTTCAGACTGAACAAGCATCTTTGCAGTCAGAAAACACACATTTTGAAAGTGAGAATCAGAA

GCTTCAACAAAAACTTAAAGTAATGATTGAATTTTATCAAGAAAATGAAATGAAACTCCAGAGGAAATTAACAGT

AGATGAAATTACCGGTTAGAAAAGGAAGAAAAACTTTCTAAAGTACACGAAAAGATCAGCCGTGCCACTGAAGAG

TTGGAGACCTATAGAAAGTGAGCCAAAGATCTTGAAGAAGAGTTGGCGAGAACTATTCATTCTTATCAAGGATGG

ATTATTTCCCACGAGAAAAAAGCACATAATAATTGGTTGGCAGCTTGGACTGCTGAAAGAAACCTCAATGGTTTA

AGGAAAGAAAGTGCTCACAACAGACAAAAATTAACTGAAGCAGAGTTTAAATTTGAACTTTTAGAAAAAGATCCT

TATGCACTTCATGTTCCAAATACAGCATTTGGCAGAGAGCATTCCCCATATGGTCCCTCACCACTGGGTCGGCCT

TCATCCTAAACAAGAGCTTTTCTCTGAGGGCCCACTGAGACTCTCATCTTTGCTAACAGGAGGAGGAGGAAGAGG

CTCAAGAGGTCCAGGGAATCCTCTGGACCATCAGATTACCAATGAAAGAGGAGAATCAAGATGTGACAGGTTAAC

CAATCCTCACAGGGCTTCTCTGACACTGGGTCCCTGTCACCTCCATGGGAACAGGACCGTAGGATGATGTTTCTT

CCACCAGGACAATCATATCCTGATTCAGCTCTTCCTCCACAAAGGCAAGACAGATTTTATTCTAATTCTGGCACA

CTGTCTGGACCAGCAGAACTCAGAAGGTTTAATATGACTTCTTTGGATAAAGTGGATGGGTCAATGCTTTCAGAA

ATGGAATCCAGCAGAAATGATACCAAAGATGACCTTGGTAATTTAAATGTGCCTGATTCATCTCTCCCTGCTGAA

AATGAAGCAACTGGCCCTTACTTTTCTCCTCCACCTCTTGCTCCAATCAGAGGTCCATTGTTTCCGGGGGATACA

AGGAGCCTGTTCATGAGAAGAGGACCTCCTTTCCCCCCACCTCCTCCAGGAACCATGTTTGGAGCTTCTCAAGAT

TATTTTCCACCAAGGGATTTCCCAGATCCACCACATGCTCCATTTGCAATGAGAAATGTCTATCCAGCGAGGCGT

TTCCTCCTTACCTTCCCCCAAAACCTGGATTTTTCCCCATAAACCCCACATTCTGAAGGTAGAAGTGAGTTCCCT

GCAGGGCTGATTCTGCCTTCAAATGAGCCTGCTACTGAACATCCAGAACCACAGCAAGAAACCTGACAATATTTT

TGCTCTCTTCAAAAGTAATTTTGACTGATCTCATTTTCAGTTTAAGTAACTGCTGTTACTTAAGTGATTACACTT

TTGCTCCCACTGAAGCTTAATGGAATTATAATTCTCAGGATAGTGTTTTCTAAATAAAGATGATTTAAATATGAA

TCTTATGAGTAAATTATTTCCATTTTATGTTATTCTGGATAGTATAACTATTTTAATTTGATAAACTAATCCACG

ATTATATAAACAATAATGGGAGTTTTATATATGTAATCTTGCAGGTAGGGAGGCTTTAAATTATAAAGGTTGTGT

CTTTATGCCAAGAACTGTATTAACTGTGGTGTAGACAAATGTGAAAGTAATTTTATGCTTCATTAAATAAATTT

TAGTTGATTTTTTTTAAAAAAAGAAAATGGTTAATCTATCATTTAGGTGCATCATCAGTTGTTTAACCATTCTC

TCTTACTGAACATTGGGTTGTTTAAAAAGTGTTGTTATTTTTGAATCATGGTTCAGTGAACAATTTTGGACACAT

AACTTTTTATCTGATGAGTTATTTCCTAAGGATCCAGCTCAGAAACTCAGCACATAAACCTAATAAGAAAAAAAC

AATTTGAAGTGGCTAACCTCTTATCCCAATAAAAATGTTGTATTTATGTTTGGATTTAGATGCCTTTCAGTGGTC

ATACCTTCACCTAACTTTTATGGATTCTACTTTTAACATGTAGAGTGACTGTTTAAATCACCTAAACTCACTGAG

TTTTAAGTTCCTTTTTATTCAACAAGACTGGATTGTATGTTCCAGCTCCTCAAACTTAGTTACCAACCACCATCC

TAGAGAAGTGAATTCACATGAGGCCTGTCCAGAAGAACAATCTCCCTTTCAGTGTCCTCATGCATGCAGTGACCA

GAGACCAACCTTGATAAATTATGGAAAAGTACAGCACATTCTGGAAGAGCCATGAAAGATCCAGATCATCTGGT

GCTGGATAAGAATATTAATGGACAGGCTGGGCGCGGTGGCTCACGCCTGTAATCCTAGCACTTTGGGAGGCCGAG
```

-continued

```
GCGGGCGGAACATGAGGTCAGGAGATCGAGACCATCCTGGCTAACACGGTGAAACCCCGTCTCTACTGAAAATAC
AAAAAATTAGCCGGGCATGGTGGCGGGCGCCTGTAGTCCCAGCTACACGAGAGGCTGAGGCAGGAGAATGGCGTG
AACCCGGGAGGCAGAGCTTGTAGTGAGCCCAGATGGCGCCATTGCACTTCAGCCTGGGCGACAGAGTGAGACTCC
GTTTCAAAAAAAAAAAAAAAAGAATATTAATGGACAAAAAGATTAATGAAAGAACATATTGAAGCATCCAATTAC
CTGGTGTCTGCTCAAATGAGGAATCGGTGAGATAGGTCAGTTAGCAGTCAAGATTTATAAAAGAGACGATGGCCT
TGGGAGGGGCTGCCCTACTCGACTTTTTAATGGCTAGAAGCTATTAAGGGCTAAGCCAGAACCCTTCAGTATGGT
TCAGTGAGGATCCCAATTTGGGGTCCAAAAGTAAATGACAACTCCCAGGAACCATTAAGAATAAAAATCATGGAG
CATTACTGAGAATTTATGTTATCTAAGTCTGAGGAAAATTAATGTTAAGGAAGCTTTCAAAAGTCTAATATTTAC
ACCGAATTCCAGGGCACCATGCTCTAAGACAAAGCACTCTGGTCCTGCCCCTCTCCTTTCCTCATGTTTTTTGGT
TCTTGGGATCCTTAAGGGTCAATGTTATTCTTAAAATACAGAGCATCCTGGAAACTAAAAAAGTGGAAGATATTC
AAATTCTAATGAATGTACTGGCAGTATTGTAGATCATGGAGTATAACATAAAGACAAGAATCCCTAGCCTCTTCC
ACCATACTTTGTAATGGTAAGGAGAAAGGATAGAATTTTGAGAAGTCTGGGAAGACAATGTATGATAACATCTGG
AGAAGCTCTGCATAAGTTACTTTTGTTCAGGCTTAAGAAAAATTCTAGCTTGCCCCTGCACTGTCATCAGGTATC
ATGAAAGTAAATAAAACCTTTAAAGATTCTTCAAGCCAGCAGACTTCTATCTTCTCTATACTATCCTGTGATCCT
AAACTCTTAACAGTTACTACGTATAATTTCCCTACATTTGCTACTAGTATTTTATCATACACAATATTACACTCA
ATATTTCAAAAGTGGATGATTCATCTCCCGAAGAGACTGCAAAATTCATGAGTTAAGATTTGAGAATACTATTTT
AGACAAGATTTAGTCAGATTTTAGAGAGTTAGAAACCTGTAACAATTCTCTAACAATACTGCTTCTCCTTTTGTG
TATTAAGGAATTTTTGTCTATCAAAGATAGTACGAGGTAGACCAGAAGATAACTTGCCTTCAAAATGTCTGGAAT
GTAAAATGGCAACAGTAGTATTTGGGGACTTCGTAGGGGATGGCCAATATACACCCATTCTTAGAGGTACTGATG
ATATAATGTATAAGACAAAATCAAGTGGTCTCCATCACCATATAATGTTTAAAATGGCAAAGAGGGAGCAGAACA
AACACCCTTTGCAAATCTCTTCATAGAATCTACCGTAATAAACTTGTACTTGCTTAAAGTGTGTCTCTTCAGTGG
TCTTATTACCACTACTTTGGGGAAAATGAGGCTGCTTAAAAGATTAACAGACATTACATTTTACATATCTGTGGC
AGAGAAAACACTATGTATTCACCAAACCACTTCTTTTCCTTCCCAGTCACTCGGGAAGAGGTCATTTCTTTGTCC
CCTTTCATCTAATTGAGGTGCCGTGACTACTTCTAGACAGGCAATGTGAGCAGAAGGTATGCACGCCACGTATAG
GCCTGGTCTTCAAAAATCCCTCAGATATGATCTTCTTCTCGTCTCTTTCATGGACAAACTACAGGCCATGTAA
TAAGGATGGTGGGGTTCCAAACTGAAAGAGCCTGGATTTCTGATTTACTGTTTTGAGAAGAGTTCACCAGGGAAA
CAGCCTGGAAATACGCACAGGAAAATATGCACAGGACCCTGTGTGAGCAAGATATAAAGATCTATTACATGGTGC
CATTAAGGTGAGAGTATTGTGCTTATAGTATCCAGCATTAATTATCCTCACTACTACAACTTCTTTGTATCCATC
ATGTGGAAAAGTAGAGTATTTAATAAATGATTATTGAGTTTATTACCTTTTTTATATTCCAATCATTGCTAATTG
TACGTTACCTCATTTCAAGGTAAAGGTGACCAAGGGCTAAAGCAGTGCTATCCAAACCAAGCCAGACATCAAAAT
CACACAAAACCTTTTGAAAATACAACTTTGAAGATGCCATTCACATAGATATTTATTCAGTGGGTTTTCAAATGG
AACCCTGGAATCTACAGTCTTTAACAAGGCTTCCCAAGTTATTCTGATATACAGCAGGCAAATCTGAGAACCACT
GGACAAGAAGAAATAAAGGCTATATCTTTCGACAACAAAGACAATGCCTTAAACATAGAATGTATTCAATTAAA
GCTTGTAGAAAGATAGGTTTGTGAACAGGCACAGGGACTAGCCTCGAGCAAATTAATAAGGGCAGCAATGTTTTT
CACTGAAACCATTATTCCCCCTATTTTATTTCTTCTGGGGCTCTGTGTTTCCTTTCTCCTATCAAAATCCATTCT
AAGGTTGGAGGTTGGGGGTATCTCTTGCCTACTCCATACAGCAAGGAATAAAATTAGTATTTCTCGAACTATCTG
TGACAGCAGACCCATTGTAGGCCAGTACTTTTGTAAAATGCAATAAAAATTAACTTCTAGAGAATGAAATTTTAA
AATCACAGACATTCAAAATACAAATTCCAATTTTTTTATTATTAACTGTAAGAAATTTAAAATTAAATCTCAATA
AATAAAATTAAAGCAAACATAAGATAGAAAAAAATAAGCATTATGGATTGGCCCAGTCTGCAAACTGTATACACT
TTGCCAAACATGGGCATAAATTACTAAGAAGCAAAATCTTCCATCTGTAAACATTTCCATTTCCATTGACAATAT
GTGTGAGGGAAAGGAGGGATGCTTCTGTTTTAGAATGCCAGGCGTCAGCTAACAAGTGAGAAATACGTATTGAGA
```

-continued

```
CTGAGATCTCCCCAGCCTCTCAGTAGTCAGCAAGAACATGTTGAGGCCTCTGTTTTTGACTAAAAAATTGGCCAG

TGCATGGGCAACATGCATAGGTCCTGAATGAAAAAAATAGCAGCAGCAGAAATTTAAAAGAATTTTCACAGCTAG

GCCACAGTAAATTCTCAAGCCCTTCATGAGAAGCCACTGTGGGGCCTCATTTATGCCTTTGTTTTTATTAAATTG

GATGTGATCTTAAGATTCTTCTGTCAAAATTCCACTAGCATGTGAAGGCACCAAAAGTTTAAAATGTAAAATTAA

CCCAAGTTAAGCTATTCCATTATTAAGCAATAGCAGATATATTTGTTATTATATGAGAAGAAAGTTAACAGGGAG

CTAAGATTGATGTTACTGATAAGAAACAGAAACAAGACTTTAAAATTAAATAAATGAATTATTTATTTAATAAGA

ACCAATTGACAGATTCTCGATAAAGACTGTAAGATGTCTTAAAACATTAGGTGTATGGAGATAACATTTGTAACT

TTGACAATTTATATGATGAGAAAAATCAAGGAATGTTATTGTTTATTGGCAGAGTTCTAGAATTACAATTCCATC

ATTCTGTTTTGGGGAAGTTTCCCTTGAAGTAAATGATAACAGGGCTTGAAATAGTACACCTCAGCATTTTGTTTA

TAAAACTGTGGAATAGGTAAGGTTTGTATTGTAACTGAACCCAGGTTCAGCTGCTTGCTGCTCTAAAGCTAGACA

TAAGAGAGGAAGGTTGGTGGGAGGAAAAGCGATTTTAATCGGAGAAGCAGCAAACCAAGAAGATGGTGAACAATA

TGCACAGAACCATCTTAAATTTTAAAATTTACCATAGAGTGTTCAAAGGAAAACTTGGTATGGGAGGCATGCAGG

AGGGGTGCAGGGGGCGGGTCTGTGTGTCTTGTTCCAATGGCTATCTGAGATAGTGACCCATCTGGAGGTCTAGT

TGGTATTATTTTGAATTCAGCCCAGTGGTGGTGGACTGTCAGTGACTCCTCGCTAAGCAGGAGGATTCTGCACTC

AGGGCTCCATGCATGGTTTGTTTCAAGATTGGCCTCTGGAATTTCTCAAGCAAGAACATAATTAAATAAGCAGGC

ATTGCCAGAGGGGAGTGTCTGGAAAGGAAAGGAATGAAGAGATGAAAGGAAAGTGGGTGGTTAAACTATATTTTT

AAAACTGAGGTTCCCAGTTATAGTATGTTTCGCACGCTCCCCCCATTTTAGCACCCCTGACAGAATTTAGTAATC

TCCTCATCTTGTCCTCTACTTGAGGTCCCCTATCTGTCCTTGTACTCTCCAGGGTTTCCTTTTCTTCTTCACGAC

CTTCCTTCCCTGCAATTTTATAAGCTATTCCTATCCCAGTGATTTAGTTTCAGCTTATAAAACTGTGTCTTTGCC

ATTGTAATCAAATTGAAGGGCCTCTGCTTCATGGTTGGATTCTGTGACCAGGAGACTCTTACGAGGAGTTGGCCA

GGTCTCTGTTAGGAAAGCAAAAAGAACAATGGAGGCAATTATCCCATTGATTTCAGCTATAAATCCTATTTTGC

CTGAATTGTCTGAACGATGAGTATTCTGTGAAAATGCTGCTCTCTAGTGCAATAGAACTGCAAATAATGCACATC

TATTTCTTATAATCTCATCCAACATACCCACAGAGATTCAGATCTAACAAAACAGAGGTGATTTGGTTATTGAAT

CATAATATAAATATGGGGAAGAGGAGGGAAATTTCAAGCCTGAGGAAACTGTAGTAGGAGTAAGTATGCTGTGTT

TAAGAGGTCACAGATAAAATTAATATTACCAATCCATCAATAGGCAATTACTAATAGCTTACTACACACACAGGA

ATAAAATGTGAAGACAGAGGAAGTGTAAAATGGAGCCGCCAACTCTACGGAGTTGTTTGCAATTTGGTCTGGTAG

AAAGCTATGAAATAAGGAAGTACATGATTGAGAGCTAGAGAATGTGGCACAGGCTCTGAACCCGGACCGTTCAAT

GTAGTAAGGTCTAGCCACACTGGAGACTTGCAATGTGGCTTGTCCAAACTGACATGTGCTTTAAGTATAAAATAT

AATCCAGATTTCTAAGACTTCAAAAAAATGGAAATATCTCATTAATAATCTTAAGTTTATTACAGGTAGAAATG

ATAGATTAAATAAACTATATTGTCAAAATTCATTTGATCTGTTTCTACAGTATAACAAACTTACTTGTGTGGTTT

GCATTTATTTCTACTGGATAACATGGCTTTAAAAATGGTATTTTAGAGGAAGGAAAGCTTGGTAGAGAATGGAC

TAATCCGGATCCCTGGAAGAAATGGACCTTGAATGGGTCTTGATGACTTGGAGAGGCAGAGAGAGAAAAAGAAAA

GTCAAACATAGGGAATTGGTTGATAAAATGAAGGTGAGGGGAGAAGGAACAGAGGGAGGAGAAGATCCAGTTTGA

GGGATATTACAGCGAGCAGCCTGAGAAAGAAGGATAAGAAAGGAGAGAAAAAATGCAAGGGAAGTAACCCTTCAA

AGCCAGTCAGAAGTTTCTGGGTTCCTCAGCAGCCAGAAAAGAAGCCGTTGAAAAGATCTGAGTAACGGAGATTCT

GGACGAAAACTGAAGTTATGGAAGGGAAGTTTAGACATGGGTTATTAAACGCTTTAGCGCATTAGAAGTTTCTTA

TGTAATCACTAAATTCAGATCCTGAAATAATGCCACAAGAACTATACAGCTCAGCCACCCAATTCAATAAGAAGT

TACAGCACAGTCTCACACATATCCAATTAACCTTGGCCTTTAGTCAACATCTGGGTTCTTTTTGTCATTTTCAAA

TACTATCACCCAGAGGTGCTATGATTTATATTGGGGAGGGGATTAAAAGAAAATAAGTAAGTTGGTGATAAGAAA

AAGCTTTCAGATGATTCCATCTGAATTAACAGCCCTCTTTAGTTGTCTAGGAAAGAGGATGCTTTTTCTTGAAAG
```

-continued

```
TGCTTTGAAATGATGATGTGCTTGTTAGTAAACATCAATTATTTTCAAATCGTAATGTTTGCAAGTTTGTCTTCC

TGTAGCTCACCCTTTATGTAGGTCCAGAATATGATTGTCACAAATATCTGGGTGAGCAAGACTATGAAATGTGGT

CATAAAGTAAGTGATTATTTCTAAACTCATCTTTGTCACTCGTAGTGCTTCACAAAGCACCTTTTCCTGGACTAC

AATTCATTTTAATTGATCCCATCAGCACTATATCTGTATCCTGAGTGACTTCACAATACCCTCTATTTCAAGAGA

AACCAATCAGGTTATGGGTTTGTTAGTAATAAAAATTACCAAGGAGCAGTTTGTGGATGGTAAAAGCAATGCAAA

TTCTAAAGAGAAGTCATAAGAGCAATAATAAGCATCCTCCTCACTTCTTGGAAGTGAACAATTCCAAGCTCCCTG

AAGCAACACTTAACCTATCATATTAAACAGTAATGGACAAATATTAGAAATGTTGATGTCAGCTTTCAGAATCTG

TGGGCATCAAAACATCACTTAAGTTCTCCGAAGTATTCTCTGTCAAGTTTCCTTCTACAGTATTCTTTTCCTACT

AGGACAGAGCCTTAAGCCCTAGAAGAATAATTTTGCTTGTGTGTTAATTATTTGTTTACTGGTTCATTCCAGAGT

GTGAGCTGGAAAAAGGGGGAAGTGTCATAAATAGTTTTTTATGGCCCATGGTTTTTCAACTACGTCACTATTGGT

AGCAGTTTCCACTGCAGGATCTATTTGCAAAGCCTAGGAAATTAGCATTAAGCAAGCTGCTAGGAAGACTTCAAC

AGTAACTAGGCCACAGGCCTCACACATTTTTCCTCCACCCCAGCCTCCTCTGGAGAGTACTTGCTAAACCTCTGT

GACACATAATGAAGCAAAGAAAGTGATAGAACAACAGAATTACACGGGCAGATCCTTGTTTCTTCTTCTCTCTCT

AAAGAATTCCTTGGACTGAAAAGCAGTTTATTTTGGAGGAGTGAGAAAGTGGTGACAGAATTAGAAGGGCCTGGG

AGGGCTTCATTTTAGGAGACAGTTTTAGGCTGAAAAGAGATTTCATGAGTGTGATTTACCTGAGGTGACTTTTGG

GGGCTCTTATAAAAAGGAAGTTCATGCTGAATGGGAGGTGGCTTCTGAGATGCAGATTCTGGTGAGCTAAGAGGG

CTCGGTAAAGAGGAGGCAGGAGTTAAGTAGCGTGAACTATGCAGTAGCAGCCTTCTTCCCCCCTTGCTTGGGGCA

GGTCATCACAACCCTTCTCAATAAAGGGGTCCAGGAACCACTAGGAATAAATGGGCATTTGCACTTCAGGTGAAA

CCCATTTGTCATAACTGCTTGGACTTTAAGCTTACAAATAAAAAGAACCACATATTTCCCTTTGCAGCTTGATTT

AGTTAATGTCATTTTGAGAAAGAAAGAAGACATTGTTATCCCGTCCCTTTTTTTTTTTTTTTTTTTTTTATGA

AGAGACTGGGACTCAGAGAAGTCAAGTGATTTTCCCAGAACCAGAAAACACAGAAGTAGCAGAGCTGAGATGACT

ACTCCGGTCTTCTGATTCCAAATTCCAAATTCATTCTTCTAAGCGATTTCCCAAAACGGGAAATGGGTTTATCTT

CTATTTATGGGAAGTGATAGTGGTATTCTATTTAGAGAACTTATATAAAATCTTACTTTAAAATAAATAATATTT

CAAAAAGTAAGCTTAATTTAAAGAAAATAATCAAGAAAGTCTGGTATATTTTTACAAATATACCAAATGACCTTG

CTCTAAAATACATCTACTTTCCAGCAAGCCAAAGTGAAACAATTTGAAATAAGTGGCATTTACTGACCACTCCCT

AAAGTTCACACAAAAGAGGTAGTACTCTAACTTAAATATACAAGGTGAAGAAATAGCTTACTCAGCCTGTTGGGC

TTCCTCTTCTACACTCTTGGGAAATGCCCTCCGTGTTAACCAAGAATTCTCAGGCCTTGGAGGGAGTTTTCCATT

CTCAGTAAACTGAGATTGCAGTTGCGGAAATTAAGAGGTATCTGTCCAGCACTTCATTCCCTTAAGGTCAGGATC

TGTGCTTTTAATAATGACAATTAGCTAACATATACAATTAAGCCATGCAAATGAAGTAAGAGAAAGCTAGAGGAG

AAATTCAGGAGCCAGTTGCCTTTTCCAGACATCTTGTACAAATAGTGTTCAAAGGACTAATTCAAAAGATGGGAT

TCTTCGCTTGAACCCAGGAGGTGGAGTTTGCAGTGAGCGGAGATCGCTCCACTGCACTCCAGCCTGGGTGACAAA

GTGAGACCCCATCCAAAAAAAAAAAAAAAAAAAAAAAAAAAAAGATGGGATTCTTTTTTAAAAAATAAATTTTACT

GCGTATTTTTAAGGTATACAACGTGATGTTATAAGATGGATATAGATAGTGAAAAGGTAACTGTAGTGAAGCAAA

TTAACATATTCATCATCTCACATAGTTATCTTTTATTTGTTTTGTTTTGATGGGATTTTTAAGATAGTAGAAAGG

AATGGTAGACAATAAACATTTGAGGGAAAGTGGGGCTTTGTAGAACTCCTAAAATGACAGCACGCACAAATGTCC

CCATTATGTCTAAAGGGTAACTCGTTCCTACTTCTAGGGACAGCTGAGGGACATCAATGTAAATTTCTAAATGAC

TTCCTGAACTTTTTATTTTATTTTTTGTATTTTAGAGGAAATTATAATAACATCAAGCCACCTCTGGACCATA

TCGCTGCTGATATCATCAGCAAATGGCACTATTCCTAAATCCTAAGATGCACTTTTCCCTTCACATTTCAACATT

TGTGAAACTCGATTGTACCTACACCTGATTTTATATACAATGCAGCCTTTCCTTTTCTTTTGTCATTGCATCTTA

CGCCTGATTTCTCCTTGGAATTGAGTAAATATAATGCTTACATGTGTTAATAAGAATTGAGGTCACTCATAATTT

TTGAAATATGCCACCAAATATAAGCCTTTCTACATATTGTTGACTTTGAAGTCATTTCTTTTTTTAACTACTAAA
```

-continued

```
CAATAACACTTTTTGTTGAGAAAAATTGCATATGAACAAGAGACCAAGCAGGTAGAGAGAAAAAAACTTTTAATA

ATCAAGAGAATCTTACTGTGTCCCAAAGGCTAAAGTCACCTTACTATCAAGAGAGAAGGACAGGAACAGAGAGAA

CCAGGTAAATTACGAATTGAAAATTCCATGGTTCATTTATCTTTATTTTTAATAATTCCATTTGTGTGATTGTGT

TGACCACAAGGTCATAATGTTACTCTTCATACTGACTTCTCATGTAAATTATAAATAAGTTTTTATGCTAATGAT

TTATGGAGTAAGCTATTCATCTTTCCGACAGAGAGTTACCTACAAAGAAATAATTATTCTACCTCTGAGATGAAA

TATCATGAAAGGAGTGGTTTCCAGATATTTTGACTTTTAAAAGCTTAAAGAATATATGTAGTATAAAATTCTAAA

GCACGCAAAATTAATCCTTTTAGCAATCAAGATAGCGGCTACTTTTGGTGAGAAGGACAAGGTAGTGATAGAGAA

GGGGCTCAGGGGTCTTTCCTGAAGACAGTGAGGTGGGCAATGGTATTTTCCTTGACCTGGATGGTGATTAAACAG

ATGTGTTTACTTTGTGATAATTGACTAGGCTGTGCACCTATGAACTGCATACTTTTCCATATATGTACTGTATTC

TTATACTTAAAAAGAAGTTTAAAAATAAATGCAACAGATATAGGACTTCCTATATTACTCGTTGACCAAAAAAAT

GGATTCATTTTTCTTTCAGGTAAAACGTACTAGTGGTTTTAATATTATATTGACCAGGGAGTAAATGTTTACCTT

AGGAACCTTAATCTTGATGTTCTCCAAAGTCATTATCTGTTCTTTCTGATTATCAGAATAGAGTATATCTCTATA

TAAATGAAAATTTCTGGTCATTCTCAAAAAATAACACTAAGCATGAAAATCAGAAATATTGATCTTGTTTTGTAA

TGATGTTTCTATTGATGTGAAGTAGTTTCTAGTAGAGTTGCTGTCCTAACACACAAATGAAATTGCACTGTTTGG

AAGACACAACTGTGAATGACTTGCTTCAGTAAGGAATTTCCAACATGATGGTTTAGGGATAGAGGTGCTCGATTC

CTCTGTCTCCGGTTACCCAGGTTATTGAGGACAGGGAGGTCAATAAGTAATGCCCTCCTCCCACCCATAGCACAA

AACAGAGCGGGGTTCAGAGAATAGGTAAGGCTTTGGCCAGGGTGTTGAGGAGACTTACATCCCTGGGAACCAGTC

AGAATGGGGGCGCTGAAAACAATGTTTTAAATTCTAGCACCCAGCAACATATGTGTGAAGATTAAATGTACTCGT

GCTAAATTCACTTGCTCCATTACTGAATTTGGGTGGTGTCTGTTAAAGATGGGAACAAAGGCATTCAGGTCCTGG

TATCTTCTACCACTCCCAGCATGAACAGACTCATGTCAGTGGGTAAGGGATGGTATTTCCCGAGAAGGCTTTGAA

CTCTTGTAGTGGGTCAAATAATGGCCCCCCACTTAAAAATGTTCATGTCCAAATCCCTGGAAGCTGTGAAAAGGG

GTTTTTGCACATGTAATTAAGTCAAAGATATTGAAATTAGATCATCCTGGATTACATAGGTGGGCCCTACATTTA

ATGACAAGTATCCTCATAACAGAAGAGGAGAAGGTGATGTGAGATTTGGAGCAGCAGAGATTGGAGTGATGTGGC

CACCAATCAAGGAAACCAAGGACTTCCAGCAGCCACCAGAAGCTGGAAGAGGCAAGGAAGGACTCTTCCCTAAAG

CCTTTAAAGGAGCACAGCCCTACTAACACCTTGCTTTTGGGCTCTGGCCCGCAAAACTGTGAAAGGATACATTGC

TGTTATTTGAAGCCACAGTTCGTAGTAAATTTATTACAGCAGCCCTAGAAACTGATACAACTCCTAAATACACCC

TTAGCAACACTGCTCAACAAGAAGTAGGCAATTTCCTCCTGACTGAAAAATACTGATACTGTTATGGGATCCTTG

GGGGTGTTGCTTTTCTGTCCAGAAACCTCTGTGGCGGTGGCACCTTTGCATGAGTTTTGCTCGGGTCCACTGGGC

CCACTCATCCTGGCAGGCTGCGCTCAGCTGACACTACTGGCGTGGATCCCATGCCTCCAAAGAGACTGGAGCGAA

GCGGTGAGGGATGTGTGAGGAAGTGAGCGTGGGGTCTGGCACACAGTCAGGCTCAATGGCTGCTACAGCGGGATG

GGCAGCTTCAGGTGCTGGCACGGGTGCTGGCTCACTGCAAGGCTGTGGCTGCACCAAGCAGCGCAGCAACGGAAC

GCATTGGTGCCTGGAAACTTGGAGACTCCAGGAACCTCAGGGCTCCAAAAGGCAAATCACAGCCCTAGCTTCGGG

AGGTCCCAGGTCTGGGCTGCCAAAGGGCTGCAGCTCTTCTCTCCTCTCTCTCTTCGCTCCTCTCCCTTTCTCT

CTTCACTCCTCCCTCTTTCTCTCTTCACTCCTCCTGTCGCCTATGAACAGCGAATTCAACCTTCCAGTTTTCAGA

CTAGGAATGCTGGAGTTGTCCTTGATTACTCTGAATTGTTCACTCCGCATATGGGCACTGAGGATACGTTGATGA

ACTACACAGACAAAAGGATAGAAATTCCTGTCAAGACTACATTCAATAGGGATGAAGCAGGCAATAATGAATAA

ACATACTAAGTTGAATATGACTATTTAAATATATATAACACATATGACTTGTATAATGTTAAATATTTTAAGTTT

TTTAAATTCTTCCCTTCATAGATTTTACATTATAGTAGAAGAGGCATTTTTGTTGTTGTTCTTTTTGTTTTGGAT

TCAGAGGGTAAATGTGCGGGGTTGTTACATGGGTATATTGCATAATGCTGATGATGGTCCCATCACCCAGGTGGT

AAACATAGTACGTAATAGGTGAATTTTTAGCCCGTGCTTCCCTCTCCCATCTAGTCGTCCTGAGTGTTTATCGTT
```

-continued

```
GCTACGTTTATGTCAATGTGTATTCAATATTTAGCTCCCACTTATAATTGAGAATATGCAGTATTTCGTTTTTG

TTCTCGTGTTAATTTGTTTAGGATAATGGCCTACAAAGAACATGATTTCATTATTTTTATGGACATGTAGTATTT

CATGGTGTATATGTACCACGGTTTCTTTATACAATCCCACTGTTGATGGGCACCTAGGTTGATTGTATTGCTGTT

GTGAATAGGGCTGCAATGAACATACAAGTGCATGTATCTTTTTGGTAACAAAAATTTTATATTTGGATTACCCAG

TAGAATTGCTGGGTTGAATAATAGTTTTGGTTTAAGTTCTCTGAGAAATCTCCAAACTGCTTTCCACAGTAGCTG

AACTAATTTACATTTCCACTAGCAGTGTATAAGCGTTCTCTTTTCTCCACAATCTTTTCACCAGCATCTGTTATG

TTTTGGCTTTTTAATAGCCTTTTGATGACTGTGAAATGGTATCTCACTGTGGTTTGGATTTCCATTTCTCTAATG

ATTAGTGAATGTTGAGCATTTTTTTCATATGTTTATTGGCCGTTTGTATGTCTTCTTTTGATAAGCGTCTGTTCA

TGTCCTTTACACATTTTCAATTAAAATATTTGTTTTTTGCTTGCTGATTTAAGTTCTTTGTATATTCTGGAAATT

AGATCTTTGTCAGATGCATAGTTTGCAAATATTTTCTCCCATTCTGTAGCCTGTTTACTCTGTTGGTAATTTCTT

TTGCTGTACAGAAACTCTTTAATTAGGTCCCACTTGCCTATTTTAGTTTTGTTGCAATTATTCTCTGGAACTTA

GCCATAAATTGTTTGCCAAAGCCAACGTGGAGAAGGATATTTTCTAGGTTTTCTTCTAGGATTTTATAGTTTAAG

TTTTACATTTAAATCTTTAATCCATCTTGAGTTAATTTTTGTATATGTTGAGAAGCAGGAGTGTAATTTCATTCT

TCTGCATAGGGCTAGCCATTATCTTGGCACCATTTATTGAATAGAGAGTCCTTTCCTTATTGCTTATTTCTGTCA

ATTTTGTTGAATATCAGATCGTCGTAGGTGTATGGGTCCATTTCTGGGTTTTCTATTCTGTTCTATTTGTCTCTG

TGTCTGTTTTTGTACCAGAACCATGCTGCTTGGTTACTGTAGCCTTTTAGTATAGTTTGAAGTTGGGTAATGTGA

TGTCTCTGGCTTCGTTCTTTTTGCTTAGGATTGCTTTGGCTATTCAGGCTCCTTTTTGGTTCCATATGAATTTTA

GAATATTTTCTGATTCTGTGAAAAATGACTTGATATTTGCTAGGGATAGCATTGGAGTGGTAACTTGCTTTGG

ACAGTGTGGCCATTTTAATGATATTGATTATTCCAATCCATGAGCATGGAGTATTTTATATTTATTCAGTCATC

TTGATTTCTTTCAGCAGTGTTTTGTAGTTCACCCTGTAGAACATTTCACTTCCATGGTTAGATGTATTCCTATTT

TGTGGCTATTGTAAATGGCATTGTATTTTTTTTATTTGGCCCTAAACTAGAATGTTATTGGTGTATAGAATTGC

TACTGATTTTGTACATTGATTTTGTATCCTTAAACTTTACTGAAGTTATTTATCAGTTCTAGGAGACTTTTGGA

GAAGTCTTTAGGGTTTTCTATGTATGAAATCATATCATCAGCAAAGAGAGACAGTTTGACTTCTTCTTCTTTTTG

GATGCCATTTATTTCTTTCTCTTGCCTAGTTGCTCTGACTAGGACTTCCAGGGCAATGCTGAATAGGAGTGGTGA

GAGTGGGCATCCTTGTCTTGTTCCAGTACTCAAGAGAAATGCTTCCAGCATTTACCTGTTTAGTATGATGTTGGC

TGTGGTTTGTCATAGGTGGATCTTATTATTCTAAGGTATATTCCTTTGATGCCTAGCCTGTCGAGGGTTTTAAT

CATGAATGGATATTGAATTTTATTGAAGGTTTTTTCTGAAACTATTGAGATGATCATATGGTTTTTGTTTTTCA

TTCTGTTTATGTGGTGAATCACACTTATTGATTTGTTATGTTGAACCAGCCTTGCATCCCAGGAATAAAGCCTAC

TTGATTGTTGTGAATTAACTTTTTGATGTGCTTCTTGATTTAGTTTGCTCATATTTTGTTGAGGATTTTCGTGTT

TATGTTAATCAGAGATATTGTCCTGAAGTTTTCTTTTTTCATTGTGTCTCTGGCAGATTTTGATATCAGGATGAT

GCTGGCATTGTAGAATGAGTTAGGGAGGAGCCCCTCTCCTTAATATTATGGAATAGTTTCAGTAAGATTACTATC

AGTTCTTCTTTGTATGCTTGGTAGAATTCAGTTGTGAATCCATCTGGTCCAGGGCTAAATTTGGTTGGTAGGTTT

TTTATTACTGATTCAATTTTGGAACTTGTTATAGGTCTGTTCAAGTTTTCACTTCCGTCCTGGTTCAATCTTGGG

AGGTTGTATGTTTCCAGGAATTTATCCATTTCCTCTAGATTTCCTACTTTGTGTGCATAGAGGTGTTCATAACGG

TCTCTGAAAATCTTTGGCATTTCTGTGGGATTGGTCGTAATGTCATTTTTGTCATTTCTTGTGCTTTTTGGAACT

TCTGTCTGTTTTTCCTCGTTTTTCTAGCTAGCAGTCTATTAGTCTTGTTTATTCTTATGAAAACCAACTCTTTG

TTTCACTAACATTTTATGGACTTTTGCATCTCAATTTTATTTAGTCATTATCTGATTTTAGTTATGTCTTTTCCT

CTGCTAGCTGTGAGATTGAATTGTGCTCTTTTTTTCTAGTTCCTCTAGTGTTATGTTAGATTGTTTAGTTGAGAT

CTTTCTAACCTCTTGATGAAGGCATTTTAGCACTATAAACTTTCCTCTTAACACTGCTTTTGCTACATCCCAAAG

ATTTTGGAAAGTTGTGTCTCTATTTTCATTAATTTCAAATAATTTTTTGATTTCTGCCTTAATTTCATTGTTCAC

CCAACAGTTATTCGGGAGCATGTGGCTTAATTTCCATGCTTTTGTGTAGTTTTGAGAGATCTTCTTGGTATTGAT
```

-continued

```
TTCTATTGTTATTTCACTATGATTTGAGAGTGGCCTTTGTATGATTTTAATTTTTTTAATTTATTGAGACTTGC

TTTATGACTGAGCATGTGGGGCAATCTTAGAATACGTTCCATGTGCATATGAGAAGAATGTGTGTTCTGTCATTG

TTGGCTTGAGTATCCTAGAGAGGTCTATTAGGTCCAACTGGTCAAGTGTCAAGTTTAATTCCAGAATTCCTTCGT

CAGTTTTCTGCCTCAGTGATCTGTCTAATGCTATCAGTGGAGTGATAAAGCCCCCACTAATATTGTGCTGCCATC

TACGTTTTATTGTAGGCCAATAATTTGTTTTATGAATCTGAGTGCTCCAGTGTTGGGTGCATATATGTTTAGAAT

AGTTAAGTCTTTTTGTTCAATTGAACCTTTTATCATTTTATAATGCCCTTCTTTGTCCTTCCTGATTGTTGTTGG

TTTAAAGTATGTTTTAATCTGATTTAAGGGTAGCAACTCCTGCTCTTTTTGTTTTTCATTTGCATGGTAGATCT

TTCTTCATTCTTTCACTTTGAGCCTGTGAGTGTCATTCATGTAGGATGCATCTTCTGAAAACAGCAGACAGTTGT

GTCTTGTCTTTTTATCCAGCTTACCACTTTATGCATTTTAAAGGGAGAGTGTAGACTGTTTACATTTAGGGTTAG

CATTGACATGTGAGATTTTGCTCCTGTGATTGTGTTGTTTAGCTGGTTGTTTTGTAGACTTCATTGTGTAATAAG

TGTATTTTTATTGGTAGCAGGTTTCGTCTTTCATTTCCATGTTTAGCAATCACTTACGGATTTCCTGTAAGAATC

ATCTGGTGGTAATGAATCTCCTTGGTGCTTGCTTGTCTGAGAAGGATTGTATTTCTCCTTCACTTATGAAACTCA

GTTTGGTGGGATATGAGTTCTTGGTTGAAATTTATTTTCTTTAATAATGCTGAAAATATAGGCCCCCCCATATCT

TCTGGCTTGTAAGGTTTCTGCTGACAGAACTGTTGCTGGCCTGATGAGGTTCTTTTTGTAGGTGACCTGACCTTT

CTCACTAGCTGCCTTAACAATTTTTTCTTTTGCATTGACCTTGGTGAATCTGATGACTATGTGACTTGGCAATGG

TTGTCTTGTATAGTGTCTCACAGGAGTTCTCTGTATTTCTTGAATTTGTATGCCCACCTCTCTGGTGAGATAGGG

GAAATTTTCATGGACTGCATCCTCAGATGTATGTTCTAAGTTGCTTACTCTCTTTCTCAGGAATGACTGTGAGTC

ATAGACTTGGTCTCTTTACATAACCTCATAAATCTTGAAGGTTTTGTTCATGTTTTAAATTCTTTTTTCTTTATT

TTTGTCCAACCAAGTTGATTCAAATAACTGGTCTTCAAACTCTGAGATTCTTTCCTCAGCTTGGTCTGTTCTGCT

GTTAATGCCTCTGACTATATTATGAAATTTTTGAAGTTGATCCCTCAATTTCTGAAGTTCAGTTTTGTTCTTTCT

TAAAATAGCTATTTCATCTTTAAGCTCTTTGATCATTTTTCTGGATTCCTTGAGTTCCTTGTATTGGGTTTCAAT

GATCTCCTGGATCTTGATGTACTTCCTTGCCATCCAGATTCTGAATTCTATGTATGTCATTTGAGTCATTTTAAT

CTGGTTAAAATCCTTTGCTGGAGGACTTGTGTGTTTGTCTGGAGGTAAGGAGACACCAGCTTTTTTGAATTGCTA

GAGTTCTTGAGATGACTCTTTAACATATGAGGGCTGGTGTTCCATTAACAATAGTGTACATTGAGTATAGTCAGT

TGGCTTCATTCTGAGTGCTTTGAAAGGGCCAAAGCTCTGTACAGCATCTTTATTTGTGGCTAGATTTTTGCTTTA

GGTTTCACAGGTGCTGTATATTGGAAAAATGTTTTTGGTGTTGTCATTTGGGGTGCAATCCAGTAGGTGATGCTT

AAGAGTGGTAGCTGGCAGATAGGCTCTTACTCAGTCCACAGCTCTTTTGTATTTGGTGCAGTCCTCAGTAGTGC

TCTGTGGTGGTAGGGAGAGATGACCCCCTCACCAGATACATTCCTGGGCCTTGGGGGAGCCCTCTCTTATTACTG

GCACTGCACTGCATTTCATTTATTAGGTGTCCTGGGCCTGCAGGGTGCCCTCAGGCAGAGGCTGCGGCTGGAAAA

TAGACCATACCCTTCCCTGGCTGGCCCTGCACAAGGAGGCACACCCTGTTCCTGAGCCAGTCCATGAACCCAGCT

GTCTCACCCCTCTCAGTCTTCTGAGAGTAGGGGATCCCCCACTGCTTGAGCACCATGAGCCCCTCCTGGCTACAG

GCAGTGGGGGTAGGTATAGTCTCTCAACCCACTGTCCAACTGATTTCCAGGGTAACAGAGAGCTGTGCCTGCCCA

CAGAGTTCAGGCAGAGGCCAGGCCATTGTGCTGGAAGCTGATGCTAAGCCTTGTCTGATGATGGGGAGTGAAGCA

ATGTAACGGCTCCCTAACTGTGGCTTCTCTCAGGGCTATGGCAGCTGGCATGAGACTGCTCCAGGTCCAAGGCCT

GTGGGACTTCCTGTGGACTTGAGTTTTGCCTCTGCAAACACTCCAGCAACTCTCTATGTCAGTCTAGAGGCCCAG

GGACACGGATCAGGTATTGGGATGAAGGGGTTCTCGAGTTCCCAGGATTTCACAGGTCCCTGTGGAAAGTGAGGA

TCCCCCAGGGGCTCTCACTCACTCACCCTTTCTCTATGTTGGGGAGCTTCCCTGGCTCCATGCCCATCTTGGGT

GGCCAGCTGCCCAGCTTCACTCTTCCCTGTTCTCTGTGTCCCCTCACTCCCTTAATTGTCCTGATATCGTTCCTT

AGGTGATCTACTTGCAGAGGCAGTGTTTACTCGCCACTTGTTTTCTCTCTGTGAGAGTAGCACACACTAGCTGCT

ACTCATCTAGCATCTTGAATTCTTCCCATCTGAAAAAGTTTCAACTGCAATCACAGTTAAAGAAATACAAAACA
```

-continued

```
ATAGCACTCTAAGTTACAACTTCTCACCTATAGAATTCAAAACATCCAAATGATTAACTAAACATTTGTTTGGT
AGATCTGTGGGAAAACATGAATTCCTTGTGAATTACTGGAGAAAATGAAAATGATGCAACACTTATGGAAGAAA
TTTGGGGATTTTTGGGGGGGAGGGGAACAATATATTTAAAACTATAAATGCATTTATCCTAGCAATTCTATGAAT
GGGGATTTATCTTAGGGTACACCTGCACACTTAGGAAATAATGTATGCAGTCATTCATTACAGAATTGTTTGTAA
TAGCAACAACCTGAAAAGCAACTCATATATCCATCCATCACACAGGGACTGGTTTCATGACTACGGTTCATGAAT
ACTCTGCAGCCCTTAGAAAGAATGAGGAAGTGGCCGGGCACGGTGGCTCATGCCTGTAATCCCAGCACTTTGGGA
GGCCGAGGCGGGTGGATCACGAGGTCAGGAGATCAAGACCATCCTGGCTAACACGGTGAAACCCCGTCTCTACTA
AAAACAATACAAAAAAATTAGCCAGGCAGGCGCCTATAGTCCCAGCTATTCGGGAGGCTGAGGCGGAGAATGGC
ATGAACCCGGGAGGCAGAGCTTGCAGTGAGCCGAGATAACGCCACTGCACTCCATCCAGCCTGGGCGACAGAGCG
AGACTCCGTCAAAAAAAAAAAAAAGAGGAAGTTCTCTATGCGCTGACATGGAAGGAAGACAGATGGTTGAATGA
AAAAAGTACATAATTAGCCATAAAGTGTAAGACTTTTTGTCTAAAAAAGAAGGGTGATATAATTGCATATTTATA
TTTTCTTCCATTTATATTAAGAGATAATAAAGGTACACAAATTGGCTAGAATAAAGTGGTTTCCTATAAAGGGTA
AGAGTAATTGAGTGGATGAAGACTAGGGTTAGGGATAGATTTCTCAGTGTATTCATTTTAATATATGTATTCATT
TTATATATGTACTAATTTTTATATATGTATTTATTTTATATTTTGATTTTCTTAACATAAATATATTATTCCTTC
ATAAAATTAAACTTGATACATTTTTGATTACTAGATATGTAGAAAGCATTATGTTCAGTACCACAGTAATACTTT
CAAACCAGCTACAATTAGTATTTATGAGCATCTATGTGCCAGACATTGTGTTCTGCTTTGGTTGGTGGGGTAGA
GGAGGAAAGGAAACCATGGCTTACATAGGAGTGGAAGTCTTGTCTTTCACTTTGCACCTCTCTCGTTCAGACCTA
GCATAAATATGACCTTAGGGGAGGCAGAACACATATGATAAAGAGATAACTAGCAAGAGACATAATAGTAGCTAA
ATAAATACTGAAGGAAAAATTCAGGAAGAGGTAGGAAGGATATGCCTCATCACTTCCACCTGTTAAGAAAAACTT
TAGACATTCTTGCCAATATTCCTTATTGCCTGTCTTTTGAACAAATGCCATTATCACTAGAGTGAAATGATATTT
CATTGTAGTTTTGATTTGCATTTCTCTCATGATCGGTGATGTTGAGCACCTTTTTATATACCTGTTTGCCATTTG
TATGTCTTCTCTTGAAAAATGTCTATTCAGATCTTTGCCCATTTTTAAATGGCGTAATACATTTTTTCCTATTGA
GTTGTTTGAGTTCTTTATATATTCTGGTTATTAATCCCTTGTCAGATGAATAATTTGCAAATATTTTCTCCCATT
CTGAGGATTACCAGAGGCTCAGAGGGGTAATGGTGGTGGGGGAGAATAAAAATGGTTAATGAGTACAAAAATATA
GATAGGAGTAATAAGATCTAGTATCTGATAGCACAACAGGGTAATTACAGCCAACAAAAATTTATTGTGCATTTC
AAAATAACTAAGAGTATAATTGGAATGTCTGTAACACAAAGAAGCAATAAATGCTTGAGGTGATGTGAGGGGATG
GATATCTAATTTACCTTGATGTGATTATTAGATATTGTATGCCTGCATCAAAATAGGTGATGTATCTTATAAGTA
TATACACCTATTATGTACCCATTAAATTTTTAAGAACTTTAAACAAATCAAATTTAACAGAGTTTAATTGGGCA
AAGAATGATTTGAGGATCAGGCAACCCCCAGAAACAGAAGAGGTTCAAAGCAACTCAGTGCTGTCACATGGTTGG
AGAGGATTTATGGGCAGAAAAGGGAAAGAGAGATACAGAAAATGGAAGTGAGGTACACAAACAGCTGGATTGGTT
ACAGCTTGCCATTTGCGTTATTTGAACATAATCTGAACAGTTGGCTGTCTTTGCTTGACCAAAACTTGGTGTTTG
GTACAAGAGCAGATTACAGTCTATTTACACATCCAGTTAGTTTACAGTTCACTATACACGAAGAAGAAACCTTTA
AGCAGAACTTAAAATATGCAAAGAGGAAGCTTTAAGTTAAACTTAATTTAACACACCCAATTATCAAAAAATGAG
TAGCTCTGCAAAAGTGGATTTTCCTGGTCATCTTTGGTACTTCCTTAAAAAAGAGAAAAGTAGTACTCACGATAA
AAAAAAAAAGTCCTCAAGTCTTTATTTTATTCCTTTCCAATTTAAAATGTTACATCATCTGAGGAAGGTTTTTC
CCTTTGACCGCTTTCATAGACATTTCTTCTGCATGGGTTGGCCAGAATCAGAAGAGTAATTGTAACTTTCTGTTC
TTGTCCTACAGTTACAAAGCGGTTTCACTTTGTAAATGCTCTTTGGATGGCAGGAACCAAGCAGCCATGAAAAGA
GGAGTTACACCTTTAAAGGAGTCATTCCATCATGACTCTCAGGACTGGAACATGGAATACCTGAATGGCCTCTTT
GGCACAGATAGGCCACCCTTGAAAGGTGTTCCAAGCTAGGAACTCACTACCACTGTTACATCGATGCAACTCTGT
GAGAAGTTTTTATCTGGTGATGGAAAATCTCATCTCTTCAACACACTGACTACTACCAGTCTCAGAACCCTGTAA
ACAAGATTCATTCATCTCAAATTGGGTTAAAGCAGTCACCCTGCCTTACATTAGTTTGGAATAAGGATGTGGGA
```

-continued

```
TGGTGGTAGAGGAGGGGAGTGGATGATGATTTTTTTATTGTTATTTGATTCTAAAGAAACTTCTATACATTTTGC
ATTTAAAATAATTATGTTTTTAACAATGTTTGGATTAATTCAAAATAGGATATTATATCCTATTATATTATATAT
ACTATTTAATCATCTTGTTGACCAAATGCAACTTAAACATGTAAAATGGTAAATAGCATAATAATTGTCTTCTAA
GCCTGCACTATAAAGTATTTCAGTGGCCTCATTATTAAAGGACCAAGGTGCCCAAAGAAACAAAATTTAGTAATC
ATAAACAAGAGACAAACCTACTTCTTTTCCCCCAGAGTTCTGGCCACATTGAAATAAGGTGTTTGAATGCTTAAT
AAGAATTATTTTGGCCCACACAGTGGCTCATGCCTGTAATCTCAGCACTTTGGGATGCCAAGGTGAGCAGATCAC
TTGAGGCCAGGAGTTCAAGACCAGCGTGGCCAACGTGGTGAAACCCCATCTCTACTAAAAATACAAAAATTAGCC
CGGTGTGGTGGTACACGCCTATAGTCCCAGCTACTCGGGAGACTGAGGTGGGAGAATCACTTGAACCCGGGAGGC
CAAGGCTGCAATATCGAGATCACACCACTGCACTCTAGCCTGGGCAACAGAGTGAGAGTGAGACTCTTTCTCGGA
AAAAAAAAAAAGAATTATTTTGAACAAAGTGCTGTCACCTAAGTTAGCAAAACTCCAAGCAAGGTTTTTGGCTC
TGTAAGGAAAGAATTAGCCTACTCATTTGGAAATTTAGTGGTGTTTGTAATGCAGAAAGTGACAGTGAGACTGGA
AAGGGATTGGCTTTGGGGCTTGTTCTGCTTTATAAATAATAATGAATCTTCTCCAACATGAAGTAATGTGAATTA
AAAAAAAAAAATCTGTCCTTAGAGTACAAAATTACTTCATAACCCAATCTGCATTTCTCCACTCCAAGCATATTT
TCTGGGAGTTCTACTTAGAGAGTGAAAGCTGCTGTGTGTGTGATAATTAATTTTAACAAACACTTGGCAAACTGA
GCTGGACTATGTATAAGCTACCCTAGACTAAGCATGAATTTGAACTGCACTTTTTATGGTGTTTTTTCCACAATG
ACATTATTTAGGCATTTAAAGTTATCTGAACTGCAATTTTTTGTTCTTTTTTTTTAATTTGACTTTTTAAAAAA
AATTATTCCTGAATAAAGAGGCAGTTTGTAAAAACTCGAGAACTGTGAGAGATAATTGGATCTTTGTGTAGCAAA
ACTAGAAGGGTGTTGGGTATCTGCTCTTTATCAAATGGACCACTTACTTTTCTTTTCTTTTTGCCCTGTGTTCA
GAAAACAAATGTGCGTGTCTCCTGATTTATAATGTATAGTTCATTAATGGAGAAAGTGCTTGAGAATTAGATCCT
AATGTCATTTCCCATGCAGCATCTTCATTCTTTTCTAAAGCACTATTTGGTAAAAACAACTGATAGTCGTCAGAG
GTGATCAGCAATGTTTGAGCACTATTTCCTTTTTATATCCTGCACATGGAATATGCACAGGCAAACAAATCATTT
CCAAGTAAGAAAATAAATTTTGAGGGAGTTAATACTATAATTTGAAAGTAATAACCTCCTATTTATCCATCTAGT
TTGTTGTTCTGTACTAAATTATTTGTGCATGTCTCTGTGTCTATAATTTATGTGAAACTTTGCACAATCTTAAAT
AGGACAAAATAGACATTCTGTAATTTCCCAGGCAAGCTATTTAAGGTGACTATCTCTCTACATATTTGAGATGAA
AAACAATAACATGACAATCCATCCCTTCTTAGGTTTTTGTAAGCAGACTTACTACCTGTGACTCAGTTTTGTTCT
CACAGGGTACTAATTAATCCTTCACGATAATAACTTGTCAAATTCCATTACTTCTGTAAAGGCAATACTTTATAT
TTGTTTGTATTCAAATTTTAAACTGATGTTAAATGCCGTGGGTGCAACTGCAGGTTAAAAATATGTGTTTGAATC
TCTTATTCTTTTTGCTTGGCAATGTATGAAATAACTGCTCTTTCTAGAAATCTTGATGATGAAGTGGCCTGTTGT
TTTGTCACCTAAAAATGCAATAATGTTCAAATTAAGCTTTTCTTTATTAACATCACTTGATTGTGTGCCATATTT
AGAGCTTAGTGAAATTTTAATCTACACATTGATTAAATACATTTTATTTATTCTTGTTTCTAATGGGAACTTTCT
GTGCTTAGAGGAAAAGCGCAGACGAAAGTGAATCAGACAAGTTCCCTGCCCTCCGGAAGCTTTCAGTCTAGTGAT
GAGAAAGACGTATACACACCTTATGTTGATTTAAAAAAAAAAAAGCTCTTACCTGGTTGCTGGCATATGAAAGT
GTTAGTTACAGATCTGCCCCAAACTAAAGGTGTCACCTCGAGTAAATCTCTTTCCCTTTCCCTTTCAATCTCTTC
ATCTATAAACTAGGGGTTGGGAATACATTTATTAACAAACACAAATTGAGCGTCTACCATGTGATAATAGTAGCT
AAACTTACTGAGCAATTACCATGGGGCAGGTATCAAGATAAACCCTTTATGATGGTAACCTCATTTAATCCTCAA
AGCAATTCCATTTTCAAGAGGAGGAAATTGAGGCTCAAAAATGTTAAGTAACTCCCCCAAGGATGCAAAGTGATT
GAGCCAGAATTCAAGACTAGGTTGGTTTGACTCCAAAACTCATGCCATTAAACCCTATTGTGTCACTGCAAACAA
CTCTAATAGTTTCAAATTATTAGTTCTATTAATATTATATTACCATTATTTGCCCCCAAAATGTAAAATGTAAAT
ACAAAGAGTTTGGTTTTTGTATTACTAGTGGAGGTTAAAGGTGCACAATGGAATTATTCAAACTGGGAAAATCCA
GGAAGACTTCATGGAGGAGGCAGCATATGGCTGCAGTTAATAAGGTTTGGTCACACAAAATGGAGAGGTGAGGAC
```

-continued

```
ATTTCAGGCAGAGAGAATTATATGAGAGGTTACAGAGCAGTAAACAGTCATGCGTCTGCAAGATCAAAGGGAAAG

GGCGGTAAGAGAGAAGCTTGAAAGTCAAGTGGAGCCAGATTGTGGAAAAACTAGAGAGTCATGCCAAGGACCTTG

ACATATAGAAAATGGGAAGGCCCTGAAAGGTGAAGAACATGAGAGTGAAATGATTAGTAACTTTTTGGTTTAGGA

CTTGTTTCTTTTGTGTTTTGGTTGCTTTCTTGTTTTGTTTTGTTTGTGGTTTTTAAATTTACAACCAATAAGAAT

ATTTAGTAAGGTTTCCAAATACATCATGAATATATAAAACTAGCCTGACTCAAGGATAATAATTCTGGGTAGTTG

GAGTGAAGTTTCAATCAGCTACGTGGCATTTGCTAATCATCTGATATGAGCTAACAATAAAGGAGTTAACAAATA

AACTGTCAGCCTACAGTCCAGGGTCTCAAATAGCATGTGACATAGTTGAGAAGCAGTTTTCCATATCATACATGA

AATAACTAAAGAAACTACTTACAAAGCACTATACCAGTAACTACAATAAAATACAACTATACATGCAAAATAATG

CTGAAAGCTGCAAGTAGAGGGGTAAAGCTAGGCCAGTTGCTCAGGGAACCATTCTGAAGTGGATTTGGGAAGTAT

GTCTAGAAGGGGAGCCATTGCTGTGAGAGTGCTGAGGCTCATCTGCTACTAGTCCCCCACTACTCAGGCATATGG

TAGGTCAGTAACAAAACCATCATTGTGCACTGTTCTTTCCATCTAAATTCCATCAAATTATGACCAACCTATCAA

GGTACTAGTTCAAATTCTCTCTTCCTCTATAAGCTAGTGCTCTTCTAAAATTTAAGAAGATCGTGCTCATCTT

CCTACTTCTTGTTCTCTTTCTTCTGTGTTTTCTGAGGCTGCAATGAACTAGGAACTTCCTCTCCCCAGAACTCTG

TATTCCAGGCCTTAGATCACTCAAAACTGTTGCTTATAAAGTGCAGAGAATCAACAGAGAAGGAATAGAGGTTAA

TGTCTGGTCAAAGATGTGATTCTCTTGTTGAAAAGTTCATTAGCTTATTATTTATAGAATCATAAGTCCCAGGAA

AAACCAAAAGGAAATATATATTGGATCCTAATGATATTCTCTTTTTTTCTTTTTTCTTTTCCCCCACTCCATTGC

CCAGGCTGGAGTGCAGTGGCATAATCTCAGCTCACTGCAACCTCCACCTCCCGGGTTCAAGGGACTCTCCTGCCT

CAGCCTTCCAAGTAGATGGGATTACAGGCATGTGCCACCACATCGGCTAATTTTTTTTGTATTTTTAGTAGAG

ATGGGGTTTCACCATGTTAGTCAGGCTGGTGTTGAACTCCTGACCTCAAATGATCCACCAGCCTCGGCCTCCCAG

TGTGCTGGGATTGCAGGCGTGAGCCACCACACCCGGCCTGATATTCTCTTGCAAGGGCATTGTTTACATTGTCTA

TCATCAGAACTGTAGAGTGTTGGCTCCAGGCACAGAACCCCTAGAGTTTTGTAAACCATTTATATCACACTGGCA

ACCAGAAGTAACTTTATATACTCAAGAATCAAGATTTCACCTAGAAGTACCTCAGGTAGGTGTTGGTTCATTCAC

ATTCCAACCAAAAGATAATGTACCATAAAGTGCATACCGCCTAGTCCGTAATGATTAAGGCAACCACATAAAATC

TCATTATTTAAAAGAAATTAAGTCCAGGCACGGTGGCTCACACCTGTAATCTCAGCACTTCGGGAGGCCAAGGAG

GGCAGATCACCTGAGGTTGGGAGTTTGAGACCAGCCTGATCAACATGGAGAAATCCCATCTCTACTAAAAATACA

AAATTAGCGGGCATGGTGGTGCATGCCTATAATCCCAGCTACTCAGGAGGCTGAGGCAGGAGAATCACTTGAAC

CCAGGAGGTGGAGGTTGAGATCGTGCCATTGCACTCCAGCCTGGACAACAAGAGTGAAACTCTGTCTCAAAAAG

AAAAAAGAAAAGAAATTAAATGCACTATGGTTTATGGAGCGGTATTCCTCCTCCATGTCCTACATAAGATCTT

TCACATGCCAGTCACAGTTAAATCTAATTTGCTGTAATCTGGATAAATGGGAGCTAATCAACAAGCTCTCAGCTC

TAGCTCTGAATCAGCAGCAGATATTGCATTTTGAAATACACTAATAGCAAGAATGCCTTCCTGACAACAACTGG

CATTTTTGACACAGCAGGAAGTTTATCTGGATTCTGATATAATAGTTATTGGAATCATACATAGGTACATAGTTT

AAAAGGCTAATAAGTCATTTGTTATTGCTTTTATTATCTCTGCATAGTTAGTAAAATTGAGATTAGAACCACTTC

TCGAATGTACTGTTCTAAATCCTTAGCTTGCTTGATCACACATGACCCTCACAATGATCCTAGGAGAAATTATTC

TGCATGCCATTTTGTAGCTGGGGAAACTGAGGCACAGAGAAATACAGTACTGCCCAAAATGTCATAACTAATCAA

AGGCAAAGACAATACTCACACCAGCTCTGATTCCAGAGCCCACTCTCTTAACCATATGCTTTTCTGCTTCCCTAG

TTGTAGAGTCTTTTTGTATGACTGCATTAATTATATGTGAAGAGTTCAAAAATTTCTATATAAGGTCTTTTAAGG

GTGTCATTCTGGTTGAAAATGGAGGACTAGGCTTCTCACTTGAAGACATATTTCTGTAGAAAAACCTATTTCAT

TTAGATGCTACAGTTACTTGATGTGGTTAATAAACCAGTTAACAGAGTATGAAAAGGATAAGGGTTAAAGCCCTC

CCAAGCCATCTTTCATGCTGCTAATATGAATCACATTACTAGATACTTAAATATCATTTTCTCTTTGGTTCCCAG

AAGACTGCATATATGCTAGAATATTTGTCCTCCTCTTTTACCCTTTCAGGCAATAAAGTATTTTGGACCACTGTA

CTATGTTATAATTATTGTTTCTCTCCTGATTTTTTTGCTCCAATCTAATGAAAGACATACAAGCTACTATACTGC
```

-continued

```
TACACAATGACTAAATACCTGTTGGATTAGGTGGGGGGAAGATACACAGTCACTGGCTAGAAAGCATCATGCATA

CAGAGCCATTTTCACCATATATTTTATTTCTCATGATCATGTAGAATTTAGGCTTTGGTGTTGATTATTTCTCTC

TTAGGAAACATAGTTGTTTCAGGGTTGATATCACAAAAAAACAGAAAAACCTATTCGAGAAAAGGAAAATTATTT

GTCTGTAGGCCAAATTTTGAAGTAGGAAAACCTGCTTTTGGAGTTGTATTCCCCTCCCAGGCACTTAATCCAAGT

TCCAGTCTTATTCTAAACTGGGGATGCTAGTATTAACCACCATAGGAGTTATCTGAGATGAGTTATCATCAACTT

GGTACCAGGTTGTTGTCCTCTGGACTCAGTGAGCTCTAGAATTGCATGAAACTGGCCTAATTTATCAAAGTATGT

AGCCTTGGGTAAATAATTCAAGCTCTCAGAGGTCCAGTTATCTCCTCTGTAAAACATATCTACATCCTAGGGATG

ACAATATCTACATCCTAGAGATGTCAGGAGGATTAAGTGTAATTTTTTTAATTGTATGTATTTAAAATGGGCAA

CATAATGTTTTGATATACACGTGTATAGTGATTACTACAGTCAAGCAAATTAACATATCCATCATTTCATAGCTA

CCTTTTATGTATGTGATAAGATTATCTAAAATCTATTCTCTTACCAAATTTCCAGTATACAATATTGATATGGTT

TGATCCATATCCCCATCCAAATCTCATGTTCAGTTGCAATCCCCAACGTTGGAGATGGAGCCTGGTTGGAGGTGA

TTGGATCACAGGGGTGGCTTCTAATGGTTCAGCACCATCCTTTCTTGGTACTGTATAGTGAGTAAGTTCTCACGA

GATCTGGTTGTTTAAAAGTGTGTAACACCTCCCCCACTTTCCCTCTCTGTTCCTCCTGCTCCCGCTATGTGAA

GTGCCAGCTCCCTCTTTGCCTTCCGCCATGATTGTAAGTTCTCTGAGGCATCCCCAGAAGCTGATGCTGCCATGC

TTCCTATACAGCCTGCAGAACCATGAGTCAATTAAACCTCTTTTCTTTGTAAATTACCCAGTCTCAAGTATTTCT

TTATAGCAATGCAAGAATGGACTAATACAGAAAATTGTTACTGAGAAGAAGGGCATTGCTATAAAGATACCTGAA

AATGTAGAAGTGACTTTGGAACCGGCTAACAGGCAGAAGTTGAAACATTTTAGAGGGCTCAGAAGAAGACAGAAA

GATGAGAGAAAGTTTGGAACTCGCTAGGAACTTGTTGAGTGGTTGTAACCAAAATACTGATAGTGATATAGACAG

TGAAGTCCAGGCTGAGGAGGTCTCAGATGGAAATGAGAAATTTATTGGGAATGAGTAAAGGTCAGGTTTGCTATG

CTTTAGCAAAGAGCTTAGCTGCATTGTTCCTCTGTTCTAGGGATCTGTGAAATCTTAGACTTAAGAATGATGATT

TAGGGTATCTGGCAGAAGAAATTTCTAAGCAGCAGAGTGTTCAAGAAGTAACCTAGCTGCTTCTAATAGCCTATG

CTCATAGGCATGAGCACAGAAATGACCTGAAATTGGAACTTACACTTAAAAGGGAAGCAGAGCATAAAAGTTTGT

AAATTTTGCAGCCTGGCCATGTGGTAGTAAAGAAAAGCTCGTTCTCAGGAGAGGAAGTCAAGCAGGCTGCATAAA

TTTGCATAACTAAAAGGAAGGCAAGGGCTGATAACCAAAACAATGGGGAGAAAGACTCATAGGACTAACAGGCAT

TTTATTTTATTTTATTTTTATTTTATTATTATTATACTTTAAGTTTTAGGGTACATGTGCACAATGTGCAGGTTA

GTTGCATATGTATACATGTGCCATGCTGGTGTGCTGCACCCATTAACTCGTCATTTAGCATTAGGTATATCTCCT

AATGCTATCCCTCCCCCCTCCCCACCCCACAACAGTCCCCAGAGTGTGATGTTCCCCTTCCTGTGTCCATGTGT

TCTCATTGTTCAATTCCCACCTATGAGTGAGAACATGTGGTGTTTGGTTTTTTGACCTTGCAATAGTTTACTGAG

AATGACGATTTCCAATTTCATCCATGTCCCTACAAAGGACATGAACTCATCATTTTTTATGGCTGCATAGTATTC

CATGGTGTATATGTGCCACATTTTCTTAATCCAGTCTATCACTGTTGGACATTTGGGTTGGTTCCAAGTCTTTGC

TATTGTGAATAGTGCCACAATAAACATAGTGTGCATGTGTCTTTATAGCAGCAGGATTTATAGTCCTTTGGGTAT

ATACCCAGTGATGGGATGGCTGGGTCAAATGGTATTTCTAGTTCTAGATCCCTGAGGAATCGCCACACTGACTTC

CACAATGGTTGAACTAGTTTACAGTCCCACCAACAGTGTAAAAGTGTTCCTAATAGGCATTTTAGGCTTTCATGG

TGGTCCCTCTCATCACAGGCCCCGAGGCCTAGGAGGACTGAATCATTTCCTGGGCCAGGCCTAGGGCCCCTGCTC

CCTCTTACAGCCTTGGGACTCTGCTCCCTGAATCCCAGCTGCTCAAAGGGGCCCAGGTACTGTTACAGTAGGTAG

CTAATCAGGCATGAGTGGGTAAGAGAGAAGTCCCCACCACCCACCAGGAATGTCAGGCAACCATCAGATGATGG

TCAGGCAGTTGTCATACTGCCTCTCTAAAATAGTAATTGGTTGCAGCCAGCACCAGGGAGAGGCAACTTCTCAAT

AGATAGAAACACCTGAAATTGGTAACTGGGCGCTTCCAATAAGATCTCAGGAACTGAGAGAGTGGGCTTAACATG

CACATTAAGAGGCAAAATGGTGAAGTATGACCTTTGGGGGCATTCCACCGGAAAAGGGAAGAAAGCCTCAGGTAA

GCATGTATACAACTCCAGTAAACACACTGCACACGCTCACCTTCCAAGTGCAAGCAGGGCACCATGCATGCGGCA
```

-continued
AGCTCACCCTTAGGGAAGGACCAAGGGAAAGGGGCACAAGATGTCAGAAGTAGGCCAGTGTATAAGATCCTAGGT

TCAAGGTCAAACAGGGCACTTGACCTCCAAGGTGCCCACTTGGGCCTCTTCCAAATGTACTTTCCTTTCATTCCT

GTTCTAAAGCTTTTTAATAAACTTTTACTCCTGCTCTGAAACTTGTCGCAGTCTCTTTTTCTGCCTTATGCCTCT

TGGTCAAATTCTTTCTTCTGAGGAGGCAAGAATTGAGGTTGCTGCAGACCCACATGGATTTGCAGCTGGTAACTC

AGATAACTTTCACCAGTAAGAATACAGTTCAGGCTGCTGCTTCACAGGGTGCCAGGCATAAGCCTTGGTGGCTTC

CATAAGCTGTGAAGCCGGCGGGCGCACATAATGCAAGAGTTGAGGCTTAAGAAGCTCTGCCTAGATTTTAGAGGA

TGTATGAAAAAGCCTGGATGTCCAGACAGAAGCCTGTTACTGGGGTGGAATCCTCATGGAGAACATCTACTAGGG

AAGCAAGGAGAAGAAATGTGGGGTTGCAGCCCCCACAGAGAGTCCCCTGGGGCACTGCCTAGCAGAGCTATGACA

AGACAGCCACCGTCCTCCAGACCCCAGAATGGTAGATCCACCAACAACTTGCACCCTGCAGCCTGGAAAAGCTGC

AAGCACTCAATGCTAGCCCATGAGAGCAGCTGTGGGAGATGAACCCTGGAAAACCACAGGGGTGGTTCTGCCCAA

GGTTTTGGGAGCCCACTCATTGCATCAGTGTTCCCTGGGTGTGAGTCAAAGGAGATTATTTCAGAGCTTTAACAT

TTAATGACTGCCCGGCTGGCTTTCAGACTTGCAATGGGGCCCTATAGCCTCTTTCTTTTGGCAGATTTCTCCCTT

TCGGAATGGCAGTATCTGCCCAATGCCTATACCCCCATTGTATCTTTGAAGCAATTACCTTGTTTTTGATTTTAC

AGGTTCATAGGTAGAAGGGACTAGCTTCGTCTCAGGTGAGACTTGGGACTTTGGACTTTTGAATGAATGCTGGAT

CGAGTTAAGACTTTGGGGAACTGTTGGTAAGGCACGACAGTATTTTGCAATATGAGAAGGACATTAGATTTGGGA

GGGGCCAGAGTTGGAATAACATGGTTTGGATCTCTGTCCCCACCCAAATCTCATGTTCAACTGTAATCCCCAGTG

TTGGAGGTTGGGCCTGGTGGGAGGTGAGTGGATTATGGGTGGCTTCTAATGGTTTTGTACAGTCCCCTCTTGGT

ACTATATAGTGAGTTCTGACAAGATCTAGTTGTTTAAACGTATGTAGCACCTCCCATTTCTCTCTTCCCCCAGTT

CCTGCCATGTGAAGTCTGGGGTCTCCCTATGCCTTCCATCATGATTTTAAGTTCCCTATGGCCTGCCCAGAAGCT

GATCCAGCCATGCTTCTTGTACAGCCTGCAGAACTGTGAGCCATTAAACTTTTCTTTATAAATTACCCAGTTTCA

GTTATTTCTTTATAGCAGTGTAAGAATGGACTAACACAATTATTAACGCTAGTCCTCATGTTGTACATTAAATCT

CTAGATGTATTAGACGTAACTGCAACTTTGTACCCTACCCTACAATTTTCTTTCCCCCCAAGCCCCCCAACCAAG

GGTCTACTCTGTTTCTATAAATTCAGTTGTTTTTTAATTCCACGTATAAGTGAAGTACAACTCAGTGTAGAAACT

TGGTAAATGCTAGCTACTTGTTATAAGCTGTCAGTCAAAATAAAAATACAGAGATGAATCTCTAAATTAAGTGAT

TTATTTGGGAAGAAAGAATTGCAATTAGGGCATACATGTAGATCAGATGGTCTTCGGTATATCCACACAACAAAG

AAAAGGGGGAGGTTTTGTTAAAAAAGAGAAATGTTACATAGTGCTCTTTGAGAAAATTCATTGGCACTATTAAGG

ATCTGAGGAGCTGGTGAGTTTCAACTGGTGAGTGATGGTGGTAGATAAAATTAGAGCTGCAGCAGGTCATTTTAG

CAACTATTAGATAAAACTGGTCTCAGGTCACAACGGGCAGTTGCAGCAGCTGGACTTGGAGAGAATTACACTGTG

GGAGCAGTGTCATTTGTCCTAAGTGCTTTTCTACCCCCTACCCCCACTATTTTAGTTGGGTATAAAAAGAATGAC

CCAATTTGTATGATCAACTTTCACAAAGCATAGAACAGTAGGAAAAGGGTCTGTTTCTGCAGAAGGTGTAGACGT

TGAGAGCCATTTTGTGTATTTATTCCTCCCTTTCTTCCTCGGTGAATGATTAAAACGTTCTGTGTGATTTTTAGT

GATGAAAAGATTAAATGCTACTCACTGTAGTAAGTGCCATCTCACACTTGCAGATCAAAAGGCACACAGTTTAA

AAAACCTTTGTTTTTTTACACATCTGAGTGGTGTAAATGCTACTCATCTGTAGTAAGTGGAATCTATACACCTGC

AGACCAAAAGACGCAAGGTTTCAAAAATCTTTGTGTTTTTTACACATCAAACAGAATGGTACGTTTTTCAAAAGT

TAAAAAAAAACAACTCATCCACATATTGCAACTAGCAAAATGACATTCCCCAGTGTGAAAATCATGCTTGAGAG

AATTCTTACATGTAAAGGCAAAATTGCGATGACTTTGCAGGGGACCGTGGGATTCCCGCCCGCAGTGCCGGAGCT

GTCCCCTACCAGGGTTTGCAGTGGAGTTTTGAATGCACTTAACAGTGTCTTACGGTAAAAACAAAATTTCATCCA

CCAATTATGTGTTGAGCGCCCACTGCCTACCAAGCACAAACAAAACCATTCAAAACCACGAAATCGTCTTCACTT

TCTCCAGATCCAGCAGCCTCCCCTATTAAGGTTCGCACACGCTATTGCGCCAACGCTCCTCCAGAGCGGGTCTTA

AGATAAAAGAACAGGACAAGTTGCCCCGCCCCATTTCGCTAGCCTCGTGAGAAAACGTCATCGCACATAGAAAAC

AGACAGACGTAACCTACGGTGTCCCGCTAGGAAAGAGAGGTGCGTCAAACAGCGACAAGTTCCGCCCACGTAAAA

-continued

```
GATGACGCTTGGTGTGTCAGCCGTCCCTGCTGCCCGGTTGCTTCTCTTTTGGGGGCGGGGTCTAGCAAGAGCAGG

TGTGGGTTTAGGAGGTGTGTGTTTTTGTTTTTCCCACCCTCTCTCCCCACTACTTGCTCTCACAGTACTCGCTGA

GGGTGAACAAGAAAAGACCTGATAAAGATTAACCAGAAGAAAACAAGGAGGGAAACAACCGCAGCCTGTAGCAAG

CTCTGGAACTCAGGAGTCGCGCGCTAGGGGCC(GGGGCC)ₙ

GGGGCCGGGGCGTGGTCGGGGCGGGCCCGGGGGCGGG

CCCGGGGCGGGGCTGCGGTTGCGGTGCCTGCGCCCGCGGCGGCGGAGGCGCAGGCGGTGGCGAGTGGGTGAGTGA

GGAGGCGGCATCCTGGCGGGTGGCTGTTTGGGGTTCGGCTGCCGGGAAGAGGCGCGGGTAGAAGCGGGGGCTCTC

CTCAGAGCTCGACGCATTTTTACTTTCCCTCTCATTTCTCTGACCGAAGCTGGGTGTCGGGCTTTCGCCTCTAGC

GACTGGTGGAATTGCCTGCATCCGGGCCCCGGGCTTCCCGGCGGCGGCGGCGGCGGCGGCGCAGGGACAAGG

GATGGGGATCTGGCCTCTTCCTTGCTTTCCCGCCCTCAGTACCCGAGCTGTCTCCTTCCCGGGGACCCGCTGGGA

GCGCTGCCGCTGCGGGCTCGAGAAAAGGGAGCCTCGGGTACTGAGAGGCCTCGCCTGGGGGAAGGCCGGAGGGTG

GGCGGCGCGCGGCTTCTGCGGACCAAGTCGGGGTTCGCTAGGAACCCGAGACGGTCCCTGCCGGCGAGGAGATCA

TGCGGGATGAGATGGGGGTGTGGAGACGCCTGCACAATTTCAGCCCAAGCTTCTAGAGAGTGGTGATGACTTGCA

TATGAGGGCAGCAATGCAAGTCGGTGTGCTCCCCATTCTGTGGGACATGACCTGGTTGCTTCACAGCTCCGAGAT

GACACAGACTTGCTTAAAGGAAGTGACTATTGTGACTTGGGCATCACTTGACTGATGGTAATCAGTTGTCTAAAG

AAGTGCACAGATTACATGTCCGTGTGCTCATTGGGTCTATCTGGCCGCGTTGAACACCACCAGGCTTTGTATTCA

GAAACAGGAGGGAGGTCCTGCACTTTCCCAGGAGGGGTGGCCCTTTCAGATGCAATCGAGATTGTTAGGCTCTGG

GAGAGTAGTTGCCTGGTTGTGGCAGTTGGTAAATTTCTATTCAAACAGTTGCCATGCACCAGTTGTTCACAACAA

GGGTACGTAATCTGTCTGGCATTACTTCTACTTTTGTACAAAGGATCAAAAAAAAAAAAGATACTGTTAAGATAT

GATTTTTCTCAGACTTTGGGAAACTTTTAACATAATCTGTGAATATCACAGAAACAAGACTATCATATAGGGGAT

ATTAATAACCTGGAGTCAGAATACTTGAAATACGGTGTCATTTGACACGGGCATTGTTGTCACCACCTCTGCCAA

GGCCTGCCACTTTAGGAAAACCCTGAATCAGTTGGAAACTGCTACATGCTGATAGTACATCTGAAACAAGAACGA

GAGTAATTACCACATTCCAGATTGTTCACTAAGCCAGCATTTACCTGCTCCAGGAAAAAATTACAAGCACCTTAT

GAAGTTGATAAAATATTTTGTTTGGCTATGTTGGCACTCCACAATTTGCTTTCAGAGAAACAAAGTAAACCAAGG

AGGACTTCTGTTTTTCAAGTCTGCCCTCGGGTTCTATTCTACGTTAATTAGATAGTTCCCAGGAGGACTAGGTTA

GCCTACCTATTGTCTGAGAAACTTGGAACTGTGAGAAATGGCCAGATAGTGATATGAACTTCACCTTCCAGTCTT

CCCTGATGTTGAAGATTGAGAAAGTGTTGTGAACTTTCTGGTACTGTAAACAGTTCACTGTCCTTGAAGTGGTCC

TGGGCAGCTCCTGTTGTGGAAAGTGGACGGTTTAGGATCCTGCTTCTCTTTGGGCTGGGAGAAAATAAACAGCAT

GGTTACAAGTATTGAGAGCCAGGTTGGAGAAGGTGGCTTACACCTGTAATGCCAGAGCTTTGGGAGGCGGAGGCA

AGAGGATCACTTGAAGCCAGGAGTTCAAGCTCAACCTGGGCAACGTAGACCCTGTCTCTACAAAAAATTAAAAAC

TTAGCCGGGCGTGGTGATGTGCACCTGTAGTCCTAGCTACTTGGGAGGCTGAGGCAGGAGGGTCATTTGAGCCCA

AGAGTTTGAAGTTACCGAGAGCTATGATCCTGCCAGTGCATTCCAGCCTGGATGACAAAACGAGACCCTGTCTCT

AAAAAACAAGAAGTGAGGGCTTTATGATTGTAGAATTTTCACTACAATAGCAGTGGACCAACCACCTTTCTAAAT

ACCAATCAGGGAAGAGATGGTTGATTTTTAACAGACGTTTAAAGAAAAAGCAAAACCTCAAACTTAGCACTCTA

CTAACAGTTTTAGCAGATGTTAATTAATGTAATCATGTCTGCATGTATGGGATTATTTCCAGAAAGTGTATTGGG

AAACCTCTCATGAACCCTGTGAGCAAGCCACCGTCTCACTCAATTTGAATCTTGGCTTCCGTCAAAAGACTGGCT

AATGTTTGGTAACTCTCTGGAGTAGACAGCACTACATGTACGTAAGATAGGTACATAAACAACTATTGGTTTTGA

GCTGATTTTTTCAGCTGCATTTGCATGTATGGATTTTTCTCACCAAAGACGATGACTTCAAGTATTAGTAAAAT

AATTGTACAGCTCTCCTGATTATACTTCTCTGTGACATTTCATTTCCCAGGCTATTTCTTTTGGTAGGATTTAAA

ACTAAGCAATTCAGTATGATCTTTGTCCTTCATTTTCTTTCTTATTCTTTTTGTTTGTTTGTTTGTTTTTT
```

```
TCTTGAGGCAGAGTCTCTCTCTGTCGCCCAGGCTGGAGTGCAGTGGCGCCATCTCAGCTCATTGCAACCTCTGCC

ACCTCCGGGTTCAAGAGATTCTCCTGCCTCAGCCTCCCGAGTAGCTGGGATTACAGGTGTCCACCACCACACCCG

GCTAATTTTTTGTATTTTTAGTAGAGGTGGGGTTTCACCATGTTGGCCAGGCTGGTCTTGAGCTCCTGACCTCAG

GTGATCCACCTGCCTCGGCCTACCAAAGAGCTGGGATAACAGGTGTGACCCACCATGCCCGGCCCATTTTTTTTT

TCTTATTCTGTTAGGAGTGAGAGTGTAACTAGCAGTATAATAGTTCAATTTTCACAACGTGGTAAAAGTTTCCCT

ATAATTCAATCAGATTTTGCTCCAGGGTTCAGTTCTGTTTTAGGAAATACTTTTATTTTCAGTTTAATGATGAAA

TATTAGAGTTGTAATATTGCCTTTATGATTATCCACCTTTTTAACCTAAAAGAATGAAAGAAAAATATGTTTGCA

ATATAATTTTATGGTTGTATGTTAACTTAATTCATTATGTTGGCCTCCAGTTTGCTGTTGTTAGTTATGACAGCA

GTAGTGTCATTACCATTTCAATTCAGATTACATTCCTATATTTGATCATTGTAAACTGACTGCTTACATTGTATT

AAAAACAGTGGATATTTTAAAGAAGCTGTACGGCTTATATCTAGTGCTGTCTCTTAAGACTATTAAATTGATACA

ACATATTTAAAAGTAAATATTACCTAAATGAATTTTTGAAATTACAAATACACGTGTTAAAACTGTCGTTGTGTT

CAACCATTTCTGTACATACTTAGAGTTAACTGTTTTGCCAGGCTCTGTATGCCTACTCATAATATGATAAAAGCA

CTCATCTAATGCTCTGTAAATAGAAGTCAGTGCTTTCCATCAGACTGAACTCTCTTGACAAGATGTGGATGAAAT

TCTTTAAGTAAAATTGTTTACTTTGTCATACATTTACAGATCAAATGTTAGCTCCCAAAGCAATCATATGGCAAA

GATAGGTATATCATAGTTTGCCTATTAGCTGCTTTGTATTGCTATTATTATAAATAGACTTCACAGTTTTAGACT

TGCTTAGGTGAAATTGCAATTCTTTTTACTTTCAGTCTTAGATAACAAGTCTTCAATTATAGTACAATCACACAT

TGCTTAGGAATGCATCATTAGGCGATTTTGTCATTATGCAAACATCATAGAGTGTACTTACACAAACCTAGATAG

TATAGCCTTTATGTACCTAGGCCGTATGGTATAGTCTGTTGCTCCTAGGCCACAAACCTGTACAACTGTTACTGT

ACTGAATACTATAGACAGTTGTAACACAGTGGTAAATATTTATCTAAATATATGCAAACAGAGAAAAGGTACAGT

AAAAGTATGGTATAAAAGATAATGGTATACCTGTGTAGGCCACTTACCACGAATGGAGCTTGCAGGACTAGAAGT

TGCTCTGGGTGAGTCAGTGAGTGAGTGGTGAATTAATGTGAAGGCCTAGAACACTGTACACCACTGTAGACTATA

AACACAGTACGCTGAAGCTACACCAAATTTATCTTAACAGTTTTTCTTCAATAAAAAATTATAACTTTTTAACTT

TGTAAACTTTTTAATTTTTTAACTTTTAAAATACTTAGCTTGAAACACAAATACATTGTATAGCTATACAAAAAT

ATTTTTTCTTTGTATCCTTATTCTAGAAGCTTTTTTCTATTTTCTATTTTAAATTTTTTTTTTACTTGTTAGTC

GTTTTTGTTAAAAACTAAAACACACACACTTTCACCTAGGCATAGACAGGATTAGGATCATCAGTATCACTCCCT

TCCACCTCACTGCCTTCCACCTCCACATCTTGTCCCACTGGAAGGTTTTTAGGGGCAATAACACACATGTAGCTG

TCACCTATGATAACAGTGCTTTCTGTTGAATACCTCCTGAAGGACTTGCCTGAGGCTGTTTTACATTTAACTTAA

AAAAAAAAAAGTAGAAGGAGTGCACTCTAAAATAACAATAAAAGGCATAGTATAGTGAATACATAAACCAGCAA

TGTAGTAGTTTATTATCAAGTGTTGTACACTGTAATAATTGTATGTGCTATACTTTAAATAACTTGCAAAATAGT

ACTAAGACCTTATGATGGTTACAGTGTCACTAAGGCAATAGCATATTTTCAGGTCCATTGTAATCTAATGGGACT

ACCATCATATATGCAGTCTACCATTGACTGAAACGTTACATGGCACATAACTGTATTTGCAAGAATGATTTGTTT

TACATTAATATCACATAGGATGTACCTTTTAGAGTGGTATGTTTATGTGGATTAAGATGTACAAGTTGAGCAAG

GGGACCAAGAGCCCTGGGTTCTGTCTTGGATGTGAGCGTTTATGTTCTTCTCCTCATGTCTGTTTTCTCATTAAA

TTCAAAGGCTTGAACGGGCCCTATTTAGCCCTTCTGTTTTCTACGTGTTCTAAATAACTAAAGCTTTTAAATTCT

AGCCATTTAGTGTAGAACTCTCTTTGCAGTGATGAAATGCTGTATTGGTTTCTTGGCTAGCATATTAAATATTTT

TATCTTTGTCTTGATACTTCAATGTCGTTTTAAACATCAGGATCGGGCTTCAGTATTCTCATAACCAGAGAGTTC

ACTGAGGATACAGGACTGTTTGCCCATTTTTTGTTATGGCTCCAGACTTGTGGTATTTCCATGTCTTTTTTTTTT

TTTTTTTTTTGACCTTTTAGCGGCTTTAAAGTATTTCTGTTGTTAGGTGTTGTATTACTTTTCTAAGATTACTT

AACAAAGCACCACAAACTGAGTCGCTTTAAACAACAGCAATTTATTCTCTCACAATTCTAGAAGCTAGAAGTCCG

AAATCAAAGTGTTGACAGGGGCATGATCTTCAAGAGAGAAGACTCTTTCCTTGCCTCTTCCTGGCTTCTGGTGGT

TACCAGCAATCCTGAGTGTTCCTTTCTTGCCTTGTAGTTTCAACAATCCAGTATCTGCCTTTTGTCTTCACATGG
```

-continued

```
CTGTCTACCATTTGTCTCTGTGTCTCCAAATCTCTCTCCTTATAAACACAGCAGTTATTGGATTAGGCCCCACTC

TAATCCAGTATGACCCCATTTTAACATGATTACACTTATTTCTAGATAAGGTCACATTCACGTACACCAAGGGTT

AGGAATTGAACATATCTTTTTGGGGACACAATTCAACCCACAAGTGTCAGTCTCTAGCTGAGCCTTTCCCTTCC

TGTTTTTCTCCTTTTTAGTTGCTATGGGTTAGGGGCCAAATCTCCAGTCATACTAGAATTGCACATGGACTGGAT

ATTTGGGAATACTGCGGGTCTATTCTATGAGCTTTAGTATGTAACATTTAATATCAGTGTAAAGAAGCCCTTTTT

TAAGTTATTTCTTTGAATTTCTAAATGTATGCCCTGAATATAAGTAACAAGTTACCATGTCTTGTAAAATGATCA

TATCAACAAACATTTAATGTGCACCTACTGTGCTAGTTGAATGTCTTTATCCTGATAGGAGATAACAGGATTCCA

CATCTTTGACTTAAGAGGACAAACCAAATATGTCTAAATCATTTGGGGTTTTGATGGATATCTTTAAATTGCTGA

ACCTAATCATTGGTTTCATATGTCATTGTTTAGATATCTCCGGAGCATTTGGATAATGTGACAGTTGGAATGCAG

TGATGTCGACTCTTTGCCCACCGCCATCTCCAGCTGTTGCCAAGACAGAGATTGCTTTAAGTGGCAAATCACCTT

TATTAGCAGCTACTTTTGCTTACTGGGACAATATTCTTGGTCCTAGAGTAAGGCACATTTGGGCTCCAAAGACAG

AACAGGTACTTCTCAGTGATGGAGAAATAACTTTTCTTGCCAACCACACTCTAAATGGAGAAATCCTTCGAAATG

CAGAGAGTGGTGCTATAGATGTAAAGTTTTTGTCTTGTCTGAAAAGGGAGTGATTATTGTTTCATTAATCTTTG

ATGGAAACTGGAATGGGGATCGCAGCACATATGGACTATCAATTATACTTCCACAGACAGAACTTAGTTTCTACC

TCCCACTTCATAGAGTGTGTGTTGATAGATTAACACATATAATCCGGAAAGGAAGAATATGGATGCATAAGGTAA

GTGATTTTTCAGCTTATTAATCATGTTAACCTATCTGTTGAAAGCTTATTTTCTGGTACATATAAATCTTATTTT

TTTAATTATATGCAGTGAACATCAAACAATAAATGTTATTTATTTTGCATTTACCCTATTAGATACAAATACATC

TGGTCTGATACCTGTCATCTTCATATTAACTGTGGAAGGTACGAAATGGTAGGTCCACATTATAGATGAAAAGCT

AAAGCTTAGACAAATAAAGAAACTTTTAGACCCTGGATTCTTCTTGGGAGCCTTTGACTCTAATACCTTTTGTTT

CCCTTTCATTGCACAATTCTGTCTTTTGCTTACTACTATGTGTAAGTATAACAGTTCAAAGTAATAGTTTCATAA

GCTGTTGGTCATGTAGCCTTTGGTCTCTTTAACCTCTTTGCCAAGTTCCCAGGTTCATAAAATGAGGAGGTTGAA

TGGAATGGTTCCCAAGAGAATTCCTTTTAATCTTACAGAAATTATTGTTTTCCTAAATCCTGTAGTTGAATATAT

AATGCTATTTACATTTCAGTATAGTTTTGATGTATCTAAAGAACACATTGAATTCTCCTTCCTGTGTTCCAGTTT

GATACTAACCTGAAAGTCCATTAAGCATTACCAGTTTTAAAAGGCTTTTGCCCAATAGTAAGGAAAAATAATATC

TTTTAAAAGAATAATTTTTTACTATGTTTGCAGGCTTACTTCCTTTTTTCTCACATTATGAAACTCTTAAAATCA

GGAGAATCTTTTAAACAACATCATAATGTTTAATTTGAAAAGTGCAAGTCATTCTTTTCCTTTTTGAAACTATGC

AGATGTTACATTGACTGTTTTCTGTGAAGTTATCTTTTTTTCACTGCAGAATAAAGGTTGTTTTGATTTTATTTT

GTATTGTTTATGAGAACATGCATTTGTTGGGTTAATTTCCTACCCCTGCCCCCATTTTTTCCCTAAAGTAGAAAG

TATTTTCTTGTGAACTAAATTACTACACAAGAACATGTCTATTGAAAAATAAGCAAGTATCAAAATGTTGTGGG

TTGTTTTTTAAATAAATTTTCTCTTGCTCAGGAAAGACAAGAAAATGTCCAGAAGATTATCTTAGAAGGCACAG

AGAGAATGGAAGATCAGGTATATGCAAATTGCATACTGTCAAATGTTTTCTCACAGCATGTATCTGTATAAGGT

TGATGGCTACATTTGTCAAGGCCTTGGAGACATACGAATAAGCCTTTAATGGAGCTTTTATGGAGGTGTACAGAA

TAAACTGGAGGAAGATTTCCATATCTTAAACCCAAAGAGTTAAATCAGTAAACAAAGGAAAATAGTAATTGCATC

TACAAATTAATATTTGCTCCCTTTTTTTTCTGTTTGCCCAGAATAAATTTTGGATAACTTGTTCATAGTAAAAA

TAAAAAAAATTGTCTCTGATATGTTCTTTAAGGTACTACTTCTCGAACCTTTCCCTAGAAGTAGCTGTAACAGAA

GGAGAGCATATGTACCCCTGAGGTATCTGTCTGGGGTGTAGGCCCAGGTCCACACAATATTTCTTCTAAGTCTTA

TTCTTACCCTCTCCTCTAGGAAAATGTGCCATGTTTATCCCTTGGCTTTGAATGCCCCTCAGGAACAGACACTAA

GAGTTTGAGAAGCATGGTTACAAGGGTGTGGCTTCCCCTGCGGAAACTAAGTACAGACTATTTCACTGTAAAGCA

GAGAAGTTCTTTTGAAGGAGAATCTCCAGTGAAGAAAGAGTTCTTCACTTTTACTTCCATTTCCTCTTGTGGGTG

ACCCTCAATGCTCCTTGTAAAACTCCAATATTTTAAACATGGCTGTTTTGCCTTTCTTTCGTTCTTTTTAGCATG
```

-continued

```
AATGAGACAGATGATACTTTAAAAAAGTAATTAAAAAAAAAAACTTGTGAAAATACATGGCCATAATACAGAACC
CAATACAATGATCTCCTTTACCAAATTGTTATGTTTGTACTTTTGTAGATAGCTTTCCAATTCAGAGACAGTTAT
TCTGTGTAAAGGTCTGACTTAACAAGAAAAGATTTCCCTTTACCCAAAGAATCCCAGTCCTTATTTGCTGGTCAA
TAAGCAGGGTCCCCAGGAATGGGGTAACTTTCAGCACCCTCTAACCCACTAGTTATTAGTAGACTAATTAAGTAA
ACTTATCGCAAGTTGAGGAAACTTAGAACCAACTAAAATTCTGCTTTTACTGGGATTTTGTTTTTTCAAACCAGA
AACCTTTACTTAAGTTGACTACTATTAATGAATTTTGGTCTCTCTTTTAAGTGCTCTTCTTAAAAATGTTATCTT
ACTGCTGAGAAGTTCAAGTTTGGGAAGTACAAGGAGGAATAGAAACTTAAGAGATTTTCTTTTAGAGCCTCTTCT
GTATTTAGCCCTGTAGGATTTTTTTTTTTTTTTTTTTGGTGTTGTTGAGCTTCAGTGAGGCTATTCATTCA
CTTATACTGATAATGTCTGAGATACTGTGAATGAAATACTATGTATGCTTAAACCTAAGAGGAAATATTTTCCCA
AAATTATTCTTCCCGAAAAGGAGGAGTTGCCTTTTGATTGAGTTCTTGCAAATCTGACAACGACTTTATTTTGAA
CAATACTGTTTGGGGATGATGCATTAGTTTGAAACAACTTCAGTTGTAGCTGTCATGTGATAAAATTGCTTCACA
GGGAAGGAAATTTAACACGGATCTAGTCATTATTCTTGTTAGATTGAATGTGTGAATTGTAATTGTAAACAGGCA
TGATAATTATTACTTTAAAAACTAAAAACAGTGAATAGTTAGTTGTGGAGGTTACTAAAGGATGGTTTTTTTTTA
AATAAAACTTTCAGCATTATGCAAATGGGCATATGGCTTAGGATAAAACTTCCAGAAGTAGCATCACATTTAAAT
TCTCAAGCAACTTAATAATATGGGGCTCTGAAAAACTGGTTAAGGTTACTCCAAAAATGGCCCTGGGTCTGACAA
AGATTCTAACTTAAAGATGCTTATGAAGACTTTGAGTAAAATCATTTCATAAAATAAGTGAGGAAAAACAACTAG
TATTAAATTCATCTTAAATAATGTATGATTTAAAAAATATGTTTAGCTAAAAATGCATAGTCATTTGACAATTTC
ATTTATATCTCAAAAAATTTACTTAACCAAGTTGGTCACAAAACTGATGAGACTGGTGGTGGTAGTGAATAAATG
AGGGACCATCCATATTTGAGACACTTTACATTTGTGATGTGTTATACTGAATTTTCAGTTTGATTCTATAGACTA
CAAATTTCAAAATTACAATTTCAAGATGTAATAAGTAGTAATATCTTGAAATAGCTCTAAAGGGAATTTTTCTGT
TTTATTGATTCTTAAAATATATGTGCTGATTTTGATTTGCATTTGGGTAGATATACTTTTTATGAGTATGGAGGT
TAGGTATTGATTCAAGTTTTCCTTACCTATTTGGTAAGGATTTCAAAGTCTTTTTGTGCTTGGTTTTCCTCATTT
TTAAATATGAAATATATTGATGACCTTTAACAAATTTTTTTATCTCAAATTTTAAAGGAGATCTTTTCTAAAAG
AGGCATGATGACTTAATCATTGCATGTAACAGTAAACGATAAACCAATGATTCCATACTCTCTAAAGAATAAAAG
TGAGCTTTAGGGCCGGGCATGGTCAGAAATTTGACACCAACCTGGCCAACATGGCGAAACCCCGTCTCTACTAAA
AATACAAAAATCAGCCGGGCATGGTGGCGGCACCTATAGTCCCAGCTACTTGGGAGGATGAGACAGGAGAGTCAC
TTGAACCTGGGAGGAGAGGTTGCAGTGAGCTGAGATCACGCCATTGCACTCCAGCCTGAGCAATGAAAGCAAAAC
TCCATCTCAAAAAAAAAAAAAGAAAAGAAAGAATAAAAGTGAGCTTTGGATTGCATATAAATCCTTTAGACATGT
AGTAGACTTGTTTGATACTGTGTTTGAACAAATTACGAAGTATTTTCATCAAAGAATGTTATTGTTTGATGTTAT
TTTTATTTTTTATTGCCCAGCTTCTCTCATATTACGTGATTTTCTTCACTTCATGTCACTTTATTGTGCAGGGTC
AGAGTATTATTCCAATGCTTACTGGAGAAGTGATTCCTGTAATGGAACTGCTTTCATCTATGAAATCACACAGTG
TTCCTGAAGAAATAGATGTAAGTTTAAATGAGAGCAATTATACACTTTATGAGTTTTTGGGGTTATAGTATTAT
TATGTATATTATTAATATTCTAATTTTAATAGTAAGGACTTTGTCATACATACTATTCACATACAGTATTAGCCA
CTTTAGCAAATAAGCACACACAAAATCCTGGATTTTATGGCAAAACAGAGGCATTTTGATCAGTGATGACAAAA
TTAAATTCATTTTGTTTATTTCATTACTTTTATAATTCCTAAAAGTGGGAGGATCCCAGCTCTTATAGGAGCAAT
TAATATTTAATGTAGTGTCTTTTGAAACAAAACTGTGTGCCAAAGTAGTAACCATTAATGGAAGTTTACTTGTAG
TCACAAATTTAGTTTCCTTAATCATTTGTTGAGGACGTTTTGAATCACACACTATGAGTGTTAAGAGATACCTTT
AGGAAACTATTCTTGTTGTTTTCTGATTTTGTCATTTAGGTTAGTCTCCTGATTCTGACAGCTCAGAAGAGGAAG
TTGTTCTTGTAAAAATTGTTTAACCTGCTTGACCAGCTTTCACATTTGTTCTTCTGAAGTTTATGGTAGTGCACA
GAGATTGTTTTTGGGGAGTCTTGATTCTCGGAAATGAAGGCAGTGTGTTATATTGAATCCAGACTTCCGAAAAC
TTGTATATTAAAAGTGTTATTTCAACACTATGTTACAGCCAGACTAATTTTTTATTTTTTGATGCATTTTAGAT
```

-continued

```
AGCTGATACAGTACTCAATGATGATGATATTGGTGACAGCTGTCATGAAGGCTTTCTTCTCAAGTAAGAATTTTT
CTTTTCATAAAAGCTGGATGAAGCAGATACCATCTTATGCTCACCTATGACAAGATTTGGAAGAAAGAAAATAAC
AGACTGTCTACTTAGATTGTTCTAGGGACATTACGTATTTGAACTGTTGCTTAAATTTGTGTTATTTTTCACTCA
TTATATTTCTATATATATTTGGTGTTATTCCATTTGCTATTTAAAGAAACCGAGTTTCCATCCCAGACAAGAAAT
CATGGCCCCTTGCTTGATTCTGGTTTCTTGTTTTACTTCTCATTAAAGCTAACAGAATCCTTTCATATTAAGTTG
TACTGTAGATGAACTTAAGTTATTTAGGCGTAGAACAAAATTATTCATATTTATACTGATCTTTTTCCATCCAGC
AGTGGAGTTTAGTACTTAAGAGTTTGTGCCCTTAAACCAGACTCCCTGGATTAATGCTGTGTACCCGTGGGCAAG
GTGCCTGAATTCTCTATACACCTATTTCCTCATCTGTAAAATGGCAATAATAGTAATAGTACCTAATGTGTAGGG
TTGTTATAAGCATTGAGTAAGATAAATAATATAAAGCACTTAGAACAGTGCCTGGAACATAAAAACACTTAATAA
TAGCTCATAGCTAACATTTCCTATTTACATTTCTTCTAGAAATAGCCAGTATTTGTTGAGTGCCTACATGTTAGT
TCCTTTACTAGTTGCTTTACATGTATTATCTTATATTCTGTTTTAAAGTTTCTTCACAGTTACAGATTTTCATGA
AATTTTACTTTTAATAAAAGAGAAGTAAAAGTATAAAGTATTCACTTTTATGTTCACAGTCTTTTCCTTTAGGCT
CATGATGGAGTATCAGAGGCATGAGTGTGTTTAACCTAAGAGCCTTAATGGCTTGAATCAGAAGCACTTTAGTCC
TGTATCTGTTCAGTGTCAGCCTTTCATACATCATTTTAAATCCCATTTGACTTTAAGTAAGTCACTTAATCTCTC
TACATGTCAATTTCTTCAGCTATAAAATGATGGTATTTCAATAAATAAATACATTAATTAAATGATATTATACTG
ACTAATTGGGCTGTTTTAAGGCTCAATAAGAAAATTTCTGTGAAAGGTCTCTAGAAAATGTAGGTTCCTATACAA
ATAAAAGATAACATTGTGCTTATAGCTTCGGTGTTTATCATATAAAGCTATTCTGAGTTATTTGAAGAGCTCACC
TACTTTTTTTGTTTTAGTTTGTTAAATTGTTTTATAGGCAATGTTTTAATCTGTTTTCTTTAACTTACAGTG
CCATCAGCTCACACTTGCAAACCTGTGGCTGTTCCGTTGTAGTAGGTAGCAGTGCAGAGAAAGTAAATAAGGTAG
TTTATTTTATAATCTAGCAAATGATTTGACTCTTTAAGACTGATGATATATCATGGATTGTCATTTAAATGGTAG
GTTGCAATTAAAATGATCTAGTAGTATAAGGAGGCAATGTAATCTCATCAAATTGCTAAGACACCTTGTGGCAAC
AGTGAGTTTGAAATAAACTGAGTAAGAATCATTTATCAGTTTATTTTGATAGCTCGGAAATACCAGTGTCAGTAG
TGTATAAATGGTTTTGAGAATATATTAAAATCAGATATATAAAAAAAATTACTCTTCTATTTCCCAATGTTATCT
TTAACAAATCTGAAGATAGTCATGTACTTTTGGTAGTAGTTCCAAAGAAATGTTATTTGTTTATTCATCTTGATT
TCATTGTCTTCGCTTTCCTTCTAAATCTGTCCCTTCTAGGGAGCTATTGGGATTAAGTGGTCATTGATTATTATA
CTTTATTCAGTAATGTTTCTGACCCTTTCCTTCAGTGCTACTTGAGTTAATTAAGGATTAATGAACAGTTACATT
TCCAAGCATTAGCTAATAAACTAAAGGATTTTGCACTTTTCTTCACTGACCATTAGTTAGAAAGAGTTCAGAGAT
AAGTATGTGTATCTTTCAATTTCAGCAAACCTAATTTTTAAAAAAAGTTTTACATAGGAAATATGTTGGAAATG
ATACTTTACAAAGATATTCATAATTTTTTTTGTAATCAGCTACTTTGTATATTTACATGAGCCTTAATTTATAT
TTCTCATATAACCATTTATGAGAGCTTAGTATACCTGTGTCATTATATTGCATCTACGAACTAGTGACCTTATTC
CTTCTGTTACCTCAAACAGGTGGCTTTCCATCTGTGATCTCCAAAGCCTTAGGTTGCACAGAGTGACTGCCGAGC
TGCTTTATGAAGGGAGAAAGGCTCCATAGTTGGAGTGTTTTTTTTTTTTTTTAAACATTTTTCCCATCCTCCA
TCCTCTTGAGGGAGAATAGCTTACCTTTTATCTTGTTTTAATTTGAGAAAGAAGTTGCCACCACTCTAGGTTGAA
AACCACTCCTTTAACATAATAACTGTGGATATGGTTTGAATTTCAAGATAGTTACATGCCTTTTTATTTTTCCTA
ATAGAGCTGTAGGTCAAATATTATTAGAATCAGATTTCTAAATCCCACCCAATGACCTGCTTATTTTAAATCAAA
TTCAATAATTAATTCTCTTCTTTTTGGAGGATCTGGACATTCTTTGATATTTCTTACAACGAATTTCATGTGTAG
ACCCACTAAACAGAAGCTATAAAAGTTGCATGGTCAAATAAGCTGAGAAAGTCTGCAGATGATATAATTCACCT
GAAGAGTCACAGTATGTAGCCAAATGTTAAAGGTTTTGAGATGCCATACAGTAAATTTACCAAGCATTTTCTAAA
TTTATTTGACCACAGAATCCCTATTTTAAGCAACAACTGTTACATCCCATGGATTCCAGGTGACTAAAGAATACT
TATTTCTTAGGATATGTTTTATTGATAATAACAATTAAAATTTCAGATATCTTTCATAAGCAAATCAGTGGTCTT
```

-continued

```
TTTACTTCATGTTTTAATGCTAAAATATTTTCTTTTATAGATAGTCAGAACATTATGCCTTTTTCTGACTCCAGC
AGAGAGAAAATGCTCCAGGTTATGTGAAGCAGAATCATCATTTAAATATGAGTCAGGGCTCTTTGTACAAGGCCT
GCTAAAGGTATAGTTTCTAGTTATCACAAGTGAAACCACTTTTCTAAAATCATTTTTGAGACTCTTTATAGACAA
ATCTTAAATATTAGCATTTAATGTATCTCATATTGACATGCCCAGAGACTGACTTCCTTTACACAGTTCTGCACA
TAGACTATATGTCTTATGGATTTATAGTTAGTATCATCAGTGAAACACCATAGAATACCCTTTGTGTTCCAGGTG
GGTCCCTGTTCCTACATGTCTAGCCTCAGGACTTTTTTTTTTTAACACATGCTTAAATCAGGTTGCACATCAAA
AATAAGATCATTTCTTTTTAACTAAATAGATTTGAATTTTATTGAAAAAAAATTTTAAACATCTTTAAGAAGCTT
ATAGGATTTAAGCAATTCCTATGTATGTGTACTAAAATATATATATTTCTATATATAATATATATTAGAAAAAAA
TTGTATTTTTCTTTTATTTGAGTCTACTGTCAAGGAGCAAAACAGAGAAATGTAAATTAGCAATTATTTATAATA
CTTAAAGGGAAGAAAGTTGTTCACCTTGTTGAATCTATTATTGTTATTTCAATTATAGTCCCAAGACGTGAAGAA
ATAGCTTTCCTAATGGTTATGTGATTGTCTCATAGTGACTACTTTCTTGAGGATGTAGCCACGGCAAAATGAAAT
AAAAAAATTTAAAAATTGTTGCAAATACAAGTTATATTAGGCTTTTGTGCATTTTCAATAATGTGCTGCTATGAA
CTCAGAATGATAGTATTTAAATATAGAAACTAGTTAAAGGAAACGTAGTTTCTATTTGAGTTATACATATCTGTA
AATTAGAACTTCTCCTGTTAAAGGCATAATAAAGTGCTTAATACTTTTGTTTCCTCAGCACCCTCTCATTTAATT
ATATAATTTTAGTTCTGAAAGGGACCTATACCAGATGCCTAGAGGAAATTTCAAAACTATGATCTAATGAAAAAA
TATTTAATAGTTCTCCATGCAAATACAAATCATATAGTTTTCCAGAAAATACCTTTGACATTATACAAAGATGAT
TATCACAGCATTATAATAGTAAAAAAATGGAAATAGCCTCTTTCTTCTGTTCTGTTCATAGCACAGTGCCTCATA
CGCAGTAGGTTATTATTACATGGTAACTGGCTACCCCAACTGATTAGGAAAGAAGTAAATTTGTTTTATAAAAAT
ACATACTCATTGAGGTGCATAGAATAATTAAGAAATTAAAAGACACTTGTAATTTTGAATCCAGTGAATACCCAC
TGTTAATATTTGGTATATCTCTTTCTAGTCTTTTTTTCCCTTTTGCATGTATTTTCTTTAAGACTCCCACCCCCA
CTGGATCATCTCTGCATGTTCTAATCTGCTTTTTTCACAGCAGATTCTAAGCCTCTTTGAATATCAACACAAACT
TCAACAACTTCATCTATAGATGCCAAATAATAAATTCATTTTTATTTACTTAACCACTTCCTTTGGATGCTTAGG
TCATTCTGATGTTTTGCTATTGAAACCAATGCTATACTGAACACTTCTGTCACTAAAACTTTGCACACACTCATG
AATAGCTTCTTAGGATAAATTTTTAGAGATGGATTTGCTAAATCAGAGACCATTTTTAAAATTAAAAAACAATT
ATTCATATCGTTTGGCATGTAAGCACAGTAAATTTTCCTTTTATTTTGACAGGATTCAACTGGAAGCTTTGTGCTG
CCTTTCCGGCAAGTCATGTATGCTCCATATCCCACCACACACATAGATGTGGATGTCAATACTGTGAAGCAGATG
CCACCCTGTCATGAACATATTTATAATCAGCGTAGATACATGAGATCCGAGCTGACAGCCTTCTGGAGAGCCACT
TCAGAAGAAGACATGGCTCAGGATACGATCATCTACACTGACGAAAGCTTTACTCCTGATTTGTACGTAATGCTC
TGCCTGCTGGTACTGTAGTCAAGCAATATGAAATTGTGTCTTTTACGAATAAAAACAAAACAGAAGTTGCATTTA
AAAAGAAAGAAATATTACCAGCAGAATTATGCTTGAAGAAACATTTAATCAAGCATTTTTTTCTTAAATGTTCTT
CTTTTTCCATACAATTGTGTTTACCCTAAAATAGGTAAGATTAACCCTTAAAGTAAATATTTAACTATTTGTTTA
ATAAATATATATTGAGCTCCTAGGCACTGTTCTAGGTACCGGGCTTAATAGTGGCCAACCAGACAGCCCCAGCCC
CAGCCCCTACATTGTGTATAGTCTATTATGTAACAGTTATTGAATGGACTTATTAACAAAACCAAAGAAGTAATT
CTAAGTCTTTTTTTTCTTGACATATGAATATAAAATACAGCAAAACTGTTAAAATATATTAATGGAACATTTTTT
TACTTTGCATTTTATATTGTTATTCACTTCTTATTTTTTTTAAAAAAAAAAGCCTGAACAGTAAATTCAAAAGG
AAAAGTAATGATAATTAATTGTTGAGCATGGACCCAACTTGAAAAAAAAAATGATGATGATAAATCTATAATCCT
AAAACCCTAGTAAACACCTTAAAAGATGTTCTGAAATCAGGAAAAGAATTATAGTATACTTTTGTGTTTCTCTTT
TATCAGTTGAAAAAAGGCACAGTAGCTCATGCCTGTAAGAACAGAGCTTTGGGAGTGCAAGGGAGGGGGATCACT
TGAGGCCAGGAGTTCCAGACCAGCCTGGGCAACATAGTGAAACCCCATCTCTACAAAAAATAAAAAAGAATTATT
GGAATGTGTTTCTGTGTGCCTCTAATCCTAGCTATTCCGAAAGCTGAGGCAGGAGGATCTTTGAGCCCAGGAGT
TTGAGGTTACAGGGAGTTATGATGTGCCAGTGTACTCCAGCCTGGGGAACACCGAGACTCTGTCTTATTTAAAAA
```

```
AAAAAAAAAAAAAATGCTTGCAATAATGCCTGGCACATAGAAGGTAACAGTAAGTGTTAACTGTAATAACCCAGG

TCTAAGTGTGTAAGGCAATAGAAAAATTGGGGCAAATAAGCCTGACCTATGTATCTACAGAATCAGTTTGAGCTT

AGGTAACAGACCTGTGGAGCACCAGTAATTACACAGTAAGTGTTAACCAAAAGCATAGAATAGGAATATCTTGTT

CAAGGGACCCCCAGCCTTATACATCTCAAGGTGCAGAAAGATGACTTAATATAGGACCCATTTTTTCCTAGTTCT

CCAGAGTTTTTATTGGTTCTTGAGAAAGTAGTAGGGGAATGTTTTAGAAAATGAATTGGTCCAACTGAAATTACA

TGTCAGTAAGTTTTTATATATTGGTAAATTTTAGTAGACATGTAGAAGTTTTCTAATTAATCTGTGCCTTGAAAC

ATTTTCTTTTTTCCTAAAGTGCTTAGTATTTTTTCCGTTTTTTGATTGGTTACTTGGGAGCTTTTTTGAGGAAAT

TTAGTGAACTGCAGAATGGGTTTGCAACCATTTGGTATTTTTGTTTTGTTTTTTAGAGGATGTATGTGTATTTTA

ACATTTCTTAATCATTTTTAGCCAGGTATGTTTGTTTTGCTGATTTGACAAACTACAGTTAGACAGGTATTCTCA

TTTTGCTGATCATGACAAAATAATATCCTGAATTTTTAAATTTTGCATCCAGCTCTAAATTTTCTAAACATAAAA

TTGTCCAAAAAATAGTATTTTCAGCCACTAGATTGTGTGTTAAGTCTATTGTCACAGAGTGATTTTACTTTTAAG

TATATGTTTTTACATGTTAATTATGTTTGTTATTTTTAATTTTAACTTTTTAAAATAATTCCAGTCACTGCCAAT

ACATGAAAAATTGGTCACTGGAATTTTTTTTTGACTTTTATTTTAGGTTCATGTGTAGATGTGCAGGTGTGTTA

TACAGGTAAATTGCGTGTCATGAGGGTTTGGTGTACAGGTGATTTCATTACCCAGGTAATAAGCATAGTACCCAA

TAGGTAGTTTTTTGATCCTCACCCTTCTCCCACCCTCAAGTAGGCCCTGGTGTTGCTGTTTCCTTCTTTGTGTCC

ATGTATACTCAGTGTTTAGCTCCCACTTAGAAGTGAGAACATGCGGTAGTTGGTTTTCTGTTCCTGGATTAGTTC

ACTTAGGATAATGACCTCTAGCTCCATCTGGTTTTTATGGCTGCATAGTATTCCATGGTGTATATGTATCACATT

TTCTTTATCCAGTCTACCATTGATAGGCATTTAGGTTGATTCCCTCTCTTTGTTATCATGAATAGTGCTGTGATG

AACATACACATGCATGTGTCTTTATGGTAGAAAAATTTGTATTCCTTTAGGTACATATAGAATAATGGGGTTGCT

AGGGTGAATGGTAGTTCTATTTTCAGTTATTTGAGAAATCTTCAAACTGCTTTTCATAATAGCTAAACTAATTTA

CAGTCCCGCCAGCAGTGTATAAGTGTTCCCTTTTCTCCACAACCTTGCCAACATCTGTGATTTTTGACTTTTTA

ATAATAGCCATTCCTAGAGAATTGATTTGCAATTCTCTATTAGTGATATTAAGCATTTTTTCATATGCTTTTTAG

CTGTCTGTATATATTCTTCTGAAAAATTTTCATGTCCTTTGCCCAGTTTGTAGTGGGGTGGGTTGTTTTTGCTT

GTTAATTAGTTTTAAGTTCCTTCCAGATTCTGCATATCCCTTTGTTGGATACATGGTTTGCAGATATTTTCTCC

CATTGTGTAGGTTGTCTTTTACTCTGTTGATAGTTTCTTTTGCCATGCAGGAGCTCGTTAGGTCCCATTTGTGTT

TGTTTTTGTTGCAGTTGCTTTTGGCGTCTTCATCATAAAATCTGTGCCAGGGCCTATGTCCAGAATGGTATTTCC

TAGGTTGTCTTCCAGGGTTTTTACAATTTTAGATTTTACCTTTATGTCTTTAATCCATCTTGAGTTGATTTTTGT

ATATGGCACAAGGAAGGGGTCCAGTTTCACTCCAATTCCTATGGCTAGCAATTATCCCAGCACCATTTATTGAAT

ACGGAGTCCTTTCCCCATTGCTTGTTTTTTGTCAACTTTGTTGAAGATCAGATGGTTGTAAGTGTGTGGCTTTAT

TTCTTGGCTCTCTATTCTCCATTGGTCTATGTGTCTGTTTTTATAACAGTACCCTCCTGTTCAGGTTCCTATAGC

CTTTTAGTATAAATCGCCTTTATGTGATGCCTCCAGCTTTGTTCTTTTTGCTTAGGATTGCTTTGGCTATTTGGG

CTCCTTTTGGGTCCATATTAATTTTAAAACAGTTTTTTCTGGTTTTGTGAAGGATATCATTGGTAGTTTATAGG

AATAGCATTGAATCTGTAGATTGCTTTGGGCAGTATGGCCATTTTAACAATATTAATTCTTCCTATCTATGAATA

TGGAATGTTTTTCCATGTGTTTGTGTCATCTCTTTATACCTGATGTATAAAGAAAAGCTGGTATTATTCCTACTC

AATCTGTTCCAAAAAATTGAGGAGGAGGAACTCTTCCCTAATGAGGCCAGCATCATTCTGATACCAAAACCTGGC

AGAGACACAACAGAAAAAGAAAACTTCAGGCCAATATCCTTGATGAATATAGATGCAAAAATCCTCAACAAAAT

ACTAGCAAACCAAATCCAGCAGCACATCAAAAAGCTGATCTACTTTGATCAAGTAGGCTTTATCCCTGGGATGCA

AGGTTGGTTCAACATACACAAATCAATAAGTGTGATTCATCACATAAACAGAGCTAAAAACAAAAACCACAAGAT

TATCTCAATAGGTAGAGAAAAGGTTGTCAATAAAATTTAACATCCTCCATGTTAAAAACCTTCAGTAGGTCAGGT

GTAGTGACTCACACCTGTAATCCGAGCACTTTGGGAGGCCAAGGCGGGCATATCTCTTAAGCCCAGGAGTTCAAG
```

-continued

```
ACGAGCCTAGGCAGCATGGTGAAACCCCATCTCTACAAAAAAAAAAAAAAAAAAAATTAGCTTGGTATGGTGAC

ATGCACCTATAGTCCCAGCTATTCAGGAGGTTGAGGTGGGAGGATTGTTTGAGCCCGGGAGGCAGAGGTTGGCAG

CGAGCTGAGATCATGCCACCGCACTCCAGCCTGGGCAACGGAGTGAGACCCTGTCTCAAAAAAGAAAAATCACAA

ACAATCCTAAACAAATAGGCATTGAAGGATACATGCCTCAAAAAAATAAGAACCATCTATGACAGACCCATAGCC

AATATCTTACCAAATGGGCAAAAGCTGGAAGTATTCTCCTTGAGAACCGTAACAAGACAAGGATGTCCACTCTCA

CCACTCCTTTTCAGCATAGTTCTGGAAGTCCTAGCCAGAGCAATCAGGAAAGAGAAAGAAAGAAAGACATTCAGA

TAGGAAGAGAAGAAGTCAAACTATTTCTGTTTGCAGGCAGTATAATTCTGTACCTAGAAAATCTCATAGTCTCTG

CCCAGAAACTCCTAAATCTGTTAAAAATTTCAGCAAAGTTTTGGCATTCTCTATACTCCAACACCTTCCAAAGTG

AGAGCAAAATCAAGAACACAGTCCCATTCACAATAGCCGCAAAACGAATAAAATACCTAGGAATCCAGCTAACCA

GGGAGGTGAAAGATCTCTATGAGAATTACAAAACACTGCTGAAAGAAATCAGAGATGACACAAACAAATGGAAAT

GTTCTTTTTAACACCTTGCTTTATCTAATTCACTTATGATGAAGATACTCATTCAGTGGAACAGGTATAATAAG

TCCACTCGATTAAATATAAGCCTTATTCTCTTTCCAGAGCCCAAGAAGGGGCACTATCAGTGCCGAGTCAATAAT

GACGAAATGCTAATATTTTTCCCCTTTACGGTTTCTTTCTTCTGTAGTGTGGTACACTCGTTTCTTAAGATAAGG

AAACTTGAACTACCTTCCTGTTTGCTTCTACACATACCCATTCTCTTTTTTTGCCACTCTGGTCAGGTATAGGAT

GATCCCTACCACTTTCAGTTAAAAACTCCTCCTCTTACTAAATGTTCTCTTACCCTCTGGCCTGAGTAGAACCTA

GGGAAAATGGAAGAGAAAAAGATGAAAGGGAGGTGGGGCCTGGGAAGGGAATAAGTAGTCCTGTTTGTTTGTGTG

TTTGCTTTAGCACCTGCTATATCCTAGGTGCTGTGTTAGGCACACATTATTTTAAGTGGCCATTATATTACTACT

ACTCACTCTGGTCGTTGCCAAGGTAGGTAGTACTTTCTTGGATAGTTGGTTCATGTTACTTACAGATGGTGGGCT

TGTTGAGGCAAACCCAGTGGATAATCATCGGAGTGTGTTCTCTAATCTCACTCAAATTTTTCTTCACATTTTTTG

GTTTGTTTTGGTTTTTGATGGTAGTGGCTTATTTTTGTTGCTGGTTTGTTTTTTGTTTTTTTTGAGATGGCAAG

AATTGGTAGTTTTATTTATTAATTGCCTAAGGGTCTCTACTTTTTTTAAAAGATGAGAGTAGTAAAATAGATTGA

TAGATACATACATACCCTTACTGGGGACTGCTTATATTCTTTAGAGAAAAAATTACATATTAGCCTGACAAACAC

CAGTAAAATGTAAATATATCCTTGAGTAAATAAATGAATGTATATTTTGTGTCTCCAAATATATATATCTATATT

CTTACAAATGTGTTTATATGTAATATCAATTTATAAGAACTTAAAATGTTGGCTCAAGTGAGGGATTGTGGAAGG

TAGCATTATATGGCCATTTCAACATTTGAACTTTTTTCTTTTCTTCATTTTCTTCTTTTCTTCAGGAATATTTTT

CAAGATGTCTTACACAGAGACACTCTAGTGAAAGCCTTCCTGGATCAGGTAAATGTTGAACTTGAGATTGTCAGA

GTGAATGATATGACATGTTTTCTTTTTAATATATCCTACAATGCCTGTTCTATATATTTATATTCGCCTGGATC

ATGCCCCAGAGTTCTGCTCAGCAATTGCAGTTAAGTTAGTTACACTACAGTTCTCAGAAGAGTCTGTGAGGGCAT

GTCAAGTGCATCATTACATTGGTTGCCTCTTGTCCTAGATTTATGCTTCGGGAATTCAGACCTTTGTTTACAATA

TAATAAATATTATTGCTATCTTTTAAAGATATAATAATAAGATATAAAGTTGACCACAACTACTGTTTTTTGAAA

CATAGAATTCCTGGTTTACATGTATCAAAGTGAAATCTGACTTAGCTTTTACAGATATAATATATACATATATAT

ATCCTGCAATGCTTGTACTATATATGTAGTAGAAGTATATATATATGTTTGTGTGTATATATATATAGTACGA

GCATATATACATATTACCAGCATTGTAGGATATATATATGTTTATATATTAAAAAAAAGTTATAAACTTAAAACG

CTATTATGTTATGTAGAGTATATGTTATATATGATATGTAAAATATATAACATATACTCTATGATAGAGTGTAAT

ATATTTTTATATATATTTTAACATTTATAAAATGATAGAATTAAGAATTGAGTCCTAATCTGTTTTATTAGGTG

CTTTTTGTAGTGTCTGGTCTTTCTAAAGTGTCTAAATGATTTTTCCTTTTGACTTATTAATGGGAAGAGCCTGT

ATATTAACAATTAAGAGTGCAGCATTCCATAGGTCAAACAACAAACATTTTAATTCAAGCATTAACCTATAACAA

GTAAGTTTTTTTTTTTTTTGAGAAAGGGAGGTTGTTTATTTGCCTGAAATGACTCAAAAATATTTTTGAAACA

TAGTGTACTTATTTAAATAACATCTTTATTGTTTCATTCTTTTAAAAAATATCTACTTAATTACACAGTTGAAGG

AAATCGTAGATTATATGGAACTTATTTCTTAATATATTACAGTTTGTTATAATAACATTCTGGGGATCAGGCCAG

GAAACTGTGTCATAGATAAAGCTTTGAAATAATGAGATCCTTATGTTTACTAGAAATTTTGGATTGAGATCTATG
```

-continued

```
AGGTCTGTGACATATTGCGAAGTTCAAGGAAAATTCGTAGGCCTGGAATTTCATGCTTCTCAAGCTGACATAAAA

TCCCTCCCACTCTCCACCTCATCATATGCACACATTCTACTCCTACCCACCCACTCCACCCCCTGCAAAAGTACA

GGTATATGAATGTCTCAAAACCATAGGCTCATCTTCTAGGAGCTTCAATGTTATTTGAAGATTTGGGCAGAAAAA

ATTAAGTAATACGAAATAACTTATGTATGAGTTTTAAAAGTGAAGTAAACATGGATGTATTCTGAAGTAGAATGC

AAAATTTGAATGCATTTTTAAAGATAAATTAGAAAACTTCTAAAAACTGTCAGATTGTCTGGGCCTGGTGGCTTA

TGCCTGTAATCCCAGCACTTTGGGAGTCCGAGGTGGGTGGATCACAAGGTCAGGAGATCGAGACCATCCTGCCAA

CATGGTGAAACCCCGTCTCTACTAAGTATACAAAAATTAGCTGGGCGTGGCAGCGTGTGCCTGTAATCCCAGCTA

CCTGGGAGGCTGAGGCAGGAGAATCGCTTGAACCCAGGAGGTGTAGGTTGCAGTGAGTCAAGATCGCGCCACTGC

ACTTTAGCCTGGTGACAGAGCTAGACTCCGTCTCAAAAAAAAAAAAAATATCAGATTGTTCCTACACCTAGTGC

TTCTATACCACACTCCTGTTAGGGGGCATCAGTGGAAATGGTTAAGGAGATGTTTAGTGTGTATTGTCTGCCAAG

CACTGTCAACACTGTCATAGAAACTTCTGTACGAGTAGAATGTGAGCAAATTATGTGTTGAAATGGTTCCTCTCC

CTGCAGGTCTTTCAGCTGAAACCTGGCTTATCTCTCAGAAGTACTTTCCTTGCACAGTTTCTACTTGTCCTTCAC

AGAAAAGCCTTGACACTAATAAAATATATAGAAGACGATACGTGAGTAAAACTCCTACACGGAAGAAAAACCTTT

GTACATTGTTTTTTGTTTTGTTTCCTTTGTACATTTTCTATATCATAATTTTTGCGCTTCTTTTTTTTTTTTT

TTTTTTTTTTTCCATTATTTTTAGGCAGAAGGGAAAAAAGCCCTTTAAATCTCTTCGGAACCTGAAGATAGACC

TTGATTTAACAGCAGAGGGCGATCTTAACATAATAATGGCTCTGGCTGAGAAAATTAAACCAGGCCTACACTCTT

TTATCTTTGGAAGACCTTTCTACACTAGTGTGCAAGAACGAGATGTTCTAATGACTTTTTAAATGTGTAACTTAA

TAAGCCTATTCCATCACAATCATGATCGCTGGTAAAGTAGCTCAGTGGTGTGGGGAAACGTTCCGCTGGATCATA

CTCCAGAATTCTGCTCTCAGCAATTGCAGTTAAGTAAGTTACACTACAGTTCTCACAAGAGCCTGTGAGGGGATG

TCAGGTGCATCATTACATTGGGTGTCTCTTTTCCTAGATTTATGCTTTTGGGATACAGACCTATGTTTACAATAT

AATAAATATTATTGCTATCTTTTAAAGATATAATAATAGGATGTAAACTTGACCACAACTACTGTTTTTTTGAAA

TACATGATTCATGGTTTACATGTGTCAAGGTGAAATCTGAGTTGGCTTTTACAGATAGTTGACTTTCTATCTTTT

GGCATTCTTTGGTGTGTAGAATTACTGTAATACTTCTGCAATCAACTGAAAACTAGAGGCTTTAAATGATTTCAA

TTCCACAGAAAGAAAGTGAGCTTGAACATAGGATGAGCTTTAGAAAGAAAATTGATCAAGCAGATGTTTAATTGG

AATTGATTATTAGATCCTACTTTGTGGATTTAGTCCCTGGGATTCAGTCTGTAGAAATGTCTAATAGTTCTCTAT

AGTCCTTGTTCCTGGTGAACCACAGTTAGGGTGTTTTGTTTATTTTATTGTTCTTGCTATTGTTGATATTCTATG

TAGTTGAGCTCTGTAAAAGGAAATTGTATTTTATGTTTTAGTAATTGTTGCCAACTTTTTAAATTAATTTTCATT

ATTTTTGAGCCAAATTGAAATGTGCACCTCCTGTGCCTTTTTTCTCCTTAGAAAATCTAATTACTTGGAACAAGT

TCAGATTTCACTGGTCAGTCATTTTCATCTTGTTTTCTTCTTGCTAAGTCTTACCATGTACCTGCTTTGGCAATC

ATTGCAACTCTGAGATTATAAAATGCCTTAGAGAATATACTAACTAATAAGATCTTTTTTTCAGAAACAGAAAAT

AGTTCCTTGAGTACTTCCTTCTTGCATTTCTGCCTATGTTTTTGAAGTTGTTGCTGTTTGCCTGCAATAGGCTAT

AAGGAATAGCAGGAGAAATTTTACTGAAGTGCTGTTTTCCTAGGTGCTACTTTGGCAGAGCTAAGTTATCTTTTG

TTTTCTTAATGCGTTTGGACCATTTTGCTGGCTATAAAATAACTGATTAATATAATTCTAACACAATGTTGACAT

TGTAGTTACACAAACACAAATAAATATTTTATTTAAAATTCTGGAAGTAATATAAAAGGGAAATATATTTATAA

GAAAGGGATAAAGGTAATAGAGCCCTTCTGCCCCCCACCCACCAAATTTACACAACAAAATGACATGTTCGAATG

TGAAAGGTCATAATAGCTTTCCCATCATGAATCAGAAAGATGTGGACAGCTTGATGTTTAGACAACCACTGAAC

TAGATGACTGTTGTACTGTAGCTCAGTCATTTAAAAAATATATAAATACTACCTTGTAGTGTCCCATACTGTGTT

TTTTACATGGTAGATTCTTATTTAAGTGCTAACTGGTTATTTTCTTTGGCTGGTTTATTGTACTGTTATACAGAA

TGTAAGTTGTACAGTGAAATAAGTTATTAAAGCATGTGTAAACATTGTTATATATCTTTTCTCCTAAATGGAGAA

TTTTGAATAAAATATATTTGAAATTTTGCCTCTTTCAGTTGTTCATTCAGAAAAAAATACTATGATATTTGAAGA
```

-continued
CTGATCAGCTTCTGTTCAGCTGACAGTCATGCTGGATCTAAACTTTTTTAAAATTAATTTTGTCTTTTCAAAGA

AAAAATATTTAAAGAAGCTTTATAATATAATCTTATGTTAAAAAAACTTTCTGCTTAACTCTCTGGATTTCATTT

TGATTTTTGAAATTATATATTAATATTTCAAATGTAAAATACTATTTAGATAAATTGTTTTTAAACATTCTTATT

ATTATAATATTAATATAACCTAAACTGAAGTTATTCATCCCAGGTATCTAATACATGTATCCAAAGTAAAAATCC

AAGGAATCTGAACACTTTCATCTGCAAAGCTAGGAATAGGTTTGACATTTTCACTCCAAGAAAAAGTTTTTTTTT

GAAAATAGAATAGTTGGGATGAGAGGTTTCTTTAAAAGAAGACTAACTGATCACATTACTATGATTCTCAAAGAA

GAAACCAAAACTTCATATAATACTATAAAGTAAATATAAAATAGTTCCTTCTATAGTATATTTCTATAATGCTAC

AGTTTAAAGAGATCACTCTTATATAATACTATTTTGATTTTGATGTAGAATTGCACAAATTGATATTTCTCCTAT

GATCTGCAGGGTATAGCTTAAAGTAACAAAAACAGTCAACCACCTCCATTTAACACACAGTAACACTATGGGACT

AGTTTTATTACTTCCATTTTACAAATGAGGAAACTAAAGCTTAAAGATGTGTAATAGACCGCCCAAGGTCACACA

GCTGGTAAAGGTGGATTTCATCCCAGACAGTTAGAGTGATTGCCATGGGCACAGCTCCTAACTTAGTAACTCCAT

GTAACTGGTACTCAGTGTAGCTGAATTGAAAGGAGAGTAAGGAAGCAGGTTTTACAGGTCTACTTGCACTATTCA

GAGCCCGAGTGTGAATCCCTGCTGTGCTGCTTGGAGAAGTTACTTAACCTATGCAAGGTTCATTTTGTAAATATT

GGAAATGGACTGATAATACGTACTTCACCAGAGGATTTAATGAGACCTTATACGATCCTTAGTTCAGTACCTGAC

TAGTGCTTCATAAATGCTTTTTCATCCAATCTGACAATCTCCAGCTTGTAATTGGGGCATTTAGAACATTTAATA

TGATTATTGGCATGGTAGGTTAAAGGTGTGATCTTGCTGTTTTCTATTTGTTCTTTTTGTTTCTCCTTACTTTT

GGATTTTTTATTCTACTATGTCTTTCTATTGTCTTATTAACTATACTCTTTGATTTATTTTAGTGGTTGTTTT

AGGGTTATACCTCTTTCTAATTTACCAGTTTATAACCAGTTTATATACTACTTGACATATAGGTTAAGAAACTTA

CTGTTCTTGTCTTTTTGCTGTTATGGTCTTAACGTTTTTATTTCTACAAACATTATAAACTCCACACTTTATTGT

TTTTTAATTTTACTTATACAGTCAATTATCTTTTAAAGATATTTAAATATAAACATTCAAAACACCCCAATTAAA

AGTCAGAGATTGTTAATACCACATGATCTCACTTACACAGAGAATTGAAAAACTTGGAACTCATAGAAGCAGAGA

GTAAAAACATGGTTACCAGGTGCTGGGGAGAGGCGGTGGGCTGGGGAGATGTTGGTCAAAGTTAGACAGGAGGAA

TAAGTTCAAGAGATCTATTGTACAACTTATTCAGTTAGATAGGAGGAATAAGCTAAAGATCAAGAGATCTATTGT

ACAATGTGACTATAACCAACAACATATATTGTACACTTGAAAATTGCTAACAGTATCTTTTAAGTGTTCTCTCTA

CAAATAAATATGTGAGGTAATGTATATATTAATTAACTGTAGTCATTTCACAATGTATACTTATTTCAAAACATC

ATATTGTATGCTATAAATATATACAACTTTTATTTTTCAATTTTAGAAATGTCCTTAAAAAATCAGATTTTCAGA

TCAGATAAAAAAGCAAGACCCAACTATATGCTGCCAACAGGAAACACACCTTAAAAATAAAGGACGAACAAACAG

ATTAAAAGTAAAAGGATGGAGAAAAGATACATCATATTGGTAATTAGAAGAAAACTGGAGTGACAATATGAAACA

AAATAGATTTCAGAGCAAAGAATATTACCAGGGGTAAAAATGATCATTTTATAATGATAAAAGAGTCAGTTCAGe

AAAAGGATATAACAGTCCTAAATGTTTTTTCACCTCATAGCTGTGTCAAAATAGATGAAGCAAAAACTGATAGAA

CTGTAAGAAGTAGACAAGTCCACAATTATGTTTGGAGATTTTTTTTTTTTTTTTTTGTCGCCCAGGCTGGAGT

GCAGTGGCAGGATCTCAGCTCACTGCAAGCTCCGCCTCCCAGGTTCACGCCATTCTCCTGCTTCAGCCTCCCCAG

TAGCTGGGACTACAGGCGGCCACCACCACGCCTGGCTAATTTTTTGTATTTTTAGTAGAGACGGGGTTTCACCG

TGTTAGCCAGGATGGTCTCGATCTCCTGACCTCGTGATCTGCCTGCCTCGGCCTCCCAAAGTGCTGGGATTACAG

GCATGAGCCACTGCACGCAGCCTGGAGATTTAATATCCTTTCAATGTTTAGTAGAACAAGAATACACAAAATCA

GTAAGGATATAGAAGATTAGAACAAGACTATCAAACAATTTGACTTAAATGACATTTGTAGAGCACAGCAGTCCC

CAACAACAATAAATCACACATTCTTTCCAAGAGTACATGAAACATGTACCAAGATAGACCGTATTTTGAGCCATG

AAACAAATCTTGATAAATTTAAAAGGATTCAAGTCATAGAAAATATGTTCTCTGACCACAATGGAATTAAATTAT

TAACCAATAACAAATATCTGGGAAAACCTCAAAAACTTGGACACCAGCGCTTTTAAAAGACTAAATAATTTCTAA

ATTATCTGTGTTGGGGGGAAAAGAGAAATGGATTAGAGAGCAAAAAGGGTATCAGAGTGCTGTGGTACGATTTTT

ATGAAGAGTGGAACAGAATCTGCCTTTGGCGTTTCCCCACTACAGCCCATTCTTCACATTGATAACAGCATGATC

-continued

```
CTTCTAAAATTAAATCTAACGATCACTTCTGCTTAATGGCTCTCCAACACTTACAGAATTAGGTCCAAAATTCTA

GCACAGTTTCTGTTCATCTTTCTAACCTTTCTTCCCACAGGTCTAGCTAGTACGTATTTCTTTTATTGCATTTAT

TACACTATTCCTTTGCTTATCTATCTCCCCACCTAGGCTAAAGAACAAGATTCTTGTCTTTTTCATTTTTGTGTC

TCAGTGCCTAGCATGGTGCCAGGCACACAGCATGCTTCCAGTAAATGTTAGCTGGATGGATGTAATGAGTATATT

AAATATTAATTTATTTGTTTTTCCCCAAAAAGAATTATTTCCTGCAAATCAAGGAAATTGCTTTCTTTATATAAT

CAAAAACTTATTTTCCCAGAAGATTCTTCATTAAAAATTAAGCCTATGCACAACCTAGCTCTAAAGTTTCAAGA

TTTTAGGCAGCAATTTTTCAATCTTTTTGAAGTAATACATTTGAATCTTTTCAAATTTCTGTTTCTGCATTTGTG

CCACACCATCTCATCTCTTGCTGAAATGTTTTTGTTAAATTAATTGCTTGATAAATTGCTAAGTACTTTTCATCA

GACCAATTAGGACAATAGTAAGTATCCATCTGTGGAGCGCGGACATTCAAGAAATCTGATCCAGTATTTAGAAAG

TCATTCCTGAGCTGAGTTGGCTCAAACTGGCACCTTCTGGCATTTGCTTGTGGGTGGGAATGTGGAATGCTTTG

AAAGCTGAATGAGTTTGTCAAGTTTTAAAATTCCCTTATGGCTAAAGGAAAACAACATTCATTGTTTAAAACAC

CATTGTTTGTTTTTTCTGCTTTTTTGTTCTTTGGAGCCTGAATCTGCAAAAACACTCACACCCAGCATTTTGCTT

CATGTACCACTCCTAAGATGTTTTTAGAGACTTGAATAGTGTCTCCGCACTACTTTTTATTGTGATTGTTCAGAA

TGTTCATAACAAATGGTAAAAAGTCAGTTTTAGTGCTCAAATTGAGTTTTATGGAGAAAGACCATAATTTATGTT

TGTCATTGTAAATTGATAGGAGAATTTTTGGAAGTTTGCGTCCTAGAACCAGATTTCCAAGGCTCAGATCCTTAT

TTTCTCACTTCCTAGCTGTGTGACCTTAGACAAGGTATTAAACCTGTCTGTGCTGCCTCAGTGTCCTCATCTATT

CTTTAAGAGTAAGAATAGAACCTACCCGATAGAGTCACTTGAAGATTAAGTGGGTTAGTAAATTCAGAATGCTTG

GAACAGTAACTAGCACAGAATAAGTGTCCAATAAAATTGGGTTGCAGCTATTATCAGTATTATTCCTGTCATAAT

CATCATCACCATTAAGCAATTAAATGTAGAGTTCCAAAATTTGATTATGAAACTACAGTTATACAGCCATGATTC

CCGGTGATACCACGTCAGTAACAAGATTATTTCCTTAGCTTGAGCCAGTCACTACCTCATTGCATGTGGCAGAGT

GTGTTGCCGTAGGCAAATGTCATTGTAGGGAATGAAAAAAAAATTGCCTGTGAGCTGCTCTCCAGAGGCCTCATC

CCATTTTCCCATCGTCCACTTTACTCCATCTCCACTGCCACTATTAGGACCTTATCATTTCTTGTCTAGATTAAT

TCAACAGCTTCCTTCCUTCTAGTCTCCATGATTTCACCCACTAGCCATCCCCTCCCCTTTGCCCAATTTTCTCCA

TTTATGGTAGAGTGATCTTTCTAATAGGAAACTCCTGACTTGCCTTAAAAAGCCCTCATTGAGGCCGGACGTGGT

GGCTCATGCCTGTAATCCCAGCACTTTGGGAGGCCGAGGCAGGTGGATCACGAGGTCAAGAGATTGAGACCATCG

TGACTAACACAGTGAAACCCCATCTGTACTAAAAATACAAGAAATTAGCCAGGCGTGGTGGCGGGTGCCTGTAGT

CGCAGCTACTTGGGAGGCTGAGGCAGGAGAATGGCGTGAACCCGGGAGGCAGAGCTTGCAGTGAGCCGAGATTGC

GCCACTGCACTCCAGCCTGGGCGACAGAGTGAGACTCCGTCTCAAAAAAAAAAAGCCCTCATTGACAACCTTCAA

CCCACAATCCATGGTGAAGCACAGGAGCCTTGGGGATCTGCCCCCAGCACACCTCTCCACCCTTGTCTCTGACTG

CTCCTGCCTTCATGGAGAGCCCTGATGAACTATTTGTAGTTTCCCCTGACTCACCTTGCTGTTACTGGGCCTGTG

TGCGTGTTGCTCCCACTACCTGCAATACGCTTACCCACTTCACCTGGGTGAACTTTACTTAGGATTCACCTTAGG

TGGGCATCATGTTCTTCCAGGCCCCTCCTCTAACTTTTAGTTGAGAGTATTCCAGACTTAAGGCTCCATGGGATA

GGGATCTTGTCTATGCACCAGCTTATTCCCAACTGCCTGGCACGTAATGCATTTATTAAATATATATTGAATTGA

TTACCCTACTTGGGGCTCTTGTTTGCTTCTACACTTACAGTTCTAGCATAGCACTTAACTCATTATCATGCATCA

TTATTATGGGTTTGTTTTGTCTCCCATTAGACTGTGAGCTCCACAAGGCTGTGTCCTTGTCTTATACATCATTGT

ATTTCCAGCTTCCAACATAGTGCTTGCCATGACACAGGAAGTCAGTAAGCTCTGAATGAATGAATAGTATCTACA

TACCATTAATCTGAGGTTTAAAGTTTCCCCAAATTCTGAAGCAAGGGGATTTACGGACTTCCCTGACAATTTTTG

GATGTCATCCCAATGATACCACTAACATTTTAAGGGACAGCTTGCATATATACATTTTTCTGGATGGCAGTTTTT

TTTCCCACAGGCTTCATCGATATTTCTCCATAGCCTTCCTCAGATTCTCAAAGGGGTCTCTGATTCCCCCAAAA

GATAAGAAACTGTCATAAAAAATTATTTCTAAATATCAATTGTTAAATAAAATGTTTGCAAAGCAGCCTGATGAA
```

```
TCATTTCAGGCCACTTGACCCCGATGAGTTAGAGAGTTTGTGCTCTGCAATCTGACTGCTTCCAGCAGTCTCACT
GCTGCTGGACTGTGGCACTTCCAATTGGCAGCAGGGCAAGTTTCTTCTGGATGAATATTCTGTCATAGGGGTCCC
CCTTCCACACATACCTGTAGGAGCAGTTTGAAACTCATATGCATGGTCTTCCTGGTTCTAGGCACATGAGTCATT
TAAGCTGCTGGAGCCAGGACCAGCTAGTATGCTAGCCCGGCATTCAGAAAGTTAAAATTTGGGGTCAAAACTGAG
AACCTTCTTTGATCCACCTTGGCCAGACATTTTCTCTGGCTTCCATTAATAGCCTCAACATTTTTTTTTTTCTG
GCCTAGACCCACACAGGCAAGAGACCAGAGCTTCTCTAAGGAGCTAAGGGAAAGCACATTTTAAAAATAACTTGA
GCAAATGAATTCATCTGGCAAAAGCAACCCCACTACGTAAAATAAACCTTTTTAGTTTCGCAATAGCAGTTCCTG
AAAATGTAAACAACCTCAGGGTCTACATGCACTGAATCATTTGCTGAACAGAAAGTCCCTGGTCCAAATTCTGCA
AGAATAAACACCTTACAAAACTAGGGGTCAATGACCTTCATATGGGAACAAGGAGGGTGTGGGGGGCAGCAACCC
ACCCTGAGGACAATGAGAAAGTCTTGAGACTTGATATTCAAAATGCTGGCTTTCTAAACCAAAAACTGGCATGAG
TGGAGGGAGAAGGGGAGGGTGGGCACAGTCTATGCCTCAGGCTCTTGCTCAGACCCTACCAGGCCCCTGCCTTCC
CTAGGGAAAGCGAGAGTCTACTCACTGTCATGAAGCCAGAGGAAGGCCCTGCAGGTTTCACTGTGTGTTCTGTTG
ACAAGATGATGGTTCCATTGAAACTGTAATAACATACTTGGCCAACTAAGCCCATACGATCGTAGTAACTTTGTA
CCCAGTCCTAGCTTTTCAAACATAATGATAATATGTTCTTTCTAATGTGGCCCATACTGTTCTAATGAACTTATG
CTGAGTTTTTCTGAGTACTAGAATAATATTCGCCATAAATAATAGATATAATTATTCTCATTTAATATTTGCGTA
GCTCTTCTTTAAAGCAGAAAGTATTTTCTCATTCCTTACTAGAACCTTTCTGTGTGAGGAGCACTGAGCTAGAAC
CCATATCTTAGAATGGTCAGAATTTGGAGAAATTCAGGGAAAAGGCACTGGACTCATTTTTAAAGACTAGAAAAT
GCAACCTCCAGAAAAAGATTCAAGAGTTTTTTACTCCCAGAGATGTAGGAAAGATTGGAGTAAATCTTAATATTA
TATTTCAGGTAAACAAAGGATCACTGTCAAAATAGCAGCATTTATTGAGTAATGGCTGTGTGCCAGGTACTTTAC
AGTTTCACATTTAACCCTCATAATAACCTTGTAAAGTGGATATCCCCTCAGTACATGATGAGAACACTGAAGCTT
AGGTTAAATGATTGTCCAAATCGGACAATCATTTTCAAAATCTCCCCCTTTTTTCTCCTTTCTTATCTGCAAGG
CAGATTGCCCTTTCCCTTTCAGTGAAACTTGTGCATGACCACATGACTCTCTTTGGCCAATGAAACATGAACAAG
CAGCGTTTATCACTTTCAGATGGAAGGCTTTGCATGAGCTTTGCCTCCTTTTCACTCTGCCACAGTGGCCACTAA
CATTCCAGATAGTGGCGCTCTGCAGGCTAGGTCCTATAGTGGGAGCTATGGGCAGAGCCCCTTTCCCACCCCCA
TCAAGATGTGCATGCTGCATAAGCCATGCATTAATCTTTGCAGTTTTAAGCCACTAAGTTTTGGAGTTATATTAA
TCATTAATCATGGTTCTCAAGAGAAACAGAGTGGGGAGTGGTATTCATTATGGGAATTGGCTTACATGATTATG
GAAGCTGAGTAGTCCCCAGTCTGCTGTTTTTGAGCTGGAGAACTAGAGGAGCCAGTGGTATAATTCAGCCCAAG
CCTGAAGGCCTGAGAAATGGGATGGGGGAATTGGGAGGGTGGGTGTGCTAGGGTAGGATAAGTCCTGAAGTTCAA
AGGCCAGCCAGAAGGTGGATGTTTCAGCACCAGAAGAGAGCAAATTCGCTTTTCTTCTGCCTTTTTGTCCTCT
CTGGGCCCTCAATGGATTGGATGATGCCCTCCCACATTGGTAAGGGTGGATCTTCTATACTCAGTCTGCTAATTT
CTTCCAGAAACATCTTCACAGACACATCCAGAAATAATGTTTTACCAGCTATCTCGGTATCCCTTAGCCTAGTCC
ATATTTAAAAATTAATGATCACAAGCAGTTGTTTGTTTCCACAGCAAAACCTGGGTGACAGACCAAGTGACCCAG
ATGACTAGAATTTGACCTTCTTTTGTTGCCCACACCATACTCTGAACTAACATGCTGTGCTGCCTTCCAAGTGGA
GAATGATGGCTAAGTATCTTCTACCTAATTTGAGTCACAGAAAAAAAAAAAAAAGGTTATTAACTGCAGTGACAA
GAATTGTGATTCCCCAGGGGGCAGATCAAGACTGATAGATAAGAGAAGTGAGGAACATCTGGGGAATGTCCATTG
AAAATTTACTCAGAAGAGAAGAATAATTAATATAATAATATGATATATTGAATTATAATAAATAATATTTTGATG
TATTTCCTTCCAGGCATGTTTAAGTTATAGACTTTGAGTATATTTTCTCAAAGGGGGTTCTATGTAAGAGACTAT
TTCTTAATATAGTTCCTAGCTTGGAATTGCTCTTGCTGGTTTAAGCTGAGCTTATTTTATTACAGACTTCACAAC
AATAACGTTTTCCTTCACTAGTCAGTACACAAGATGGTCTTCATTTCCAGTTTGGAATCCCACACTATCAGAGCC
TGAGACAAGGACTAGTATGCAGTTAGTTTGTTTGGGAGGTGATTCCAGGAAGTGGGAATGAGAGATCAGTCAGCC
TGCAACACGAAGGAGGAAAAGTCAATATAAGGATGAATTTGGCAATTGGCCGTTTCATGCAACTGGGGCTAAATT
```

-continued

```
TTGCTTGGCTCTCTAAGAAATGTAAAGAATGCCTCCCGTAATTGCTCACCTCAAGTATTTATTCATTGGCTCTCA

TGCTCCATTGGTTGTCCATGAGAACTTTAGCCCTCCCTCGCTGCAGCACAGACACTGTGCTTTCTCCTAGGCTGA

GCAAGCTCCTGCATCTGTGGAAACCGTCCCGGGGCAGATAGTGAAATAATGACTGCTGCGTGCTTGAGATCGGG

AAAGAGGCCACATCATAAGTGCACTGAAATCAGAGATGTGTCAAGAGATGTGACACAGGGCATCTGAGGTGTCTA

CTGCACCAGCTATAACTCCCTAAACGCTAATCTCAGTTCTTACAGAGGGGATGGATGCAAGGGAACAGTCATGAT

TGAGAGCACCGAAGAAGCTCTGTATGAACCTTAGGCAAGTTTCCTAATCTCCAAAATGAAGGTAATAATACCCAC

CATCCAAGATCTTCGGGAGGAATAGATGAACTAATGTATGTGAAAATGTCCAGCACAGGTCCTAACCCATAGTAG

GTGCTCACCAAATGTTAGTTCCCTGCCCTCCACGTTGTGTGTATCCGGAGCTGCACTAGATGCTGAGGCAAATGG

TCTCAAATGTACTTTAACACTTAATGACTGAGATTTTTTCTGAGCTGCCTACAGGTTATTGACTATATTCATTAT

TAATAATAATATATATGGCCACTTCAGGCAACTGGGGCTAAATTTTGCTTGGCTCTCTAAGAAATGTAAAGAATG

CCTCCTGTAATTGCTCACCTCAAGTATTTATTCATTGGCTCTCGTGCTTTATTGGTTGTCCCTGAGGACTTTAGC

CCTCTCTCACTGCAGCACAGACACTGTGCTTTCTCCTAGTTTCTGTGGCAAGTGACAGGAGCCCACCTCAAACTA

AAGCAAAAGGGACTTCATTGGCTCTTGTAGCTAGGAATTCCAGGGTTGGCACTGGCTTTGGGCACTACTGGATGC

AGGAATTCAAACAATGTCTTGAACTCTTTCTTTTGGTGTTTCTCTCAGCTGTGCTTCTCTTGTCGTTTCTTTTTC

CCATTTTACAGATAAGTTCATCCGTAACTGAGAGAGGTGAAAAGGGGATGGCTGCAGAGAACTCTGGCTTATATC

ATCCTTGCTTGCTGACCTCAAGGTCCATGTATAAATTCTCAGAGAAGAAGCCCTCTGGTTGGTGATGCTTGGAAC

ATGCCCTGGAGGGTGGGCCCCTTGAAGTGGAGCTTGCTGGAACCACATGGGCTGGAGCAAGGCGCTAGGGCCAGA

AGAGAGAGGTAGGCAGGGCTGCTGGCCAGGCACTCTTCACCAAGACAAGGCAAGAGGAGGGGCATGATTGAGGCA

GTGATACAGAAAGCAGACAGTAGAGGTCGTGGCAAGTGTGCCGTTACTTGCTACCTGTGGTTGATGGGAGAGTCA

CACCACATTTAGGAGGAGAGAATCCATTTGCCACTTCTGACAATGCCACAAGAATCACATATTTCATCCAGAGGT

TGAATTTGGCCCATGCTGAGCTTTAAAATACAGAGCTGTCTTGGAACAATGGCTCAGTACATTCATTTGGTGTCC

AACAAAGCCTGCCTCTGTTGCCTTCCCTCTCTCTGTGTGCCCTTCAAGATCTTCATTGTGCTTTGGGGAGAGAAA

GAGAAAATGTCATATCAGGGTAGCTCACCCCATGTGTCCTGGACTCAGGAAAAGAGTATCTTATCACCTTACTCT

TTTGTTATTATAAAAAATAAAGTTGAACGTCTTCAAATAAAATAAAGAAGTATAGAAAAATTTTAAATTAACCT

GTTATGATTCTACCTAGAGAACCATTGTCAACATCTTGGTATATGTACTTCCAGATACTTTCCTATGAATATATA

CATTGTAGATTTTTTAATATTAAAAGGCTATCATGCTGCTTTGTATACAGGCTTTCTTTACTGATATGTAATATA

ATACACAGACAAATATACAAATCCTAAGCCATCAACTCATTGAATTTTTATTCATTGTTTTTAATACCTGCATTG

TGTTCCATTGTTAGGCTATGTCACAACATATTTAATTAAGCCCCTATTGATGAATATTAATTTACTCTATTTGCC

AGTTCATTCCAGTCCAACATTTATTGAGTGTCTACTTACGGGCCAGGCACTCTTGTATTCATCAAGATCACCACA

TTATCTGTATCAGTTATTTATTGCCACAATAAAACTGCATAACAAATCACTCCAAAATGTAGCACCTTAAAACTA

CAACTACTTATTATTTCTCAAGAGTCAATGGGTCAGCTGAGCAGTTCTGCCGATAGGGGTCAAGGTCAACACATT

TCAACTAGACTACTTGTAAAAAGAATGAGTGTCTGGGTAGGTGTGTTCTTCTAAAAATAAAACAAGGAATGAGG

AAATTGCAGGTAGGATAAGAGGGGTGGTTGGCAACCAAACCCCACAAAAGGCAGACAAATTTTAAGGAAACATAA

TGCCAGACTCCTATGTCATCATCCAAGTAGATGCAGTGAAGTATAACCTGGGGCGTAGTAGGGTAGGAGTGGGA

GAGCAGAGGAGAAGGAAGGGAGATTGCTTTTCATCACTTTTGGATTCCCTAATAACAGACATGACTGCCAGTATT

AAAATTTAACAAAGGATATCTGATCATTAATTTTCCTGTATAAGTCACTGGTGATCTTCAACATCTCTCCCTCCC

TTCCTCCCTTCCTTCCTCCCACCCTCCCTTCCTTCCTTCTTTCCTCTTTTGCTTTCAACTTCCTTTTCTCGTTTC

CTTTTGCTTTCTTTCTCTTCTCCCTTTTTTCTGTCACTCTGGGCGTATGTAGTAGTGTAAAAAGGTTGACAGAGA

AATCAAATATAACAGGAGCAGGGCCCTGAGAAAAGCACCTGGCATCCTGTAGGCAAACCATTGTTTCTAAAAGAA

GGGACTGAGAGATTGAGGAGCTCAGGACATTGCCAAATGAACAAGGCAAGCACATTTATTCAGTACCAAACAAAC
```

-continued

```
GGAAAACGGCCTTTCCAAATAACTGACCTATAAAACAGCCTTTTCACAAGAGTACCGTAATTACTGGCCAACAGC

AACAATGAAAAACAACTCCCAAACAAAGAAATATTTCTGGATTAAAAGCCATGAGATCTGGATTCTAACAAGCTG

TGCTCCTCAAACTACAAGTACAAAATCTGGCTCTAAACTAACAAGCTATGAGCCTCAAACTGATGACTGGCATGT

TTGGGTCTCCATCTCCTTCTTGGGGGTTGGGGTCTTAGAGACCCTTTTCCACGCCCTGATTCTCTTACTAGTGTG

TATGCTTTCCTTTTGACTTCTCATGCTGACCGTCTGAGCAGGAGTGAGAAGCAATTTCAAAGGAAAACATCGTTT

ATCATCTGCTGAAAGAAACCAAAAAGAACACAGGAAAACAAAAAGACAAGGAAAGGGAATGAAAATGTAATTCAT

TTTATTAAAAGAAGAATTATTCTTCTGGGACACTGGATAGAAACCTTAATGAGTTACCTAGCTATCATAAATCC

TCTAACAGAGAAGAGAAGAGAAAGAAACAAAGACGGAAGAGGGCAGGATAAAAGAAAGAAAAAAGGAAGGGAAAA

ATGAAGGAAGGAAGTTATCTATTCATTTCTACAGAGACTCTGCTGAGCAGTAGACAAGAAGACTTGGGAAAAATT

TAACTGAAACTTTTCCAAAAATCTTTTCAGAGGGATTTTTTCCCTCTGAAAAGCATCATTAGAGGCTGTTCAATA

CCCAAGGCAAGCCTCTTTCATATTACTTACTGTACATGAAACACTCATGCAATTGAGGCTAGCCAGAGGCCATTT

AGAAATTCAATAATTATTCAACCCAAGGGGCTTTCCAAATGGTGAAGTAGCTTCTTAAGAGGAAATTAATATTGA

GCAGTATAGCAAACCTAATTGGAATCTTGAGAAAATAGTTCTGTGTCGTTAGAACAGCTAGAGGCTAAAGAAGAT

CAGGTTGGATGATACCTTCATTTTTGTCTCTTTCCTTAATTATGATGTAAAGGGAAAAATCTTGTTTATTTTCTA

TGCCAGGAGGGTAGAGGGTGATTTGGAGAGGTTCCAAGTTTATCAAAATCTACCTTCAGTCTGGCAGTAGAAAAG

TTTACTTCCTTCATTTCTTTCCTATAGACATTCAAAGAGAGCTAAGGAGATCCAAAAACCTTTTTTTCTATATTT

GCAATGCAAGGCAGTTGGGAATTAATGACTGATTTGTTGGTGAGGGCAGTGGGCATTGATCACAAAAGCAGTAAA

GCTGTGTTTCTCAAAGAGAGAAAGTCTCTTTGAGATCTTCATTATTTTACTATTTAGAAGAGAAAGGGGCGTTAT

ATCACGTTGGAAGCATCCATGAGTCACTAGTCTCTTCTCTATCTTTCTATGCCTTTCTGTATTAATTACTTTGAA

AGCACAACATTCCAAACCCATTGAGCACACAGTGGTCTGATTTCTCCACTTGTGAAAGGTGCTAAAGTCTCACTG

TAGGATTAATTTGGGGGTCCAGGCTATGGGCTTGTAGATATGACTACCTTAGACTTTGGTTCTCCTGGCAACTAA

CCCTTTTTGGATCGTATCTAAGTTGACCTGTTTCACAGTGAGAGAACTCCTCTCCATTACTCAGAATACTGAGGC

AGATCACAAGTGTACCACACCTGGCTAATGTTAAGCCAGACAGAAAGATCAGGCTCATCTCTTGAGAAGAAGGGT

CGCTTATTAAGGATACAAACTATTTTTTTTTTTTTTTTGAGACAGGGTCTCATTGCCCAGGTTAGAGTGCAGT

GGTGCAATCATAGCTCACTGCAGCCTCAACCACATGGGTATTTTTAAATAAGAAAAAAATACCATCTGATAGATA

TGAAGGAGCATTGGGTCACTATAAACAAAACAGATTCTAAGAGCAGGAAGAAAGAGTACAGTCTCTTTTCAATAA

TTTTTTTTAAACTTGGGAAAGAACACTCACTCTATTCCTATAGACCAGAAAGCAGATAATTGTCCATTATGATT

CCACATGACACTATCTTGTTCAGCTGTCACTGAAACAACTTTGAACACTGTCATATGTTCTTCCCAGCTCCTGAA

CTCTGACCTTTTTATGCCTTAGTTCCACTTTCACAAAAAGGGATTGATGTAATGTGCATTTCAGAGGAAACGACT

ATAGACATTTAGTGTCATTATAAATGTTGAGAAGTATGCTGGCAGAAATTATGCCTTAAGATCATATATGGATTC

TTGTATGGTTTGAAATTGCTTAAAAGATATATATGATCTCTAAAATGTGTGTATATATATATGATGTCTTCTT

ATATATCTATATGTGATATATTTATATATATATAAATCTGTGTATATCACATATATAAATTTGCTGTTATTTGAA

TTGCCATTACCTCAGTGCTTAGGGGAAGCCATGCACGTTTGTTTGTTTTCAGTACCCAGAGTTAATTAACATAAG

TTATCACAGAAGCTCCCATAAGCATTGAGACAATTTCTCTATACCTGTGACTATTTAAGGTTTTGAAAACAAAAC

AGAAGCAGGTAAGGAGGAAGTACGCTTTACTATTGAAGATTTATTAGGTACACATTTAGATTTGTGAACTCACAT

TGCTTAGGATGAAAGGGACTCTTGAGGATGTCTGCTGTTTGTTAGTGAACTGCCTGTAACAATTACAATTAGCAC

ACACATGAGCACAATGAACTGGGTAGTCAGACTCAGCCAAAATGAATAGAAATAGCCTCTTACCAAATTTACTTT

GAGTAGCCCTTGGACTCTGAGCACTGCTGCCCAGAGGAATATGACTGTAGGTCCAAGTTTGTCAATGAGTATGCA

AATGTGCTTTCTTCGCTTTTACTCTATTGTCATCTGTCTATTACAATGTTGCTATGGTGACACCTTTCCAATATC

CCTGTGCTTCTTTGGTATCCTCTAAGGGGAAGCTGTAATGAAGTGGCTTGGCAAAAGAATCCTCTTGGAATTTTT

TTTTTTTCATATGCTACTGAAAACCAGCATGATTTTCCTCTTATGGGAAATGTATAAAGTATGAGTTGGAAATGA
```

-continued

```
TGGAAATTAATCTGTACTGACTTGGGCAAGGAATGTGAATGTTATTCATTCGTTCCAAACTACCTGAAAATATT
CTCTTTCTGTTCCTACTTTCCAGGAGATAACATCTTAAGGGACACTGAAGCTTGTGCGTGTGTGAGTAGAACACG
TGCTGGGGGCTCTTGAGCTCATGAGGGAGGGGCTACATGTCGGTGGGGTGATAACTGTATGCTGGAAACAATGAT
AGGTGGTGACCCTGGAGCACTTACCATGTGACAGGTGTTATGCTAAGCATGTTGTATGCATTCCTTCATTGAATG
ACAGCTACCTATATTATCCTCATTTTATAAGATGAGGTAACAGAGCTTCAGAAAGGTTAGACTCAGCTGCTATGG
GTCTGTCTGACTCTGGTGTTCTTCCTCTTAAAAACTGGGGCACTTTGGAAATGAGATTCCTCGGTGATGAACAGA
AATATTGCTTAGCGGCTGTATTTTTGTATCTGGCAGTTTTCCCATATTTGAGTCTTATATTCACAATCGGTATCT
TTACATTACACAAAAGTGACACAGAATTAGAGTCATTTAATCCAGGGTTGATATCATTAAGTCATGACTATTTAT
TAAATGTTTCTTACAATATCTGAGATGATATTGCAAAAGATGTAAGTGATTTTAGAAGTTCTCACTTCGTAGTTA
GTTGCAGAAACCTCTTTTGGAGGAGGGATGTTTTCTCTATATATCCTAATTTCTACTTAATATATTTCCACACCT
CTTTGAAGTGTGTAGTAAGAATGGTAAAATGCAGTACTTCGTCATTTGGTACAGTTCAATCAATATGCATTAAGA
TGTGATCATATGGGTAATAGAAAAATGTGAAAGATCCAATTCTTTTTCTCCAGAAGGCAGGAAGCTCATATTTGA
TTTCTGTTACTATAAACTATAAAAACGTTTCAAATGTAGTTTACCCGTAACCATCACCCTGCAAGGGTGATATTG
CTCCCCGCCAATTTACGGAGGAGAATACTGAGGCTTTAAGGTTGTAGATAGACCAAGACCACACAAGTAGAGAGT
GGCGGGCTGTGGGTTGAGCTTTAAAATCCAGGTTCATCCATGACTCCCAGTGTGTTCTAGTAAATCCACTAGAAT
CTGAGTATTTTCCAATGATTTATGCTCCGCTCTGTGTCAGGCAGTTCATGGTATTTTTCAACAATCAGAAAATCC
TGGGGAAGGCAAACTGTTTCCCCCTCTCTAGGTGCCTTGGAAGTGGCCGTTGTGGACCCAGAGATCATCCTTTCT
GATCTGACACCTTCTTCACTGCCCTGGCCCAGTGTCTTTTCTGCAAGGCTGGAAGCCCCCTTAGACTGGTCATGT
CCCATCTCTTTCCGGAGGGAAGATGATCCCAAAGACGACTTTTCTCTCCACGGTGCTGCCATACCGCAGGCGGCC
GCCAGGGGTCCCCGCTCGGCGTCCCCGCGAGACAGTCGAGCCCCGGCCGGCTGCGCGGCGCGCTGGGTGCATGAG
GGGGCTGCTCCGGAGCGACGGCGGCTGCAGCTGGAGCCAGGCGCTCGCCCGTCCGCCGGTTGGCTCGCCGGGACC
TCGCGCACCGGCGGCAGAGTCCCTTGCGTGGATTGGCAAGCGACGCCCCACCTGCCCCGAGCTCACCATTTTCTT
TCGCGCTGGCTGCAGCTGACCCGGCGAAGGGAGCCGACCGGGCCCTGGGCTGGAGGTAAAACCCCACGGTGAGTA
AGAACCCGCTCCAAGCTAGGGGAGGCGGCGCAGCCCGGTGGCTGCTCGCTCCCGATCTCGCCCGGGCGGGCGGCG
AGGTTTGGGGCGCACCTGGGCGCGGGTGCAAGAAGGTGCGGGAGGCGGCGGACCGGTCTTCTGCCCGCCGGCCAC
GGGCTTCCGGGGCTGGAGTCCTCTTCAGACCCCTGCCGGCGCCTGGGTTTCTGGCCGGCTCCTCGTGTGCACTTC
CCGGCAGGAACAAGGGTCGCCCACTTTCCACCCCGGGATCTTGATTTGTCCTTGATTTGAAAAGATATAAATCAA
TAAGATCGTCCTTCTTTCGGGGTGCAAGACTCCGAGCCCATCCCCAGCCGCGGACGCCTGCAGGGTGCGTGTTGG
GCTGTGGGTGGCGGGAAGACAAACTTTTACAAAAGTGCGCCTGGGCTGGGGGACAACGCTTGGGCGTCCTGATCC
TGAGGGAGGAGTCTCGGCTTGGGGCAGCGTAGGGGAAGTCCGCACCGTCAGCCAGGTCGCCCCCGGGGCTGACGA
TGCCTCACGGAGGTGGGGAGCGTGTAAAGGCCGTACAAATCGCGCTTAACTTTGGGGCCAACAACTGTCAAACAT
CTGGAATCCCAGCCCCTCCCTTTCCCTGAACTGGGGAAGAAGGTGAAAACCCTTCAAGTTTTCTTTGATTGCCCC
TTCCCACCTTCAGACCCCTGCTGGAGGGTAAAGCGCCGACCCCTGGTGCCTGGCAAGTACCAGAGACTCTAAAT
CTCTCGGGATCCCCCCCCTCGCGCTCTTTCCTGACCCTCTCCCCTAACCCTCCCCACAGAGATCTCTCTACGCAG
CCGACTGAGATCGTGGCGAATGGCCTTTTGTTTCTCCGCGTTTCCCCTATTGTTTGCCTTTCCAACATCTGGCGG
GGCTTGGGGAGAGAAGGAAGCCCCTCTGGTCCCCCTCCCCGGCCCCACGCCAGCTCCGGCAGGGGATCCCAGCT
GGGAAAGTGGAGGAGCCCGACCCCAGCGAGGCCGCCCCACCCCGCCCTTGTGGTTAGAGGGCGGAGGGAAAGTTG
TTCCTTCCCCGCCTCCGCTGCTGCCTGTGGCCCAGGGCGCATTTCTCAGATCTCAGCCCAGGCGCGCCGCAAAGG
CTCAAATCCGAGAAGGTGCTGCTTTCGAGACAGTGGAAGCGCGTTCCGCCCCAATCCAGAGCGTCCAGTGGTTGG
TTCCAGAGGATTTCAATCTCTAGCCAAAGGCGTTGGGGCTGGGCCGCTGCTAGGGCAGTGGGAGGGGATCGGGGC
```

```
-continued
ACCTTTGGTAGGCGGAAAGCTGAGATTCTGGGGTCCACAAGTTTCCAAGGGCGGGAGGGCAGGCTAGTCGCCAAA

AAGAGAACGAAGATGCAAATAACGAGGAAGCCTTATGACGTTGCCTGGAAATAGTAGTGTGGTGGTTCACTCCGG

AATGAACGTGGAGTTCTGGCTTTGAGTACCGCTCCAAGTTTAAATCCCAAGTCCCCTTTCTTCATTGTAGAAAAA

GAGGACTCAGACGACGCAACACAGATACGGCTAGAGCACAGTTCCTGCTTCCACGTCCCAGAGAACAAGTGGCTT

AGGATGGTCCCGAGTTCCCCTGTGGGTGCGCTTGTTGGGTTGCAGGCGGCCCTGTTTCCCTGCACAAGTCAGATG

CTTACACATTGTGTTCATTCTTAGTGTGGATTATTGATTAAAGAACTGGGGCAAAAGCAAAGTAGCTACTCTGAG

AAGTCAGGGTCCCCAGATGGTGCCCAGCGAGTTGTCTTGCCTCTGAGGGGAGGCTGACTGAGACTGTGCACCTGT

TAGAACCTATGCTACCCCATAGCCTTGCAGTTGACTTGCTGTTGCCAGCTTTTCCTGTGGGATCCCCAATGAGTC

CCTCTTCCAAGGAAGCTCAATTACACTTTTGATTCCTCCTCAACCCAGGGGAAGAAAGAGGCTTCTGTAGGAACA

TTATGATCTATGTACCCACTCAGACATTGTCAGTGGATACCAGAAGCTTGGCTCTGCACAGCTCTGAGAGTTTTC

CCTTTGCGAACTCAACAGAACTTTTGAGTTTCCATTTAACATAAAAGAAGTGAGACTGCTAAGCCAGGAATGCGA

CACATAGAGCACTTTCTCTAGTGATTTCTGGGTATTATATCTCTTTACCTTCCCAACGGTGGAACCAGGAAAAGA

AAAAAAAGCAACATCTTTGAAGTACTGCAAGGCACTTTACAAACATTTCATTATGAAAATGATCCCCAAGGAAGG

ATTCCTTTGAAATTTAGCAGCAGCAACCCAGAAGCAACAAAAAAGACCAAAGTTACTCAAGAAGTACCCAAAGGC

ATCATTAACAAAATAAAAGAGCATTTCTTGTCTTGGCCTACCCCGCTAAGGAAAACAGGGTAATTATAGTGGAAG

TTAAGCTTG
```

In some embodiments, the human C9ORF72 gene and flanking sequences comprise a sequence that is, e.g., at least 75, 80, 85, 90, 95, 96, 97, 98, or 99% identical to the sequence above. As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence.

In some embodiments, the number of GGGGCC hexanucleotide repeats (e.g., (GGGGCC)$_n$ in SEQ ID NO: 63) is 300-800.300-700, 400-600, or 500-600. In some embodiments, the number of GGGGCC hexanucleotide repeats (e.g., (GGGGCC)$_n$ in SEQ ID NO: 63) is 500-600. In some embodiments, the number of GGGGCC hexanucleotide repeats (e.g., (GGGGCC)$_n$ in SEQ ID NO: 63) is greater than 300, 400, 500, 600, 700 or 800. In some embodiments, the number of GGGGCC hexanucleotide repeats (e.g., (GGGGCC)$_n$ in SEQ ID NO: 63) is greater than 500. In some embodiments, the transgenic mouse is an FVB, balb-C or C57B/6 strain mouse. In some embodiments, the transgenic mouse is an FVB strain mouse. In some embodiments, the mouse can be used to screen for therapies for the treatment of ALS or FTD, e.g., a therapy described herein or a candidate therapeutic agent.

A transgenic mouse as described herein can be made using any method known in the art or described herein, e.g., Example 4 (see also, e.g., PCT Publication Number WO2001010199 and WO2013022715; and US Publication Number US20110113496 and 20060031954, each of which are incorporated by reference herein). For example, a transgenic mouse described herein may be produced by introducing transgenes (e.g., the human C9ORF72 gene, optionally with flanking sequences) into the germline of the mouse. Embryonal target cells at various developmental stages can be used to introduce transgenes. Different methods are used depending on the stage of development of the embryonal target cell. The specific line(s) of any animal used to practice this disclosure are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). The line(s) may themselves be transgenics, and/or may be knockouts (e.g., obtained from animals which have one or more genes partially or completely suppressed). The transgene construct may be introduced into a single stage embryo. The zygote is the preferred target for micro-injection. The use of zygotes as a target for gene transfer has a major advantage in that in most cases the injected DNA will be incorporated into the host gene before the first cleavage (Brinster et al. (1985) PNAS 82:4438-4442). Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, the exogenous genetic material should be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane.

Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter. Any technique which allows for the addition of the exogenous genetic material into nucleic genetic material can be utilized so long as it is not destructive to the cell, nuclear membrane, or other existing cellular or genetic structures. Introduction of the transgene nucleotide sequence into the embryo may be accomplished by any means known in the art such as, for example, microinjection, electroporation, or lipofection. The exogenous genetic material is preferentially inserted into the nucleic genetic material by microinjection. Microinjection of cells and cellular structures is known and is used in the art. In the mouse, the male pronucleus reaches the size of approximately 20 micrometers in diameter which allows reproducible injection of 1-2 pl of DNA solution. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout: where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

Aspects of the disclosure also relate to polynucleotides, e.g., a bacterial artificial chromosome (BAC) vector, comprising SEQ ID NO: 63.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Figure 3:
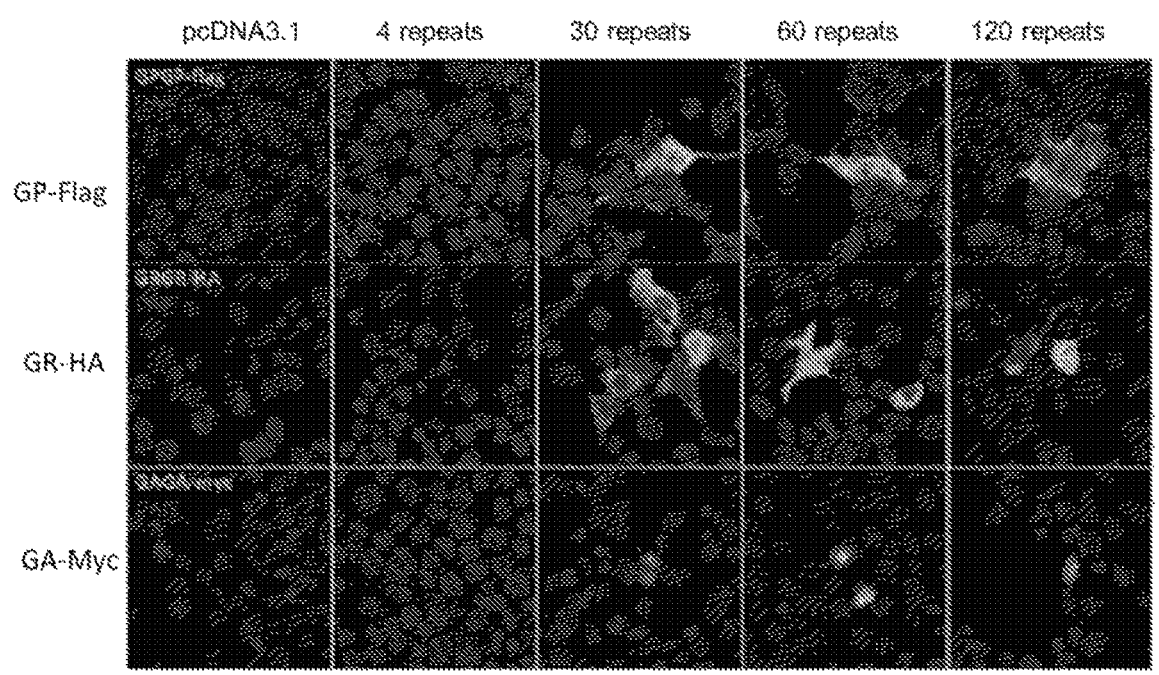
FIG. 3 is a photograph of an immunofluorescence staining of cells expressing GP, OR, or GA RAN proteins in cells transfected with 30, 60 or 120 GGGGCC repeat sequences.

A construct containing a CMV promoter, a (GGGGCC) expansion motif containing either 4, 30, 60, or 120 repeats of GGGGCC, and an HA, FLAG, or MYC tag were transfected into cells (FIG. 2A). It was shown by western blot that poly-(GR) and poly-(GP) proteins were produced in cells transfected with constructs containing 30, 60 or 120 repeats of GGGGCC (FIG. 2B). It was further shown using immunofluorescence of cells that GP-flag, GR-HA, and GA-Myc proteins were expressed in cells transfected with constructs containing 30, 60 or 120 repeats of GGGGCC (FIG. 3). These results show that GGGGCC repeat regions are capable of initiating translation independent of an AUG start codon (repeat-associated non-ATG (RAN) translation), and that poly-(GP), -(GR), and (GA)-repeat proteins are produced.

Figure 4:
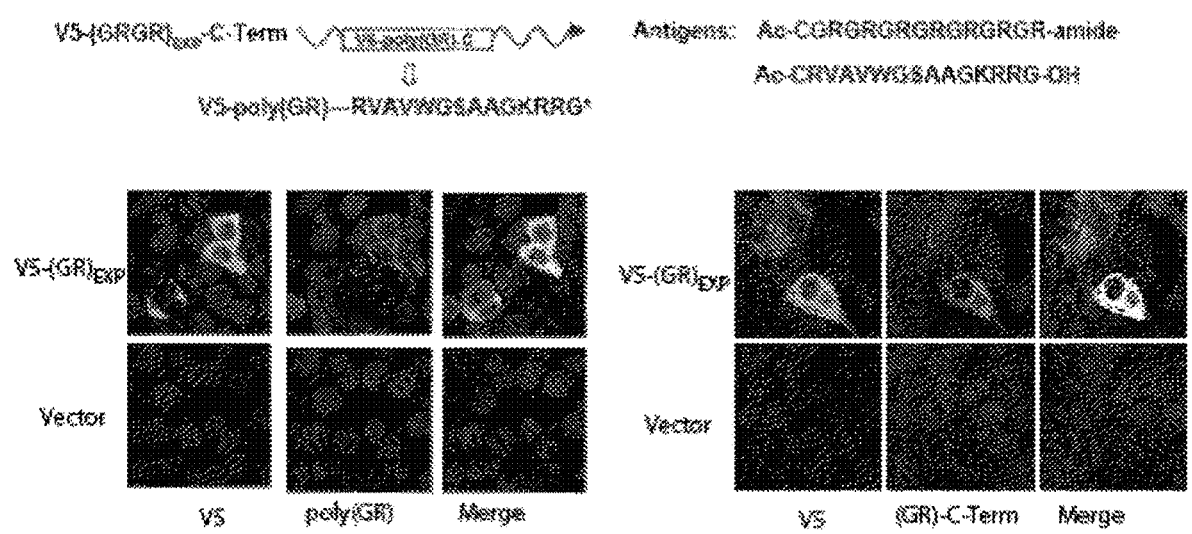
FIG. 4 is a diagram of the poly-(OR) and OR-c-terminus antigens and a series of photographs of immunofluorescence staining showing that the poly-(OR) and (GR)-c-terminal antibodies detect poly-(GR) RAN proteins.

Antibodies to a poly-(GR) sequence or to the C-terminus of the poly-(GR)-repeat protein were generated. Fluorescent staining using these antibodies showed that these antibodies were capable of detecting the poly-(GR) repeat protein (FIG. 4).

Figure 5:
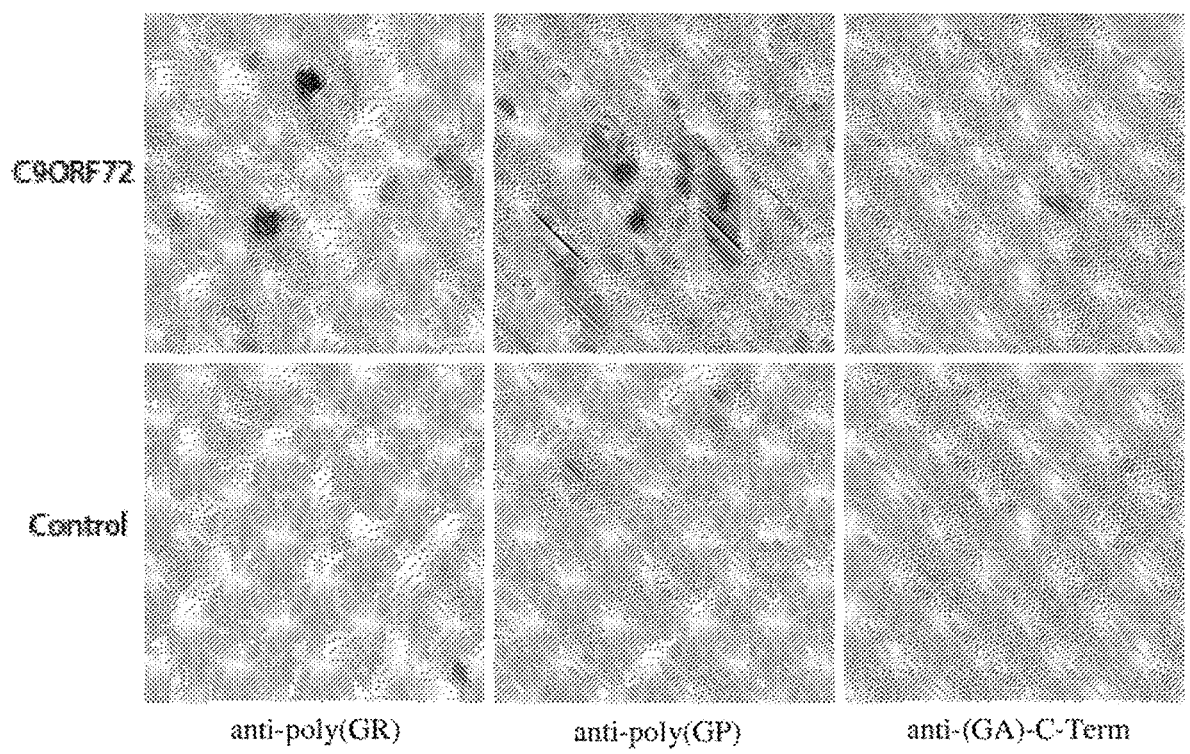
FIG. 5 is a series of photographs of tissue from C9ORF72 ALS patients or control patients showing that poly-(OR), poly-(GP), and poly-(GA) di-amino acid-repeat-containing proteins are expressed by C9ORF72 ALS patients.

Antibodies were further generated to a poly-(GP) sequence and the C-terminus of the poly-(GA)-repeat protein. The anti-poly-(GR), anti-poly-(GP), and anti-poly-(GA)-C-term antibodies were then used to stain sections of brain tissue from patients with C9ORF72 ALS or controls (FIG. 5).

Figure 6:
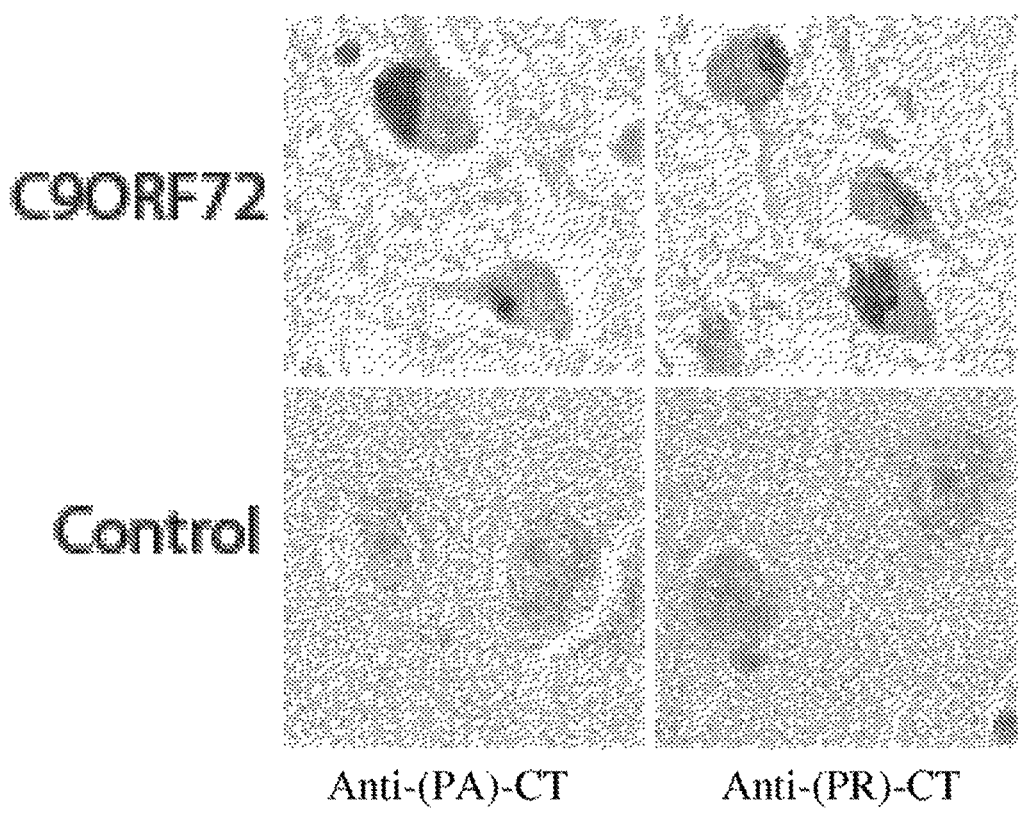
FIG. 6 is a series of photographs of tissue from C9ORF72 ALS patients or control patients showing that poly-(PA) and poly-(PR) di-amino acid-repeat-containing proteins are expressed by C9ORF72 ALS patients.

It was then hypothesized that transcripts of C9ORF72 may be produced in both a sense and anti-sense direction (see FIG. 1). It was further hypothesized that these anti-sense transcripts may also undergo RAN translation to produce further repeat proteins from the 5'-GGCCCC-3' repeats present in the anti-sense transcript. As shown in FIG. 6, both poly-(PA) and poly-(PR) proteins were detectable in brain tissue samples from patients with C9ORF72 ALS but not in controls. These results indicate that di-amino acid-repeat-containing proteins, such as RAN proteins are produced from both a sense and anti-sense transcript produced from the C9ORF72 locus.

Figure 7A:
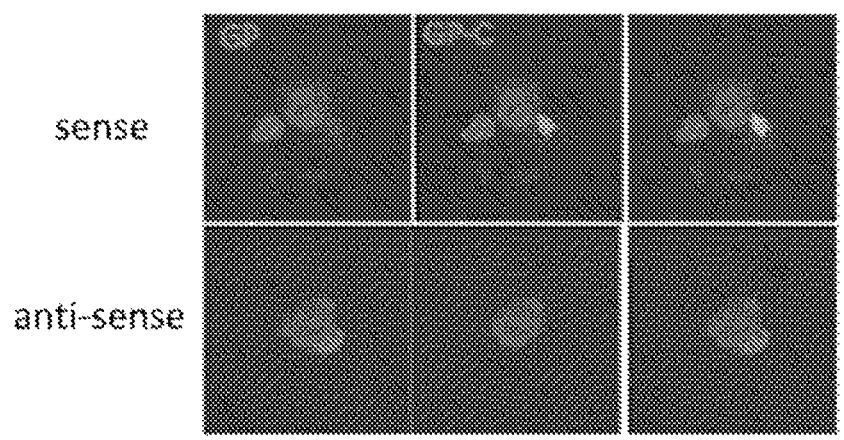
FIG. 7A is a series of photographs of immunofluorescence staining showing antibodies generated to recognize the GP repeat motif (GP) or the unique C-terminal region of the same GP-RAN proteins (GP-C) colocalize in 20% of patient cells. Cells that stain for and GP-C and GP express GP-RAN protein in the sense direction and that cells showing only GP staining express RAN-GP or Met . . . GP from the anti-sense strand.
Figure 7B:
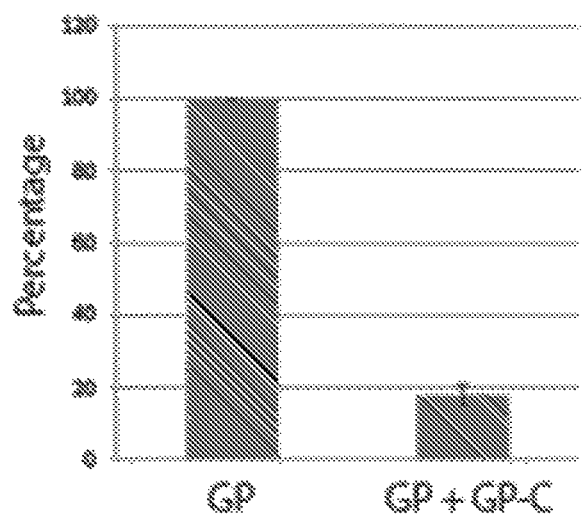
FIG. 7B is a graph depicting the percentage of GP and GP+GP-C in patient cells.

FIG. 7 shows that approximately 20% of aggregates detected with the anti-GP antibody (GP) also co-localize with antibodies directed against the unique C-terminus of the sense GP protein (GP-C). Consistent with the increases levels of antisense transcripts that seen in affected brains, these co-localization data suggest the more ~80 percent of the GP dipeptide aggregates are expressed from C9ORF72 antisense transcripts.

Figure 12:
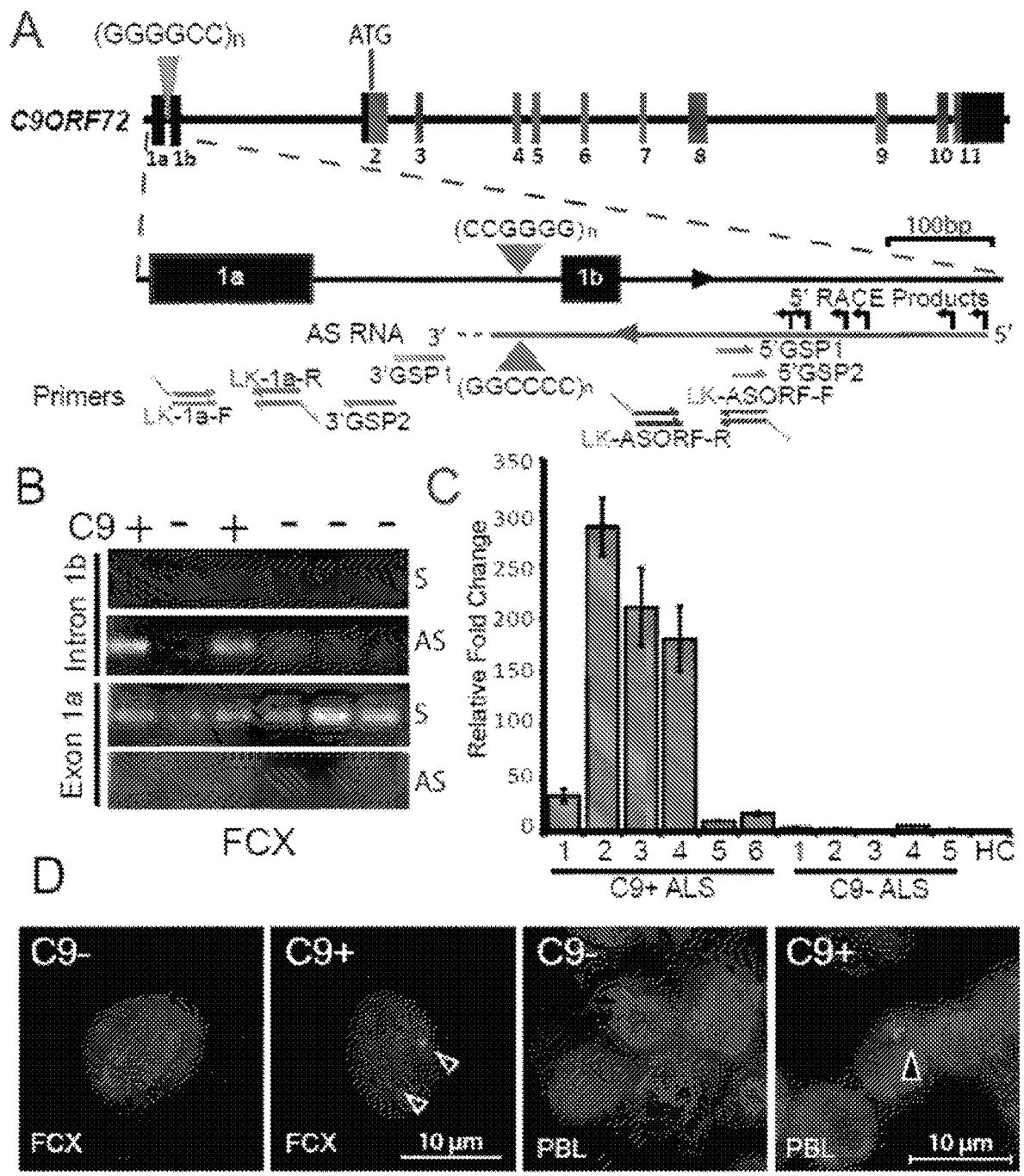
FIG. 12 is a series of schematics, graphs and images showing that G2C4 antisense transcripts are elevated by strand specific RT-PCR and accumulate as RNA foci in C9ORF72 patient tissues. (A) Schematic diagram of C9ORF72 gene and antisense transcripts and relative location of primers for strand-specific RT-PCR and RACE primers. (B) Strand-specific RT-PCR of sense (S) and antisense (AS) transcripts (across intron 1b and exon 1) from frontal cortex of C9(+) and C9(−) ALS patients. (C) strand-specific qRT-PCR showing elevated antisense mRNA in C9(+) compared to C9(−) ALS patients. (D) In situ hybridization with G4C2-Cy3 probe showing G2C4 antisense RNA foci (arrowheads) in C9(+) frontal cortex and peripheral blood leukocytes (PBLs) which are absent in C9(−) cases. Nuclear foci in FCX are indicated by arrow heads. FCX=frontal cortex. PBL=peripheral blood leukocytes.

Additionally, the anti-sense transcript was found to be dramatically elevated in subjects with ALS compared to controls (FIG. 12). The primers for the qPCR assay for detecting the anti-sense transcript levels are shown in the table below.

| | | |
|---|---|---|
| ORF F2 | AGTCGCTAGAGGCGAAAGC (SEQ ID NO: 36) | primer in c9orf72 antisense orf |
| ORF R2 | CGACTTGGGTGAGTGAGGAG (SEQ ID NO: 37) | |
| ORF F2 + IK | CGACTGGAGCACGAGGACACT GAAGTCGCTAGAGGCGAAAGC (SEQ ID NO: 38) | |
| ORF R2 + 1k | CGACTGGAGCACGAGGACACT GACGAGTGGGTGAGTGAGGAG (SEQ ID NO: 39) | for RT 1st strand |
| Linker | CGACTGGAGCACGAGGACACT GA (SEQ ID NO: 40) | for RT-per with ORF F1 and F2 |

Further, di-amino acid repeat-containing proteins were found to be present in the blood (including in the serum and plasma) and in the brain of subjects with ALS (FIGS. 9 and 10) but not in control subjects.

Example 2

Figure 8:
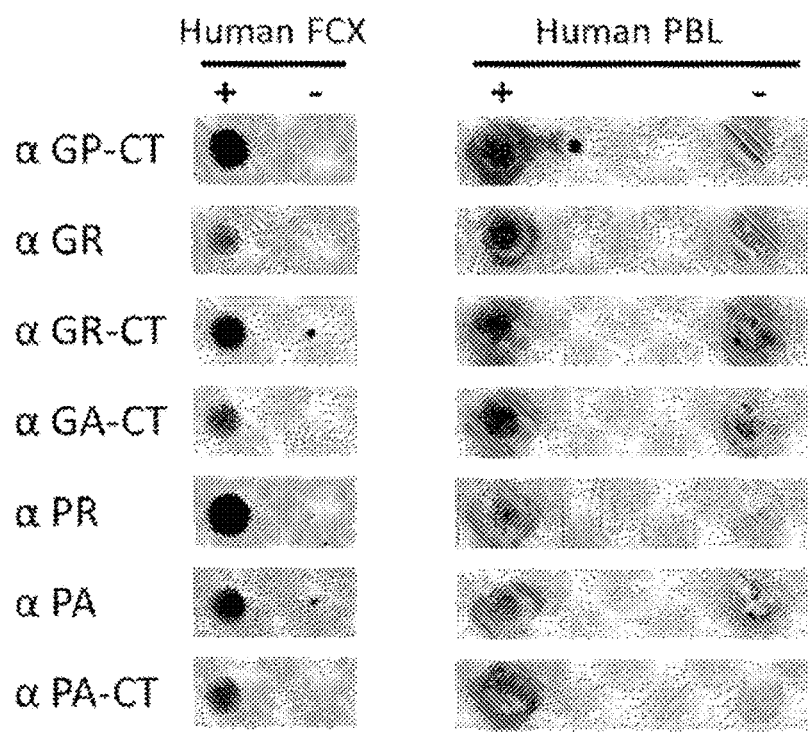
FIG. 8 is a picture of a dot blot showing that di-amino acid repeat-containing proteins are found in the blood (PBL) and the brain (FCX, frontal cortex) of subjects with ALS, but not controls.
Figure 9:
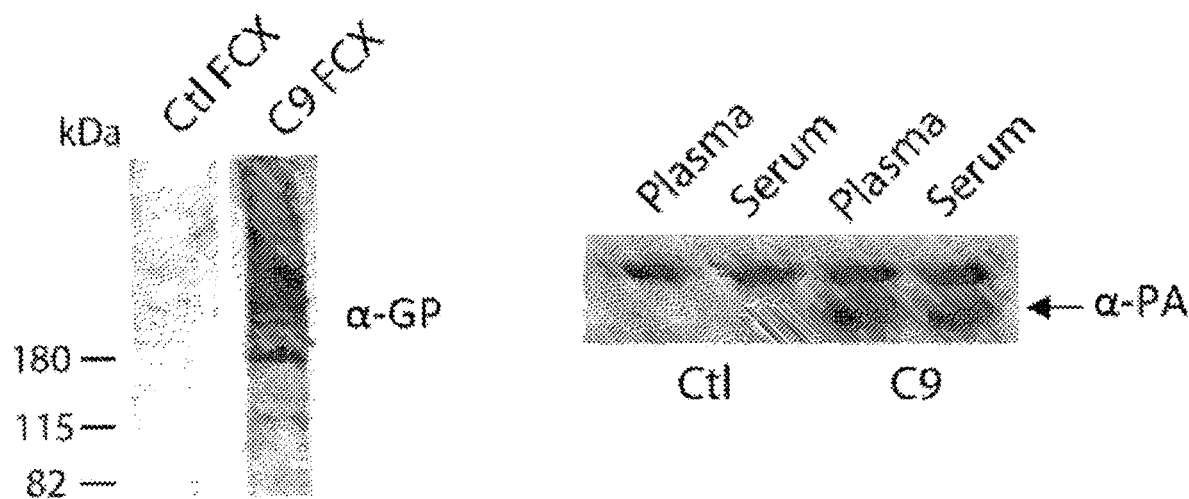
FIG. 9 is a photograph of a western blot showing that GP-repeat proteins are present in the brain (FCX) of subjects with ALS but not controls and that PA-repeat proteins are present in the plasma and serum of subjects with ALS but not controls.

According to some aspects of the disclosure, di-amino acid repeat-containing protein (such as RAN protein) accumulation in blood and cerebral spinal fluid (CSF) substantively contribute to C9ORF72 ALS/FTD and that plasmapheresis and bone marrow transplantation will reverse progression of the disease. According to some aspects of the disclosure, di-amino acid repeat-containing protein accumulation in blood and circulating CSF infiltrates the brain parenchyma and leads to protein accumulation, neuroinflammatory changes, CNS dysfunction and neuronal death. Aspects of the disclosure are based in part on the following. First, blood brain barrier (BBB) impairment is an early feature of disease in ALS patients (4, 5) and higher rates of ALS and other neurological diseases are found in patients who have had traumatic brain injuries (6). In some embodiments, without wishing to be bound by theory, ALS is in part caused by BBB disruptions that allow for the CNS entry of immune cells and other harmful substances that accelerate ALS/FTD. Secondly, as described herein di-amino acid repeat-containing proteins were found to accumulate in ALS patient blood samples (FIGS. 8 and 9).

Although plasmapheresis and bone marrow transplants have been tested as therapeutic strategies for ALS in the past, it is not clear if any of these cases were C9ORF72 positive or if treatment was early enough to have an effect. Accordingly, in some embodiments, ALS treatment (e.g., plasmapheresis or BMT) is initiated when above-normal levels of one or more di-amino acid repeat-containing proteins are detected in the blood of a subject.

The data presented herein on di-amino acid repeat-containing protein accumulation in C9ORF72 ALS patient tissues and blood indicates that reduction of blood (and perhaps also CSF) di-amino acid repeat-containing-protein load may help treat ALS in C9ORF72 ALS patients. According to some aspects of the disclosure, reduction may be achieved, for example, using plasmapheresis or a bone marrow transplant.

Methods

A detailed evaluation is performed on gene carriers from a C9ORF72 family (CNSA-1) and patients in the clinic including a gene-positive patient with early signs of motor neuron disease or fronto-temporal cognitive dysfunction, or both. Di-amino acid repeat-containing protein expression is correlated with repeat length in CNSA family samples and additional samples collected in clinic. Di-amino acid repeat-containing protein expression in blood is determined in longitudinally collected samples and correlated with disease onset and clinical severity. These methods are expected to characterize di-amino acid repeat-containing protein expression in C9ORF72 positive expansion study subjects and to determine if di-amino acid-repeat-containing protein expression occurs throughout life or increases with age and if di-amino acid repeat-containing protein levels quantitatively correlate with disease severity.

Plasmapheresis is tested to determine if lower di-amino acid repeat-containing-protein load in the blood and CSF reverses signs of the disease. Plasmapheresis is performed on five C9ORF72 positive individuals with early signs of the disease. Six plasmaphereses, each with 2-litter exchange with normal human albumin, is performed over two weeks, followed by one plasmapheresis weekly for the next six months. The study may be prolonged, if required. The primary outcome measure is the Appel ALS Rating Scale (AALSRS). Clinical evaluations including neurological examination, speech evaluation, neuropsychological testing, the ALS Functional Rating Scale (ALSFRS), EMG, and needle muscle biopsy for immunohistopathological evaluations of the vastus lateralis muscle are performed to assess disease progression immediately before and after the treatment period. Venipuncture and lumbar puncture are also performed before and after the 6-month (or if applicable, also after the prolonged) treatment period to assess the concentration of serum and CSF levels of RAN translation and ATG-translation products.

Bone marrow transplant in an animal model is tested to determine if BMT prevents di-amino acid repeat-containing-protein accumulation in blood and the brain. In a first cohort of animals, bone marrow from RANT-positive mice are ablated and replaced with wild-type donor marrow to test if protein aggregate load in the brain decreases. In a parallel set of experiments, RANT-negative animals are transplanted with RANT-positive bone marrow to test if CNS protein accumulation occurs in animals that only express the transgene in hematopoietic cells. Both groups of treated animals are compared to wild-type and untreated RANT control animals using a combination of behavioral, functional and neuropathological assessments.

Figure 10:
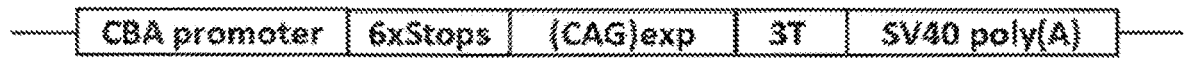
FIG. 10 is a schematic of the RAN translation mouse model construct containing 6× stops, a CAG repeat region, tags for detecting each CAG repeat frame, and a terminator sequence.
Figure 11:
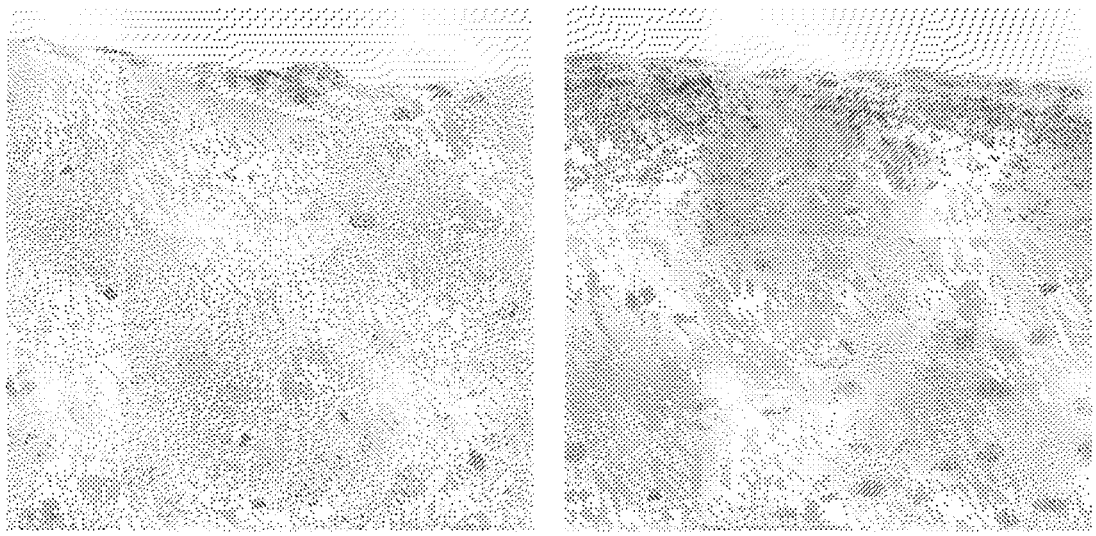
FIG. 11 depicts two photographs showing that poly-Gln proteins accumulated in the brain of RAN translation (RANT) mice containing the construct in FIG. 10, but not in control mice.

A RAN translation mouse model has been generated. Transgenic mice were generated using a construct containing 6 stop codons (two in each reading frame) immediately upstream of a CAG expansion mutation and followed by 3 separate epitope tags in each reading frame (FIG. 10). The CAG repeat generates poly-Gln RAN proteins, which have been previously associated with diseases in humans such as fragile X syndrome. The RANT mouse model produced poly-Gln RAN proteins, which were found to localize at high levels under the pia surface in the brain which is exposed to the cerebral spinal fluid (FIG. 11). This RANT mouse model is used in the studies outlined in Example 2. Accordingly, detection of poly-amino acid repeat containing proteins (e.g., mono- or di-amino acid repeat containing proteins) may be indicative of a risk for a brain disorder associated with the poly-amino acid repeat containing proteins. Accordingly, methods described herein may be used to detect or treat other neurological diseases.

Example 3

Introduction

The chromosome 9p21-linked form of ALS/FTD, the most common cause of familial FTD and ALS identified to date, is caused by an expanded GGGGCC ($G_4C_2$) hexanucleotide repeat in intron 1 of chromosome 9 open reading frame 72 (C9ORF72) (1, 2). The C9ORF72 mutation is found in 40% of familial and 7% of sporadic ALS cases and 21% of familial and 5% of sporadic FTD patients (3). The discovery of the C9ORF72 expansion has generated substantial excitement because it connects ALS and FTD to a large group of disorders caused by microsatellite expansion mutations (4).

Traditionally, microsatellite expansion mutations located in predicted coding- and noncoding regions were thought to cause disease by protein gain-, or loss-, of-function or RNA gain-of-function mechanisms (4). Protein loss-of-function has been proposed to underlie C9ORF72-driven ALS/FTD because the expansion mutation leads to decreased levels of variant 1 transcripts and potential decreases in C9ORF72 protein expression (1, 2). Additionally, because the C9ORF72 $G_4C_2$ expansion mutation is located in an intron, several studies have pursued the hypothesis that C9-linked ALS-FTD results from a toxic RNA gain-of-function mechanism in which $G_4C_2$ expansion RNAs sequester important cellular factors in nuclear RNA foci. Multiple $G_4C_2$ RNA binding proteins have been identified, but so far there is no demonstration that any of these candidates directly bind endogenous expansion transcripts or co-localize with RNA foci observed in patient cells or autopsy tissue (5-8).

In this mechanism, hairpin-forming microsatellite expansion transcripts express proteins in one or more reading frames without an AUG-initiation codon (9). While a variety of names have recently been ascribed to these RAN translated proteins (e.g. homopolymeric, dipeptide, RANT), it is proposed that all proteins expressed across microsatellite expansion mutations in the absence of an ATG-initiation codon be referred to as RAN proteins to prevent confusion as additional expansion mutations that undergo RAN translation are identified.

Here it is shown that C9ORF72 ALS/FTD antisense transcripts containing the GGCCCC ($G_2C_4$) expansion accumulated in patient brains as nuclear, and infrequent cytoplasmic, foci. Additionally, a novel panel of antibodies directed to both the repeat motifs and unique C-terminal regions was developed and both sense and antisense RAN proteins were demonstrated to accumulate in C9ORF72 patient CNS autopsy tissue. The discovery of antisense $G_2C_4$ RNA foci and three novel antisense RAN proteins in C9ORF72 patient brains suggests that bidirectional transcription and RAN translation are fundamental pathologic features of C9ORF72 ALS/FTD.

Results

Antisense RNA Foci in C9ORF72-Expansion Patients

Figure 19D:
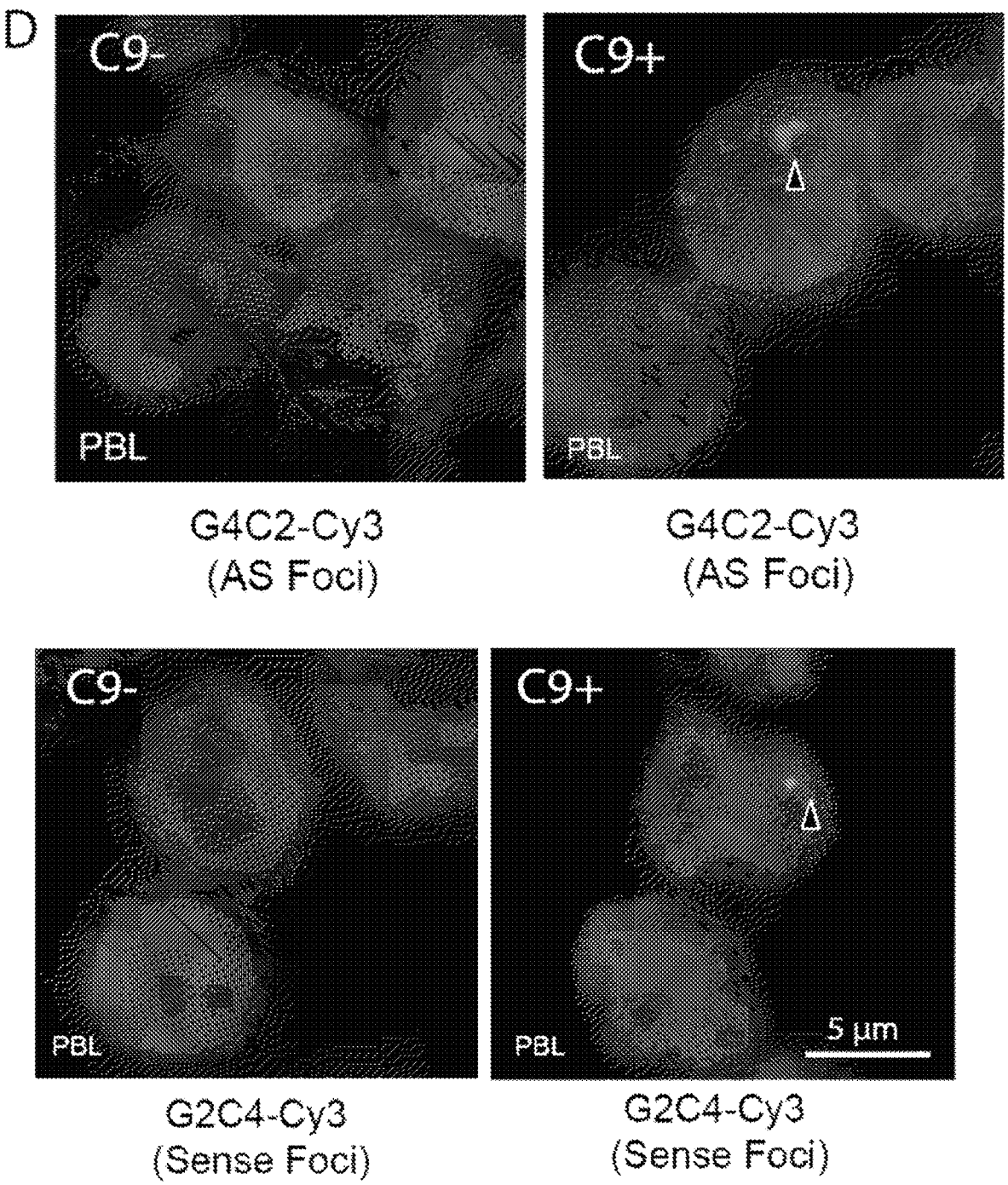

A series of experiments was performed to test the hypotheses that antisense (AS) C9ORF72 expansion transcripts form AS $G_2C_4$ RNA foci and express AS proteins by RAN translation or from short AS open-reading frames (AS-ORFs). First, it was confirmed that C9ORF72 antisense transcripts are expressed using a linkered strand-specific RT-PCR strategy to compare expression of the sense and antisense transcripts in intron 1b, 5' of the antisense $G_2C_4$ expansion, and exon 1a. For the antisense strand in intron 1b, strand-specific RT-PCR was performed using LK-ASORF-R primer for the RT reaction and ASORF-F and the LK for PCR to specifically amplify antisense-cDNAs (FIG. 12A). Similar strategies were used to amplify sense transcripts from the same region of intron 1b and sense and antisense transcripts in exon 1a. Intron 1b antisense transcripts were detected by RT-PCR in frontal cortex from C9(+) ALS/FTD patients but not C9(−) ALS/FTD or normal controls (FIG. 12B) and qRT-PCR shows these transcripts are dramatically increased among six C9(+) ALS/FTD cases (FIG. 12C). In contrast, intron 1b sense transcripts were not detected by RT-PCR (FIG. 12B) in frontal cortex. In blood, both intron 1b sense and antisense transcripts are detectable and the dramatic C9(+) elevation of the intron 1b antisense transcripts was not observed. 5' RACE showed intron 1b AS transcripts begin at varying sites 251-455 basepairs (bp) upstream of the $G_2C_4$ repeat (FIGS. 12A, 19B). In contrast, 3'RACE, using 3'GSP1 or 3'GSP2 primers located 40 and 90 bp 3' of the $G_2C_4$ repeat, did not detect transcripts. These data showed that the 3' end of the AS transcript does not overlap the sense exon 1a region, located 170 bp 3' of the antisense $G_2C_4$ repeat. Consistent with this result, sense but not antisense transcripts are detected by strand specific linkered-RT-PCR using primers overlapping exon 1a (FIG. 12B). To determine if antisense transcripts include the $G_2C_4$ repeat expansion, RNA fluorescence in situ hybridization (FISH) was performed using a Cy3-labelled (G4C2)4 probe to detect putative antisense $G_2C_4$ RNA foci. The results showed nuclear (FIG. 12D) and rare cytoplasmic (FIG. 19C) $G_2C_4$ RNA foci accumulate in C9(+) but not C9(−) ALS frontal cortex. The detection of foci in the cytoplasm showed that antisense expansion transcripts can be found in the same cellular compartment as the protein translation machinery, presumably where RAN translation occurs. Because RNA foci in peripheral tissues may provide biomarkers of the disease, peripheral blood leukocytes (PBLs) were examined and both sense and antisense RNA foci were detected in C9(+) but not C9(−) PBLs (FIG. 12D, FIG. 19D). It was discovered that the RNA-FISH signal from the Cy3-G4C2 probe detecting AS-foci may be competed with excess unlabeled G4C2 oligo, and these foci were resistant to DNase I and sensitive to RNase I digestion (FIG. 19E, F). Taken together, this shows that C9ORF72 antisense transcripts are elevated in the frontal cortex in C9(+) ALS but not C9(−) ALS or normal controls. It was also shown for the first time that antisense transcripts containing the $G_2C_4$ expansion mutation are expressed and accumulate in nuclear and rare cytoplasmic RNA foci in C9(+) frontal cortex. Additionally, it was shown that sense and antisense foci accumulate in blood, providing potential biomarkers of C9ORF72 ALS/FTD in a readily accessible tissue.

RAN Translation of GGCCCC Repeat Expansion In Vitro

To test if the antisense $G_2C_4$ expansions undergo RAN translation, a triply tagged $G_2C4$ minigene was generated, $(G_2C_4)_{EXP}$-3T, lacking an ATG initiation codon, by inserting a 6X STOP codon cassette (two stops in each frame) upstream of $G_2C_4$ expansions of 40 or 70 repeats and three different C-terminal epitope 8 tags to monitor protein expression in all reading frames [e.g., ($G_2C_4$EXP transcripts translated in three frames results in Gly-Pro (GP), Pro-Ala (PA) and Pro-Arg (PR) RAN proteins] (FIG. 13A). Immunoblotting detected two epitope-tagged RAN proteins, PR-Myc and GP-Flag, but not PAHA (FIG. 13B). The (PR)40- and (PR)70-3×Myc proteins migrated at approximately their predicted sizes of 20 and 27 kDa, respectively. In contrast, the (GP)40- and (GP)70-3×Flag proteins migrated substantially higher than their predicted sizes (10-15 kDa) at 50 and 75 kDa, respectively (FIG. 13B). The faint lower molecular weight bands on this blot may result from repeat contractions seen during bacterial culture or differences in translational start site. Immunofloresence (IF) showed antisense RAN proteins are expressed in all three reading frames (FIG. 13C). The detection of PA-HA by IF but not western blotting may be caused by a lower frequency of cells expressing RAN PA-HA from these constructs. Additionally, recombinant GP-Flag and PA-HA proteins had a cytoplasmic localization whereas PR-Myc proteins were distributed in both the nucleus and cytoplasm. These localization differences may result from different properties of the repeat motifs or the C-terminal flanking sequences found in this epitope tagged construct. In an additional series of experiments also it was shown that sense G4C2-expansion constructs containing 30, 60 and 120 repeats express GP-Flag, GR-HA and GA-Myc RAN proteins (FIG. 20). In summary, these data showed that recombinant $G_2C_4$ and $G_4C_2$ expansion transcripts express RAN proteins in all six reading frames.

Dual Immunological Strategy to Detect RAN Proteins

Figure 23C:
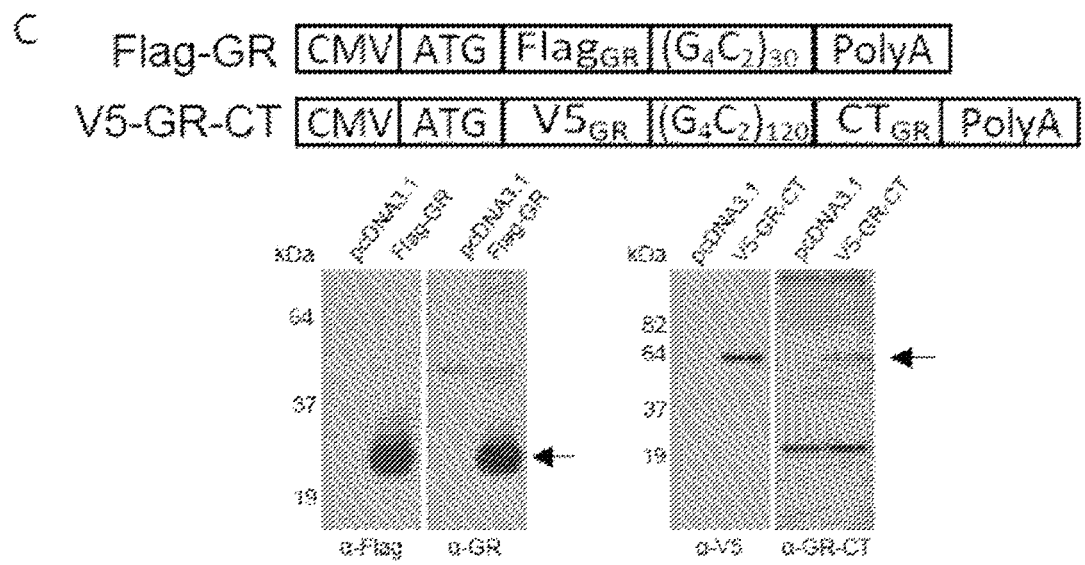

Since amino acid repeats can be found in a range of different proteins, a dual immunological strategy was used and antibodies that recognize the predicted repeat motifs described herein or their corresponding unique C-terminal regions were developed. A schematic diagram showing eight putative C9ORF72 RAN proteins is shown in FIGS. 13D and 21. Predicted proteins include six putative RAN proteins and two putative proteins with additional ATG-initiated N-terminal sequence. Unique C-terminal regions are predicted in five of the six predicted reading frames. To test for the accumulation of these proteins in vivo a series of polyclonal antibodies against the predicted repeat motifs or available corresponding C-terminal regions, were developed (FIGS. 13D, 21). Antibodies to test for putative antisense proteins [rabbit α-PA, α-PA-CT, α-PR, α-PR-CT, α-GP α-GP-CT(sense), and mouse α-GP] were generated and their specificities demonstrated in cells transfected with constructs expressing epitope-tagged recombinant protein by western blot and IF detection (FIGS. 13E, 22). Additional antibodies detecting repeat and C-terminal regions expressed in the sense direction are characterized in FIG. 23.

Antisense $G_2C_4$ RAN Proteins Accumulate in Brain

Figure 24:
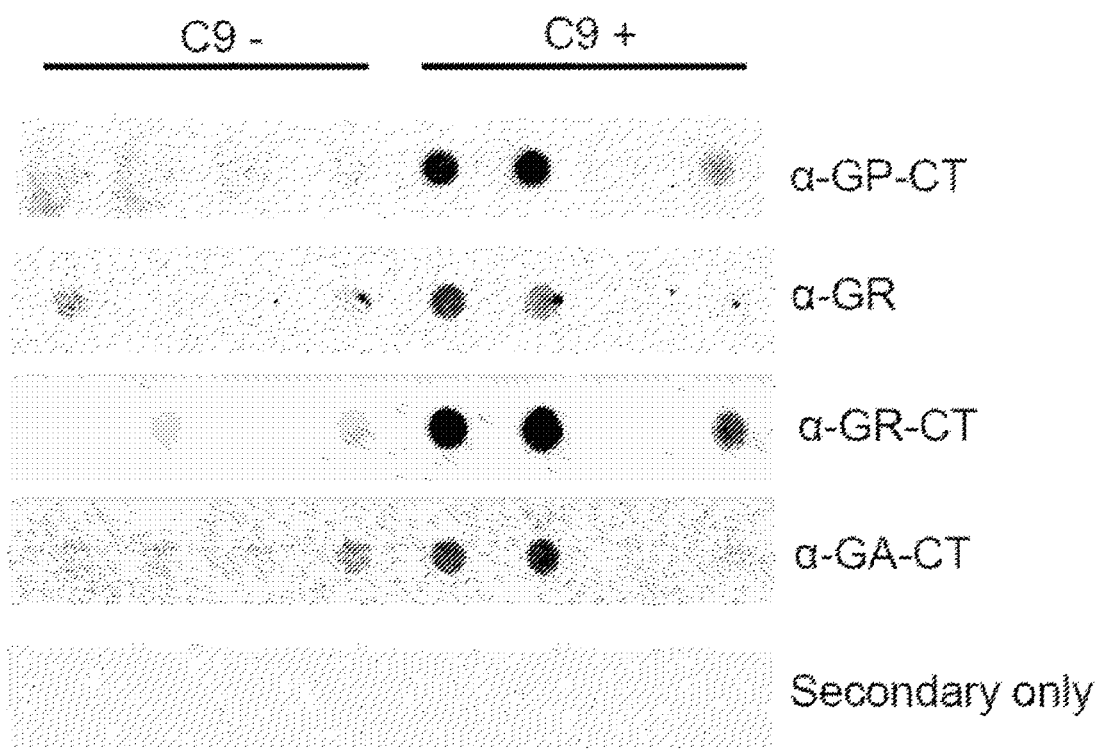
FIG. 24 is a series of images of immunoblots of 2% soluble lysates from C9(+) and C9(−) ALS frontal cortices with α-GP-CT, α-GR, α-GR-CT and α-GA antibodies.
Figure 25:
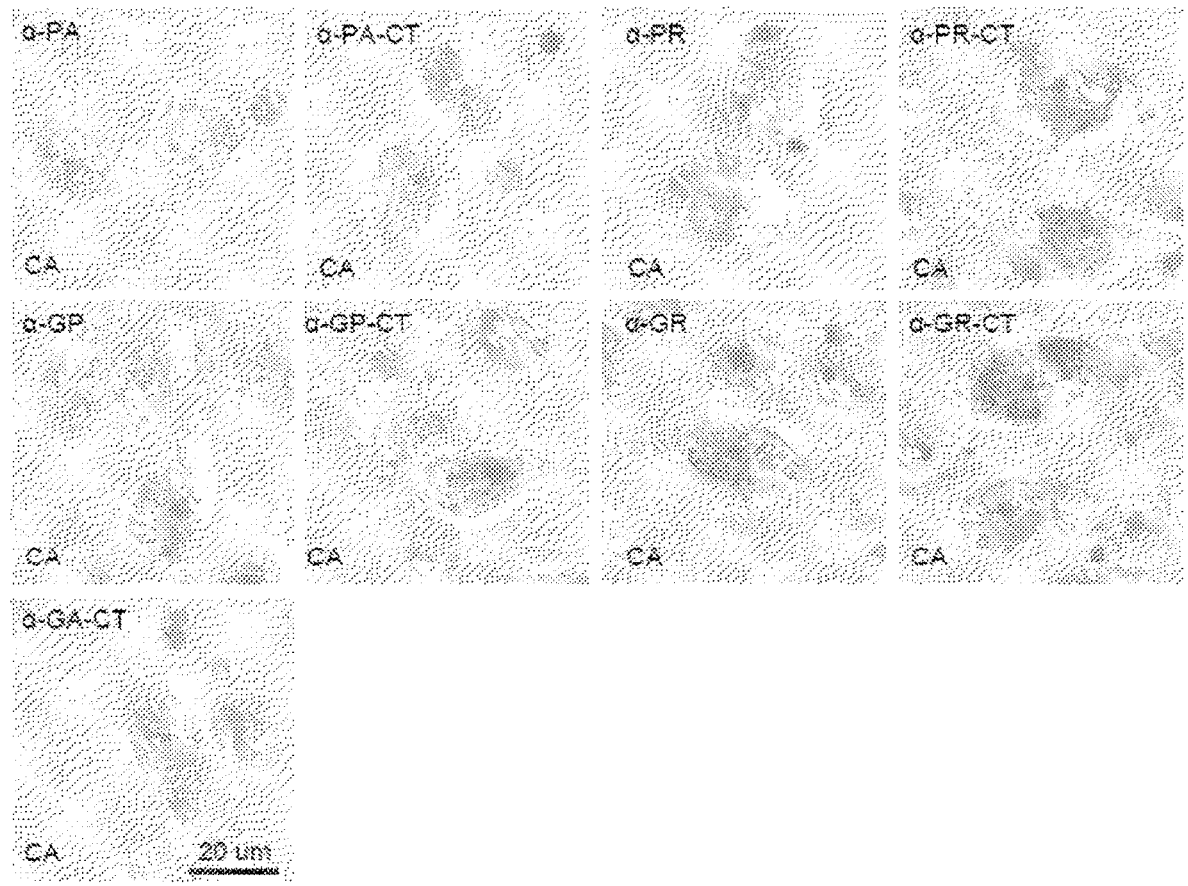
FIG. 25 is a series of images showing negative IHC staining of C9(−) ALS/FTD hippocampal sections with antibodies against sense and antisense proteins.

Several approaches were used to determine if novel antisense (AS) proteins are expressed in C9ORF72 expansion positive autopsy tissue. To overcome the obstacle that aggregated proteins are difficult to isolate from human brain, a sequential protein extraction protocol (23) was used on frozen C9(+) and C9(−) ALS frontal cortex autopsy samples. Antisense PA and PR proteins were detected with α-PA, α-PA-CT, α-PR, α-PR-CT on immuno-dot blots of 1% Triton-X100 insoluble, 2% SDS soluble extracts from a subset of C9(+) but not C9(−) ALS patients (FIG. 14A). Additional immuno-dot blots showing evidence for sense-RAN protein (GP, GR, GA) 10 accumulation in C9(+) ALS/FTD frontal cortex are shown in FIG. 24. α-PA, α-PR and α-GP antibodies also detected high molecular weight smears in 2% SDS insoluble fractions from C9(+) ALS frontal cortex samples after resuspending the pellets in sample buffer containing 8% SDS (23) (FIG. 3B). The differences in migration pattern seen for the recombinant proteins (FIG. 13B), which migrate as one or more bands, and the smears observed in patient tissue extracts (FIG. 14B) reflect differences in the RAN proteins due to much longer repeat tracts in patient samples and their extraction from highly insoluble aggregates. Immunohistochemistry (IHC) was next used to show that protein aggregates were detectable in the perikaryon of hippocampal neurons from C9(+) ALS/FTD autopsy tissue but not in C9(−) ALS patients or control subjects using antibodies against the repeat motifs (α-PA, α-PR, α-GP) as well as antibodies directed to predicted C-terminal sequences beyond the PA and PR repeat tracts (α-PA-CT and α-PR-CT) (FIG. 14C, 25). Previous studies using antibodies directed against the GP repeat motif, detected aggregates, which were assumed to be expressed from the sense strand (10, 11). It is noted that GP repeat-containing proteins are predicted to be expressed from both sense and antisense transcripts (FIG. 13D) In the sense direction the predicted RAN GP protein contains a unique C-terminal (CT) sequence. In contrast, the antisense GP protein has a stop codon immediately after the repeat. To distinguish sense-GP RAN proteins from antisense-GP proteins, a double label IF experiments was performed on C9(+) human hippocampal autopsy sections using rabbit α-GP-CT to detect the CT region of the sense-GP protein and mouse α-GP to detect both sense and antisense GP expansion proteins. Double labeling showed two types of inclusions: a) putative sense inclusions double labeled with mouse α-GP and rabbit α-GP-CT sense and; b) putative antisense inclusions singly labeled with mouse-α-GP (FIG. 14D). Approximately 18% of inclusions showed the sense pattern with double labeling and 82% 11 of inclusions showed the antisense pattern and were positive for α-GP and negative for α-GP-CT sense (FIG. 14E,F). These data showed the importance of characterizing protein aggregates with both repeat and C-terminal antibodies. Taken together, these results show that insoluble, aggregate-forming antisense-RAN proteins are expressed from all three antisense reading frames.

$G_2C_4$ Expansions and RAN Proteins are Toxic to Cells

Figure 13:
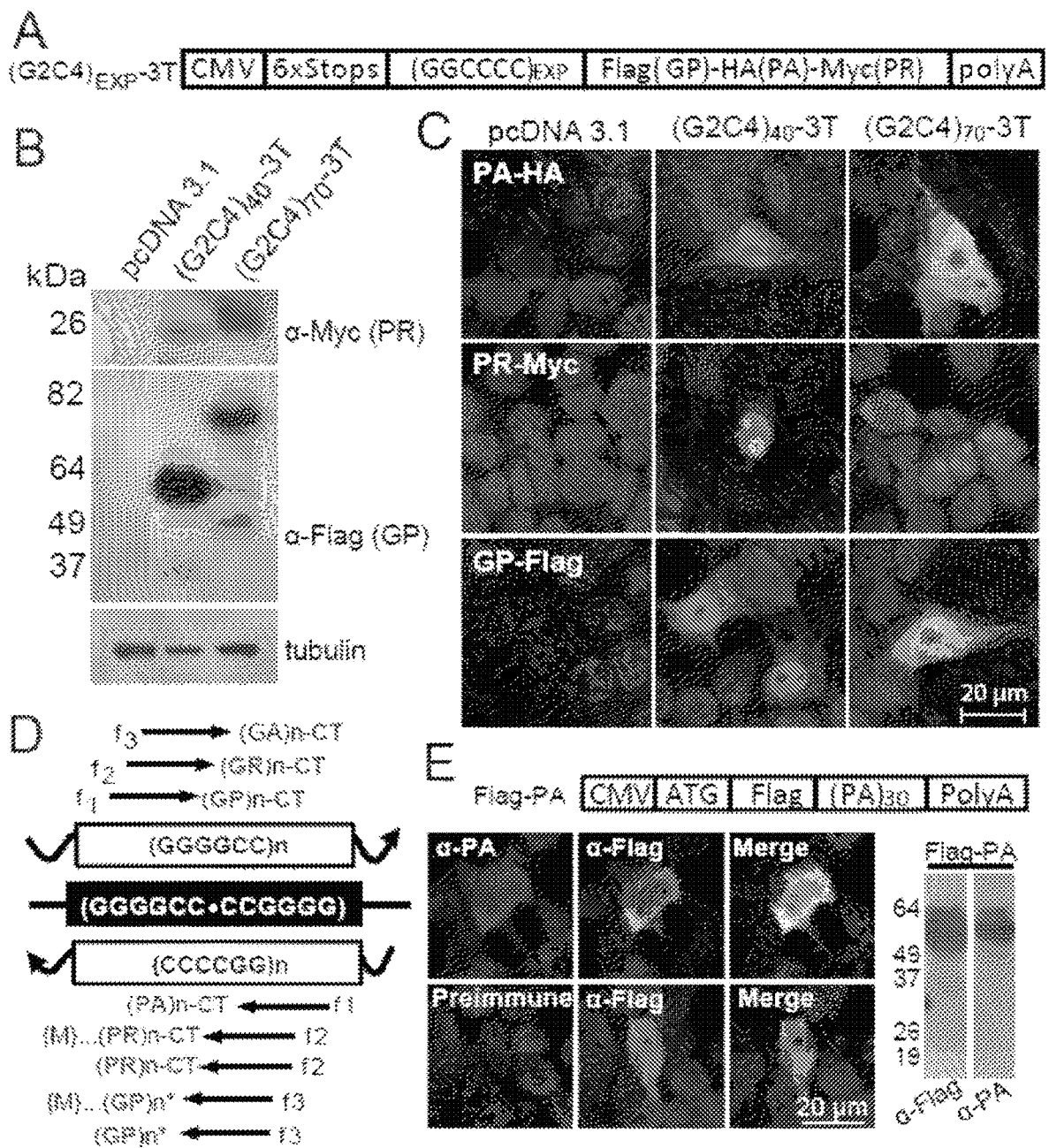
FIG. 13 is a series of schematics, graphs and images showing in vitro evidence for RAN translation of antisense $G_2C_4$ expansion and dual immunological detection strategy. (A-C) Immunoblots (B) and IF staining (C) of HEK293T cells 48 hours post-transfection with the $(G_2C_4)_{EXP}$-3T construct (A). (B) PR and GP expansion proteins detected by western and (C) PA, PR and GP detected by IF in transfected cells. (D) Diagram of putative proteins translated from sense and antisense transcripts. CT=C-terminal, f1-3: reading frame 1-3. (E) Abbreviated example of validation of α-PA rabbit polyclonal antibody. IF staining of HEK293T cells transfected with constructs with 5' Flag epitope tagged PA protein and corresponding immunoblots. See FIGS. 22 and 23 for additional controls and validation of eight additional antibodies generated against repeat motifs and CT regions.
Figure 14A:
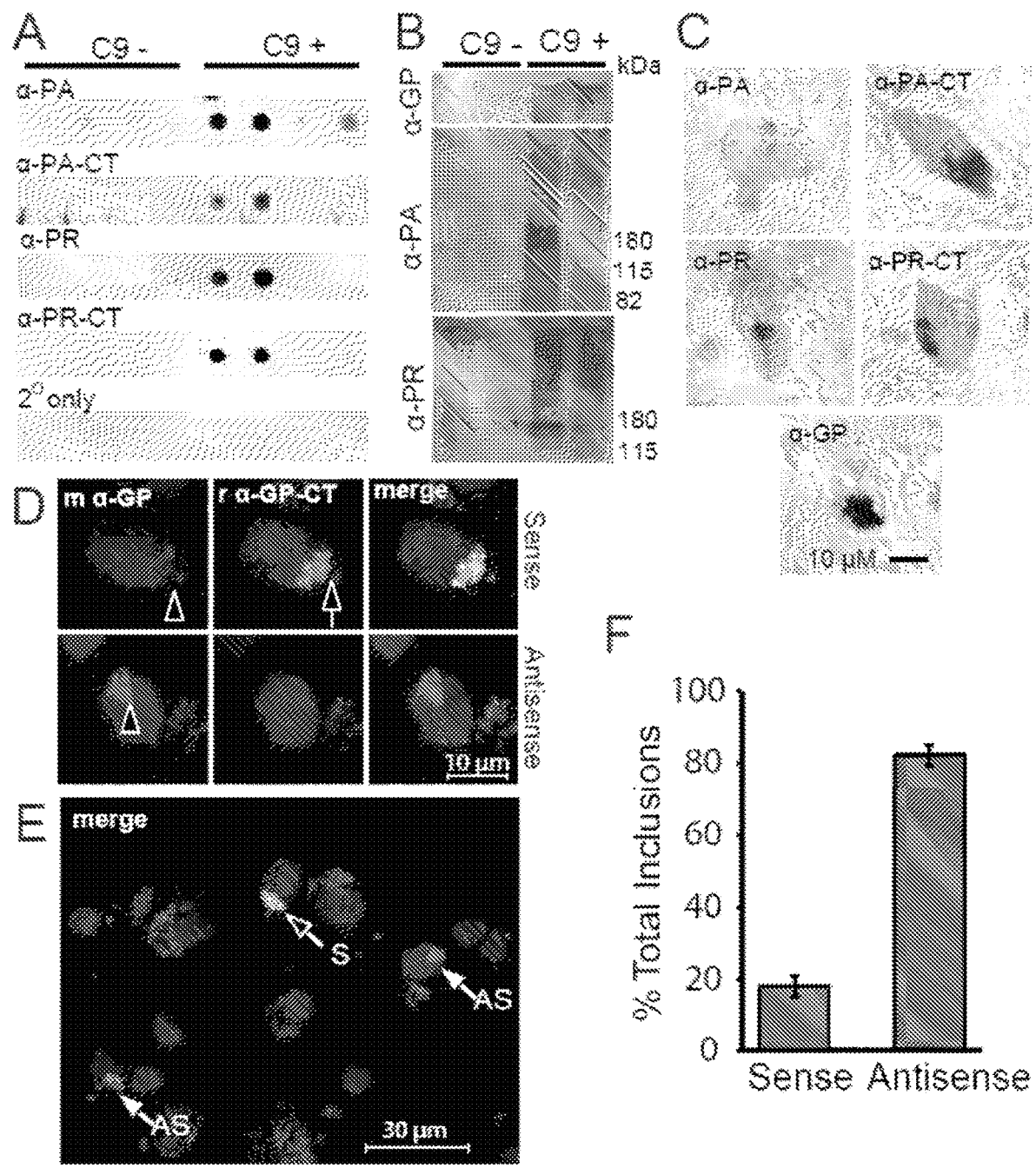
FIGS. 14A and 14B are a series of images and graphs showing in vivo evidence for RAN-translation of the $G_2C_4$ AS repeat and toxicity studies. (A) Dot blot of C9(+) and C9(−) frontal cortex lysates probed with α-PA, α-PA-CT, α-PR, α-PR-CT antibodies. (B) Immunoblots of C9(+) and C9(−) ALS frontal cortex lysates. (C) IHC detection of PA, PR and GP protein aggregates in hippocampal neurons from C9(+) ALS patients detected with α-PA, α-PA-CT, α-PR, α-PRCT and α-GP antibodies. (D)IF staining with mouse α-GP (arrowhead) and rabbit α-GP-CT (arrow) of C9(+) hippocampal tissue with sense inclusions positive for both antibodies (upper panel) and antisense inclusions positive for only GP repeat antibody (lower panel). (E) IF staining of larger region showing sense (S) and antisense (AS) staining. (F) Quantitation of double (sense) and single (antisense) labeled aggregates. (G-J) RAN and PR toxicity studies (G) $G_2C_4$ expansion constructs (+/−ATG-PR-3T) +/−ATG initiation codon in PR frame and 3'epitope tags. (H) Protein blots showing levels of PR and GP in cells transfected with constructs in (G). (I) LDH and (J) MTT assays of transfected HEK293T cells.
Figure 14B:
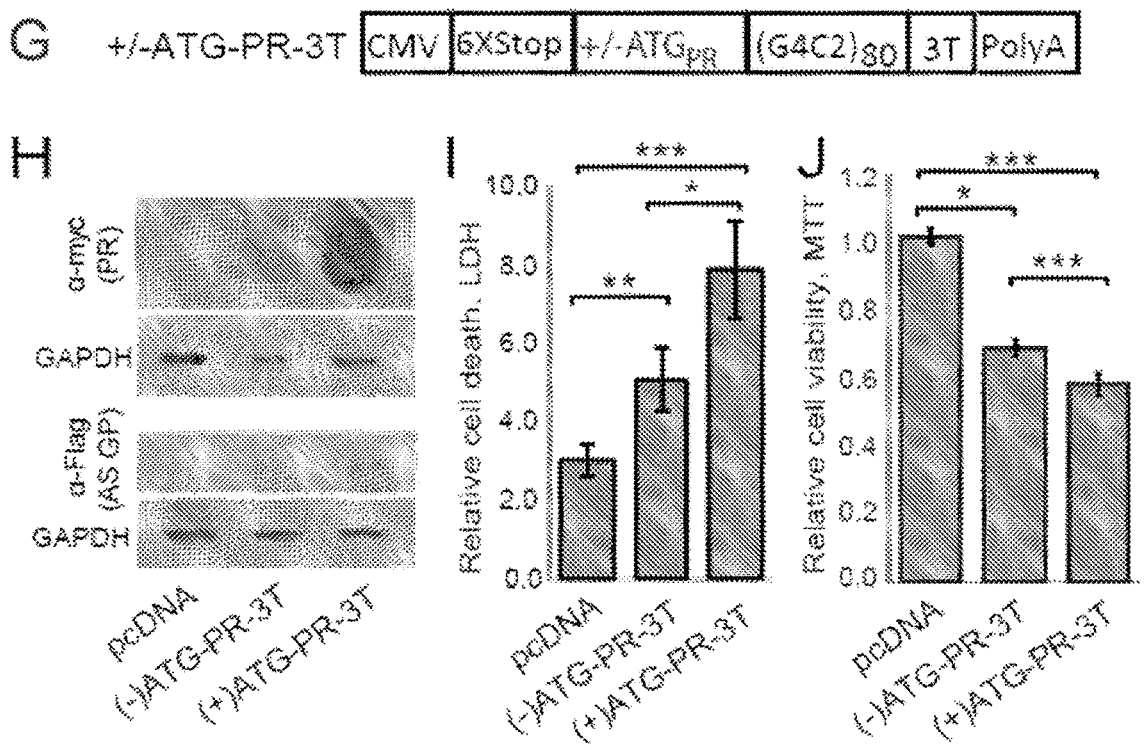
Figure 26A:
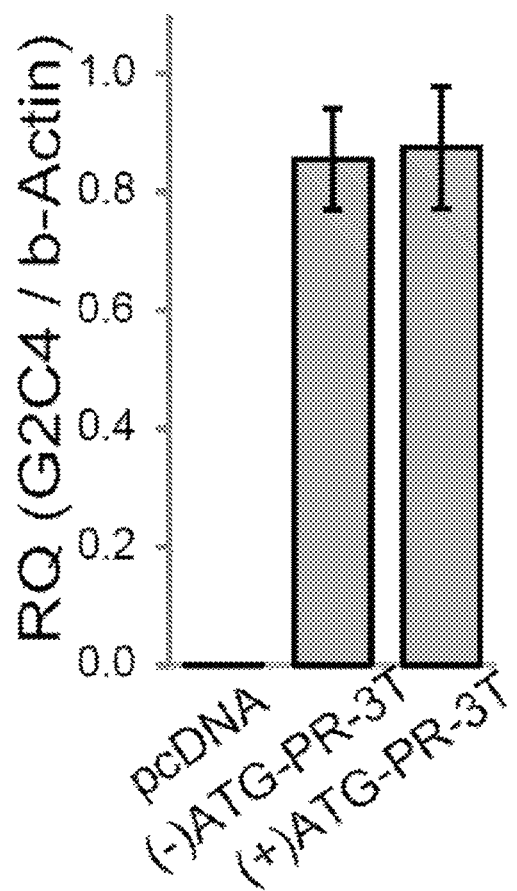
Figure 26D:
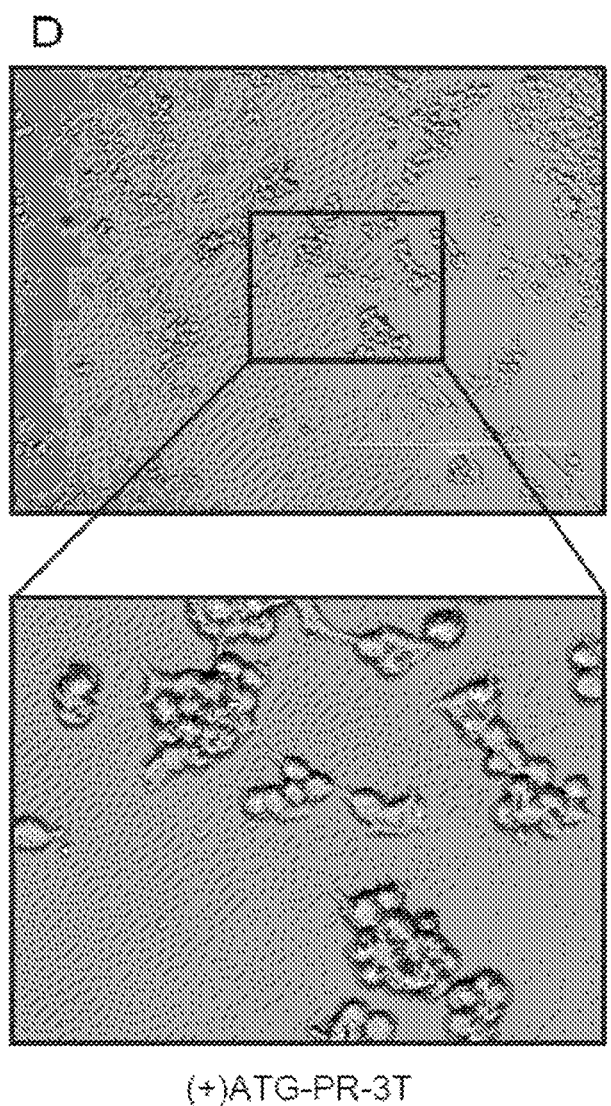

In addition to antisense GP and PR RAN proteins expressed by RAN translation, two of the antisense reading frames have upstream ATG initiation codons that may result in both ATO-initiated OP and PR proteins (M-GPAS and M-PRAS) (FIGS. 13D and 21). It was shown that the presence of an ATO-initiation codon does not prevent RAN translation from also occurring in all three reading frames (9). Therefore antisense GP and PR proteins may be expressed by both AUG-initiated and/or RAN translation. To explore the effects that an AT-initiation codon has on RAN protein expression for the $G_2C_4$ expansion, an additional minigene construct was generated by placing an ATG initiation codon in front of the $G_2C_4$ repeat (FIG. 14G). The PR frame was selected for analysis because an ATG initiation codon naturally occurs in this reading frame. Western blotting shows that HEK293T cells transfected with (+)ATG-PR-3T express substantially higher levels of PR protein compared to (−)ATO-PR-3T transfected cells (FIG. 14H). In contrast, qRT-PCR and Western blotting showed transcript levels (FIG. 26A) and levels of RAN-translated GP (FIG. 14H) were comparable. Similar to FIG. 13, RAN-translated PA was not detectable by Western blot. The effects of these constructs on cell viability was then tested using complementary assays; lactate dehydrogenase (LDH) detection and methylthiazol tetrazolium (MTT). For the LDH assay, cells transfected with the (−)ATG-PR-3T or (+)ATG-PR-3T construct showed 1.9 and 2.9 fold increases in cell death compared to vector control cells (p=0.008 and 0.001), respectively. Additionally, (+)ATG-PR-3T transfected cells, which express elevated levels of PR protein showed a 1.5 fold increase in cell 12 death compared to cells transfected with the (−)ATG-PR-3T construct (p=0.034). The MTT assay showed similar results. Cells transfected with (−)ATG-PR-3T and +ATG-PR-3T constructs showed dramatic decreases in the number of metabolically active cells, 33% (p<0.00001) and 43% (p<0.00001), respectively compared to untreated cells or empty vector controls (FIG. 14J). Additionally, elevated PR expression in cells transfected with (+)ATG-PR-3T had significantly lower levels of metabolic activity compared to (−)ATG-PR-3T cells (p<0.05). By light microscopy cell detachment and changes in cell morphology were evident in -ATG-PR-3T compared to control cells and these phenotypes worsened in (+)ATG-PR-3T cells which express elevated levels of PR (FIG. 26B-D). Taken together, these data demonstrated that: 1) the $G_2C_4$ expansion mutation is toxic to cells—this toxicity may be caused by effects of the DNA, $G_2C_4$ RNA and/or RAN-translated PR, GP or PA proteins; 2) increased PR protein expressed in cells transfected with the (+)ATG-PR-3T construct increases cell toxicity and death above levels caused by the DNA, $G_2C_4$ RNA and RAN protein effects. Therefore the PR protein was shown to be intrinsically toxic to cells.

All Six RAN Proteins Form Aggregates in the Brain

Figure 15A:
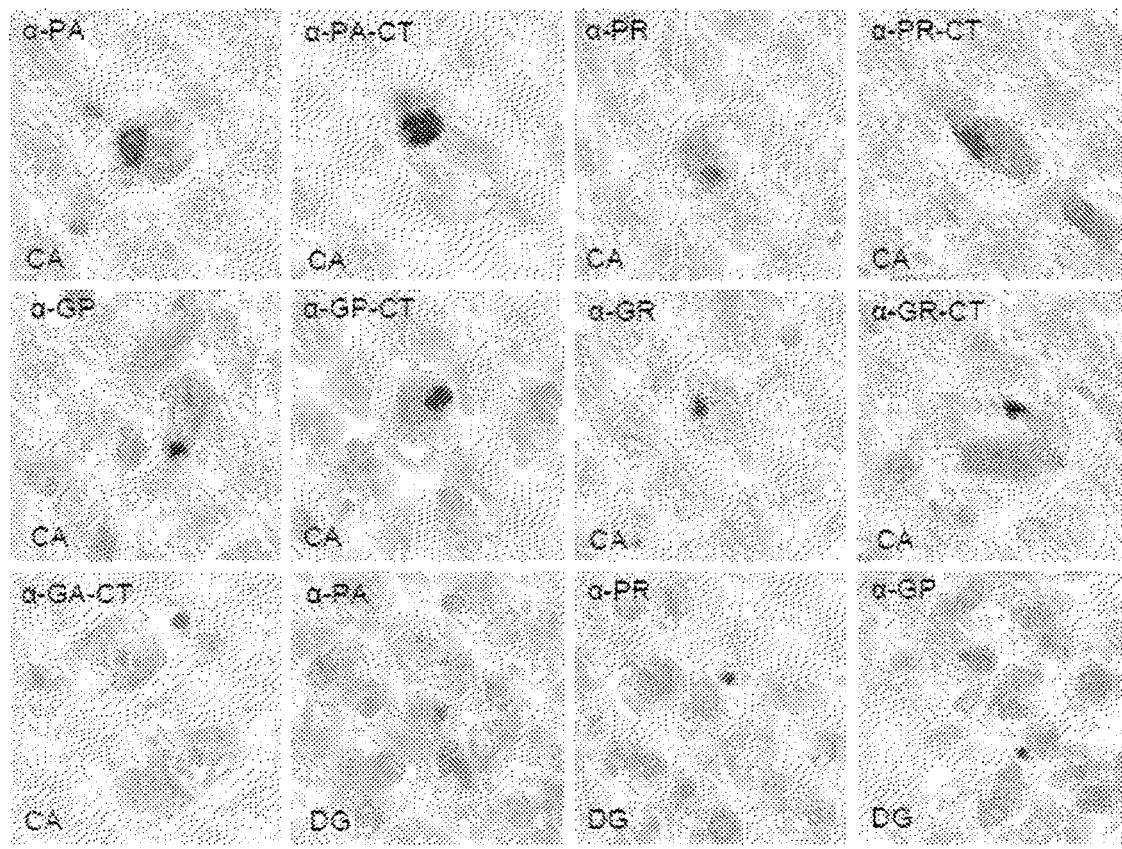
FIGS. 15A and 15B are a series of images showing in vivo evidence for RAN translation in both antisense and sense directions of C9ORF72. Cytoplasmic inclusions detected by IHC using antibodies against sense (α-GR, α-GR-CT, α-GA, α-GP-CT) and antisense (α-PA, α-PA-CT, α-PR, α-PR-CT) and α-GP which recognizes GP proteins made in both the sense and antisense directions. Aggregates were found in neurons of cornu ammonis (CA) and dentate gyrus (DG) regions of the hippocampus and the motor cortex (MC) of C9(+) ALS autopsy tissue.
Figure 15B:
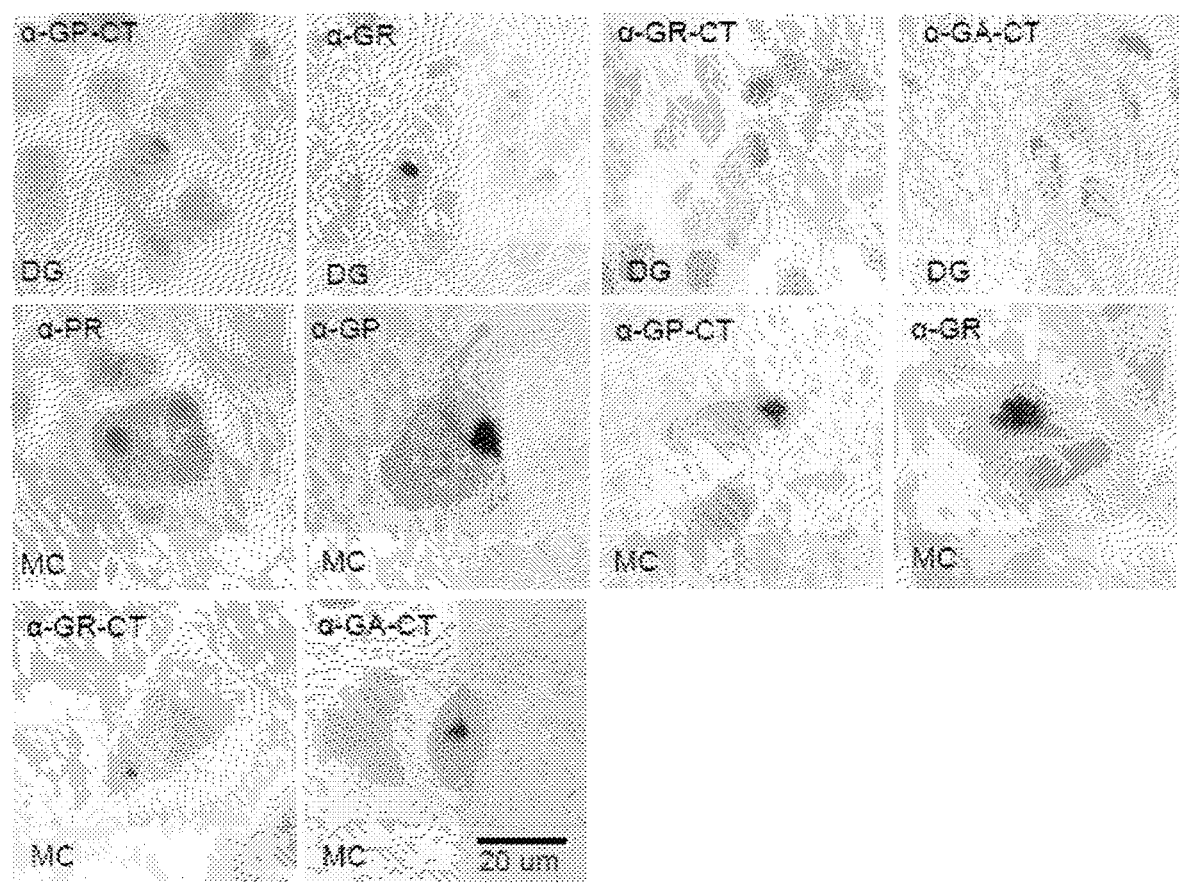

To determine if all six RAN proteins from both sense and antisense RNA strands are expressed in C9(+) ALS patients, IHC staining was performed on sections of paraffin-embedded brain tissues using nine polyclonal antibodies against repeat-expansion and/or C-terminal sequences of these proteins. In C9(+) cases there were abundant globular and irregular-shaped neuronal cytoplasmic inclusions (NCIs) in the hippocampus, the majority of which were in the dentate gyrus and in pyramidal cells in the CA regions. These RAN inclusions were also detected in C9(+) motor cortex (FIG. 15). GP positive inclusions were detected in all examined C9(+) cases but not in C9(−) cases or normal control sections in the hippocampus as well as in the motor cortex using α-GP. In the CA regions of the 13 hippocampus and in the motor cortex, clusters of aggregates were frequently found in C9(+) cases with aggregates in >20% of neurons (FIG. 27). Fewer aggregates were detected with the α-GP-CT sense antibody, consistent with double labeling experiments (FIG. 14D-F) that showed most GP aggregates are translated from C9ORF72 antisense strand. PA inclusions were detected in hippocampus in four out of six C9(+) cases tested and in one out of two motor cortex samples (FIG. 27). In C9(+) cases, the frequency of PA inclusions were significantly lower in the hippocampus and motor cortex compared with GP inclusions, but high-intensity regional staining with extremely large PA inclusions found in >50% of neurons were found in one patient (FIG. 27). PR positive inclusions were also seen in hippocampus in all C9(+) cases examined and in motor cortex in one out of two C9(+) cases tested. Similar to the PA staining, PR inclusions are less frequent but intense regional staining was occasionally observed. In the sense direction, GR positive inclusions were found in the hippocampus and motor cortex in all C9(+) cases examined, but appeared less frequent than the GP aggregates. GA inclusions were only occasionally detected by IHC as small perinuclear inclusions in hippocampus and in motor cortex (FIG. 15, 27). The apparent differences in the frequency of various types of aggregates may result from differences in protein conformation and epitope availability or differences in the affinities of these antibodies, which were designed to different epitopes. Taken together, this data showed that all six RAN proteins form aggregates in the C9(+) autopsy brains.

Inclusions of RAN Proteins in Upper and Lower Motor Neurons

Figure 16A:
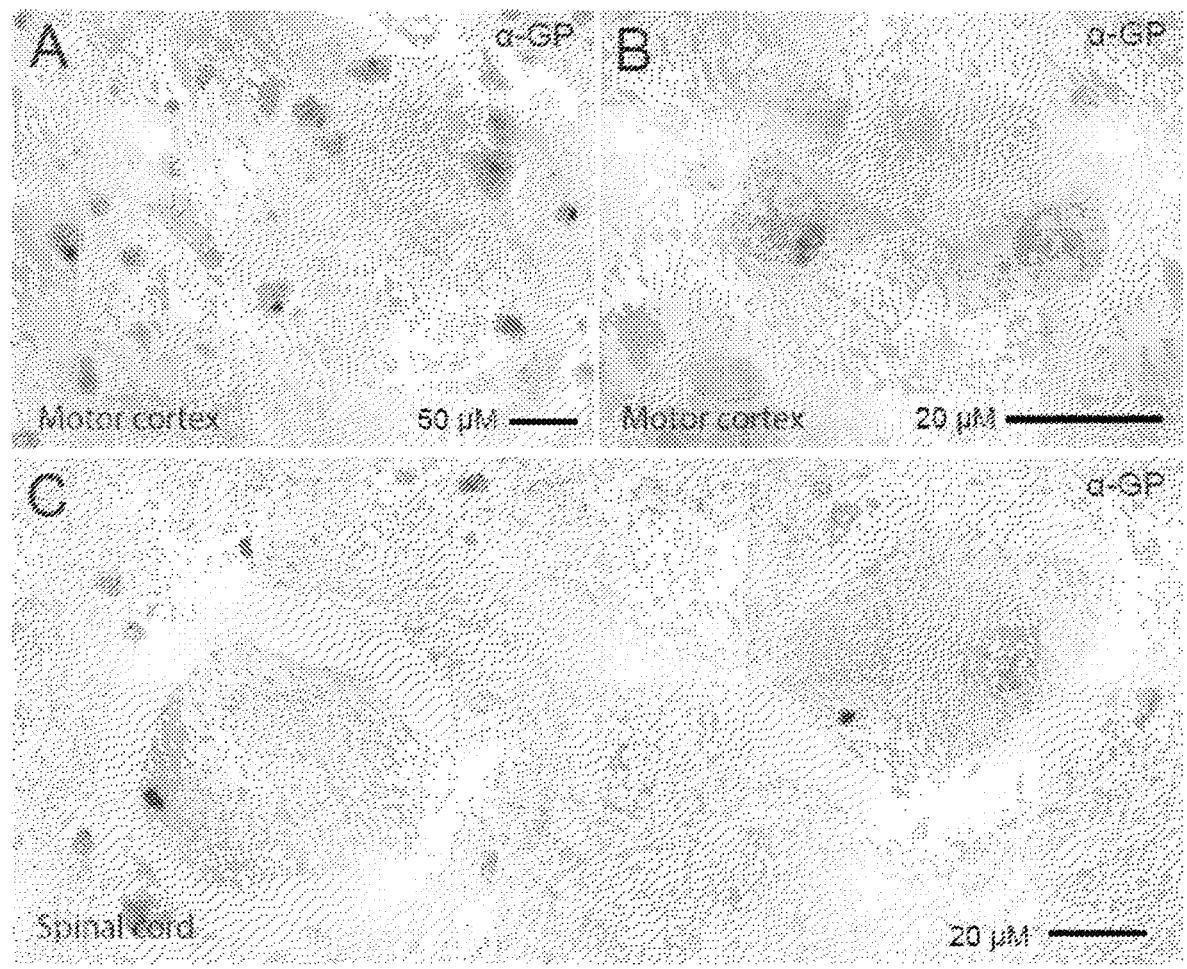
FIGS. 16A and 16B are a series of images of clustered RAN protein aggregates and RAN aggregates in motor neurons. IHC showing cytoplasmic α-GP aggregates in: (A) in layer III of motor cortex. (B) upper motor neuron in layer V of the motor cortex; (C) lower motor neurons in the spinal cord (L-S.C). (D) in cornu ammonis, CA, (E) and dentatus gyrus, DG regions of the hippocampus. (F and G) IHC showing abundant PA and PR cytoplasmic inclusions in the pre-subiculum (PrSub) from one patient.
Figure 16B:
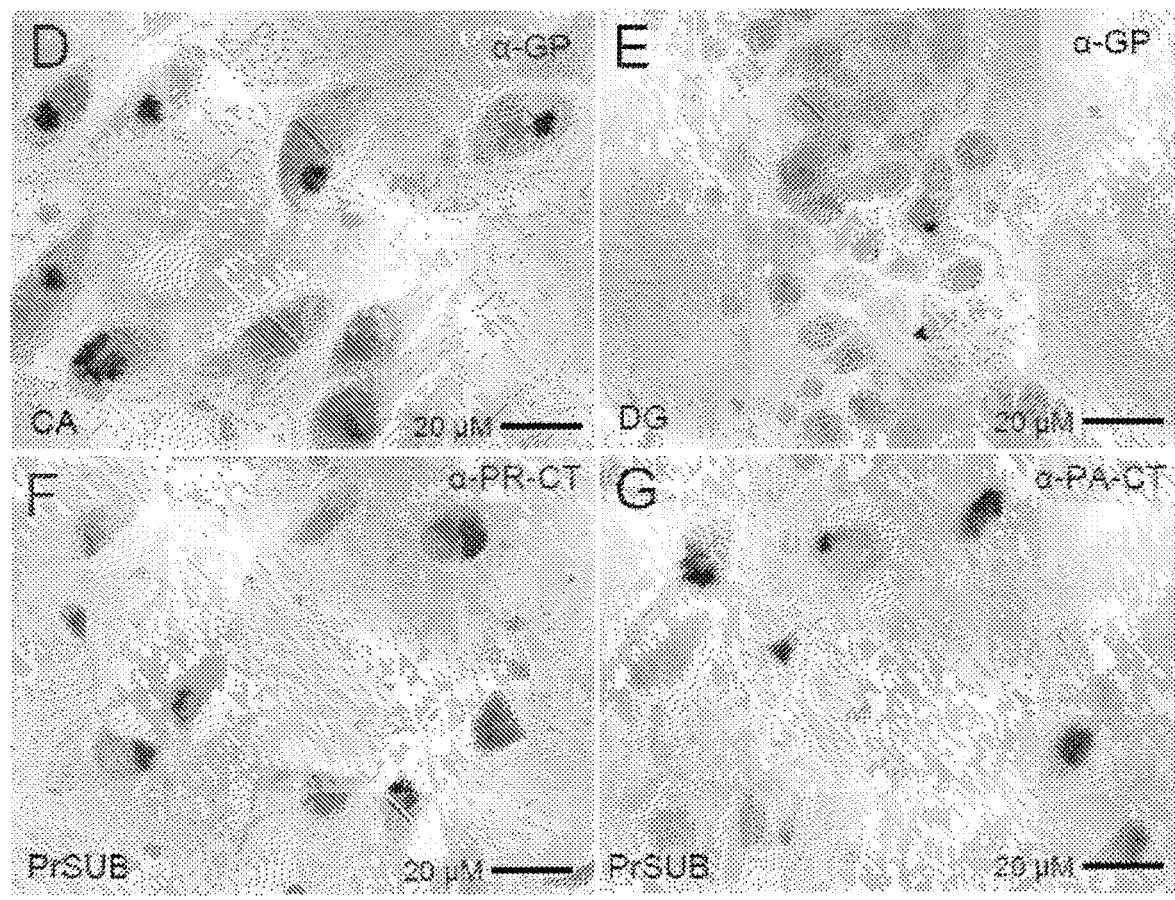

A central feature of ALS is the gradual degeneration and death of upper motor neurons in motor cortex and lower motor neurons in the brain stem and spinal cord. To test if RAN proteins accumulate in upper and lower motor neurons, IHC was performed using all nine antibodies against predicted proteins in both sense and antisense directions. In C9(+) cases, abundant GP-positive neuronal cytoplasmic inclusions were seen in all layers of motor cortex, with frequent GP aggregates in pyramidal neurons of layer II and throughout layer V (FIG. 16A). Although cell death and atrophy made motor-neurons in layer V difficult to identify, GP inclusions in remaining upper motor neurons were found (FIG. 16B). Additionally, PA-, PR-, GR- and GA-positive inclusions were also found in the motor cortex (FIG. 15, 27). Using a similar series of experiments performed in spinal cord sections, GP aggregates in all three cases examined and aggregates in lower motor neurons in two out of three C9(+) patients were detected, but not in C9(−) ALS cases or normal controls (FIG. 16C). This is the first report of RAN protein accumulation in motor neurons. The discovery of GP-aggregates in both upper and lower motor neurons links C9 RAN-protein accumulation to the neurons selectively vulnerable in ALS.

High Density Clustering of RAN-Protein Aggregates

Figure 17:
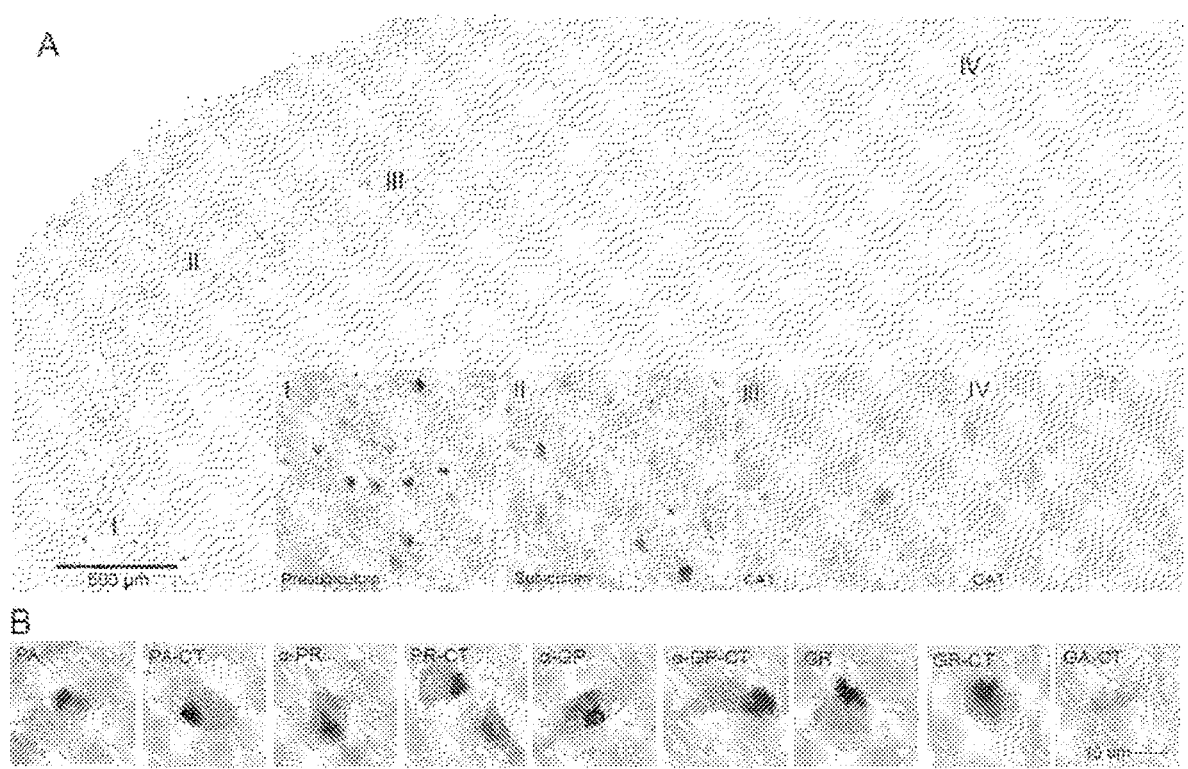
FIG. 17 is a series of images of clustered staining of RAN proteins. (A) Low power image of IHC staining with α-PA-CT shows variations in staining intensity (dark spots are positive) in regions I-IV with insets showing higher-power images. (B) Examples of aggregates from region I show immunoreactivity against all nine antibodies with similar staining for antibodies against repeat and unique C-terminal epitopes.

Both sense and antisense proteins accumulated in neurons of C9ORF72 autopsy brains. In general, two types of aggregation patterns were observed: 1) isolated cytoplasmic aggregates and 2) high-density clustered cytoplasmic aggregates in which ~10 to more than 50% of neurons were positive. Clustered aggregates were most frequently detected for GP and were found in the dentate gyrus (DG) and CA1-4 of the hippocampus (FIG. 16D, E). The clustered GP aggregates in DG were smaller and less frequent than the large cytoplasmic aggregates in CA regions. Additional clustered GP aggregates were frequently found in subiculum and presubiculum of the hippocampus as well as 15 the motor cortex. Immunostaining of serial sections showed that multiple proteins are often found in the same region. For example, intense clustered staining for PA, PR, GP, GA and OR proteins was found in the same region of the presubiculum in serial sections from one C9 (+) patient (see FIG. 16F,G). Immunostaining for PA showed that some brain regions have abundant aggregates whereas other regions in the same section are relatively spared. For example, FIG. 17A illustrates a gradient of PA inclusions (presubiculm>subiculum>CA1) across hippocampal regions in a single section in one patient. PA inclusions in this patient were numerous (>50% of neurons) in presubiculum (I), moderate in subiculum (II), and rare in CA1 hippocampal regions (III and IV). Consistent with the focal regional staining seen in this section, PA staining was not detected in sections from a separate block of hippocampal tissue taken from the same patient. These data shows that expression of the PA RAN protein is variable from cell to cell or that aggregation of PA in one cell triggers aggregation in neighboring cells as has been proposed in a mouse model of Parkinson's disease (24). Next, serial sections from this C9(+) case were used to show that antibodies directed against both the repeat motifs (α-PA, α-PR, α-GP, α-GR) and corresponding C-terminal regions (α-PA-CT, α-PR-CT, α-GP-CT, α-GR-CT α-GA-CT) detect aggregates in the same densely staining region of the presubiculum (region I) (FIG. 17B). These results showed that both sense and antisense RAN protein aggregates accumulate in this region. The detection of similar aggregates in using antibodies that recognize either the repeat motifs or specific C-terminal regions confirms that these antibodies are recognizing proteins expressed across both the $G_2C_4$ and $G_4C_2$ expansion transcripts and provides new tools to understand the biological impact of RAN translation in C9ORF72 ALS/FTD.

Discussion

There has been much excitement about the discovery that an intronic microsatellite expansion mutation in C9ORF72 causes a common form of both familial and sporadic ALS/FTD (1, 2). The three major pathological mechanisms being considered for this disease include haploinsufficiency (1, 2), RNA gain-of-function (5-8), and RAN translation (9, 11-13). To date, efforts to understand the molecular mechanisms of this disease have focused exclusively on understanding the consequences of the C9ORF72 expansion mutation in the sense direction. The results reported here show that C9ORF72 expansion mutation is also expressed in the antisense direction and show that antisense RNA foci and antisense RAN proteins contribute to C9ORF72 ALS/FTD. We show for the first time: 1) antisense C9ORF72 but not sense transcripts are elevated in C9(+) autopsy tissue; 2) antisense $G_2C_4$ expansion transcripts form RNA foci that accumulate in C9+ brain and blood; 3) RAN translation occurs across antisense $G_2C_4$ expansion constructs in cell culture; 4) that sense and antisense RAN proteins accumulate in C9(+) autopsy brains using a dual immunological approach with both repeat and C-terminal antibodies; 5) RAN protein aggregates accumulate in upper and lower motor neurons linking RAN translation directly to the key pathologic feature of ALS. Since the initial report that $G_4C_2$ RNA foci accumulate in C9ORF72 ALS/FTD patient tissues (1, 2), a leading hypothesis is that $G_4C_2$ sense transcripts sequester and dysregulate RNA binding proteins similar to the sequestration of MBNL proteins in DM1, DM2 and SCA8 (4). Several groups have already reported $G_4C_2$ binding proteins and are testing their potential role in disease (5-8). The discovery that antisense $G_2C_4$ foci also accumulate in patient cells shows that $G_2C_4$ antisense RNAs and binding proteins may play a role. Additionally, the discovery of sense and antisense foci in C9(+) peripheral blood may prove useful as an easily accessible biomarker of C9ORF72 ALS/FTD. Biomarkers that monitor both sense and antisense transcripts may be particularly important as therapies that decrease expression of one strand may increase expression of the other strand. Using a dual immunological approach it was shown that $G_2C_4$ antisense transcripts express novel antisense proteins (PA, PR, GP) by RAN translation and/or from two short ORFs (Met-AS-PR and Met-AS-GP).

Materials and Methods
 cDNA constructs.
 CCCGGGGCC(GGGGCC)$_2$GGGGCCC (SEQ ID NO: 64) and CCCGGGGCC(GGGGCC)$_1$GGGGCCC (SEQ ID NO: 65) fragments that contain upstream 6×Stop codons were synthesized and cloned into pIDTSmart vector by Integrated DNA Technologies. 6×Stops-(GGGGCC)$_{4-3}$T and 6×Stops-(GGGGCC)$_{30}$-3T constructs were generated by subcloning Nhe/XhoI fragment into pcDNA3.1 vector containing triple epitopes. To expand the size of the GGGGCC repeats, SmaI/XhoI fragment was subcloned into PspOMI blunted with T4 DNA polymerase/XhoI of pcDNA-6×Stops-(GGGGCC)$_{EXP}$-3T. To reverse the orientation of GGGGCC repeats in pcDNA-6×Stop-3T construct, SmaI/ClaI fragment was subcloned into pBluescript SK+ to generate pBluescript-(GGGGCC)$_{EXP}$. The AfeI/XhoI fragment pBluescript-(GGGGCC)$_{EXP}$ was subcloned into pcDNA-6× Stop-3T to make pcDNA-6×Stop-(GGCCCC)$_{EXP}$-3T construct.
 RT-PCR.
 1) Strand-specific RT-PCR in autopsy tissues: Total RNA was isolated from Frontal cortex autopsy tissues and peripheral blood lymphocytes (PBL) of ALS patients and healthy controls with TRIzol (Invitrogen). To detect transcripts from both strands, cDNA was generated from 0.25 µg of total RNA using the SuperScript III system (Invitrogen) with linkered strand specific reverse primers and PCR with strand specific forward and linker (LK) primers. The PCR reactions were done as follows: 94° C. for 3 min, then 35 cycles of 94° C. for 45 s, 58° C. for 45 s and 72° C. for 1 min followed by 6 min at 72° C. Bands were cloned and sequence to verify their specificity of the PCR amplification. 2) RT-PCR for toxicity assay in 293T cells: Total RNA from cells was extracted using miRNeasy Mini kit (Qiagen) according to the manufacturer's protocol. Total RNA was reverse transcribed using the Superscript III RT kit (Invitrogen) and random-hexamer primers. The expression of the different G4C2-3×Tag constructs were analyzed by RT-PCR and qPCR using primer set: 3×Tag-Fw and 3×Tag-Rv. β-Actin expression was used as a reference gene amplified with primer set ACTB3 and ACTB4. Primer sequences are listed in FIG. 27.
 Real Time RT-PCR.
 Two step quantitative PCR was performed on a MyCycler Thermal Cycler system (Bio-Rad) using SYBER Green PCR Master Mix (Bio-Rad) and ASORF strand-specific cDNA and primer sets. Control reactions were performed with human beta-actin primers ACTB3 and ACTB4 using oligo dT synthesized total cDNA as template. Two stage PCR was performed for 40 cycles (95° C. 30 s, 60° C. 30 s) in an optical 96 well plate with each sample cDNA/primer pair done in triplicate. The relative fold changes were generated by first normalizing each experimental Ct value to their beta actin Ct value and then normalized to the healthy control antisense ΔΔCt. Primer sequences are listed in FIG. 28.
 Rapid Amplication of 5' and 3' cDNA Ends (5' and 3' RACE).
 Four µg of total RNA from 2 C9(+) ALS patients and 2 C9(−) ALS patients frontal cortex autopsy tissues were used for 5' and 3' RACE (5' RACE systems and 3' RACE: Life Technologies). In 5'RACE, Primer ASORF R was used for gene specific first strand cDNA synthesis and nested reverse primers are 5'GSP1 and 5'GSP2. In 3'RACE, nested forward primers are 3'GSP1 and 3'GSP2. The 3' RACE and 5' RACE products were gel-extracted, cloned with TOPO TA Cloning (Invitrogen) and sequenced. Primer sequences are listed in FIG. 28.
 Production of Polyclonal Antibodies.
 The polyclonal rabbit antibodies were generated by New England Peptide and the polyclonal mouse antibody was generated by the Interdisciplinary Center for Biotechnology Research (ICBR) at the University of Florida. In sense strand (GGGGCC), antisera were raised against synthetic poly(GP), poly(GR) peptides and C terminal regions of predicted GP, GR, and GA RAN proteins (FIG. 21). In antisense strand (GGCCCC), antisera were raised against synthetic poly(PA), poly(PR) peptides and the C terminal regions of predicted PA and PR RAN proteins. Peptides used to generate antibodies to both antisense and sense proteins and their use for Western blot, immunofluorescence (IF) and immunohistochemistry (IHC) is summarized in Table S3.
 Cell Culture and Transfection.
 HEK293T cells were cultured in DMEM medium supplemented with 10% fetal bovine serum and incubated at 37° C. in a humid atmosphere containing 5% CO2. DNA transfections were performed using Lipofectamine 2000 Reagent (Invitrogen) according to the manufacturer's instructions.
 Human Samples.
 Frozen frontal cortex tissue samples for biochemical and histological analysis included samples from six C9(+) ALS, five C9(−) ALS controls and one normal control were used in this research. Additionally, paraffin embedded fixed tissues from C9(+) ALS/FTD and C9(−) ALS/FTD cases as well as a normal control. Peripheral blood lymphocytes (PBL) were isolated from the buffy coat of freshly collected whole blood following brief centrifugation at 2000×g. Red blood cells (RBC) were preferentially lysed and removed using RBC Lysis Buffer (Roche), PBLs centrifuged, washed once with PBS and dried on slides. This study was conducted in compliance with the Declaration of Helsinki. Institutional review boards of the University of Florida and Johns Hopkins University approved the study. Written, informed consent was obtained from participants or relevant parties at the time of enrollment.

Immunofluorescence.

The subcellular distribution of polymeric proteins was assessed in transfected HEK293T cells by immunofluorescence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum in PBS for 30 min. After blocking, the cells were incubated for 1 hour at RT in blocking solution containing the rabbit anti-Myc (Abcam), mouse anti-HA (Covance), mouse anti-Flag (Sigma), rabbit anti-OR and rabbit anti-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen).

RNA-FISH.

Slides with cells were fixed in 4% PFA in PBS for 10 min and incubated in prechilled 70% ethanol for 30 min on ice. Following rehydration in 40% formamide in 2×SSC for 10 min, the slides were blocked with hybridization solution (40% formamide, 2×SSC, 10 mg/ml BSA, 100 mg/ml dextran sulfate and 10 mg/ml yeast tRNA) for 10 minutes at 55° C. and then incubated with 200 ng/ml denatured RNA probe in hybridization solution at 55° C. for 2 hours. After hybridization the slides were washed 3 times with 40% formamide in 2×SSC and briefly washed one time in PBS. Autofluorescence of lipofuscin was quenched by 0.25% of Sudan Black B in 70% ethanol and the slides were mounted with mounting medium containing DAPI (Invitrogen). The specificity of the RNA foci was determined by treating cells prior to FISH detection with either RNAse (100 ug/mL in 2×SSC), DNase (1 U/ul in DNaseI buffer) or Protease K (120 ug/mL in 2 mM CaCl2, 20 mM Tris, pH 7.5). Treated cells were incubated at 37° C. for 30 minutes, washed 3 times with PBS then 3 times with 2×SSC. Subsequent FISH detected was performed as described above. Antisense foci specificity was determined using standard FISH detection to first hybridize slides with 10-fold excess unlabeled (G4C2)4 oligo followed by hybridization with either G4C2-cy3 (antisense probe) or $G_2C_4$-cy3 (sense probe). Subsequent treatment and detection were performed as described above.

Western Blotting.

Transfected cells in each well of a six-well tissue-culture plate were rinsed with PBS and lysed in 300 μL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham). Sequential extraction of patient frontal cortex autopsy tissue was performed as follows: tissue was homogenized in PBS containing 1% Triton-X100, 15 mM MgCl2, 0.2 mg/ml DNase I and protease inhibitor cocktail and centrifuged at 16,000×g for 15 min at 4° C. The supernatant was collected. The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS, 62.5 mM Tris-HCl pH 6.8, 10% glycerol and 20% 2-Mercaptoethanol for protein blotting (25).

Protein Slot Blot.

1% Triton-X100 soluble fraction and 2% SDS soluble fraction from the sequential extraction was immobilized onto nitrocellulose membranes with Bio-Dot 96-well microfiltration system (Bio-Rad) under vacuum. The membranes were washed in PBS-T and blotted with each rabbit polyclonal antibody (1:2000) using the same protocol as western blotting.

Immunohistochemistry.

Ten-micrometer sections were deparaffinized in xylene and rehydrated through graded alcohol, incubated with 95-100% formic acid for 5 min, and washed with distilled water for 10 min. HIER was performed by steaming sections in citrate buffer, pH 6.0, at 90° C. for 30 min. To block nonspecific immunoglobulin binding, a serum-free block (Biocare Medical) was applied for 30 min. Rabbit polyclonal antibodies were applied at a dilution of from 1:5000 to 1:15,000 in serum-free block (Biocare Medical) and incubated overnight at 4° C. linking reagent (streptavidin and/or alkaline phosphatase, Covance) was applied for 30 min at room temperature. These sections were incubated in 3% H2O2 for 15 min to bleach endogenous peroxidase activity. Then labeling reagent (HRP, Covance) was applied for 30 min at room temperature. Peroxidase activity was developed with NovaRed substrate (Vector) and sections were counterstained with hematoxylin.

Cell Toxicity Assays.

All the transfection experiments were performed using Lipofectamine 2000 (Invitrogen), according to the manufacturer's instruction and at a 60% cell confluence. 500 ng of each vector was transfected in 35 mm wells. Cell death was determined by measuring Lactate dehydrogenase (LDH) cell release, using CytoTox 96 non-radioactive cytotoxicity assay (Promega) according to the manufacturer's instructions. Absorbance was recorded at 490 nm and total LDH release was measured by lysing the cells with 1% Triton X-100. In each experiment, determinations were performed in quintuplicates for each experimental condition and average data calculated. Statistical significance was determined using the two tailed unpaired Student t test for single comparisons (p<0.05) and the analysis of variance (ANOVA) when multiple pairwise conditions were compared.

Cell Viability Assays.

HeK293T cells were transfected in 96 well plates and cell viability was determined 42 hours post-transfection with the 3-(4,5-dimethylthiazol-2-yl)-2,5-diphenyl tetrazolium bromide (MTT) assay. MTT was added to cell culture media at 0.5 mg/mL final concentration and incubated for 45 minutes at 37° C. Cells were then lysed with 100 μL of DMSO upon medium removal and absorbance was measured at 595 nm.

In each experiment, determinations were performed in quintuplicates. Statistical significance was determined using Student's t test (p<0.05).

Example 4. BAC Transgenic Mouse Model of C9ORF72 ALS to Test the Hypothesis that Both Sense and Antisense Transcripts Contribute to ALS/FTD Rationale: A mouse model of C9ORF72 ALS/FTD that recapitulates the sense and antisense transcripts is critical for modeling this disease. BAC clones were isolated from a human patient which contain ~800 G4C2 repeats. These BAC clones were used to generate 8 founder lines. These mice are useful, for example, to answer the following questions: Does both RAN protein expression and RNA gain of function contribute to C9ORF72 ALS/FTD? Are sense and antisense mechanisms both important in C9ORF72 pathogenesis?

Figure 30:
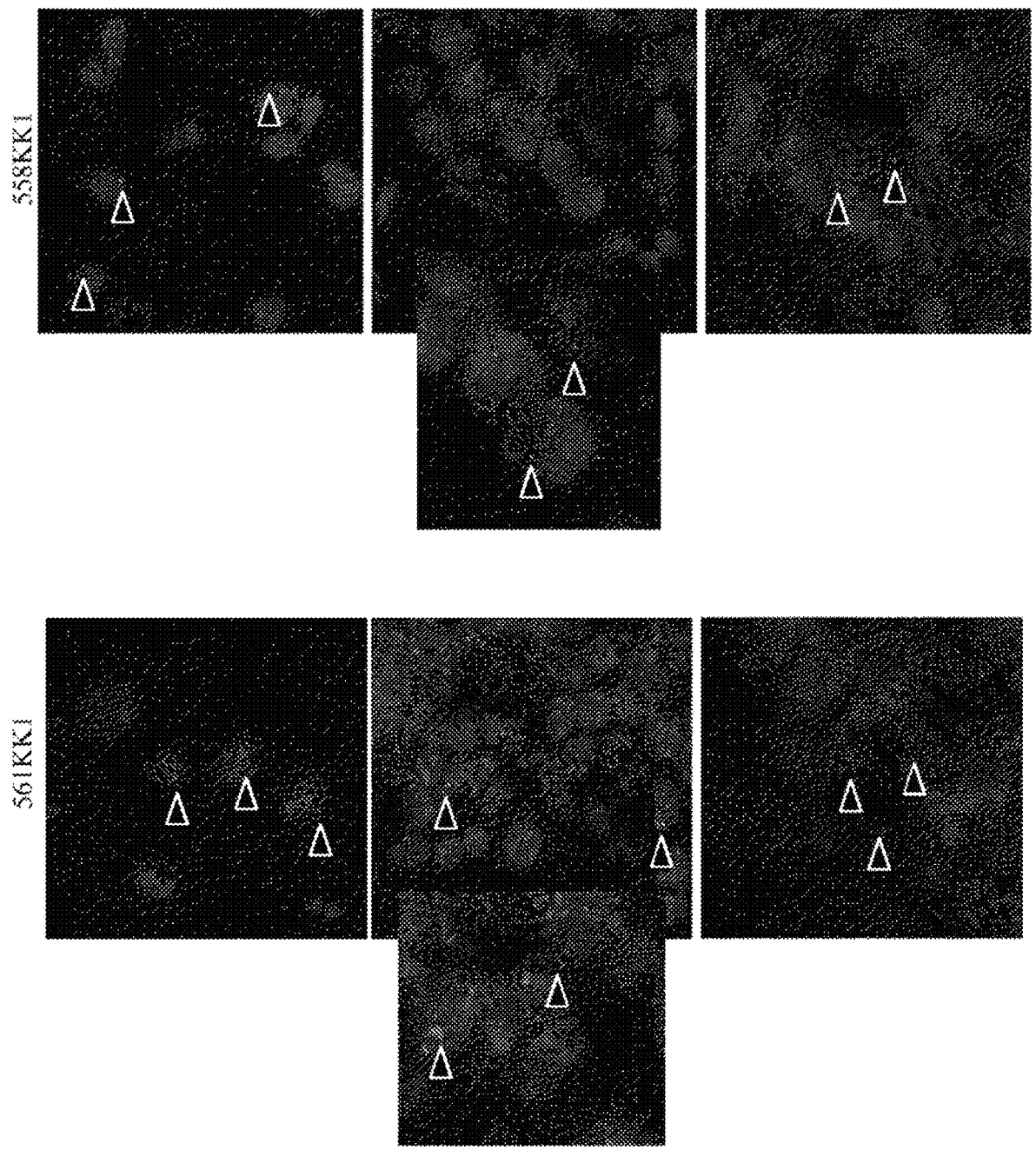
FIG. 30 is a series of photographs showing sense RNA foci in transgenic mice expressing a human C9ORF72 gene containing GGGGCC repeats. Exemplary foci are indicated by arrowheads.
Figure 31:
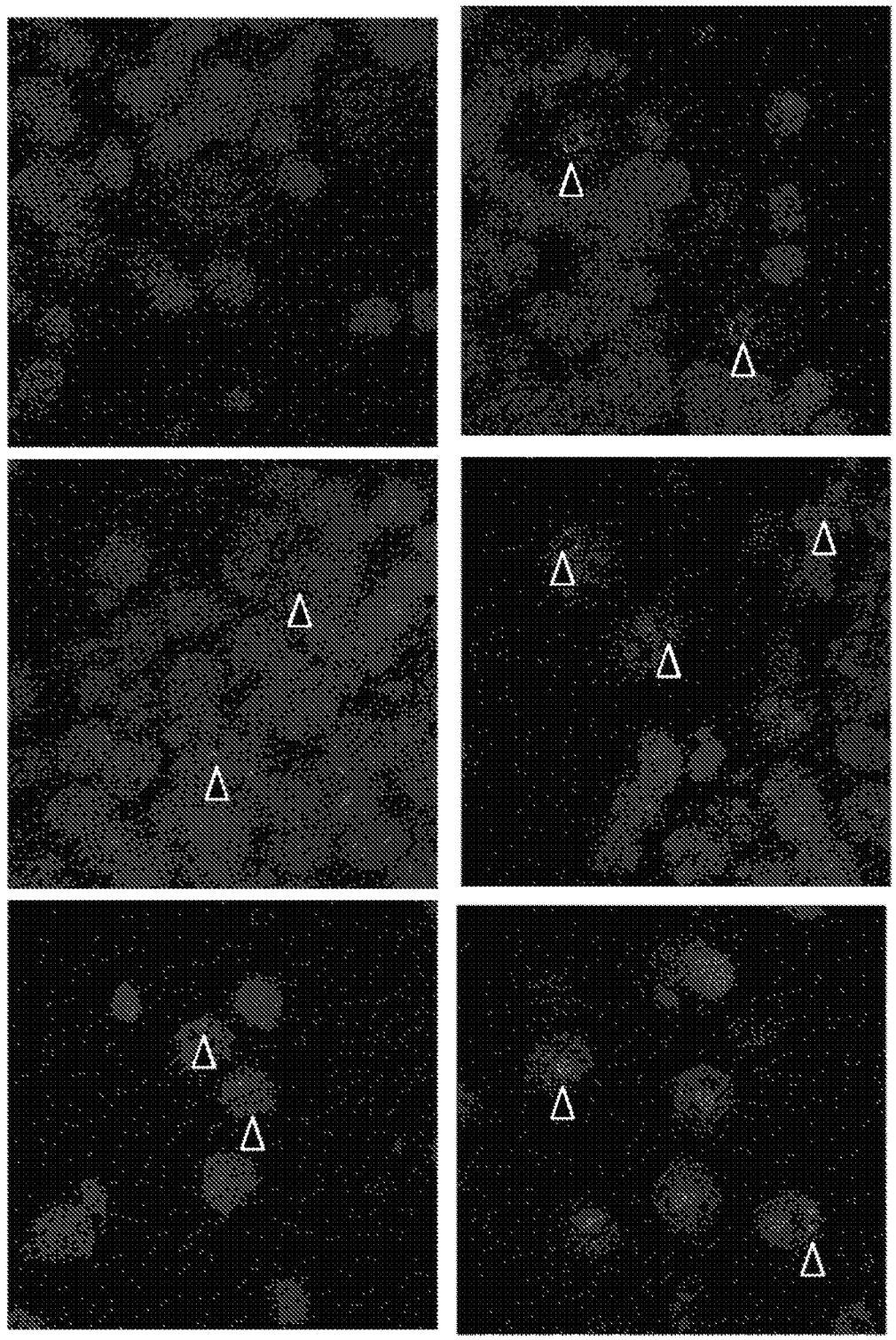
FIG. 31 is a series of photographs showing anti-sense (AS) RNA foci in transgenic mice expressing a human C9ORF72 gene containing GGGGCC repeats. Exemplary foci are indicated by arrowheads.

Approach:

BAC clones containing the full human C9ORF72 gene plus flanking sequences were isolated from a human patient with ~800 GGGGCC repeats and inserted into the pCCI BAC™ plasmid (Epicentre®). The BAC insert chosen for use in the mouse extended from bp27,625,470 to 27,527,137 of human genome reference sequence on Chromosome 9 (FIG. 29). The coordinates above do not include extra repeats from this patient. It was found that the BAC insert DNA contained about 800 repeats in some clone preps but was very unstable. Pronuclear injections were performed and 8 FVB founder lines were generated—2 independent lines which were confirmed expansion mutations. The BAC repeat size in the mice was ~500 repeats but varied between progeny and may grow or shrink in size as the mouse colony is expanded and additional generations of mice are propagated in the laboratory. BAC expansion mice expressed both sense and antisense versions of the C9ORF72 gene. Sense and anti-sense GGGCC RNA foci were present in mice that had the GGGGCC repeats, but not in control mice (FIGS. 30-31).

At least two expansion and two control lines are selected for detailed characterization. Behavioral characterization includes rotorod analysis, grip strength, balance beam and open field assessments. Molecular characterization of sense and antisense transcripts and RAN proteins are performed by RT-PCR, RACE, immunoblot, immunohistochemistry and immunofluorescence. Immunohistochemistry, immunofluorescence and FISH studies are performed to correlate sites of RNA foci and C9-RAN proteins accumulation with pathological changes. RAN-protein accumulation in the CNS, CSF, muscle, blood and other tissues are examined at various times during development.

Relevance:

Results from these studies will lead to a better understanding of the role that RAN translation plays in C9ORF72 ALS/FTD. Additionally, these studies will help to prioritize individual protein targets by determining which proteins are found most frequently in autopsy tissue and identifying overt differences in the toxicities of individual RAN proteins. Information from cellular and mouse models will also inform future studies on the effectiveness of various treatment strategies.

REFERENCES

1. DeJesus-Hernandez M, et al (2011) Expanded GGGGCC hexanucleotide repeat in noncoding region of C9ORF72 causes chromosome 9p-linked FTD and ALS. *Neuron* 72(2):245-256.
2. Renton A E, et al (2011) A hexanucleotide repeat expansion in C9ORF72 is the cause of chromosome 9p21-linked ALS-FTD. *Neuron* 72(2):257-268.
3. Majounie E, et al. (2012) Frequency of the C9orf72 hexanucleotide repeat expansion in patients with amyotrophic lateral sclerosis and frontotemporal dementia: a cross-sectional study. *Lancet Neurol* 11(4):323-330.
4. Nelson D L, Orr H T, & Warren S T (2013) The unstable repeats—three evolving faces of neurological disease. *Neuron* 77(5):825-843.
5. Reddy K, Zamiri B, Stanley S Y, Macgregor R B, Jr., & Pearson C E (2013) The disease-associated r(GGGGCC)n repeat from the C9orf72 gene forms tract length-dependent uni and multimolecular RNA G-quadruplex structures. *J Biol Chem* 288(14):9860-9866.
6. Mori K, et al. (2013) hnRNP A3 binds to GGGGCC repeats and is a constituent of p62-positive/TDP43-negative inclusions in the hippocampus of patients with C9orf72 mutations. *Acta Neuropathol* 125(3):413-423.
7. Xu Z, et al. (2013) Expanded GGGGCC repeat RNA associated with amyotrophic lateral sclerosis and frontotemporal dementia causes neurodegeneration. *Proc Natl Acad Sci USA* 110(19):7778-7783.
8. Almeida S, et al. (2013) Modeling key pathological features of frontotemporal dementia with C9ORF72 repeat expansion in iPSC-derived human neurons. *Acta Neuropathol*.
9. Zu T, et al. (2011) Non-ATG-initiated translation directed by microsatellite expansions. *Proc Natl Acad Sci USA* 108(1):260-265.
10. Ash P E, et al. (2013) Unconventional translation of C9ORF72 GGGGCC expansion generates insoluble polypeptides specific to c9FTD/ALS. *Neuron* 77(4):639-646.
11. Mori K, et al (2013) The C9orf72 GGGGCC Repeat is Translated into Aggregating Dipeptide—Repeat Proteins in FTLD/ALS. *Science*.
12. Todd P K, et al. (2013) CG repeat-associated translation mediates neurodegeneration in fragile X tremor ataxia syndrome. *Neuron* 78(3):440-455.
13. Ash P E A, et al. (2013) Unconventional Translation of C9ORF72 GGGGCC Expansion Generates Insoluble Polypeptides Specific to c9FTD/ALS *Neuron*.
14. Strausberg R L, et al. (2002) Generation and initial analysis of more than 15,000 full-length human and mouse cDNA sequences. *Proc Natl Acad Sci USA* 99(26):16899-16903.
15. Venter J C, et al. (2001) The sequence of the human genome. *Science* 291(5507):1304-1351.
16. Beausoleil S A, Villen J, Gerber S A, Rush J, & Gygi S P (2006) A probability-based approach for high-throughput protein phosphorylation analysis and site localization. *Nat Biotechnol* 24(10):1285-1292.
17. Sopher B L et al. (2011) CTCF regulates ataxin-7 expression through promotion of a convergently transcribed, antisense noncoding RNA. *Neuron* 70(6):1071-1084.
18. Chung D W, Rudnicki D D, Yu L, & Margolis R L (2011) A natural antisense transcript at the Huntington's disease repeat locus regulates HTT expression. *Hum Mol Genet* 20(17):3467-3477.
19. Wilburn B, et al (2011) An antisense CAG repeat transcript at JPH3 locus mediates expanded polyglutamine protein toxicity in Huntington's disease-like 2 mice. *Neuron* 70(3):427-440.
20. Ladd P D, et al (2007) An antisense transcript spanning the CGG repeat region of FMR1 is upregulated in premutation carriers but silenced in full mutation individuals. *Hum Mol Genet* 16(24):3174-3187.
21. Moseley M L et al. (2006) Bidirectional expression of CUG and CAG expansion transcripts and intranuclear polyglutamine inclusions in spinocerebellar ataxia type 8. *Nat Genet* 38(7):758-769.
22. Cho D H, et al. (2005) Antisense transcription and heterochromatin at the DM1 CTG repeats are constrained by CTCF. *Mol Cell* 20(3):483-489.
23. Li H, Wyman T, Yu Z X, Li S H, & Li X J (2003) Abnormal association of mutant huntingtin with synaptic vesicles inhibits glutamate release. *Hum Mol Genet* 12(16):2021-2030.
24. Luk K C, et al. (2012) Pathological alpha-synuclein transmission initiates Parkinson-like neurodegeneration in nontransgenic mice. *Science* 338(6109):949-953.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method of producing an antibody, the method comprising administering to a subject a di-amino acid repeat-containing protein antigen consisting of a poly-(Gly-Pro) di-amino acid repeat peptide.

2. The method of claim 1, wherein the di-amino acid repeat-containing protein antigen comprises the sequence set forth in SEQ ID NO: 21.

3. The method of claim 1, further comprising the step of isolating the antibody from the subject.

* * * * *